(12) United States Patent
Onishi

(10) Patent No.: US 12,329,797 B2
(45) Date of Patent: Jun. 17, 2025

(54) METHOD FOR IMPROVING HEALTH CONDITION OF MAMMAL OR FARM ANIMAL

(71) Applicant: Takao Onishi, Fukuoka (JP)

(72) Inventor: Takao Onishi, Fukuoka (JP)

( * ) Notice: Subject to any disclaimer, the term of this patent is extended or adjusted under 35 U.S.C. 154(b) by 0 days.

(21) Appl. No.: 18/844,892

(22) PCT Filed: Apr. 27, 2023

(86) PCT No.: PCT/JP2023/016737
§ 371 (c)(1),
(2) Date: Sep. 6, 2024

(87) PCT Pub. No.: WO2024/075330
PCT Pub. Date: Apr. 11, 2024

(65) Prior Publication Data
US 2025/0114421 A1    Apr. 10, 2025

(30) Foreign Application Priority Data

Oct. 4, 2022  (JP) .................................. 2022-160431
Oct. 4, 2022  (JP) .................................. 2022-160432

(51) Int. Cl.
| | |
|---|---|
| A61K 36/00 | (2006.01) |
| A23K 10/30 | (2016.01) |
| A23K 20/163 | (2016.01) |
| A23K 50/10 | (2016.01) |
| A61K 31/704 | (2006.01) |
| A61K 31/7048 | (2006.01) |
| A61K 36/484 | (2006.01) |
| A61P 1/12 | (2006.01) |
| A61P 1/14 | (2006.01) |
| A61P 3/00 | (2006.01) |

(52) U.S. Cl.
CPC ............ *A61K 36/484* (2013.01); *A23K 10/30* (2016.05); *A23K 20/163* (2016.05); *A23K 50/10* (2016.05); *A61K 31/704* (2013.01); *A61K 31/7048* (2013.01); *A61P 1/12* (2018.01); *A61P 1/14* (2018.01); *A61P 3/00* (2018.01)

(58) Field of Classification Search
CPC .................................................... A61K 36/48
See application file for complete search history.

(56) References Cited

U.S. PATENT DOCUMENTS

2018/0360899 A1 * 12/2018 Okumura .............. A23L 33/105

FOREIGN PATENT DOCUMENTS

| | | |
|---|---|---|
| CN | 103636948 A | 3/2014 |
| JP | 2007070240 A | 3/2007 |
| JP | 2018161144 A | 10/2018 |
| WO | 2018185214 A1 | 10/2018 |

OTHER PUBLICATIONS

International Search Report for PCT/JP2023/016737 dated for Jun. 13, 2023.
Supplementary European Search Report for EP23874465 dated Jan. 17, 2025.
Office Action for related European Patent Application No. 23874465 dated Jan. 29, 2025.

* cited by examiner

*Primary Examiner* — Qiuwen Mi
(74) *Attorney, Agent, or Firm* — Csaba Henter; MILLEN, WHITE, ZELANO & BRANIGAN

(57) ABSTRACT

A method for improving health conditions of mammals or livestock by feeding, to the mammals or livestock, a licorice extract including: (A) glycyrrhizic acid, a glycyrrhizic acid derivative, glycyrrhetinic acid, and/or a glycyrrhetinic acid derivative; (B) licorice saponins other than (A); and (C) licorice flavonoids; (B) including at least a licorice saponin H2, a licorice saponin G2, and macedonoside A, (C) including at least liquiritin apioside, isoliquiritin apioside, and isoliquiritin, where feeding is of 0.017 g/day/head or more of the licorice saponin H2, 0.002 g/day/head or more of the licorice saponin G2, and 0.002 g/day/head or more of the macedonoside A, 0.001 g/day/head or more of the liquiritin apioside, 0.001 g/day/head or more of the isoliquiritin apioside, and 0.001 g/day/head or more of the isoliquiritin.

19 Claims, 48 Drawing Sheets

AVERAGE WEIGHTS OF 10 MALES UPON SHIPPING TO AUCTION MARKET IN TEST 1.

AVERAGE WEIGHT OF 10 FEMALES UPON SHIPPING TO AUCTION MARKET IN TEST 1.

AVERAGE WEIGHT OF 8 MALES UPON SHIPPING TO AUCTION MARKET IN TEST 1.

AVERAGE WEIGHT OF 8 FEMALES UPON SHIPPING TO AUCTION MARKET IN TEST 1.

COMPARISON OF AVERAGE TOTAL CHOLESTEROL VALUES OF 8 MALES IN TEST 4.

COMPARISON OF AVERAGE TOTAL CHOLESTEROL VALUES OF 8 FEMALES IN TEST 4.

METHOD FOR IMPROVING HEALTH CONDITION OF MAMMAL OR FARM ANIMAL

TECHNICAL FIELD

The present invention relates to generally to methods for improving health conditions of mammals or livestock and, in particular, to a method for improving health conditions of mammals or livestock by feeding a licorice extract obtained by extracting components of licorice.

BACKGROUND ART

Conventionally, licorice has been used as one of raw materials of food additives and medicinal drugs. In particular, attention is paid to actions of glycyrrhizic acid and licorice flavonoids contained in the licorice and thus, there may be cases where the licorice is used for peculiar applications.

For example, described in Japanese Patent No. 6589102 (Patent Literature 1) is that with attention paid to glycyrrhizic acid contained in licorice, for the purpose of a feed additive for mammals and an improvement method, which aim at improving the quality of embryos obtained after superovulation treatment, a licorice extract having at least a 13% content of the glycyrrhizic acid is fed to Japanese Black Cattle continuously for a period of 60 to 90 days until collection of the embryos.

In addition, for example, described in Japanese Patent Application Laid-Open Publication No. H02-204417 (Patent Literature 2) is that in order to provide a hydrophobic licorice flavonoid preparation, an extract obtained from licorice root pulverized matter with ethanol used as an extracting solvent is refined by using adsorbing resin or the like, a refined extract having an approximately 50% content of the hydrophobic licorice flavonoid is obtained, a medium-chain fatty acid triglyceride is added to the refined extract to produce emulsion, and the emulsion is powderized by drying the emulsion.

In addition, described in Japanese Patent Application Laid-Open Publication No. 2015-70823 (Patent Literature 3) is a fruit or vegetable sugar content improver which utilizes licorice flavonoids contained in a crystallization mother liquor after crystallizing glycyrrhizic acid from a licorice extract liquid, a method for manufacturing the fruit or vegetable sugar content improver, and a method for improving a sugar content.

Described in Japanese Patent Application Laid-Open Publication No. 2018-161144 (Patent Literature 4) is a health fatness maintenance agent which contains a licorice processed product as an active ingredient and it is described therein that the licorice processed product contains glycyrrhizic acid, 22-beta-acetoxyglycyrrhizin, a licorice saponin G2, a licorice saponin H2, liquiritin, liquiritigenin, isoliquiritin, isoliquiritigenin, and the like.

Described in Japanese Patent Application Laid-Open Publication No. 2009-203182 (Patent Literature 5) is that a food composition having excellent hyaluronidase inhibitory actions attained by using a licorice extract containing a licorice saponin H2 is provided, thereby solving problems such as acne vulgaris and skin roughening.

CITATION LIST

Patent Literature

Patent Literature 1: Japanese Patent No. 6589102
Patent Literature 2: Japanese Patent Application Laid-Open Publication No. H02-204417
Patent Literature 3: Japanese Patent Application Laid-Open Publication No. 2015-70823
Patent Literature 4: Japanese Patent Application Laid-Open Publication No. 2018-161144
Patent Literature 5: Japanese Patent Application Laid-Open Publication No. 2009-203182

SUMMARY OF THE INVENTION

Technical Problem

However, effect of the conventional licorice extracts to perform a plurality of functions required to maintain or enhance health conditions of, for example, mammals or livestock has not been sufficient.

Therefore, an object of the present invention is to provide a method for improving health conditions of mammals or livestock.

Solution to Problem

The present inventor has devoted himself to earnest research. As a result, the present inventor found out that instead of individually using glycyrrhizic acid and licorice flavonoids, which have conventionally been used as active ingredients, in high purity or at high concentration, in various applications, due to composite actions of licorice saponins other than the glycyrrhizic acid in addition to the glycyrrhizic acid and the licorice flavonoids, high effects which cannot be expected in a case where the glycyrrhizic acid, the licorice flavonoids, and the licorice saponins are individually used can be obtained, and the licorice extract can be used as a multifunctional raw material. Based on the above-described findings, the present invention is constituted as described below.

A method for improving health conditions of mammals or livestock according to the present invention by feeding, to the mammals or livestock, a licorice extract including: (A) one or more selected from the group consisting of glycyrrhizic acid, a glycyrrhizic acid derivative, glycyrrhetinic acid, and a glycyrrhetinic acid derivative; (B) licorice saponins other than the (A); and (C) licorice flavonoids, the (B) including at least a licorice saponin H2, a licorice saponin G2, and macedonoside A, the (C) including at least liquiritin apioside, isoliquiritin apioside, and isoliquiritin, by feeding, to the mammals or livestock, 0.017 g/day/head or more of the licorice saponin H2, 0.002 g/day/head or more of the licorice saponin G2, and 0.002 g/day/head or more of the macedonoside A, and by feeding, to the mammals or livestock, 0.001 g/day/head or more of the liquiritin apioside, 0.001 g/day/head or more of the isoliquiritin apioside, and 0.001 g/day/head or more of the isoliquiritin, the method for improving the health conditions of the mammals or livestock by at least one selected from the group consisting of an increase in dietary intakes of the mammals or livestock, an increase in total cholesterol values in the blood of the mammals or livestock, an increase in vitamin A values in the blood of the mammals or livestock, a reduction in GOT values in the blood of the mammals or livestock, an increase in weights of the mammals or the livestock, prevention of diarrhea for the mammals or livestock, a reduction in numbers of treatment days of the diarrhea for the mammals or the livestock, prevention of colds for the mammals or livestock, and a reduction in numbers of treatment days of the colds for the mammals or livestock.

Thus, a method for improving health conditions of mammals or livestock can be provided.

DESCRIPTION OF EMBODIMENT

Figure 1:
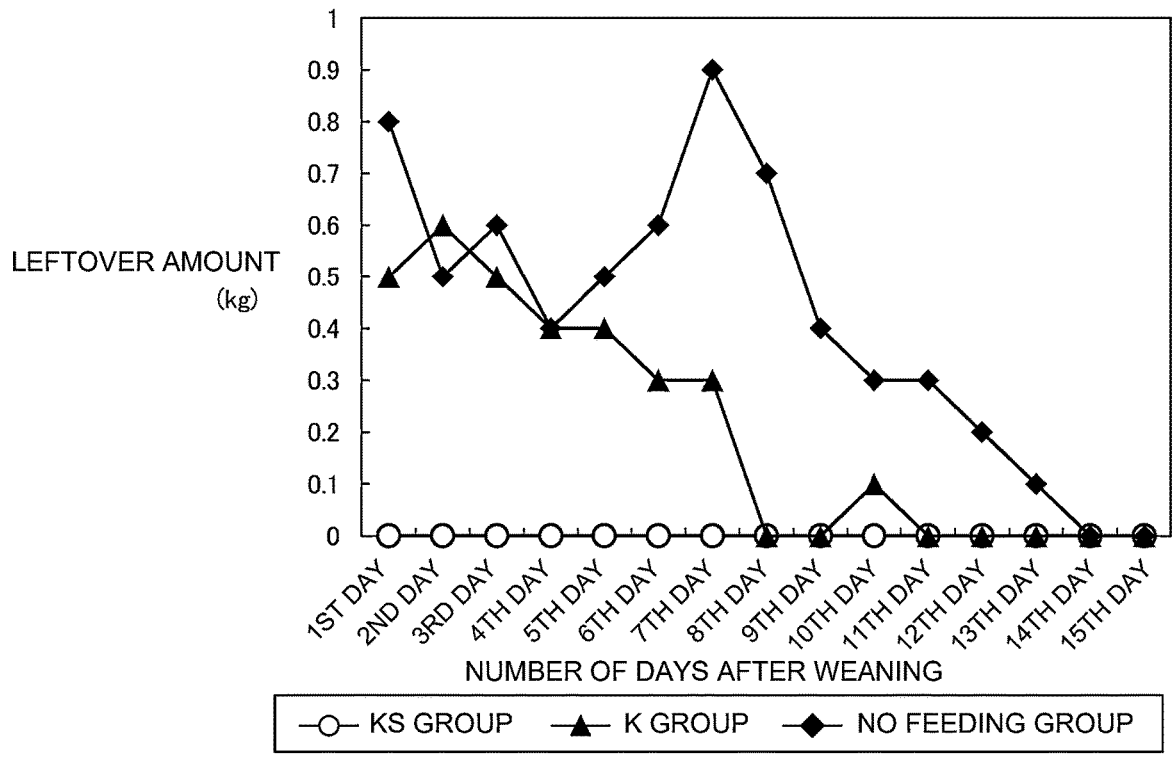
FIG. 1 is a graph showing comparison of average leftover amounts of 10 males in each group in Test 1.

Hereinafter, a licorice extract of the present invention will be described in detail with reference to specific examples. The present invention is not limited to the below-described embodiment and a variety of modifications can be made without departing from the technical idea of the present invention.

In the present invention, licorice refers to a plant which belongs to *Glycyrrhiza*. The *Glycyrrhiza* is a leguminous perennial plant which grows naturally in the Mediterranean region, Asia Minor, southern Russia, central Asia, northern China, North America, and the like. In the present invention, for example, *Glycyrrhiza acanthocarpa, G. aspera, G. astragalina, G bucharica, G. echinata (Glycyrrhiza echinata), G. eglandulosa, G. foetida, G. foetidissima, G. glabra (Glycyrrhiza glabra), G gontscharovii, G. iconica, G. inflate, G. korshinskyi, G lepidota (Glycyrrhiza lepidota), G. pallidiflora, G. squamulosa, G. triphylla, G. uralensis (Glycyrrhiza uralensis), G. yunnanensis, and G. inflata (Glycyrrhiza inflata)* can be used. One kind of these or two or more kinds of these in combination can be used.

The licorice extract in the present invention includes: (A) one or more selected from the group consisting of glycyrrhizic acid, a glycyrrhizic acid derivative, glycyrrhetinic acid, and a glycyrrhetinic acid derivative; (B) licorice saponins other than the above-mentioned (A); and (C) licorice flavonoids, and the (B) includes a licorice saponin H2, a licorice saponin G2, and macedonoside A.

In the present invention, the glycyrrhizic acid derivative is not limited and for example, is dipotassium glycyrrhizinate. The glycyrrhetinic acid derivative is not limited and for example, dipotassium glycyrrhetinate. In the licorice extract of the present invention, it is preferable that the (A) is glycyrrhizic acid. It is preferable that the licorice extract includes 9% by mass or more of (A) one or more selected from the group consisting of the glycyrrhizic acid, the glycyrrhizic acid derivative, the glycyrrhetinic acid, and the glycyrrhetinic acid derivative; it is preferable that the licorice extract includes 10% by mass or more thereof; it is more preferable that the licorice extract includes 14% by mass or more thereof; and it is further preferable that the licorice extract includes 15% by mass or more thereof. More specifically, it is preferable that the licorice extract includes 9.7% by mass or more of the (A) one or more selected from the group consisting of the glycyrrhizic acid, the glycyrrhizic acid derivative, the glycyrrhetinic acid, and the glycyrrhetinic acid derivative; it is more preferable that the licorice extract includes 10.6% by mass or more thereof; it is further preferable that the licorice extract includes 14.5% by mass or more thereof; and it is particularly preferable that the licorice extract includes 15.3% by mass or more thereof.

It is preferable that the licorice extract includes 2% by mass or more of the licorice saponins other than the above-mentioned (A); it is more preferable that the licorice extract includes 3% by mass or more thereof; and it is further preferable that the licorice extract includes 9% by mass or more thereof. More specifically, it is preferable that the licorice extract includes 2.8% by mass or more of the licorice saponins other than the above-mentioned (A); it is more preferable that the licorice extract includes 3.1% by mass or more thereof; it is further preferable that the licorice extract includes 3.6% by mass or more; and it is particularly preferable that the licorice extract includes 9.7% by mass or more thereof.

It is preferable that the (B) licorice saponins other than the above-mentioned (A) includes 1.7% by mass or more of the licorice saponin H2; it is more preferable that the (B) licorice saponins other than the above-mentioned (A) includes 2.1% by mass or more thereof; it is further preferable that the (B) licorice saponins other than the above-mentioned (A) includes 2.9% by mass or more thereof; and it is particularly preferable that the (B) licorice saponins other than the above-mentioned (A) includes 6.3% by mass or more thereof.

It is preferable that the (B) licorice saponins other than the above-mentioned (A) include 0.2% by mass or more of the licorice saponin G2; it is more preferable that the (B) licorice saponins other than the above-mentioned (A) include 0.5% by mass or more thereof; and it is particularly preferable that the (B) licorice saponins other than the above-mentioned (A) include 0.8% by mass or more thereof.

It is preferable that the (B) licorice saponins other than the above-mentioned (A) include 0.2% by mass or more of the macedonoside A; it is more preferable that the (B) licorice saponins other than the above-mentioned (A) include 0.5% by mass or more thereof; it is further preferable that the (B) licorice saponins other than the above-mentioned (A) include 0.9% by mass or more thereof; and it is particularly preferable that the (B) licorice saponins other than the above-mentioned (A) include 2.6% by mass or more thereof.

The (B) licorice saponins other than the (A) may include licorice saponins other than the licorice saponin H2, the licorice saponin G2, and the macedonoside A.

It is preferable that the licorice extract includes 4% by mass or more of the (C) licorice flavonoids; it is more preferable that the licorice extract includes 10% by mass or more thereof; and it is further preferable that the licorice extract includes 19% by mass or more thereof. More specifically, it is preferable that the licorice extract includes 4.6% by mass or more of the above-mentioned (C) licorice flavonoids; it is more preferable that the licorice extract includes 4.7% by mass or more thereof; it is further preferable that the licorice extract includes 10.8% by mass or more thereof; and it is particularly preferable that the licorice extract includes 19.8% by mass or more thereof.

It is preferable that as the (C) licorice flavonoids, the licorice extract includes liquiritin apioside, liquiritin, liquiritigenin, isoliquiritin apioside, isoliquiritin, and isoliquiritigenin. As the (C) components, other licorice flavonoids may be included.

It is preferable that the (C) licorice flavonoids include 0.1% by mass or more of the liquiritin apioside; it is more preferable that the (C) licorice flavonoids include 0.9% by mass or more thereof; it is further preferable that the (C) licorice flavonoids include 2.4% by mass or more thereof; and it is particularly preferable that the (C) licorice flavonoids include 5.6% by mass or more thereof.

It is preferable that the (C) licorice flavonoids include 0.1% by mass or more of the isoliquiritin apioside; it is more preferable that the (C) licorice flavonoids include 0.4% by mass or more thereof; and it is further preferable that the (C) licorice flavonoids include 1.8% by mass or more thereof.

It is preferable that the (C) licorice flavonoids include 0.1% by mass or more of the isoliquiritin; it is more preferable that the (C) licorice flavonoids include 0.3% by mass or more thereof; and it is further preferable that the (C) licorice flavonoids include 2.7% by mass or more thereof.

It is preferable that the (C) licorice flavonoids include 0.9% by mass or more of the liquiritin; it is more preferable that the (C) licorice flavonoids include 2.1% by mass or more thereof; it is further preferable that the (C) licorice flavonoids include 5.7% by mass or more thereof; and it is particularly preferable that the (C) licorice flavonoids include 7.9% by mass or more thereof.

It is preferable that the (C) licorice flavonoids include 0.2% by mass or more of the liquiritigenin; it is more preferable that the (C) licorice flavonoids include 1.1% by mass or more thereof; it is further preferable that the (C) licorice flavonoids include 1.3% by mass or more thereof; and it is particularly preferable that the (C) licorice flavonoids include 2.0% by mass or more thereof.

It is preferable that the (C) licorice flavonoids include 0.1% by mass or more of the isoliquiritigenin; it is more preferable that the (C) licorice flavonoids include 0.5% by mass or more thereof; it is further preferable that the (C) licorice flavonoids include 1.2% by mass or more thereof; and it is particularly preferable that the (C) licorice flavonoids include 2.0% by mass or more thereof.

As to the contents of the (A), the (B), the (C), and the components of the licorice extract, the above-mentioned values can be optionally combined.

For example, it is preferable that the licorice extract includes 1.7% by mass or more of the licorice saponin H2, includes 0.2% by mass or more of the licorice saponin G2, includes 0.2% by mass or more of the macedonoside A, includes 0.1% by mass or more of the liquiritin apioside, includes 0.1% by mass or more of the isoliquiritin apioside, and includes 0.1% by mass or more of the isoliquiritin. It is preferable that the licorice extract further includes 9.7% by mass or more of the (A) one or more selected from the group consisting of glycyrrhizic acid, the glycyrrhizic acid derivative, the glycyrrhetinic acid, and the glycyrrhetinic acid derivative. It is preferable that the licorice extract further includes 2.1% by mass or more of the liquiritin. It is preferable that the licorice extract further includes 1.1% by mass or more of the liquiritigenin. It is preferable that the licorice extract further includes 0.5% by mass or more of the isoliquiritigenin. It is preferable that the licorice extract includes 2.8% by mass or more of the (B) licorice saponins other than the above-mentioned (A). It is preferable that the licorice extract includes 4.7% by mass or more of the (C) licorice flavonoids.

In addition, it is preferable that the licorice extract includes 1.7% by mass or more of the licorice saponin H2, includes 0.2% by mass or more of the licorice saponin G2, includes 0.9% by mass or more of the macedonoside A, includes 0.1% by mass or more of the liquiritin apioside, includes 0.1% by mass or more of the isoliquiritin apioside, and includes 0.1% by mass or more of the isoliquiritin. It is preferable that the licorice extract further includes 15.3% by mass or more of the (A) one or more selected from the group consisting of the glycyrrhizic acid, the glycyrrhizic acid derivative, the glycyrrhetinic acid, and the glycyrrhetinic acid derivative. It is preferable that the licorice extract further includes 2.1% by mass or more of the liquiritin. It is preferable that the licorice extract further includes 1.1% by mass or more of the liquiritigenin. It is preferable that the licorice extract further includes 1.2% by mass or more of the isoliquiritigenin. It is preferable that the licorice extract includes 2.8% by mass or more of the (B) licorice saponins other than the above-mentioned (A). It is preferable that the licorice extract includes 4.7% by mass or more of the (C) licorice flavonoids.

In addition, it is preferable that the licorice extract includes 2.9% by mass or more of the licorice saponin H2, includes 0.5% by mass or more of the licorice saponin G2, includes 0.2% by mass or more of the macedonoside A, includes 0.9% by mass or more of the liquiritin apioside, includes 0.1% by mass or more of the isoliquiritin apioside, and includes 0.1% by mass or more of the isoliquiritin. It is preferable that the licorice extract further includes 9.7% by mass or more of the (A) one or more selected from the group consisting of glycyrrhizic acid, the glycyrrhizic acid derivative, the glycyrrhetinic acid, and the glycyrrhetinic acid derivative. It is preferable that the licorice extract further includes 7.9% by mass or more of the liquiritin. It is preferable that the licorice extract further includes 1.3% by mass or more of the liquiritigenin. It is preferable that the licorice extract further includes 0.5% by mass or more of the isoliquiritigenin. It is preferable that the licorice extract includes 3.6% by mass or more of (B) licorice saponins other than the above-mentioned the (A). It is preferable that the licorice extract includes 10.8% by mass or more of the (C) licorice flavonoids.

In addition, it is preferable that the licorice extract includes 6.3% by mass or more of the licorice saponin H2, includes 0.8% by mass or more of the licorice saponin G2, includes 2.6% by mass or more of the macedonoside A, includes 5.6% by mass or more of the liquiritin apioside, includes 1.8% by mass or more of the isoliquiritin apioside, and includes 2.7% by mass or more of the isoliquiritin. It is preferable that the licorice extract further includes 14.5% by mass or more of the (A) one or more selected from the group consisting of the glycyrrhizic acid, the glycyrrhizic acid derivative, the glycyrrhetinic acid, and the glycyrrhetinic acid derivative. It is preferable that the licorice extract further includes 5.7% by mass or more of the liquiritin. It is preferable that the licorice extract further includes 2.0% by mass or more of the liquiritigenin. It is preferable that the licorice extract further includes 2.0% by mass or more of the isoliquiritigenin. It is preferable that the licorice extract 9.7% by mass or more of the (B) licorice saponins other than the above-mentioned (A). It is preferable that the licorice extract includes 19.8% by mass or more of the (C) licorice flavonoids.

The licorice extract of the present invention is a licorice extract such as a licorice extractive obtained by extracting, separating, and refining the component of the licorice. A form of the licorice extract is not limited and is selected from forms such as a starch syrup form, a viscid liquid form, a liquid form, a suspension form, a powder form, a granule form, a pill form, a spherical form, and a ball form in accordance with properties and use application. It is preferable that the form of the licorice extract is the powder form.

One example of a method for manufacturing a licorice extract as one example of the licorice extract of the present invention will be described. It is preferable that processes of manufacturing the licorice extract of the present invention include at least one or more of processes A to C.

Process A

A process A is a process of obtaining an extract liquid from a licorice root or licorice roots. One kind or two or more kinds of licorice roots is or are dried and crushed, and water and ammonia are added thereto, thereby obtaining an extract liquid from the licorice root or licorice roots. Sulfuric acid is added to the extract liquid and the resultant is precipitated, thereby separating a viscid extract and supernatant. The viscid extract is dried, thereby obtaining a primary extract as a licorice extract (condensed licorice).

Process B

A process B is a process of separation and refinement. The condensed licorice obtained in the process A is dissolved in an ethanol aqueous solution and the resultant is filtrated, thereby removing insoluble matter. Ammonia is added to the obtained extract liquid and the licorice saponin is crystallized (formed to be crystalline) as ammonium salt and the resultant is filtrated, thereby separating crystals and extract mother liquor. The extract mother liquor is condensed under a reduced pressure, the ethanol is collected, and sodium carbonate or potassium carbonate is added thereto, thereby adjusting pH to 6 to 7. The obtained concentrated liquid is dried by spray-dry and is mixed, thereby obtaining a licorice extract.

Process C

A process C is another process of separation and refinement. Activated carbon is added to the extract mother liquor obtained in the process B, thereby removing impurities and the obtained liquid is dried by spray-dry, thereby allowing a licorice extract to be obtained.

The licorice extract, for example, may be a licorice extract manufactured by only the process A, may be a licorice extract manufactured by implementing the process A and the process B continuously, may be a licorice extract manufactured by implementing the processes A to C continuously, may be a mixture of the licorice extract manufactured by only the process A and the licorice extract manufactured by the processes A and B continuously, may be a mixture of the licorice extract manufactured by only the process A and the licorice extract manufactured by implementing the processes A to C continuously, may be a mixture of the licorice extract manufactured by only the process A, the licorice extract manufactured by implementing the processes A and B, and the licorice extract manufactured by implementing the processes A to C continuously, and may be a mixture of the licorice extract manufactured by implementing the processes A and B continuously and the licorice extract manufactured by implementing the processes A to C continuously. In addition, the number of times at which the respective processes are repeated is also optional. In addition, the licorice extract may be a licorice extract manufactured by mixing the licorice extract which is manufactured by any of the above-mentioned processes by using some raw material licorice and one or more licorice extracts which is or are manufactured by the above-mentioned processes by using different raw material licorice.

The licorice extract may be packed as needed.

An extracting solvent of the licorice extract is not limited and for example, water, alcohol (for example, methanol, ethanol, n-propanol, n-butanol, or the like), acetone, ethyl acetate, or the like can be used. In addition, in a case where dry powder is obtained, for example, the heretofore known method such as drying under a reduced pressure and spray drying can be employed for the above-described licorice extract.

In the manufacturing of the licorice extract, each of the processes of the processes A to C can be repeated and/or omitted such that each of the components attains a desired concentration. In addition, a new licorice extract can also be obtained by mixing the licorice extracts obtained in the processes of the processes A to C such that each of the components attains the desired concentration.

The licorice extract of the present invention can be used directly or by adding other components or additives thereto, can be used as food, a supplement, a feed additive, or the like. For example, the licorice extract and licorice root powder obtained by crushing a dried licorice root are combined and are used as a licorice processed product.

The licorice extract of the present invention can be manufactured directly or by adding other components or additives thereto, supplements or feed additives can be manufactured. By adding the licorice extract of the present invention to feed as the supplement or the feed additive or by adding, to feed, the supplement or feed additive which includes the licorice extract of the present invention, a plurality of functions required to maintain and enhance health of mammals or livestock can be concurrently imparted to feed. The content of the licorice extract in the supplement or the feed additive of the present invention may be 100% by mass.

In the present invention, the mammals are not limited and for example, may be monkeys, dogs, cats, goats, sheep, pigs, cattle, guinea pigs, rabbits, mice, rats, or humans and preferably, are cattle. In the present invention, as the livestock, in addition to the mammals, birds such as chickens, pigeons, and canards are included.

In the present invention, the feed means every compound, preparation, mixture, or composition which is suited to be ingested by the mammals or the livestock or is intended to be ingested by the mammals or the livestock. In the present invention, the feed additive refers to an additive agent which is used for the purpose of providing nutrition for the livestock or the like and is added to fodder (feed) to be used for quality preservation of feed and as supplemental nutrition.

A dosage form of the supplement or the feed additive is not limited and is selected from forms such as a starch syrup form, a viscid liquid form, a liquid form, a suspension form, a powder form, a granule form, a pill form, a spherical form, and a ball form in accordance with properties and use application.

The content of the licorice extract of the present invention in the supplement or the feed additive is not limited, it is preferable that the content thereof is 1 g/day/head or more, it is preferable that the content thereof is less than 10 g/day/head, and it is more preferable that the content thereof is 5 g/day/head or less. Although conventionally, the licorice extract used as the feed additive has been added in an amount of, for example, 10 g to 40 g/day/head, the licorice extract of the present invention allows a plurality of functions to be imparted to feed in a further small amount.

In other words, in a case where 1 g/day/head or more of the licorice extract of the present invention is fed to the mammals or the livestock, 0.017 g/day/head or more of the licorice saponin H2, 0.002 g/day/head or more of the licorice saponin G2, 0.002 g/day/head or more of the macedonoside A, 0.001 g/day/head or more of the liquiritin apioside, 0.001 g/day/head or more of the isoliquiritin apioside, and 0.001 g/day/head or more of the isoliquiritin are fed thereto.

In a case where 5 g/day/head or more of the licorice extract of the present invention are fed to the mammals or the livestock, 0.085 g/day/head or more of the licorice saponin H2, 0.01 g/day/head or more of the licorice saponin G2, 0.01 g/day/head or more of the macedonoside A, 0.005 g/day/head or more of the liquiritin apioside, 0.005 g/day/head or more of the isoliquiritin apioside, and 0.005 g/day/head or more of the isoliquiritin are fed thereto.

In a case where 10 g/day/head or more of the licorice extract of the present invention are fed to the mammals or the livestock, 0.17 g/day/head or more of the licorice saponin H2, 0.02 g/day/head or more of the licorice saponin G2, 0.02 g/day/head or more of the macedonoside A, 0.01 g/day/head or more of the liquiritin apioside, 0.01 g/day/head or more of the isoliquiritin apioside, and 0.01 g/day/head or more of the isoliquiritin are fed thereto.

It is preferable that 0.017 g/day/head or more of the licorice saponin H2 to the mammals to the livestock, it is more preferable that 0.02 g/day/head or more thereof is fed thereto, it is further preferable that 0.029 g/day/head or more thereof is fed thereto, and it is particularly preferable that 0.063 g/day/head or more thereof is fed thereto.

It is preferable that 0.002 g/day/head or more of the licorice saponin G2 is fed to the mammals or the livestock, it is more preferable that 0.005 g/day/head or more thereof is fed thereto, and it is further preferable that 0.008 g/day/head or more thereof is fed thereto.

It is preferable that 0.002 g/day/head or more of the macedonoside A is fed to the mammals or the livestock, it is more preferable that 0.005 g/day/head or more thereof is fed thereto, it is further preferable that 0.009 g/day/head or more thereof is fed thereto, and it is particularly preferable that 0.026 g/day/head or more thereof is fed thereto.

It is preferable that 0.001 g/day/head or more of the liquiritin apioside is fed to the mammals or the livestock, it is more preferable that 0.009 g/day/head or more thereof is fed thereto, it is further preferable that 0.024 g/day/head or more thereof is fed thereto, and it is particularly preferable that 0.056 g/day/head or more thereof is fed thereto.

It is preferable that 0.001 g/day/head or more of the isoliquiritin apioside is fed to the mammals or the livestock, it is more preferable that 0.004 g/day/head or more thereof is fed thereto, and it is further preferable that 0.018 g/day/head or more thereof is fed thereto.

It is preferable that 0.001 g/day/head or more of the isoliquiritin is fed to the mammals or the 1 livestock, it is more preferable that 0.003 g/day/head or more thereof is fed thereto, and it is further preferable that 0.027 g/day/head or more thereof is fed thereto.

It is preferable that 0.009 g/day/head or more of the liquiritin is fed to the mammals or the livestock, it is more preferable that 0.021 g/day/head or more thereof is fed thereto, it is further preferable that 0.057 g/day/head or more thereof is fed thereto, and it is particularly preferable that 0.079 g/day/head or more thereof is fed thereto.

It is preferable that 0.002 g/day/head or more of the liquiritigenin is fed to the mammals or the livestock, it is more preferable that 0.011 g/day/head or more thereof is fed thereto, it is further preferable that 0.013 g/day/head or more thereof is fed thereto, and it is particularly preferable that 0.020 g/day/head or more thereof is fed thereto.

It is preferable that 0.001 g/day/head or more of the isoliquiritigenin is fed to the mammals or the livestock, it is more preferable that 0.005 g/day/head or more thereof is fed thereto, it is further preferable that 0.012 g/day/head or more thereof is fed thereto, and it is particularly preferable that 0.020 g/day/head or more thereof is fed thereto.

It is preferable that 0.09 g/day/head or more of the (A) one or more selected from the group consisting of glycyrrhizic acid, the glycyrrhizic acid derivative, the glycyrrhetinic acid, and the glycyrrhetinic acid derivative is fed to the mammals or the livestock, it is more preferable that 0.14 g/day/head or more thereof is fed thereto, and it is further preferable that 0.15 g/day/head or more thereof is fed thereto.

It is preferable that 0.02 g/day/head or more of the (B) licorice saponins other than the above-mentioned (A) is fed to the mammals or the livestock, it is more preferable that 0.03 g/day/head or more thereof is fed thereto, and it is further preferable that 0.09 g/day/head or more thereof is fed thereto.

It is preferable that 0.04 g/day/head or more of the (C) licorice flavonoids is fed to the mammals or the livestock, it is more preferable that 0.10 g/day/head or more thereof is fed thereto, and it is further preferable that 0.19 g/day/head or more thereof is fed thereto.

As to amounts of the (A), the (B), the (C), and the components which are fed to the mammals or the livestock, the above-mentioned values can be optionally combined.

For example, it is preferable that the licorice extract feeds 0.017 g/day/head or more of the licorice saponin H2, 0.002 g/day/head or more of the licorice saponin G2, 0.002 g/day/head or more of the macedonoside A, 0.001 g/day/head or more of the liquiritin apioside, 0.001 g/day/head or more of the isoliquiritin apioside, and 0.001 g/day/head or more of the isoliquiritin. It is preferable that the licorice extract further feeds 0.097 g/day/head or more of the (A) one or more selected from the group consisting of the glycyrrhizic acid, the glycyrrhizic acid derivative, the glycyrrhetinic acid, and the glycyrrhetinic acid derivative. It is preferable that the licorice extract further feeds 0.021 g/day/head or more of the liquiritin. It is preferable that the licorice extract further feeds 0.011 g/day/head or more of the liquiritigenin. It is preferable that the licorice extract further feeds 0.005 g/day/head or more of the isoliquiritigenin. It is preferable that the licorice extract feeds 0.028 g/day/head or more of the (B) licorice saponins other than the above-mentioned (A). It is preferable that the licorice extract feeds 0.047 g/day/head or more of the (C) licorice flavonoids.

In addition, it is preferable that the licorice extract feeds 0.017 g/day/head or more of the licorice saponin H2, 0.002 g/day/head or more of the licorice saponin G2, 0.009 g/day/head or more of the macedonoside A, 0.001 g/day/head or more of the liquiritin apioside, 0.001 g/day/head or more of the isoliquiritin apioside, and 0.001 g/day/head or more of the isoliquiritin. It is preferable that the licorice extract further feeds 0.153 g/day/head or more of the (A) one or more selected from the group consisting of the glycyrrhizic acid, the glycyrrhizic acid derivative, the glycyrrhetinic acid, and the glycyrrhetinic acid derivative. It is preferable that the licorice extract further feeds 0.021 g/day/head or more of the liquiritin. It is preferable that the licorice extract further feeds 0.011 g/day/head or more of the liquiritigenin. It is preferable that the licorice extract further feeds 0.012 g/day/head or more of the isoliquiritigenin. It is preferable that the licorice extract feeds 0.028 g/day/head or more of the (B) licorice saponins other than the above-mentioned (A). It is preferable that the licorice extract feeds 0.047 g/day/head or more of the (C) licorice flavonoids.

In addition, it is preferable that the licorice extract feeds 0.029 g/day/head or more of the licorice saponin H2, 0.005 g/day/head or more of the licorice saponin G2, 0.002 g/day/head or more of the macedonoside A, 0.009 g/day/head or more of the liquiritin apioside, 0.001 g/day/head or more of the isoliquiritin apioside, and 0.001 g/day/head or more of the isoliquiritin. It is preferable that the licorice extract further feeds 0.097 g/day/head or more of the (A) one or more selected from the group consisting of glycyrrhizic acid, the glycyrrhizic acid derivative, the glycyrrhetinic acid, and the glycyrrhetinic acid derivative. It is preferable that the licorice extract further feeds 0.079 g/day/head or more of the liquiritin. It is preferable that the licorice extract further feeds 0.013 g/day/head or more of the liquiritigenin. It is preferable that the licorice extract further feeds 0.005 g/day/head or more of the isoliquiritigenin. It is preferable that the licorice extract 0.036 g/day/head or more of the (B) licorice saponins other than the above-mentioned (A). It is preferable that the licorice extract feeds 0.108 g/day/head or more of the (C) licorice flavonoids.

In addition, it is preferable that the licorice extract feeds 0.063 g/day/head or more of the licorice saponin H2, 0.008 g/day/head or more of the licorice saponin G2, 0.026 g/day/head or more of the macedonoside A, 0.056 g/day/head or more of the liquiritin apioside, 0.018 g/day/head or more of the isoliquiritin apioside, and 0.027 g/day/head or more of the isoliquiritin. It is preferable that the licorice extract further 0.145 g/day/head or more of the (A) one or more selected from the group consisting of glycyrrhizic acid, the glycyrrhizic acid derivative, the glycyrrhetinic acid, and the glycyrrhetinic acid derivative. It is preferable that the licorice extract further feeds 0.057 g/day/head or more of the liquiritin. It is preferable that the licorice extract further feeds 0.020 g/day/head or more of the liquiritigenin. It is preferable that the licorice extract further feeds 0.020 g/day/head or more of the isoliquiritigenin. It is preferable that the licorice extract feeds 0.097 g/day/head or more of the (B) licorice saponins other than the above-mentioned (A). It is preferable that the licorice extract 0.198 g/day/head or more of the (C) licorice flavonoids.

In the supplement or the feed additive, water-soluble dietary fiber may be optionally included. The water-soluble dietary fiber comes to be in a viscous sol state when added to water. The water-soluble dietary fiber is not limited, *Plantago ovata* seed coats (*psyllium*), carrageenan, xanthan gum, curdlan, pectin, Arabian gum, alginic acid, chitin, chitosan, guar gum, glucomannan, gellan gum, tara gum, tamarind gum, tragacanth gum, pullulan, indigestible dextrin, polydextrose, or the like can be used, and it is preferable that the glucomannan is used. The glucomannan may be refined by water, moisture ethanol, or the like and thereafter, may be used or as a glucomannan-containing material, konjac powder may be used. Although an average particle diameter of general konjac powder is approximately 420 μm (wholly passing through 35-mesh) and the particle diameter is comparatively large, it is preferable that the konjac powder or powdery glucomannan which has an average particle diameter of approximately 177 μm (wholly passing through 80-mesh) or less is used for the feed additive of the present invention. Thus, a surface area of the particles is increased, affinity with water is heightened, and a swelling speed of the glucomannan is increased. By adding the glucomannan thereto, intestinal regulation action of the licorice processed product can be enhanced.

It is preferable that the licorice extract and the water-soluble dietary fiber are included in the supplement or the feed additive of the present invention in a mass ratio of the licorice extract:the water-soluble dietary fiber of 10:90 to 40:60. It is preferable that the supplement or the feed additive of the present invention further includes a starch decomposition product. In a case where the starch decomposition product is included, it is preferable that a mass ratio of the licorice extract:the water-soluble dietary fiber:the starch decomposition product is 10:30:60.

By feeding the licorice extract of the present invention or the supplement or the feed additive which includes the licorice extract thereof to mammals or livestock, in order to improve health conditions by at least one selected from the group consisting of an increase in dietary intakes of the mammals or the livestock, an increase in total cholesterol values in the blood thereof, an increase in vitamin A values in the blood thereof, a reduction in GOT values in the blood thereof, an increase in weights thereof, prevention of diarrhea therefor, a reduction in numbers of treatment days of diarrhea therefor, prevention of colds therefor, and a reduction in numbers of treatment days of colds therefor, the licorice extract or the supplement or the feed additive which includes the licorice extract can be fed.

It is preferable that the mammals or the livestock to which the licorice extract of the present invention or the supplement or the feed additive which includes the licorice extract thereof is fed is livestock for meat production, and in order to increase carcass weights, to improve carcass yield rates, and/or to reduce liver discard rates of meat animals, the licorice extract or the supplement or the feed additive which includes the licorice extract can be fed.

It is preferable that the mammals or the livestock to which the licorice extract of the present invention or the supplement or the feed additive which includes the licorice extract thereof is livestock for meat production, and in order to enhance feed efficiency, the licorice extract or the supplement or the feed additive which includes the licorice extract can be fed.

The present invention is summarized as follows.

(1) In one aspect, the licorice extract according to the present invention includes; the (A) one or more selected from the group consisting of the glycyrrhizic acid, the glycyrrhizic acid derivative, the glycyrrhetinic acid, and the glycyrrhetinic acid derivative; the (B) the licorice saponins other than the (A); and the (C) licorice flavonoids, and the (B) includes at least 1.7% by mass or more of the licorice saponin H2, 0.2% by mass or more of the licorice saponin G2, and 0.2% by mass or more of the macedonoside A, and the (C) includes at least 0.1% by mass or more of the liquiritin apioside, 0.1% by mass or more of the isoliquiritin apioside, and 0.1% by mass or more of the isoliquiritin.

(2) It is preferable that in the licorice extract according to the present invention, the (B) includes at least 1.7% by mass or more of the licorice saponin H2, 0.2% by mass or more of the licorice saponin G2, and 0.9% by mass or more of the macedonoside A and (C) includes at least 0.1% by mass or more of the liquiritin apioside, 0.1% by mass or more of the isoliquiritin apioside, and 0.1% by mass or more of the isoliquiritin.

(3) It is preferable that in the licorice extract according to the present invention, the (B) includes at least 2.9% by mass or more of the licorice saponin H2, 0.5% by mass or more of the licorice saponin G2, and 0.2% by mass or more of the macedonoside A and the (C) includes at least 0.9% by mass or more of the liquiritin apioside, 0.1% by mass or more of the isoliquiritin apioside, and 0.1% by mass or more of the isoliquiritin.

(4) It is preferable that in the licorice extract according to the present invention, the (B) includes at least 2% by mass or more of the licorice saponin H2, 0.5% by mass or more of the licorice saponin G2, and 0.5% by mass or more of the macedonoside A and the (C) includes at least 2.4% by mass or more of the liquiritin apioside, 0.4% by mass or more of the isoliquiritin apioside, and 0.3% by mass or more of the isoliquiritin.

(5) It is preferable that in the licorice extract according to the present invention, the (B) includes at least 6.3% by mass or more of the licorice saponin H2, 0.8% by mass or more of the licorice saponin G2, and 2.6% by mass or more of the macedonoside A and the (C) includes at least 5.6% by mass or more of the liquiritin apioside, 1.8% by mass or more of the isoliquiritin apioside, and 2.7% by mass or more of the isoliquiritin.

(6) It is preferable that the licorice extract according to the present invention includes 9% by mass or more of the (A), and/or 2% by mass or more of the (B), and/or 4% by mass or more of the (C).

(7) It is preferable that the licorice extract according to the present invention includes 15% by mass or more of the (A), and/or 2% by mass or more of the (B), and/or 4% by mass or more of the (C).

(8) It is preferable that the licorice extract according to the present invention includes 9% by mass or more of the (A), and/or 3% by mass or more of the (B), and/or 10% by mass or more of the (C).

(9) It is preferable that the licorice extract according to the present invention includes 14% by mass or more of the (A), and/or, 9% by mass or more of the (B), and/or 19% by mass or more of the (C).

(10) It is preferable that the feed additive for the mammals or the livestock according to the present invention includes the licorice extract according to any one of the above mentioned (1) to (9).

(11) It is preferable that the feed additive according to the present invention includes the water-soluble dietary fiber.

(12) It is preferable that the feed additive according to the present invention includes the licorice extract and the water-soluble dietary fiber in the mass ratio of the licorice extract: the water-soluble dietary fiber=10:90 to 40:60.

(13) It is preferable that in the feed additive according to the present invention, the water-soluble dietary fiber is the glucomannan.

(14) It is preferable that a method for raising mammals or livestock according to the present invention improves health conditions by at least one selected from the group consisting of an increase in dietary intakes of the mammals or the livestock, an increase in total cholesterol values in the blood thereof, an increase in vitamin A values in the blood thereof, a reduction in GOT values in the blood thereof, an increase in weight thereof, prevention of diarrhea therefor, a reduction in numbers of treatment days of diarrhea therefor, prevention of colds therefor, and a reduction in numbers of treatment days of colds therefor by feeding the feed additive described in the above-mentioned (10) to the mammals or the livestock.

(15) It is preferable that in the method for raising mammals or livestock according to the present invention, the mammals or the livestock is the livestock for meat production and by feeding the feed additive described in the above-mentioned (10) to the mammals or the livestock, carcass weights are increased, carcass yield rates are improved, and/or liver discard rates of meat animals are reduced.

(16) It is preferable that in the method for increasing the feed efficiency according to the present invention, the mammals or livestock is the livestock for meat production and by feeding the feed additive described in the above-mentioned (10) to the mammals or the livestock, the feed efficiency is increased.

(17) In another aspect, the method for improving the health conditions of the mammals or livestock according to the present invention improves the health conditions of the mammals or the livestock by at least one selected from the group consisting of an increase in dietary intakes of the mammals or the livestock, an increase in total cholesterol values in the blood thereof, an increase in vitamin A values in the blood thereof, a reduction in GOT values in the blood thereof, an increase in weights thereof, prevention of diarrhea therefor, a reduction in numbers of treatment days of the diarrhea therefor, prevention of colds therefor, and a reduction in numbers of treatment days of the colds therefor by feeding, to the mammals or the livestock, the licorice extract which includes: the (A) one or more selected from the group consisting of the glycyrrhizic acid, the glycyrrhizic acid derivative, the glycyrrhetinic acid, and the glycyrrhetinic acid derivative; the (B) licorice saponins other than the (A); and the (C) licorice flavonoids, the (B) including at least the licorice saponin H2, licorice saponin G2, and the macedonoside A, the (C) including at least the liquiritin apioside, the isoliquiritin apioside, and the isoliquiritin, by feeding, to the mammals or the livestock, 0.017 g/day/head or more of the licorice saponin H2, 0.002 g/day/head or more of the licorice saponin G2, and 0.002 g/day/head or more of the macedonoside A and feeding, thereto, 0.001 g/day/head or more of the liquiritin apioside, 0.001 g/day/head or more of the isoliquiritin apioside, and 0.001 g/day/head or more of the isoliquiritin.

(18) It is preferable that the method according to the present invention includes feeding, to the mammals or the livestock, 0.017 g/day/head or more of the licorice saponin H2, 0.002 g/day/head or more of the licorice saponin G2, 0.009 g/day/head or more of the macedonoside A, 0.001 g/day/head or more of the liquiritin apioside, 0.001 g/day/head or more of the isoliquiritin apioside, and 0.001 g/day/head or more of the isoliquiritin.

(19) It is preferable that the method according to the present invention includes feeding, to the mammals or the livestock, 0.029 g/day/head or more of the licorice saponin H2, 0.005 g/day/head or more of the licorice saponin G2, 0.002 g/day/head or more of the macedonoside A, 0.009 g/day/head or more of the liquiritin apioside, 0.001 g/day/head or more of the isoliquiritin apioside, and 0.001 g/day/head or more of the isoliquiritin.

(20) It is preferable that the method according to the present invention includes feeding, to the mammals or the livestock, 0.02 g/day/head or more of the licorice saponin H2, 0.005 g/day/head or more of the licorice saponin G2, 0.005 g/day/head or more of the macedonoside A, 0.024 g/day/head or more of the liquiritin apioside, 0.004 g/day/head or more of the isoliquiritin apioside, and 0.003 g/day/head or more of the isoliquiritin.

(21) It is preferable that the method according to the present invention includes feeding, to the mammals or the livestock, 0.063 g/day/head or more of the licorice saponin H2, 0.008 g/day/head or more of the licorice saponin G2, 0.026 g/day/head or more of the macedonoside A, 0.056 g/day/head or more of the liquiritin apioside, 0.018 g/day/head or more of the isoliquiritin apioside, and 0.027 g/day/head or more of the isoliquiritin.

(22) It is preferable that the method according to the present invention includes feeding, to the mammals or the livestock, 0.09 g/day/head or more of the (A), and/or 0.02 g/day/head or more of the (B), and/or 0.04 g/day/head or more of the (C).

(23) It is preferable that the method according to the present invention includes feeding, to the mammals or the livestock, 0.15 g/day/head or more of the (A), and/or 0.02 g/day/head or more of the (B), and/or 0.04 g/day/head or more of the (C).

(24) It is preferable that the method according to the present invention includes feeding, to the mammals or the livestock, 0.09 g/day/head or more of the (A), and/or 0.03 g/day/head or more of the (B), and/or 0.10 g/day/head or more of the (C).

(25) It is preferable that the method according to the present invention includes feeding, to the mammals or the livestock, 0.14 g/day/head or more of the (A), and/or 0.09 g/day/head or more of the (B), and/or 0.19 g/day/head or more of the (C).

(26) It is preferable that the method according to the present invention improves the health conditions of the mammals or the livestock by at least an increase in dietary intakes of the mammals or the livestock, an increase in total cholesterol values in the blood thereof, an increase in vitamin A values in the blood thereof, a reduction in GOT values in the blood thereof, an increase in weights thereof, prevention of diarrhea therefor, a reduction in numbers of treatment days of the diarrhea therefor, prevention of colds therefor, and a reduction in numbers of treatment days of the colds therefor.

(27) It is preferable that in the method according to the present invention, the mammals or the livestock is the livestock for meat production.

(28) It is preferable that the method according to the present invention is further the method for increasing carcass weights, improving carcass yield rates, and/or reducing edible liver discard rates.

(29) It is preferable that the method according to the present invention is further the method for increasing carcass weights, improving carcass yield rates, and reducing edible liver discard rates.

(30) It is preferable that the method according to the present invention is further the method for increasing the feed efficiency.

(31) It is preferable that in the method according to the present invention, the licorice extract includes: the (A) one or more selected from the group consisting of the glycyrrhizic acid, the glycyrrhizic acid derivative, the glycyrrhetinic acid, and the glycyrrhetinic acid derivative; the (B) the licorice saponins other than the (A); and the (C) the licorice flavonoids, the (B) including at least 1.7% by mass or more of the licorice saponin H2, 0.2% by mass or more of the licorice saponin G2, and 0.2% by mass or more of the macedonoside A, the (C) including at least 0.1% by mass or more of the liquiritin apioside, 0.1% by mass or more of the isoliquiritin apioside, and 0.1% by mass or more of the isoliquiritin.

(32) It is preferable that in the method according to the present invention, in the licorice extract, the (B) includes at least 1.7% by mass or more of the licorice saponin H2, 0.2% by mass or more of the licorice saponin G2, and 0.9% by mass or more of the macedonoside A, and the (C) includes at least 0.1% by mass or more of the liquiritin apioside, 0.1% by mass or more of the isoliquiritin apioside, and 0.1% by mass or more of the isoliquiritin.

(32) It is preferable that in the method according to the present invention, in the licorice extract, the (B) includes at least 2.9% by mass or more of the licorice saponin H2, 0.5% by mass or more of the licorice saponin G2, and 0.2% by mass or more of the macedonoside A, and the (C) includes at least 0.9% by mass or more of the liquiritin apioside, 0.1% by mass or more of the isoliquiritin apioside, and 0.1% by mass or more of the isoliquiritin.

(33) It is preferable that in the method according to the present invention, in the licorice extract, the (B) includes at least 2% by mass or more of the licorice saponin H2, 0.5% by mass or more of the licorice saponin G2, and 0.5% by mass or more of the macedonoside A, and the (C) includes at least 2.4% by mass or more of the liquiritin apioside, 0.4% by mass or more of the isoliquiritin apioside, and 0.3% by mass or more of the isoliquiritin.

(34) It is preferable that in the method according to the present invention, in the licorice extract, the (B) includes at least 6.3% by mass or more of the licorice saponin H2, 0.8% by mass or more of the licorice saponin G2, and 2.6% by mass or more of the macedonoside A, and the (C) includes at least 5.6% by mass or more of the liquiritin apioside, 1.8% by mass or more of the isoliquiritin apioside, and 2.7% by mass or more of the isoliquiritin.

(32) It is preferable that in the method according to the present invention, the licorice extract includes 9% by mass or more of the (A), and/or 2% by mass or more of the (B), and/or 4% by mass or more of the (C).

(33) It is preferable that in the method according to the present invention, the licorice extract includes 15% by mass or more of the (A), and/or 2% by mass or more of the (B), and/or 4% by mass or more of the (C).

(34) It is preferable that in the method according to the present invention, the licorice extract includes 9% by mass or more of the (A), and/or 3% by mass or more of the (B), and/or 10% by mass or more of the (C).

(35) It is preferable that in the method according to the present invention, the licorice extract includes 14% by mass or more of the (A), and/or 9% by mass or more of the (B), and/or 19% by mass or more of the (C).

(36) It is preferable that in the method according to the present invention, the licorice extract is included in the feed additive.

(37) It is preferable that in the method according to the present invention, the feed additive includes the water-soluble dietary fiber.

(38) It is preferable that in the method according to the present invention, the feed additive includes the licorice extract and the water-soluble dietary fiber in the mass ratio of the licorice extract:the water-soluble dietary fiber=10:90 to 40:60.

(39) It is preferable that in the method according to the present invention, the water-soluble dietary fiber is the glucomannan.

EXAMPLES

A licorice extract and a method for raising mammals or livestock according to the present invention in which a feed additive or a supplement, which includes the licorice extract, is used will be described in further detail.

<Manufacturing of Licorice Extracts>

By using a species of *Glycyrrhiza glabra* (*glabra*), a species of *Glycyrrhiza uralensis* (*uralensis*), and a species of *Glycyrrhiza inflata* (*inflata*) as licorice, licorice extracts were manufactured by the following processes. In Examples 1, 2, 4, 5, 7, and 8 and Comparative Example 1, the species of *Glycyrrhiza glabra* (*glabra*) was used. In Example 9, the species of *Glycyrrhiza inflata* (*inflata*) was used. In Example 3, the species of *Glycyrrhiza glabra* (*glabra*) and the species of *Glycyrrhiza uralensis* (*uralensis*) were used. In Examples 6 and 10, the species of *Glycyrrhiza glabra* (*glabra*) and the species of *Glycyrrhiza inflata* (*inflata*) were used. In Examples 11 and 20, the species of *Glycyrrhiza inflata* (*inflata*) was used. In Examples 12, 13, 14, 15, 16, and 17, the species of *Glycyrrhiza glabra* (*glabra*) was used. In Examples 18 and 19, the species of *Glycyrrhiza glabra* (*glabra*) and the species of *Glycyrrhiza inflata* (*inflata*) were used.

Process A

One kind, two kinds, or three kinds of licorice roots were dries and crushed. Approximately 8 to 10 L of water at an ordinary temperature and ammonia water in adequate amounts were added to one kg of the crushed licorice roots and extraction was performed, thereby obtaining an extract liquid. At that time, in order to achieve pH in the vicinity of 9, the added amount of the ammonia water was adjusted. Sulfuric acid was added to the obtained extract liquid, components were precipitated, and viscid extract and supernatant (supernate) were separated. At that time, an amount of the sulfuric acid was adjusted so as to achieve pH of precipitation sludge in the vicinity of 1.8. The separated viscid extract was dried and the obtained primary extract was made to be a licorice extract (condensed licorice). The process A was repeated until desired component contents were obtained as needed.

Process B

Ethanol in the vicinity of 90% in an amount of 600 to 800 mL was added to 100 g of the condensed licorice obtained in the process A, extraction was performed therefor, and unwanted substances were filtrated and thereby removed, thereby obtaining an extract liquid. The extract liquid was heated to 50° C. to 60° C., ammonia was added thereto, a licorice saponin was crystallized (formed to be crystalline) as ammonium salt. The resultant was cooled to ordinary temperature, and thereafter, the ammonium salt of the licorice saponin was centrifuged to be separated and was removed, thereby obtaining an extract mother liquor (licorice extract liquid). At that time, the added amount of the ammonia water was adjusted so as to achieve pH of the crystallized sludge in the vicinity of 5. The process up to here was repeated until desired component contents were obtained as needed. The extract mother liquor (licorice extract liquid) was condensed under a reduced pressure, the ethanol was collected, and approximately 100 mL of a residual liquid was obtained. A sodium carbonate or a potassium carbonate was added to the extract mother liquor (licorice extract liquid) condensed under a reduced pressure and pH of the resultant was adjusted to 6 to 7. The obtained liquid was dried by spray-dry, thereby obtaining a licorice extract.

Process C

Activated carbon was added to the extract mother liquor (licorice extract liquid) obtained in the process B, impurities were thereby removed, and this process was conducted at one to two times, thereby obtaining an extract mother liquor (licorice extract liquid). The obtained liquid was dried by spray-dry, thereby obtaining a licorice extract.

The licorice extracts obtained in each of the processes A to C or the processes of combined processes A to C were mixed so as to achieve desired amounts of the component contents as needed.

Licorice extracts in Examples 1 to 6 were manufactured by the process A and the process B. Licorice extracts in Examples 7 and 8 were manufactured by mixing the licorice extracts obtained by each of the processes A to C. Licorice extracts in Examples 9 and 10 were manufactured by the process A. A licorice extract in Comparative Example 1 was manufactured by the processes A to C. Licorice extracts in Examples 11 to 17 were manufactured by the process A and the process B. Licorice extracts in Examples 18 and 19 were manufactured by the process A, the process B, and the process C. A licorice extract in Example 20 was manufactured by the process A.

<Measurement of Components in Licorice Extracts>

The glycyrrhizic acid of the (A) one or more selected from the group consisting of the glycyrrhizic acid, the glycyrrhizic acid derivative, the glycyrrhetinic acid, and the glycyrrhetinic acid derivative and the (B) the licorice saponin H2, the licorice saponin G2, and the macedonoside A in each of the licorice extracts in Examples and Comparative Example were measured under the following conditions by an HPLC analysis.

<Preparation of Measurement Samples>

Preparation of measurement samples was conducted in accordance with (1) for water-soluble licorice extracts and (2) for water-insoluble licorice extracts.

(1) Water-Soluble Licorice Extracts

Each sample in an amount of approximately 200 mg was taken and water was added thereto to precisely adjust an amount thereof to 100 mL, thereby obtaining each sample solution. Separately, by using a standard solution prepared by using a glycyrrhizic acid reference standard, an analysis was conducted by liquid chromatography. However, a collection quantity of each sample was corrected in terms of dry matter %.

(2) Water-Insoluble Licorice Extracts

Each sample in an amount of 0.1 g was taken and three drops of ammonia water (28%) and water were added thereto to precisely adjust an amount thereof to 50 mL, thereby obtaining each sample solution. Separately, diluted ethanol was added to a glycyrrhizic acid reference standard, thereby preparing a standard solution. An analysis was conducted by using the standard solution by liquid chromatography. However, a collection quantity of each sample was corrected in terms of dry matter % by Equation 1.

[Equation 1]

$$A \text{ content of a substance to be obtained } (\%) = \frac{A_T}{A_S} \times \frac{W_S}{W_T} \times 100 \quad \text{(Equation 1)}$$

AT: area of sample solution
AS: area of standard solution
WS: concentration of standard solution
WT: concentration of sample solution converted in terms of dry matter <Measurement of Glycyrrhizic Acid>

Test conditions of measurement of the glycyrrhizic acid (HPLC coping with high pressure (LC1290 manufactured by Agilent Technologies, Inc.)) were as follows.
Detector: ultraviolet absorptiometer (a measurement wavelength: 254 nm)
Column: Tosoh TSK Gel ODS80TsQA
Column temperature: a constant temperature in the vicinity of 30° C.
Flow rate: adjusted such that a retention time of the glycyrrhizic acid was approximately 7 to 8 minutes.
Mobile phase: 2% acetic acid: acetonitrile=60:40
Injected amount: 20 μL <Measurement of Licorice Saponins>

Test conditions of measurement of the licorice saponins (HPLC coping with high pressure (LC1290 manufactured by Agilent Technologies, Inc.)) were as follows.
Detector: ultraviolet absorptiometer (a measurement wavelength: 254 nm)
Column: Tosoh TSK Gel ODS80TsQA
Column temperature: a constant temperature in the vicinity of 30° C.
Flow rate: 0.8 mL/minute
Mobile phase: mobile phase A: 0.1% formic acid (water)/ mobile phase B: 0.1% formic acid (acetonitrile)
Injected amount: 20 μL
As to a concentration gradient of the mobile phase, the flow ratio was changed from A:B=90:10 (0 to 3 minutes) to 10:90 (3 to 60 minutes).

<Measurement of Licorice Flavonoids>

The licorice flavonoids in Examples and Comparative Example were measured under the following test conditions by an HPLC analysis. Measurement samples were prepared in a manner similar to the manner in which the above-described glycyrrhizic acid and the other licorice saponins were measured. By using, as standard solutions, a glycyrrhizic acid standard solution (measurement wavelength: 254 nm), a liquiritin standard solution (a measurement wavelength: 280 nm), an isoliquiritigenin standard solution (a measurement wavelength: 355 nm), and an isoliquiritin standard solution (a measurement wavelength: 355 nm), the sample solutions and the standard solutions were subjected to a gradient analysis by liquid chromatography, thereby obtaining flavonoid contents. However, the flavonoid contents were corrected in terms of dry matter % of the samples.

The measurement conditions (HPLC coping with high pressure (LC1290 manufactured by Agilent Technologies, Inc.)) were as follows.
Detector: ultraviolet absorptiometer (a measurement wavelength: 280 nm, 355 nm)
Column: TSK Gel ODS80TsQA
Column temperature: a constant temperature in the vicinity of 30° C.
Flow rate: 0.8 mL/minute
Mobile phase: mobile phase A: 0.1% formic acid (water)/ mobile phase B: 0.1% formic acid (acetonitrile)
Injected amount: 20 μL
As to a concentration gradient of the mobile phase, the flow ratio was changed from A:B=90:10 (0 to 3 minutes) to 10:90 (3 to 60 minutes).

Main components of the obtained licorice extracts are shown in Table 1 and Table 2. Note that "%" in Table 1 and Table 2 means % by mass.

TABLE 1

| | Example 1 | Example 2 | Example 3 | Example 4 | Example 5 | Example 6 | Example 7 | Example 8 | Example 9 | Example 10 | Comparative Example 1 |
|---|---|---|---|---|---|---|---|---|---|---|---|
| (A) Glycyrrhizic acid | 10.6% | 11.2% | 11.2% | 12.6% | 14.5% | 17.0% | 19.7% | 20.1% | 25.4% | 25.8% | 13.4% |
| Licorice saponin H2 | 2.1% | 7.6% | 5.4% | 4.5% | 6.3% | 6.5% | 6.2% | 6.9% | 3.6% | 7.3% | 1.0% |
| Licorice saponin G2 | 0.5% | 0.9% | 1.6% | 0.7% | 0.8% | 1.1% | 1.2% | 1.2% | 2.5% | 1.3% | 0.5% |
| Macedonoside A | 0.5% | 2.6% | 4.5% | 1.4% | 2.6% | 2.3% | 1.9% | 1.9% | 1.9% | 2.2% | 0.2% |
| Liquiritin apioside | 2.8% | 7.0% | 5.8% | 2.4% | 5.6% | 5.2% | 3.6% | 3.1% | 2.5% | 3.2% | 0.0% |
| Liquiritin | 0.9% | 8.8% | 15.0% | 1.1% | 5.7% | 10.4% | 2.2% | 2.1% | 4.2% | 3.7% | 0.0% |
| Liquiritigenin | 0.3% | 2.4% | 0.5% | 0.2% | 2.0% | 2.6% | 1.1% | 1.0% | 0.6% | 1.4% | 0.0% |
| Isoliquiritin apioside | 0.9% | 1.9% | 0.4% | 0.5% | 1.8% | 1.0% | 1.0% | 0.4% | 0.4% | 0.5% | 0.0% |
| Isoliquiritin | 0.4% | 3.4% | 2.4% | 0.3% | 2.7% | 1.3% | 0.8% | 0.4% | 1.2% | 1.2% | 0.0% |
| Isoliquiritigenin | 0.2% | 1.3% | 0.1% | 0.1% | 2.0% | 1.2% | 0.5% | 0.3% | 0.2% | 0.6% | 0.0% |

TABLE 1-continued

|  | Example 1 | Example 2 | Example 3 | Example 4 | Example 5 | Example 6 | Example 7 | Example 8 | Example 9 | Example 10 | Comparative Example 1 |
|---|---|---|---|---|---|---|---|---|---|---|---|
| (B) Total of licorice saponins except glycyrrhizic acid | 3.1% | 11.1% | 11.5% | 6.6% | 9.7% | 9.9% | 9.3% | 10.0% | 8.0% | 10.8% | 1.7% |
| (C) Total of licorice flavonoids | 5.5% | 24.8% | 24.2% | 4.6% | 19.8% | 21.7% | 9.2% | 7.3% | 9.1% | 10.6% | 0.0% |
| Total of (B) and (C) | 8.6% | 35.9% | 35.7% | 11.2% | 29.5% | 31.6%v | 18.5% | 17.3% | 17.1% | 21.4% | 1.7% |

TABLE 2

|  | Example 11 | Example 12 | Example 13 | Example 14 | Example 15 | Example 16 | Example 17 | Example 18 | Example 19 | Example 20 |
|---|---|---|---|---|---|---|---|---|---|---|
| (A) Glycyrrhizic acid | 9.7% | 15.3% | 14.1% | 15.8% | 16.3% | 27.0% | 13.8% | 22.4% | 27.6% | 23.6% |
| Licorice saponin H2 | 2.9% | 1.7% | 5.9% | 6.3% | 5.5% | 6.2% | 4.8% | 2.2% | 3.7% | 4.1% |
| Licorice saponin G2 | 0.5% | 0.2% | 0.8% | 0.9% | 0.7% | 1.6% | 0.7% | 2.4% | 1.4% | 1.8% |
| Macedonoside A | 0.2% | 0.9% | 3.7% | 3.8% | 3.8% | 2.1% | 1.5% | 0.3% | 0.4% | 2.3% |
| Liquiritin apioside | 0.9% | 0.1% | 0.4% | 0.4% | 0.4% | 2.9% | 1.5% | 1.2% | 0.9% | 0.1% |
| Liquiritin | 7.9% | 2.1% | 4.1% | 3.4% | 3.1% | 2.0% | 6.2% | 6.0% | 4.6% | 5.0% |
| Liquiritigenin | 1.3% | 1.1% | 1.5% | 1.2% | 1.3% | 0.8% | 0.9% | 1.1% | 0.8% | 1.2% |
| Isoliquiritin apioside | 0.1% | 0.1% | 0.5% | 0.5% | 0.4% | 0.6% | 0.2% | 0.1% | 0.1% | 0.1% |
| Isoliquiritin | 0.1% | 0.1% | 0.6% | 0.7% | 0.5% | 0.6% | 0.5% | 0.4% | 0.3% | 0.2% |
| Isoliquiritigenin | 0.5% | 1.2% | 0.9% | 0.7% | 0.4% | 0.3% | 0.8% | 0.5% | 0.4% | 0.2% |
| (B) Total of licorice saponins except glycyrrhizic acid | 3.6% | 2.8% | 10.4% | 11.0% | 10.0% | 9.9% | 7.0% | 4.9% | 5.5% | 8.2% |
| (C) Total of licorice flavonoids | 10.8% | 4.7% | 8.0% | 6.9% | 6.1% | 7.2% | 10.1% | 9.3% | 7.1% | 6.8% |
| Total of (B) and (C) | 14.4% | 7.5% | 18.4% | 17.9% | 16.1% | 17.1% | 17.1% | 14.2% | 12.6% | 15.0% |

In order to confirm effects by the licorice extracts of the present invention, the following tests targeted for cattle which is livestock for meat production as the mammals or the livestock were conducted.

Test 1. From Five Days of Age after Birth Up to Approximately 240 Days of Age to Approximately 270 Days of Age Calves after birth are nurtured by being fed with high-concentration substitute milk, and thereafter, the calves are gradually weaned from approximately 80 days of age after birth, and the nurturing is switched to nurturing by being provided with feed. When burdens are applied to digestive organs thereof by the high-concentration substitute milk, a reduction and variation in feed intakes are caused. In addition, the reduction and variation in the feed intake are caused also by stress due to environmental changes from the milk-nurturing frame to the feed nurturing frame upon being weaned, stress due to group feeding, and stress due to switching from the substitute milk to formula feed or coarse feed. Development of the digestive organs, for example, development of rumina in the stomachs can be retarded by the above-mentioned burdens on the digestive organs, the stress, and the reduction and variation in the feed intakes. The reduction and variation in the feed intakes and the retard of the development of the digestive organs retard growing and reduce feed efficiency.

Therefore, by feeding the licorice extracts of the present invention as feed additives to calves from five days of age after birth up to approximately 240 days of age to approximately 270 days of age, influence of the licorice extracts of the present invention exerted on a reduction in leftover amounts of feed upon being weaned (an increase in dietary intakes), nutrition states (total cholesterol values, vitamin A values, and GOT values in blood tests), and weights was examined.

Ordinarily, with weaning at approximately 90 days of age as a rough standard, while the substitute milk and creep feed are gradually decreased starting from approximately 80 days of age after birth, feeding amounts of rice straws, oat hay, and formula feed are increased. However, in the present test, in order to clearly confirm the effects by the licorice extracts, complete weaning was conducted at approximately 80 days of age.

Targets were a total of 60 head of Japanese Black Cattle including 30 male calves and 30 female calves at five days of age to 10 days of age after birth up to days of age upon shipping to an auction market (male calves at 241 to 261 days of age and female calves at 246 to 291 days of age). The targets were divided into three groups.

TABLE 3

|  | Male | Female | Total |
|---|---|---|---|
| KS group | 10 head | 10 head | 20 head |
| K group | 10 head | 10 head | 20 head |
| No feeding group | 10 head | 10 head | 20 head |

In the KS group, the licorice extract in Example 5 was added to feed as a feed additive from approximately five days of age after birth, and in the K group, the licorice extract in Comparative Example 1 was added to feed as a feed additive. In no feeding group, any licorice extract was not added to feed. As to feed other than the licorice extracts (substitute milk, artificial milk, formula feed, and coarse feed such as pasture), feed shown in Table 4 (feed fed to one male head of cattle) and feed shown in Table 5 (feed fed to one female head of cattle) were fed with each amount shown therein divided into three parts a day, and the formula feed, the rice straws, and the oat hay were fed at and after 81 days of age in this order with the same amount fed to each of the groups at the same time. The creep feed and the oat hay were fed from approximately two weeks after birth.

TABLE 4

|  | Substitute milk Artificial milk | Creep feed | Formula feed | Rice straws | Oat hay |
|---|---|---|---|---|---|
| 0 to 30 days | Fed | 0.3 kg | — | — | 0.03 kg |
| 31 to 60 days | Fed | 1.5 kg | — | — | 0.2 kg |
| 61 to 80 days | Fed | 3.2 kg | — | — | 0.4 kg |
| 81 to 120 days | — | — | 4.5 kg | 0.4 kg | 1.8 kg |
| 121 to 150 days | — | — | 5.5 kg | 0.4 kg | 2.5 kg |
| 151 to 180 days | — | — | 4.5 kg | 0.4 kg | 4.0 kg |
| 181 to 210 days | — | — | 4.5 kg | 0.4 kg | 4.5 kg |
| 211 to 240 days | — | — | 4.5 kg | 0.4 kg | 5.0 kg |

TABLE 5

|  | Substitute milk Artificial milk | Creep feed | Formula feed | Rice straws | Oat hay |
|---|---|---|---|---|---|
| 0 to 30 days | Fed | 0.3 kg | — | — | 0.03 kg |
| 31 to 60 days | Fed | 1.5 kg | — | — | 0.2 kg |
| 61 to 80 days | Fed | 3.0 kg | — | — | 0.4 kg |
| 81 to 120 days | — | — | 4.0 kg | 0.4 kg | 1.5 kg |
| 121 to 150 days | — | — | 4.5 kg | 0.4 kg | 3.5 kg |
| 151 to 180 days | — | — | 4.0 kg | 0.4 kg | 4.0 kg |
| 181 to 210 days | — | — | 4.0 kg | 0.4 kg | 4.5 kg |
| 211 to 240 days | — | — | 4.0 kg | 0.4 kg | 4.5 kg |
| (241 to 270 days) | — | — | (4.0 kg) | (0.4 kg) | (4.5 kg) |

In the KS group, the licorice extract in Example 5 was added to feed as a feed additive and fed in an amount of 1 g/day/head from approximately five days after birth, in an amount of 2 g/day/head from approximately 41 days after birth, and in an amount of 3 g/day/head from approximately 81 days after birth up to approximately 240 days to approximately 270 days after birth. In the K group, the licorice extract in Comparative Example 1 was fed was added to feed as a feed additive and fed in an amount of 1 g/day/head from approximately five days after birth, in an amount of 2 g/day/head from approximately 41 days after birth, and in an amount of 3 g/day/head from approximately 81 days after birth up to approximately 240 days to approximately 270 days after birth.

1.1 Leftover Amounts

As described above, since the formula feed, the rice straws, and the oat hay were fed as the feed in the order of the rice straws and the oat hay at and after approximately 81 days of age, in a case where remaining feed is caused, the oat hay becomes the remaining feed. Accordingly, weights of the remaining feed of the oat hay were measured as leftover amounts. The first day when the approximately 81-day-old calves were weaned is defined as the first day, and transition of leftover amounts is shown in FIGS. 1 and 2.

As shown in FIG. 1, in the KS group, the male calves had no leftovers from the first day of weaning and kept complete eating. In the K group, although the male calves once completely ate for two days from the eighth day to the ninth day, the leftover was caused again, and it took 11 days until complete eating was continued. In the no feeding group, it took 14 days until the complete eating was continued.

Figure 2:
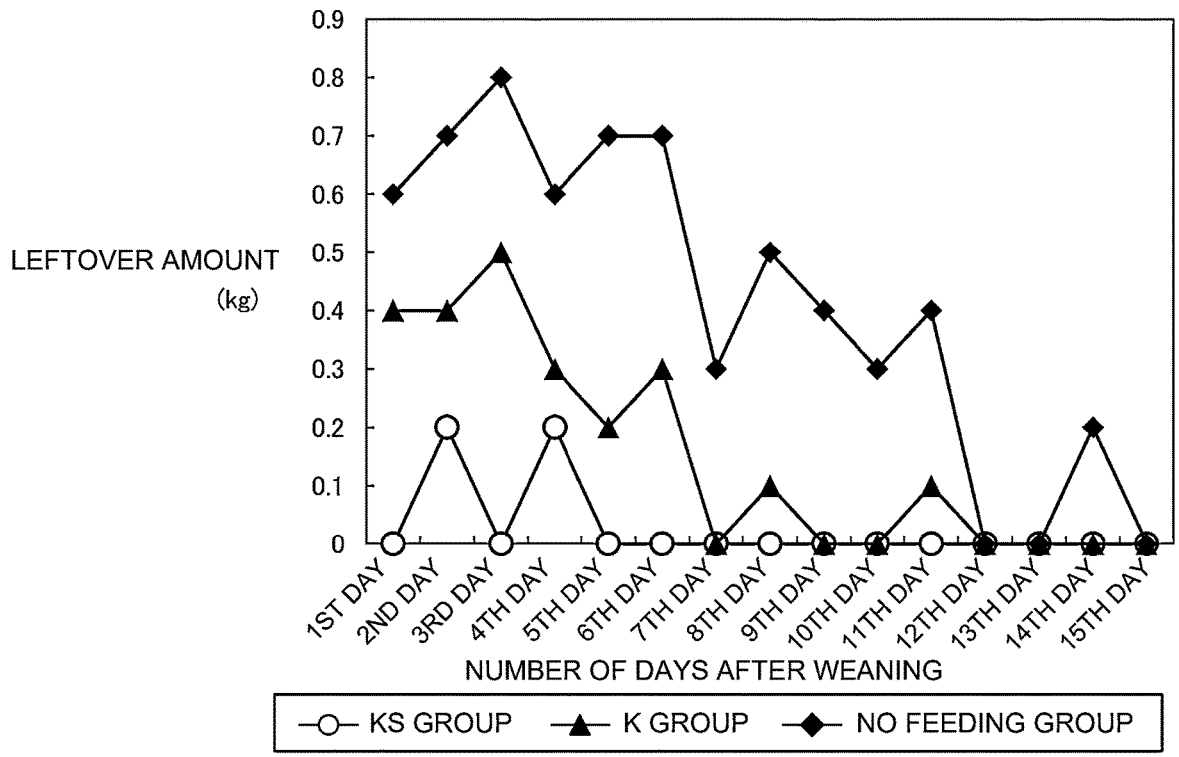
FIG. 2 is a graph showing comparison of average leftover amounts of 10 females in each group in Test 1.
Figure 3:
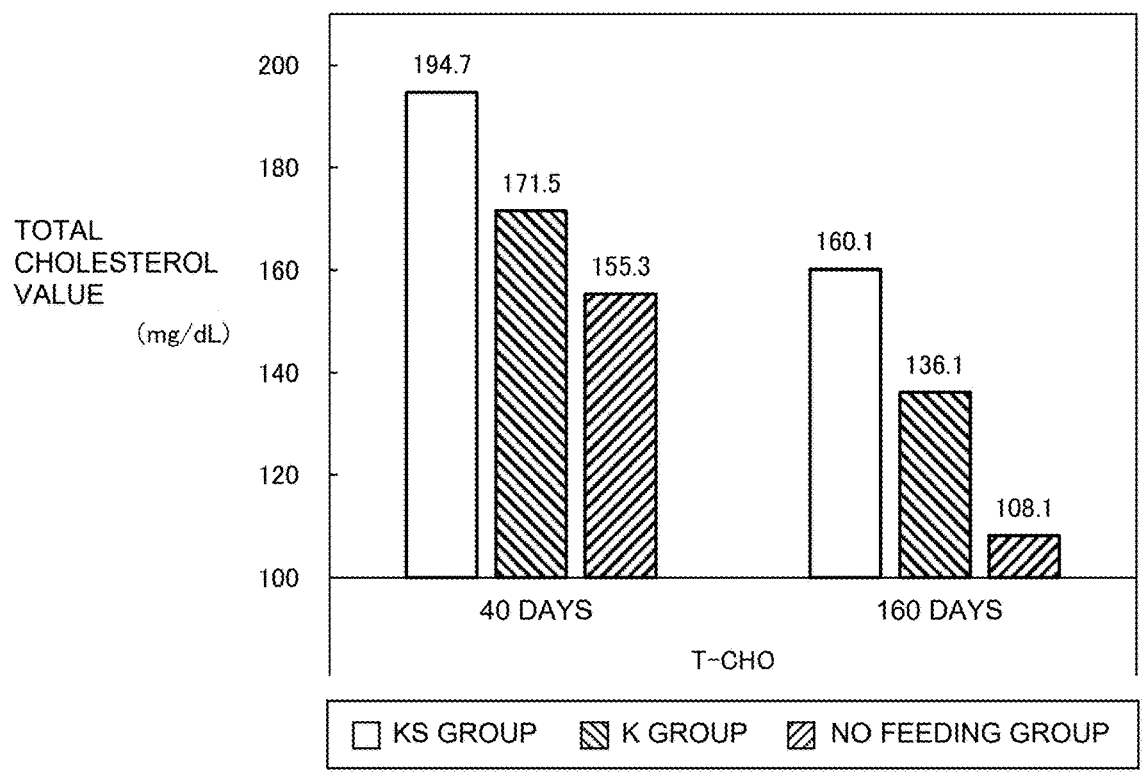
FIG. 3 is a graph showing average total cholesterol values of 10 males in each group in Test 1.
Figure 4:
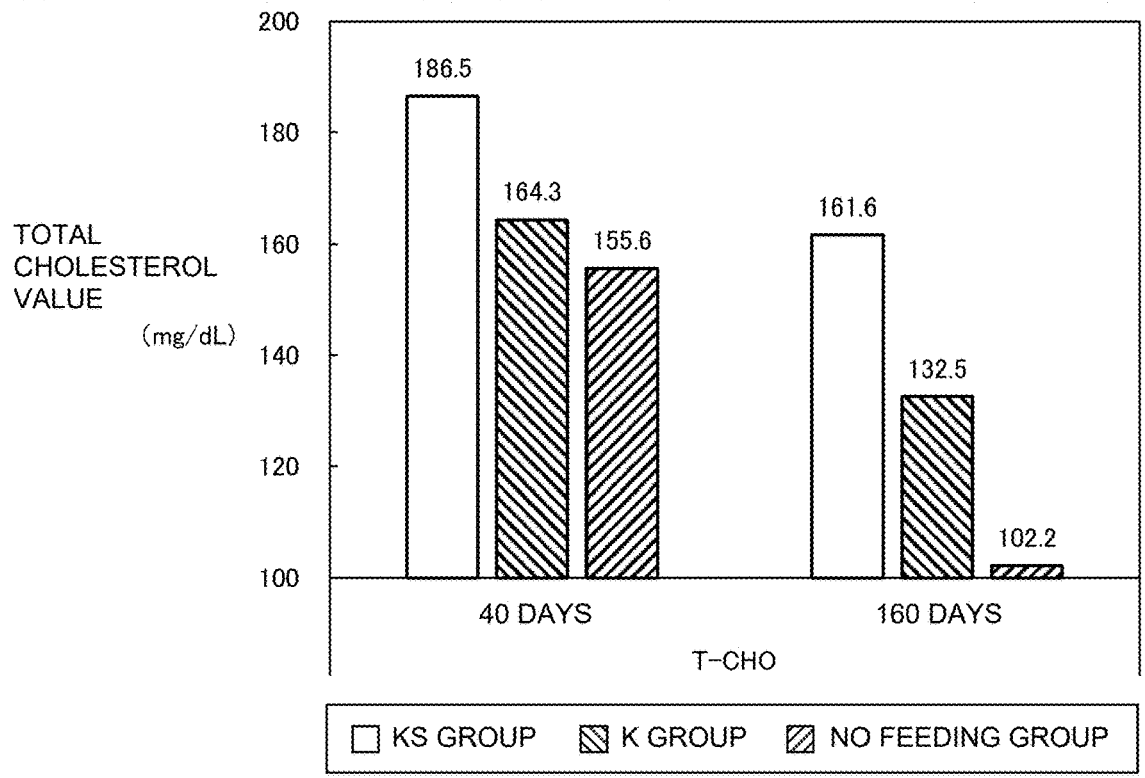
FIG. 4 is a graph showing average total cholesterol values of 10 females in each group in Test 1.
Figure 5:
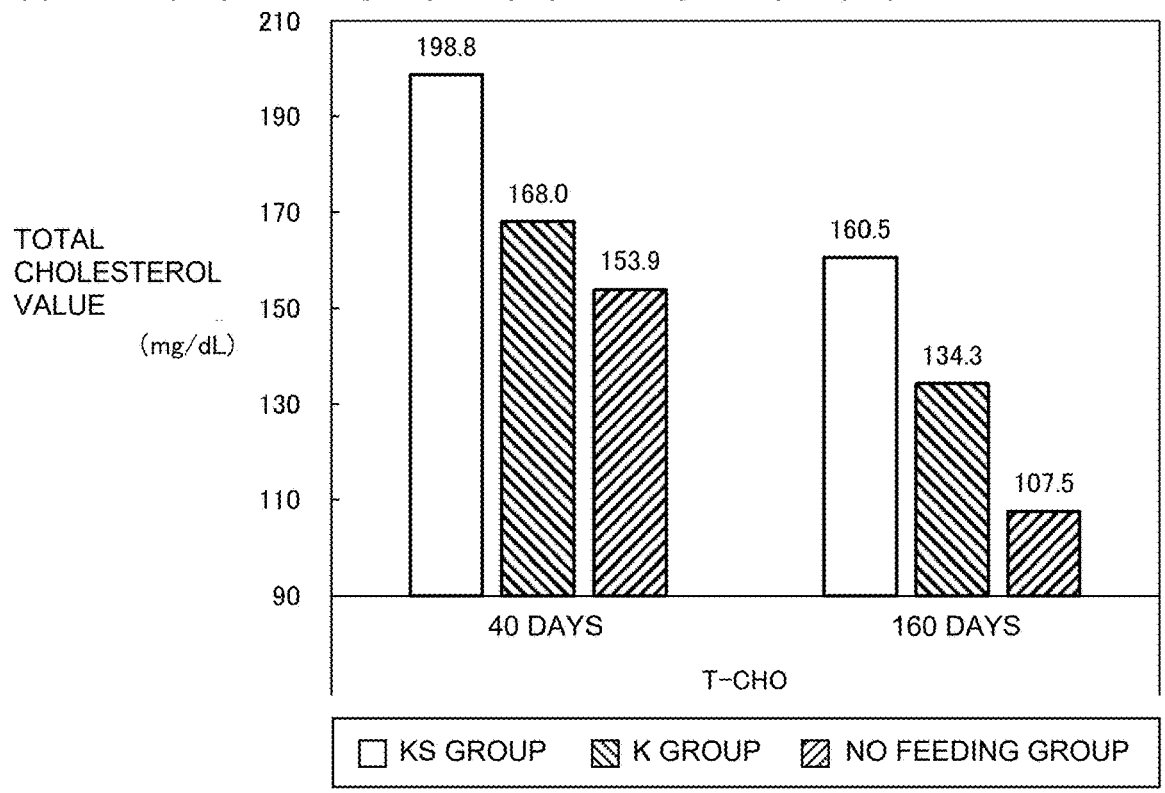
FIG. 5 is a graph showing average total cholesterol values of eight males in each group in Test 1.
Figure 6:
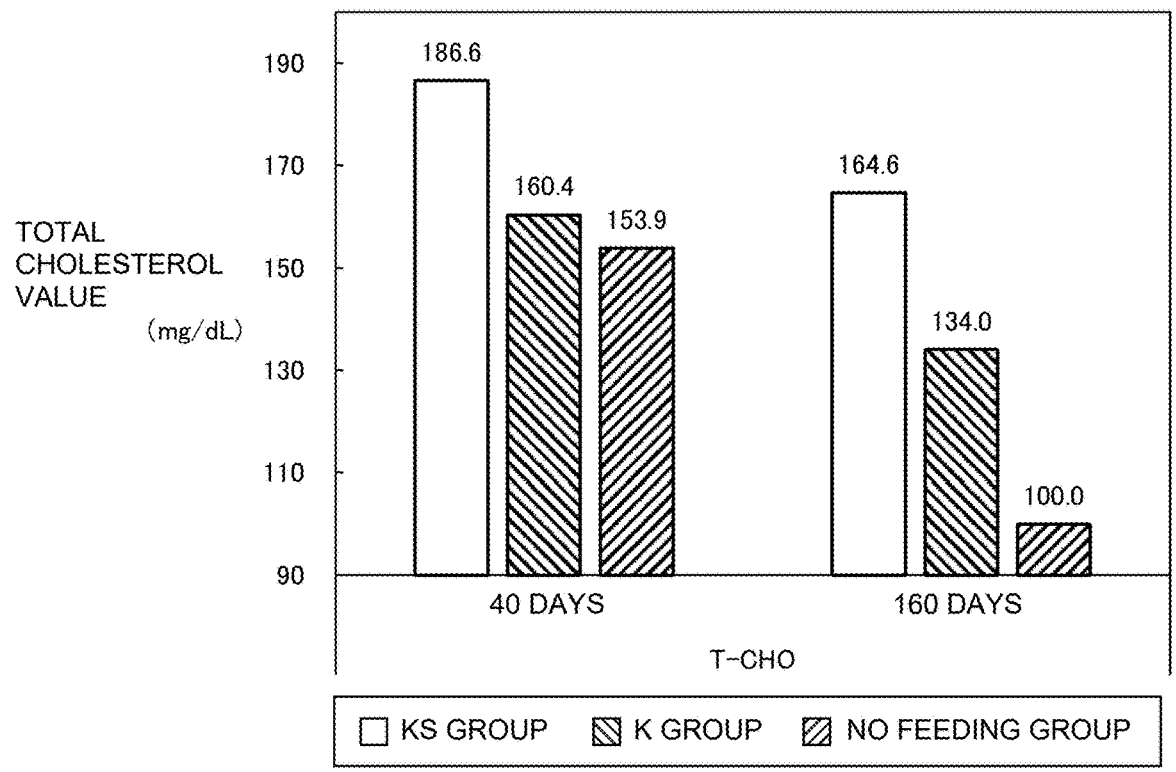
FIG. 6 is a graph showing average total cholesterol values of eight females in each group in Test 1.
Figure 7:
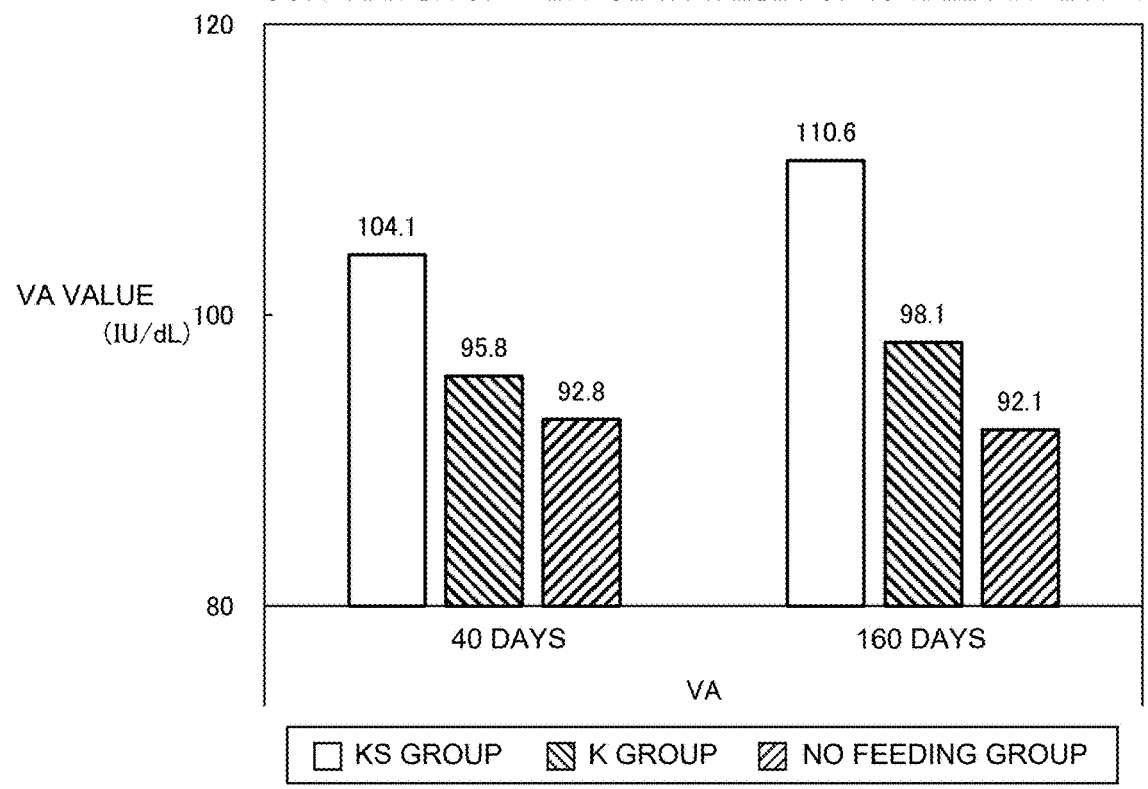
FIG. 7 is a graph showing average vitamin A values of 10 males in each group in Test 1.
Figure 8:
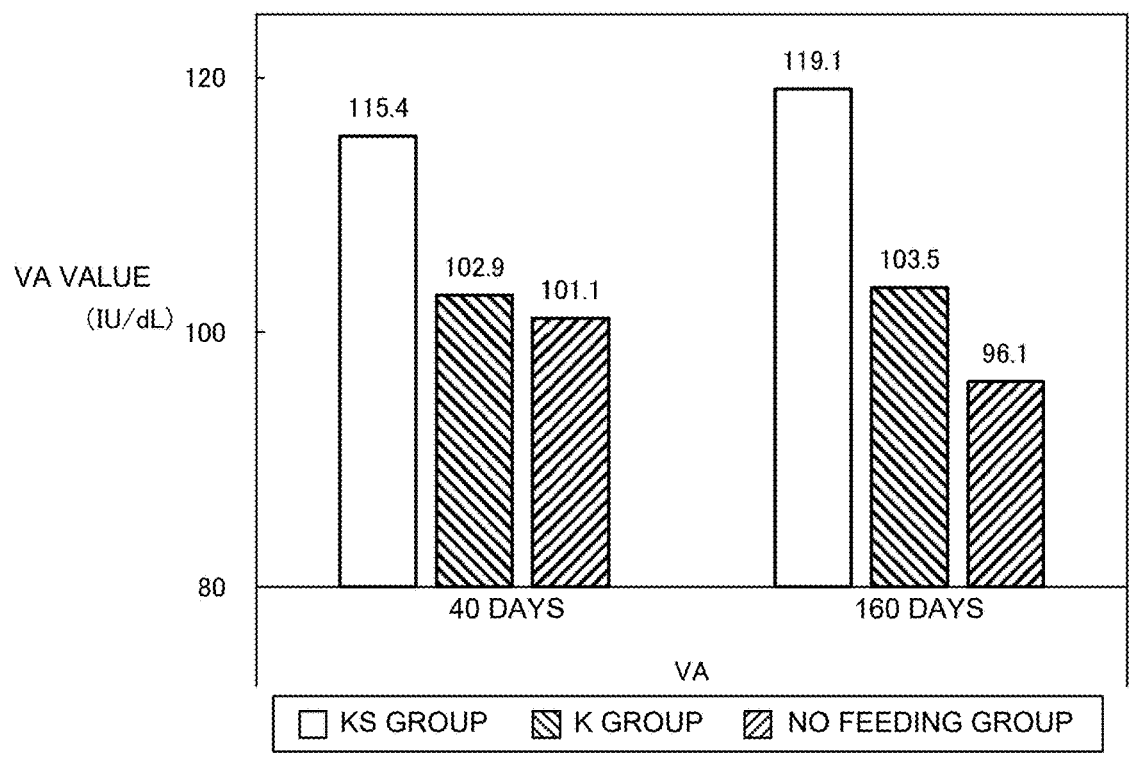
FIG. 8 is a graph showing average vitamin A values of 10 females in each group in Test 1.
Figure 9:
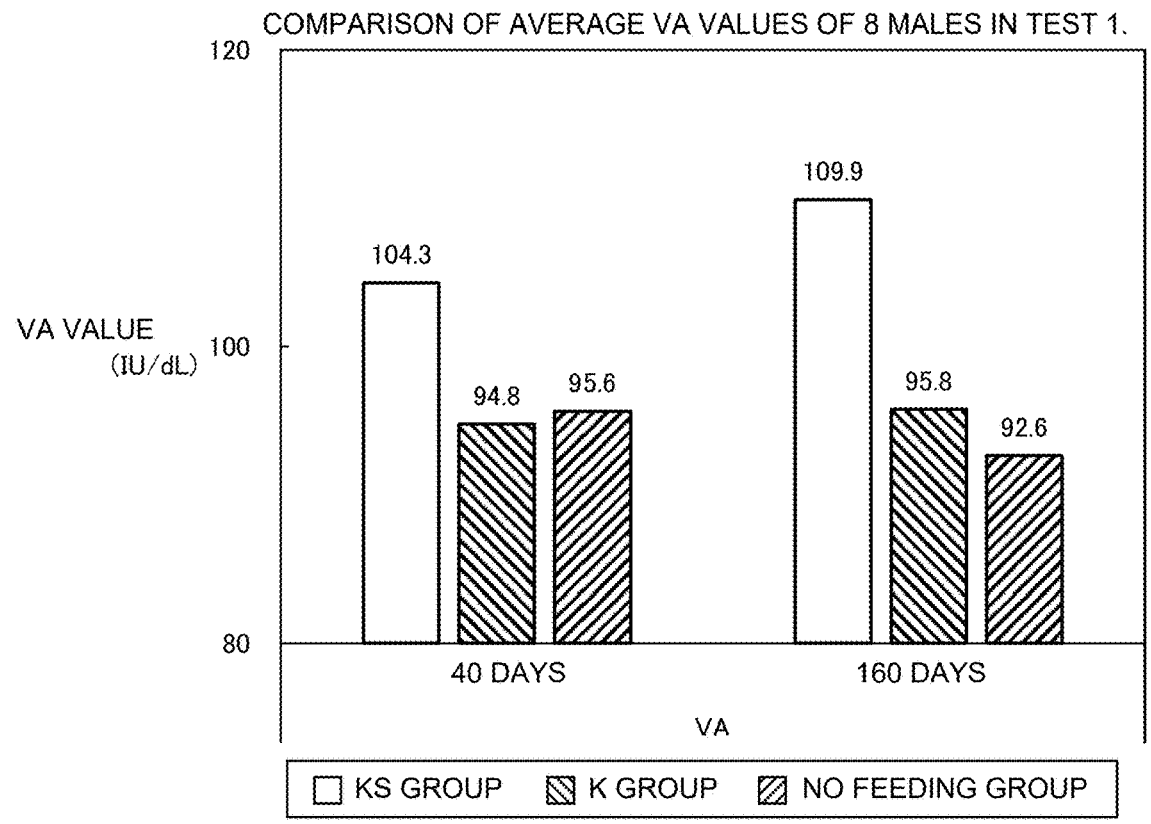
FIG. 9 is a graph showing average vitamin A values of eight males in each group in Test 1.
Figure 10:
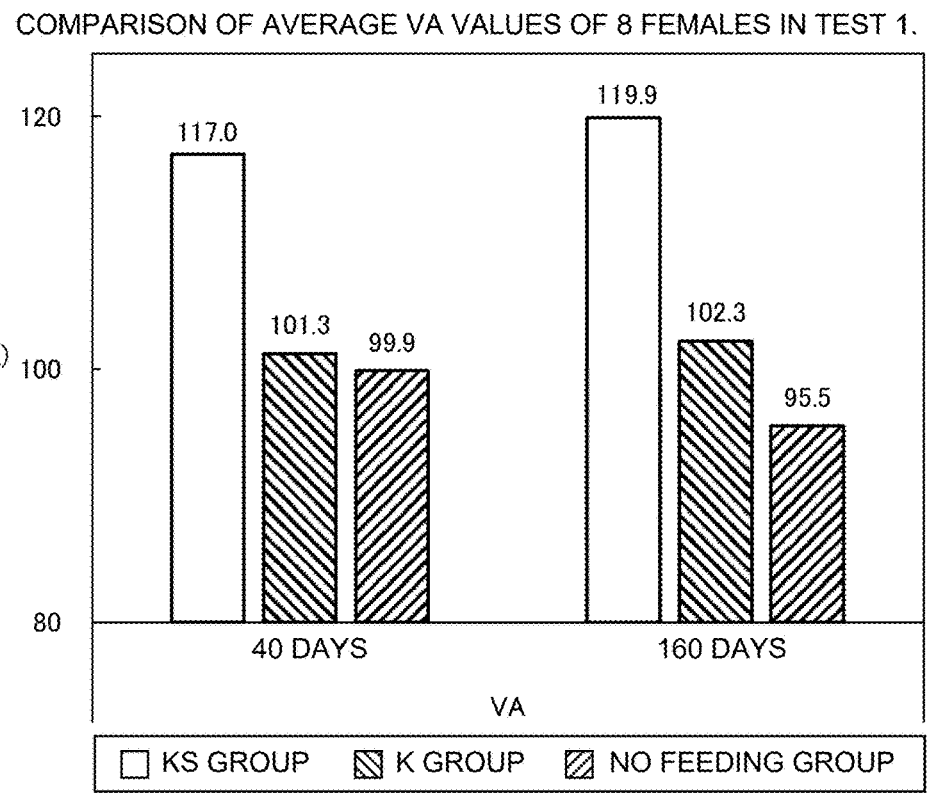
FIG. 10 is a graph showing average vitamin A values of eight females in each group in Test 1.
Figure 11:
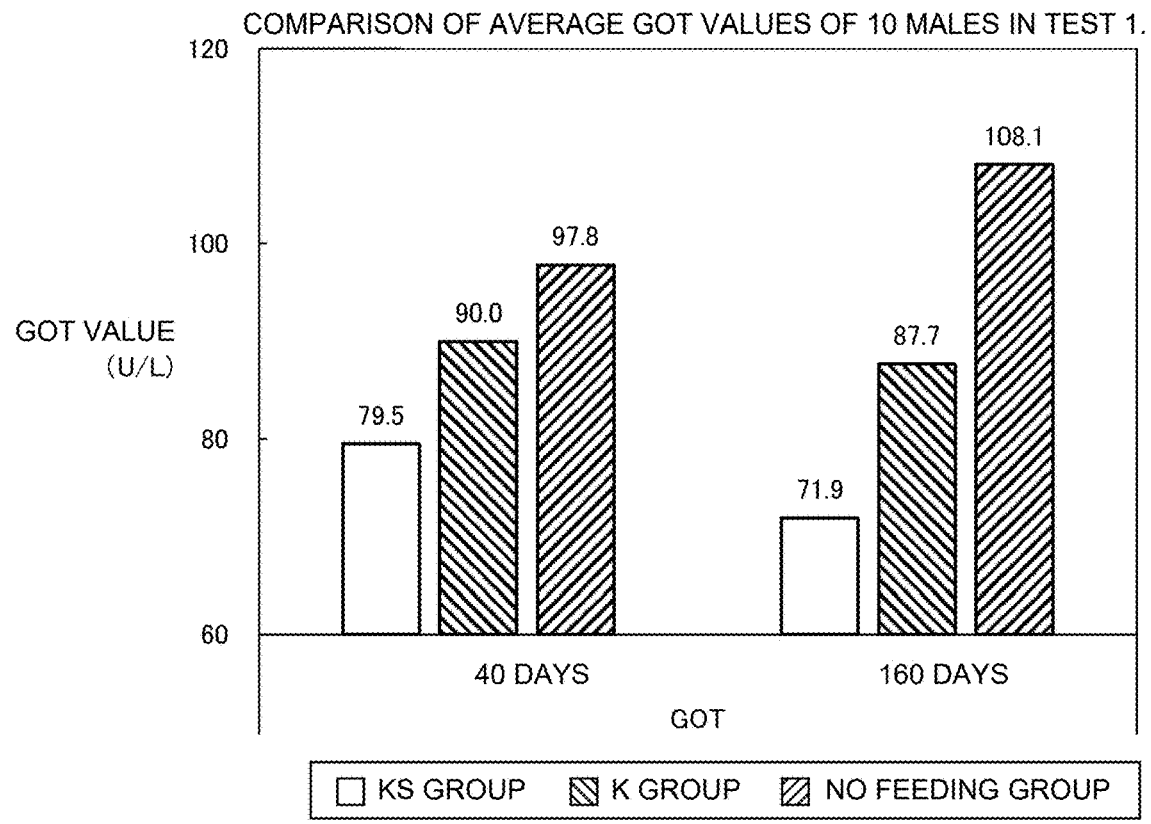
FIG. 11 is a graph showing average GOT values of 10 males in each group in Test 1.
Figure 12:
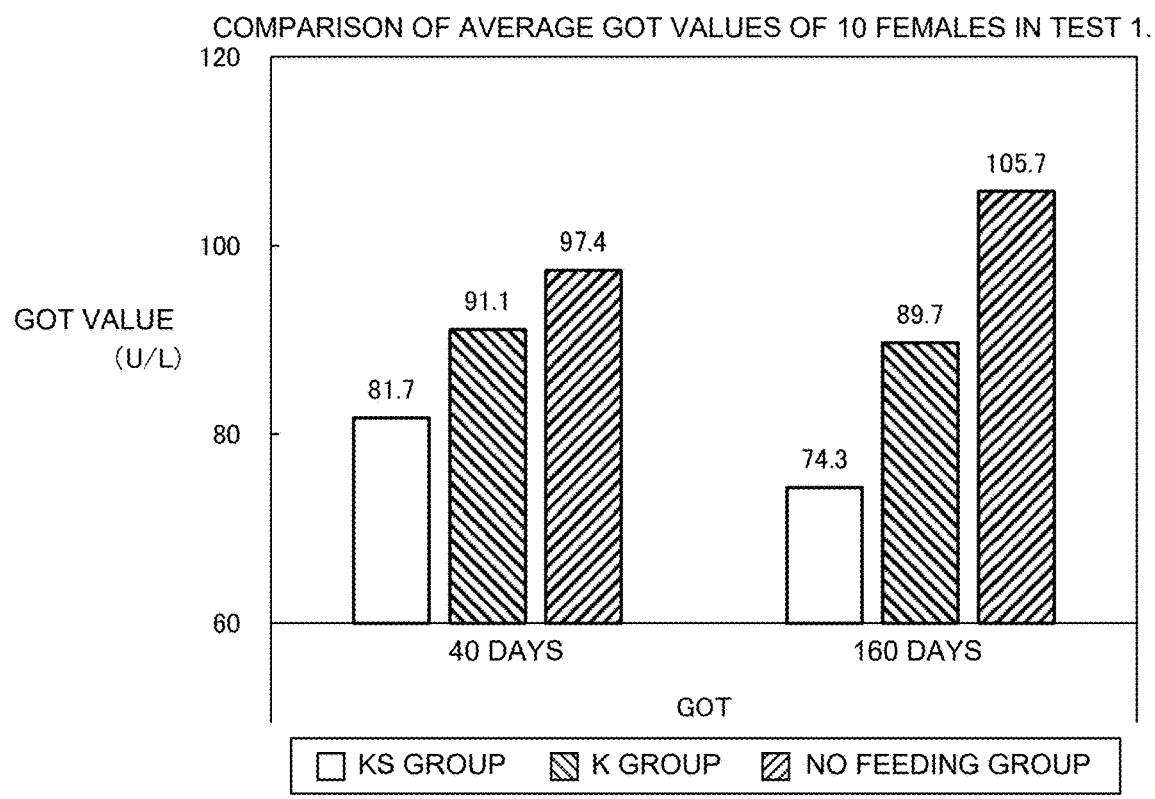
FIG. 12 is a graph showing average GOT values of 10 females in each group in Test 1.
Figure 13:
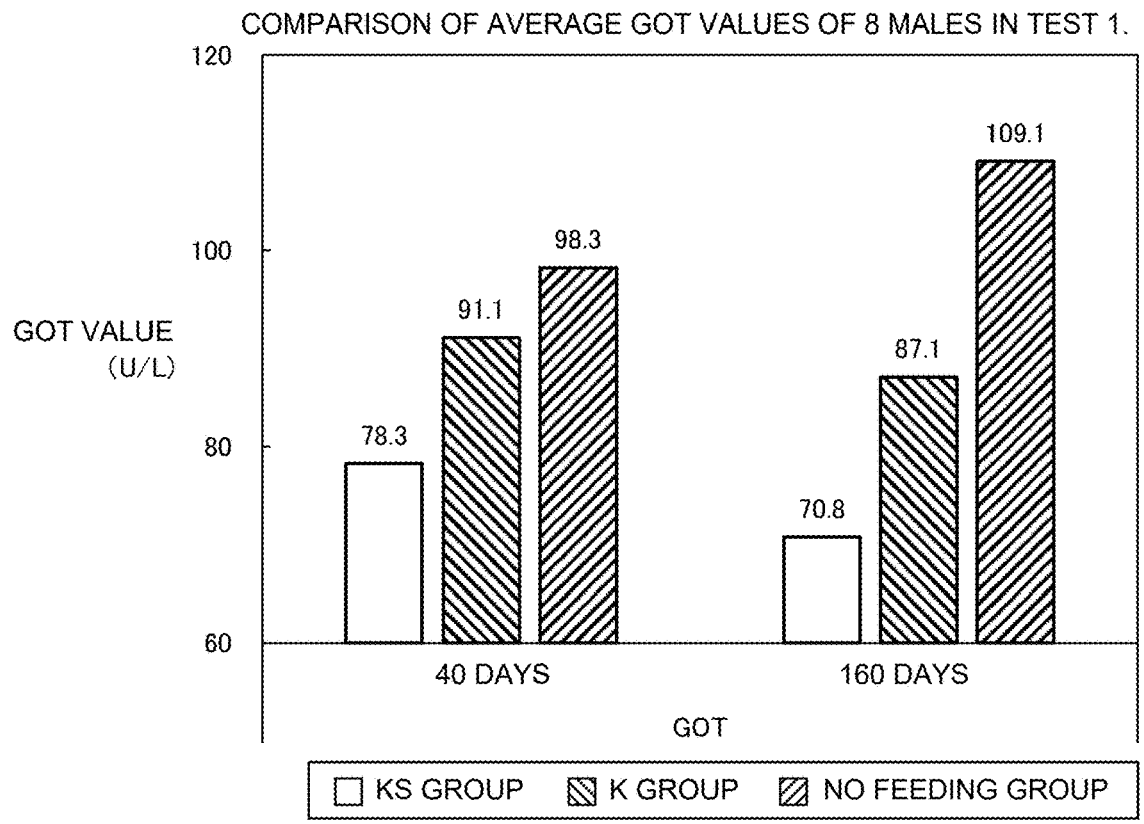
FIG. 13 is a graph showing average GOT values of eight males in each group in Test 1.
Figure 14:
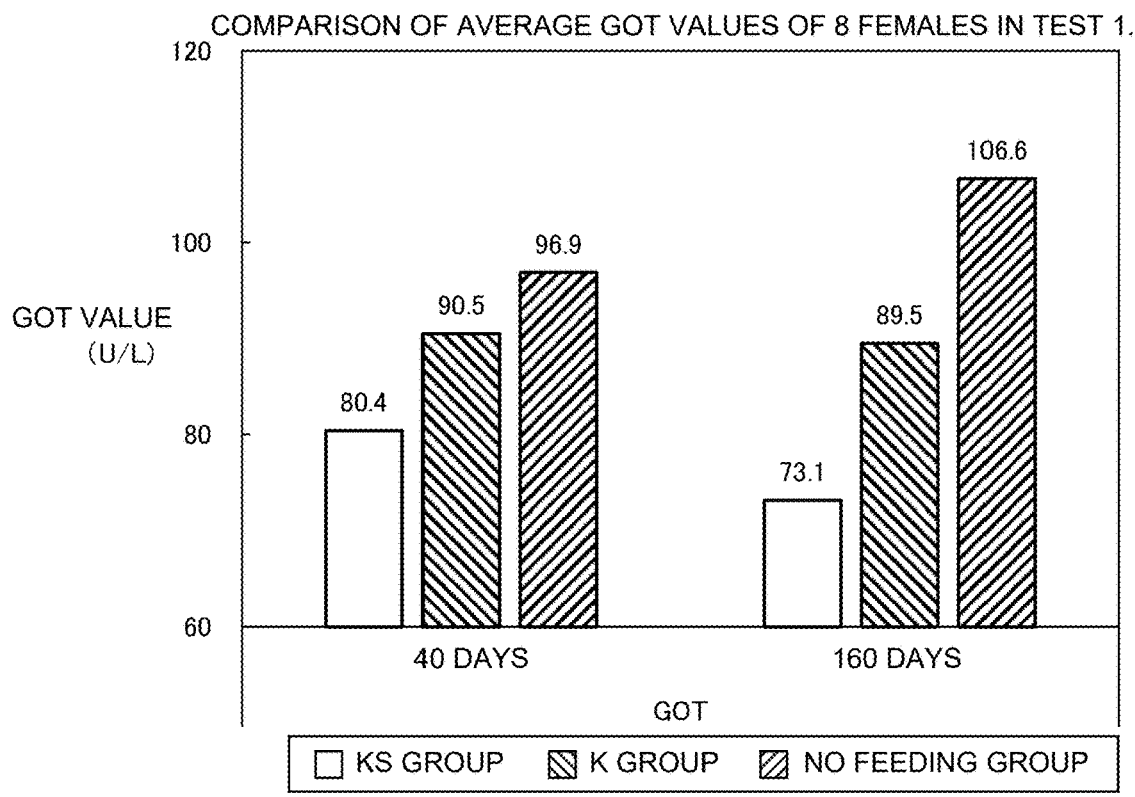
FIG. 14 is a graph showing average GOT values of eight females in each group in Test 1.
Figure 15:
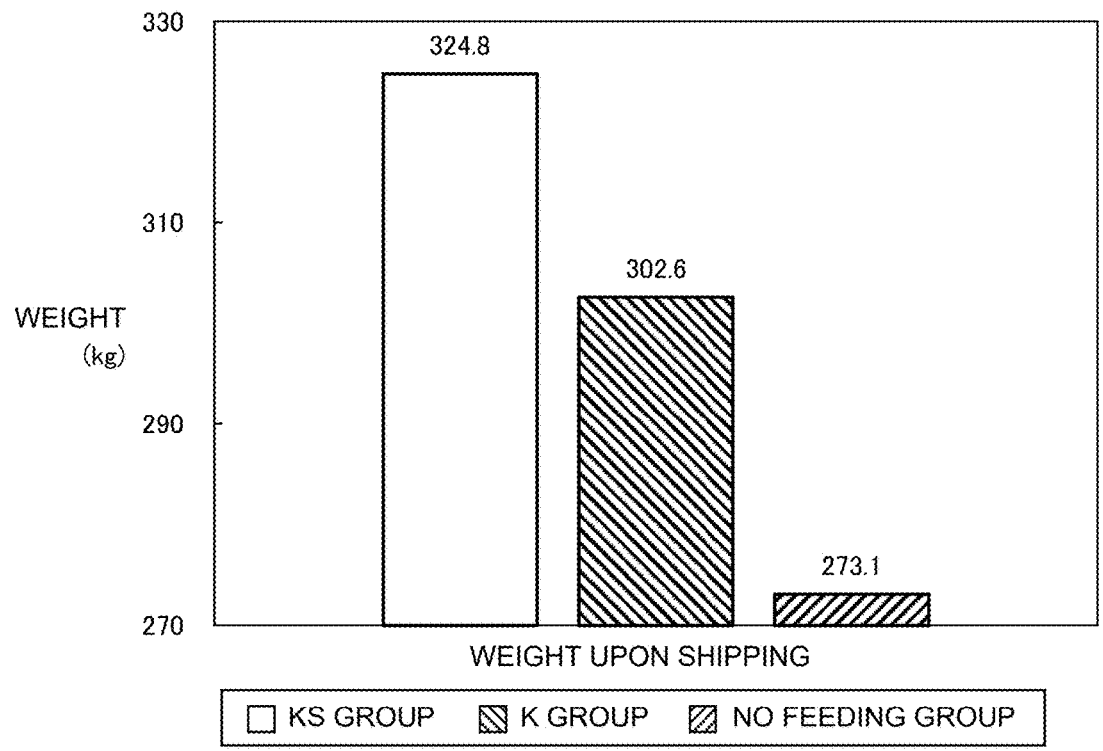
FIG. 15 is a graph showing an average weight of 10 males in each group upon shipping to an auction market in Test 1.
Figure 16:
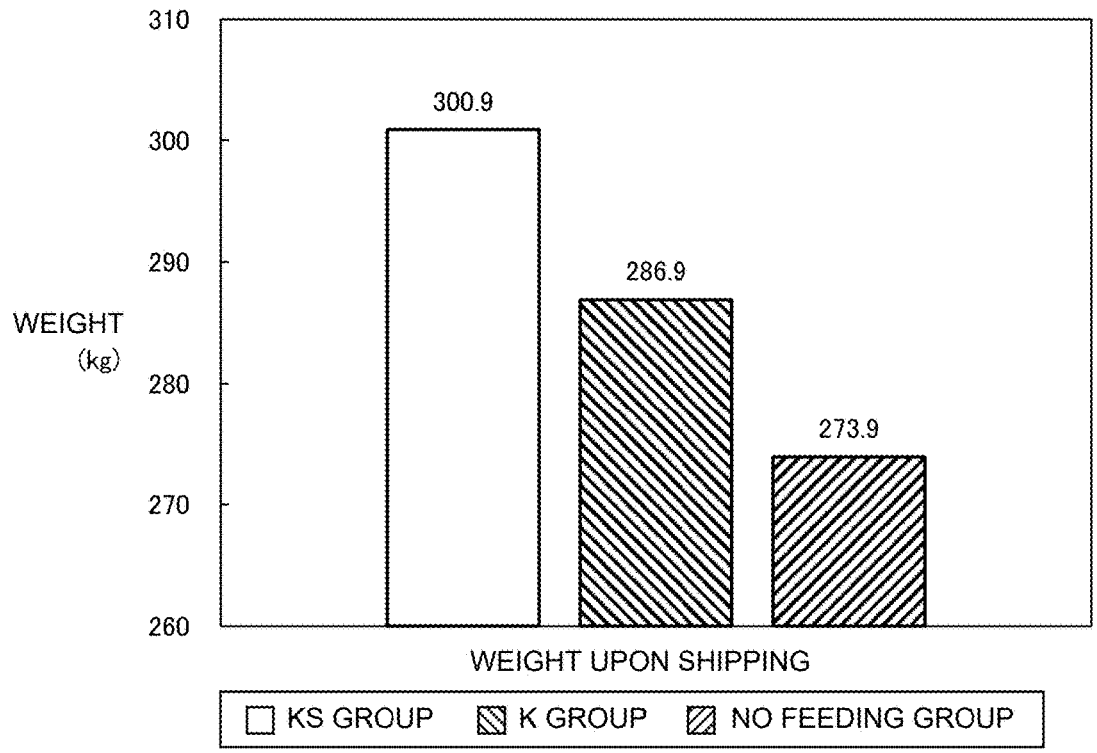
FIG. 16 is a graph showing an average weight of 10 females in each group upon shipping to the auction market in Test 1.
Figure 17:
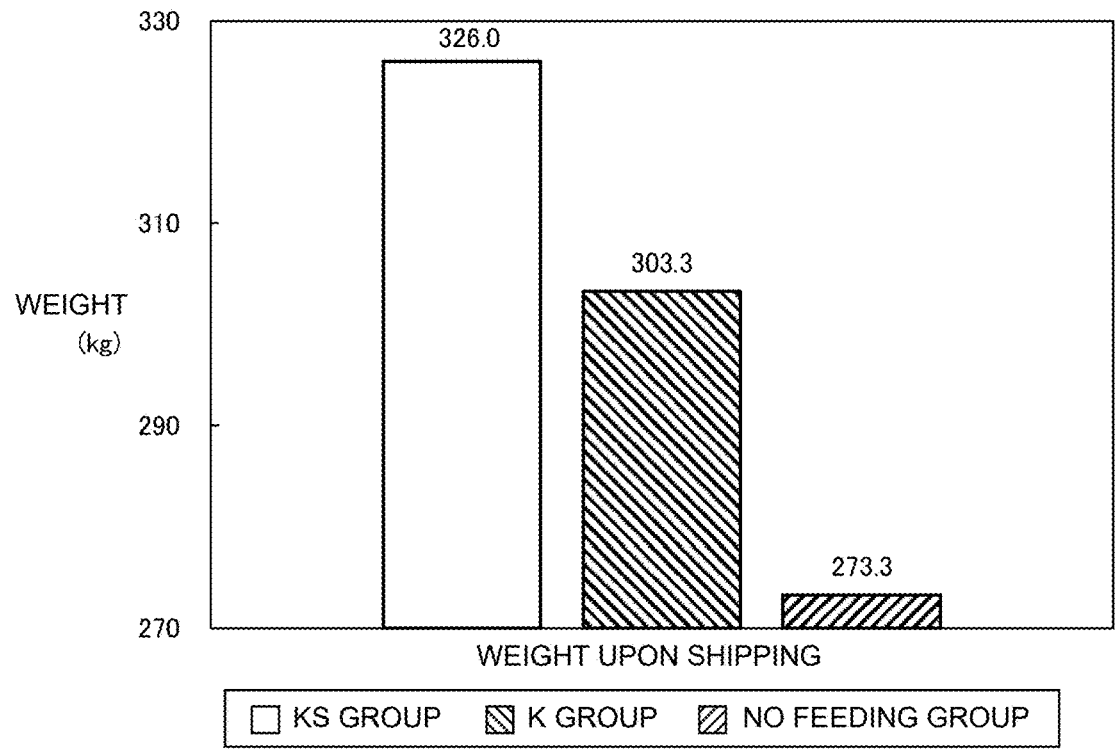
FIG. 17 is a graph showing an average weight of eight males in each group upon shipping to the auction market in Test 1.
Figure 18:
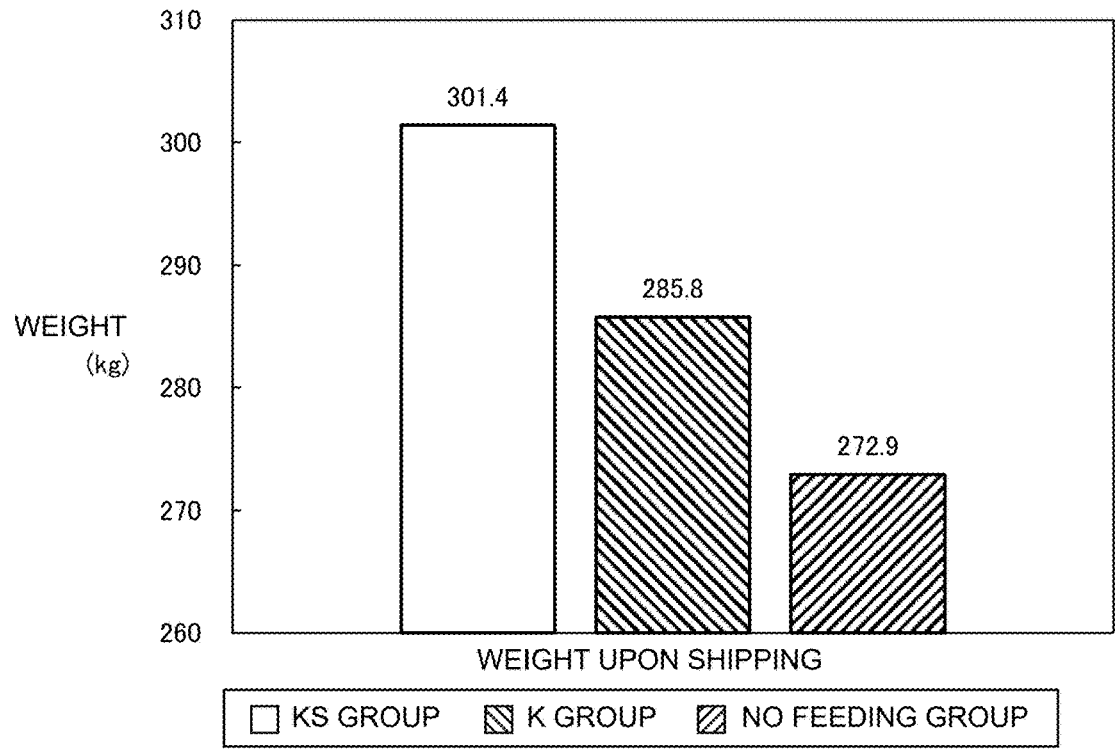
FIG. 18 is a graph showing an average weight of eight females in each group upon shipping to the auction market in Test 1.

As shown in FIG. 2, in the KS group, the female calves completely ate on the first day of weaning (approximately 81 days of age) and the third day, leftover was caused on the second day and the fourth day, and complete eating was continued from the fifth day. In the K group, while variation in the complete eating was exhibited, the complete eating was continued from the 12th day. In the no feeding group, it took 15 five days until the complete eating was continued.

In the KS group to which the licorice extract in Example 5 was fed from approximately five days of age after birth, effects by feeding of the licorice extract was exhibited from approximately 81 days of age after weaning. Even as compared with the K group to which the licorice extract including 13% or more of the glycyrrhizic acid was fed, high effects were confirmed, whereby synergy effect of the glycyrrhizic acid, the licorice saponins, and the licorice flavonoids included in the licorice extract in Example 5 with respect to the reduction in the leftover amounts (an increase in dietary intakes) was confirmed.

As described above, it is considered that the feed intakes reflect the stress exerted on the calves, the burdens on the digestive organs, and degrees of development of the digestive organs. It is considered that in the KS group in which the calves completely ate immediately after the weaning and the amounts of the feed intakes were large, as compared with the K group and the no feeding group, the stress of the calves was reduced, the burdens exerted on the digestive organs were decreased, and development states of the digestive organs were fine.

1.2 Blood Test Results (Total Cholesterol Values, VA Values, and GOT Values)

In order to comprehend nutrition states and metabolism states of the cattle, blood tests were conducted and total cholesterol values, vitamin A values (VA values), and GOT values were measured. The total cholesterol values reflect overall nutrition intake conditions. The VA values relate to growth and development and deficiency in vitamin A incurs development disorders and lowering of immune strength. The GOT values serve as information for making a decision of acute hepatic disorder and organ disorder. In particular, in a case where a GOT value is high, a liver disease is suspected.

The blood tests (total cholesterol values, VA values, and GOT values) on all of the cattle were conducted twice at approximately 40 days of age and approximately 160 days of age after birth.

Average values of 10 males and 10 females and average values of values of eight males and females excluding two males and two females among 10 males and 10 females, each of which had the highest value and the lowest value, in each of the groups are shown in FIGS. 3 to 6 (total cholesterol values), FIGS. 7 to 10 (VA values), and FIGS. 11 to 14 (GOT values).

As shown in FIGS. 3 to 6, in the KS group to which the licorice extract of the present invention was fed starting from approximately five days of age after birth before the weaning, values of both of the males and females were high at both of the approximately 40 days of age and approximately 160 days of age, as compared with the other groups. It is considered that the high total cholesterol values show that nutrition intake states are fine and metabolism is promoted. On the other hand, in the no feeding group, nutritional deficiency is suspected. The nutritional deficiency lowers immune strength and increases a risk of contracting diseases. It was found that the licorice extract of the present invention improves the nutrition states and the metabolism.

As shown in FIGS. 7 to 10, in the KS group, the VA values of both of the males and the females were high. The vitamin A is an essential component for growing and the VA values exert influence on somatic growth (a weight increase amount of livestock). However, since the VA cannot be synthesized in the body, the VA must to be taken into the body by food. When the VA extremely decreases, development disorders or lowering of immune strength is caused and there may be a case where diseases such as colds and diarrhea are developed. In the KS group, the VA values at both of the approximately 40 days of age and the approximately 160 days of age after birth were higher than those in the other groups and in particular, the VA values at the approximately 160 days of age after birth were further higher, as compared with those in the other groups, and it is shown that the KS group is advantageous for the somatic growth. It was found that the licorice extract of the present invention can increase and maintain the VA values needed for the somatic growth.

As shown in FIGS. 11 to 14, in the KS group, the GOT values at both of the approximately 40 days of age after birth and the approximately 160 days of age after birth were low, as compared with those in the other groups. In the KS group, further, the GOT values at the approximately 160 days of age after birth were lower than those at the approximately 40 days of age after birth. On the other hand, in the K group, the GOT values at the approximately 40 days of age after birth and those at the approximately 160 days of age after birth remained nearly at the same level. In the no feeding group, in the blood tests at the approximately 40 days of age after birth, the GOT values were higher than those in the other groups and at the approximately 160 days of age after birth, the further increased high GOT values were confirmed. It was found that the licorice extract of the present invention has effects to enhance a liver function.

It was found from the above-described results that the licorice extract (Example 5) in the KS group, which contains the licorice flavonoids and the licorice saponins other than the glycyrrhizic acid, exerts more favorable influence on the nutrition states, the metabolism (total cholesterol values), the growing states (vitamin A values), and the liver function (GOT values) by composite effects of the glycyrrhizic acid, the licorice saponins other than the glycyrrhizic acid, the licorice flavonoids, not by the effects of the glycyrrhizic acid, than the licorice extract (Comparative Example 1) in the K group, which contains the large amount of the glycyrrhizic acid.

1.3 Weights

Upon shipping to an auction market, individual weights of cattle are invariably measured at the auction market. Average values of the weights of 10 males and 10 females in the groups, measured upon shipping to the auction market, and average values of the weights of 8 males and 8 females in the groups, measured thereupon, which excluded two males and two females, each of the two males and two females each having the highest value and the lowest value, are shown in FIGS. 15 to 18. Note that since auction market dates are limited, there are some differences in days of age upon shipping.

As shown in FIGS. 15 to 18, weights of both of the males and the females in the KS group were larger than those in the other groups. As described above, it is considered that by feeding the licorice extract of the present invention as the feed additive, in the KS group, the feed intakes are large, as compared with the other groups, and since the nutrition states, the metabolism, the growing states, and the liver function are fine, the immune strength is not lowered and contraction of diseases can be prevented, and for example, anorexia due to diseases and a reduction in dietary intakes can also be prevented, thereby leading to the somatic growth.

The large somatic growth makes it possible to shorten days of age upon shipping to an auction market, that is, to shorten a raising period, thereby leading to a reduction in costs such as labor costs and feed costs. In addition, it is seen that by feeding the licorice extract of the present invention as the feed additive, feed efficiency can be increased because despite the feeding manner in which in the KS group, the K group, and the no feeding group, the same kinds of the feed, other than the licorice extract, in the same amounts were fed, the somatic growth in the KS group was larger than those in the other groups.

In a period between approximately five days of age after birth up to approximately 240 days of age to approximately 270 days of age, there are a suckling period, a weaning period, and the subsequent growth process, and kinds of feed, feeding contents, feeding methods change. Although it is known that the cattle strongly feel psychological and physical stress by petty environmental changes and changes in physical conditions are thereby caused, by feeding the licorice extract of the present invention as the feed additive, it was made possible to reduce adverse influence exerted by changes in the environment and the stress on the feed intakes, the nutrition states, the metabolism, the growing, and the liver function can be reduced and to enable the somatic growth.

Test 2. From Time of Introduction of Fattening to Shipping to Carcass Market

Calves shipped to an auction market from growing farmers are thereafter introduced to fattening farmers. In this period, the calves are moved from the growing farmers to a calf auction site by truck transportation and after auction purchase successful bid, the calves are moved to ranches of new fattening farmers by trucks, and the calves receive stress due to the movement by the trucks and stress of environmental changes due to changes of growing places, raisers, and the like. The calves are often moved for long distances from markets in Hokkaido to ranches in Kagoshima, Miyazaki, and the like. Furthermore, the calves receive stress due to changes in kinds and amounts of given feed, starting from when the calves are introduced to fattening ranches and receive heat stress and cold stress (stress in a heat period and a cold period) in fattening ranches and also stress due to group feeding and the like. The above-mentioned kinds of stress can exert adverse influence on feed intakes, nutrition states, metabolism, growing, and a liver function of the cattle. In addition, it is often the case that upon the introduction to the fattening ranches, for the purpose of somatic growth, the calves have already been fed with high-concentration formula feed, a wide variety of additive agents, and the like, and digestive organs, internal organs, and a liver function in particular are damaged.

Therefore, by feeding the licorice extract of the present invention as a feed additive to cattle from when fattening was introduced to when the cattle were shipped to carcass markets for the purpose of selling, influence exerted by the licorice extract of the present invention on leftover amounts, nutrition states (total cholesterol values, vitamin A values, and GOT values in blood tests), weights, liver discard rates, carcass weights, and carcass yield rates upon the introduction of fattening was examined.

Targets were a total of 60 head of Japanese Black Cattle including 30 males of Japanese Black Cattle at approximately nine months of age to approximately 10 months of age (from 266 days of age to 308 days of age after birth) and 30 females of Japanese Black Cattle at approximately nine months of age to approximately 10 months of age (from 274 days of age to 304 days of age after birth). Based on results of weights measured upon purchasing at a calf auction market, the targets were divided into three groups shown in Table 6 such that individual weights and days of age were substantially equalized.

TABLE 6

|  | Male | Female | Total |
| --- | --- | --- | --- |
| KS group | 10 head | 10 head | 20 head |
| K group | 10 head | 10 head | 20 head |
| No feeding group | 10 head | 10 head | 20 head |

In the KS group, the licorice extract in Example 5 was added to feed as a feed additive, and in the K group, the licorice extract in Comparative Example 1 was added to feed as a feed additive. In the no feeding group, any licorice extract was not added to feed. As to feed other than the licorice extracts, feed shown in Table 7 (feed fed to one male head of cattle) and feed shown in Table 8 (feed fed to one female head of cattle) were fed with the same amount fed to each of the groups at the same time by dividing each amount shown therein into three parts a day. After the introduction to the fattening ranch, the feed other than the licorice extract was fed in the order of formula feed, rice straws, beer lees, and oat hay until complete eating.

TABLE 7

|  | Formula feed | Rice straws | Beer lees (moisture 50%) | Oat hay |
| --- | --- | --- | --- | --- |
| 0 to 1 month | 2.5 kg | 0.3 kg | 2.0 kg | 4.0 kg |
| to 2 months | 3.5 kg | 0.3 kg | 2.0 kg | 4.0 kg |
| to 3 months | 5.0 kg | 0.3 kg | 2.0 kg | 5.0 kg |
| to 4 months | 6.5 kg | 0.3 kg | 2.0 kg | 5.0 kg |
| to 5 months | 8.0 kg | 0.3 kg | 3.0 kg | 4.0 kg |
| to 6 months | 9.0 kg | 2.0 kg | 3.0 kg | 3.0 kg |
| to 7 months | 9.0 kg | 2.5 kg | 3.0 kg | — |
| to 12 months | 10.0 kg | 2.5 kg | 4.0 kg | — |
| to 13 months | 11.0 kg | 2.5 kg | 2.0 kg | — |
| to 19 months | 11.0 kg | 2.5 kg | — | — |

TABLE 8

|  | Formula feed | Rice straws | Beer lees (moisture 50%) | Oat hay |
| --- | --- | --- | --- | --- |
| 0 to 1 month | 1.8 kg | 0.2 kg | 2.0 kg | 3.5 kg |
| to 2 months | 2.5 kg | 0.2 kg | 2.0 kg | 3.5 kg |
| to 3 months | 3.5 kg | 0.2 kg | 2.0 kg | 3.5 kg |
| to 4 months | 4.5 kg | 0.2 kg | 2.0 kg | 3.0 kg |
| to 5 months | 5.5 kg | 0.2 kg | 2.0 kg | 3.0 kg |
| to 6 months | 6.5 kg | 2.0 kg | 2.0 kg | 2.5 kg |
| to 14 months | 7.0 kg | 3.0 kg | 3.0 kg | — |
| to 19 months | 9.0 kg | 3.0 kg | — | — |

In the KS group, the licorice extract in Example 5 was added to feed as a feed additive and was fed in an amount of 3 g/day/head for approximately 19 months from the day of the introduction to the fattening ranch. In the K group, the licorice extract in Comparative Example 1 was added to feed as a feed additive and was fed in an amount of 3 g/day/head for approximately 19 months from the day of the introduction to the fattening ranch.

2.1 Leftover Amounts

As described above, since the feed was fed in the order of the formula feed, the rice straws, the beer lees, and the oat hay, in a case where remaining feed is caused, the oat hay becomes the remaining feed. Accordingly, weights of the remaining feed of the oat hay were measured as leftover amounts. Transition of the leftover amounts is shown in FIGS. 19 to 20.

Figure 19:
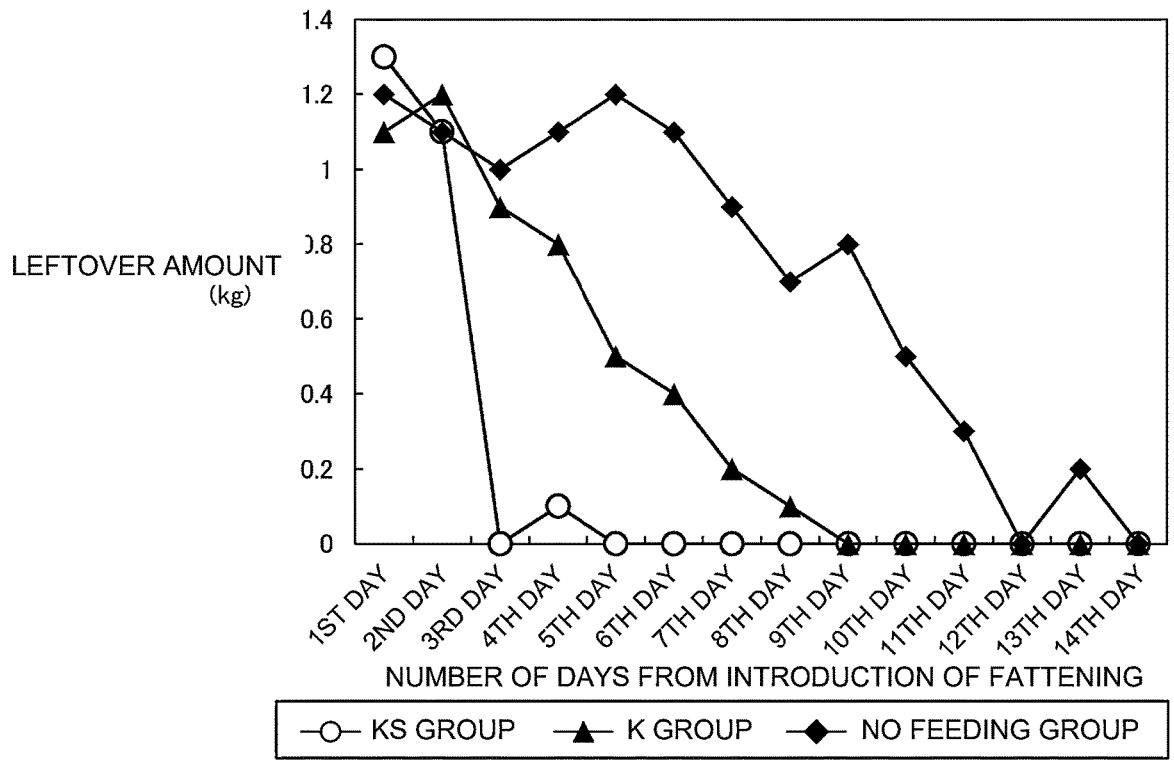
FIG. 19 is a graph showing comparison of average leftover amounts of 10 males in each group in Test 2.

As shown in FIG. 19, in the KS group, it took five days for males to completely eat after the feeding was started; in the K group, it took nine days for males to completely eat; and in the no feeding group, it took 14 days for males to completely eat.

Figure 20:
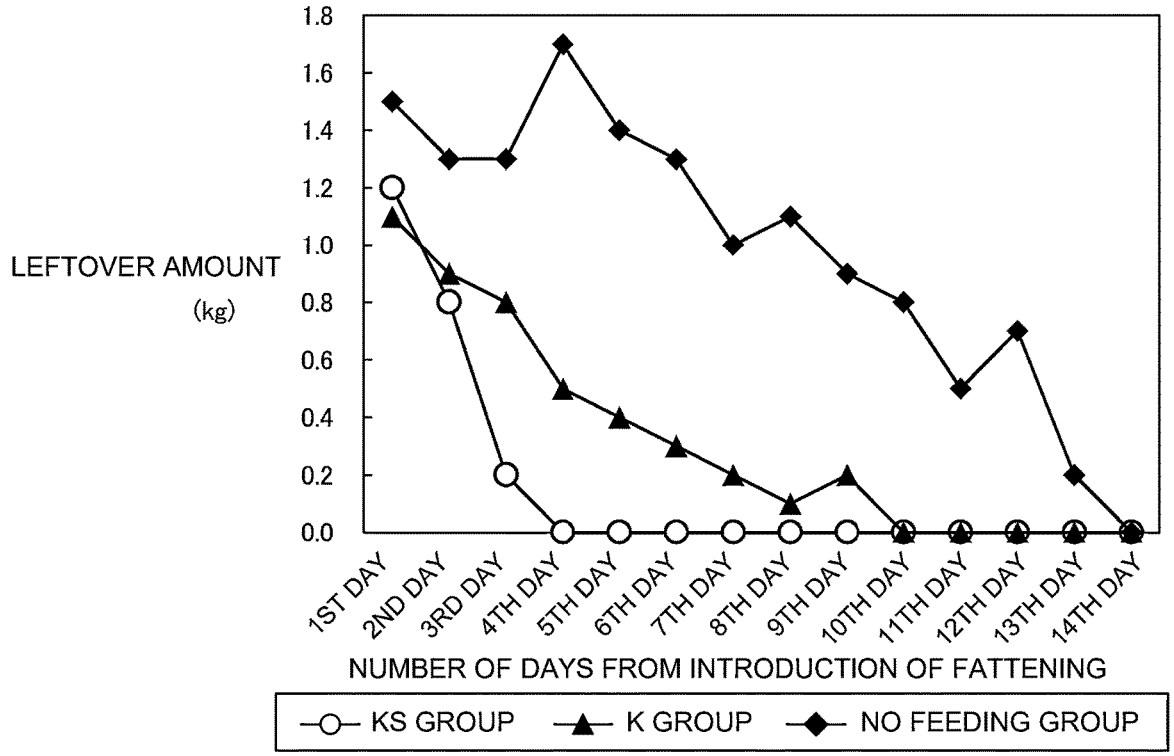
FIG. 20 is a graph showing comparison of average leftover amounts of 10 females in each group in Test 2.
Figure 21:
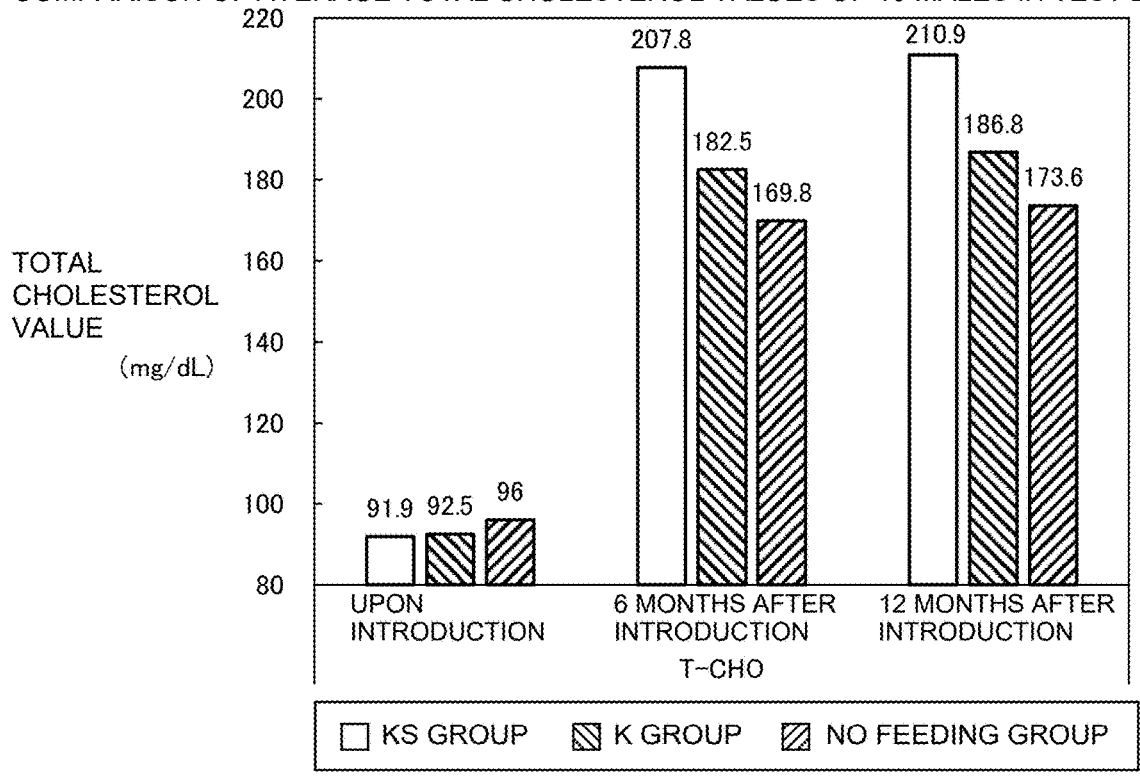
FIG. 21 is a graph showing average total cholesterol values of 10 males in each group in Test 2.
Figure 22:
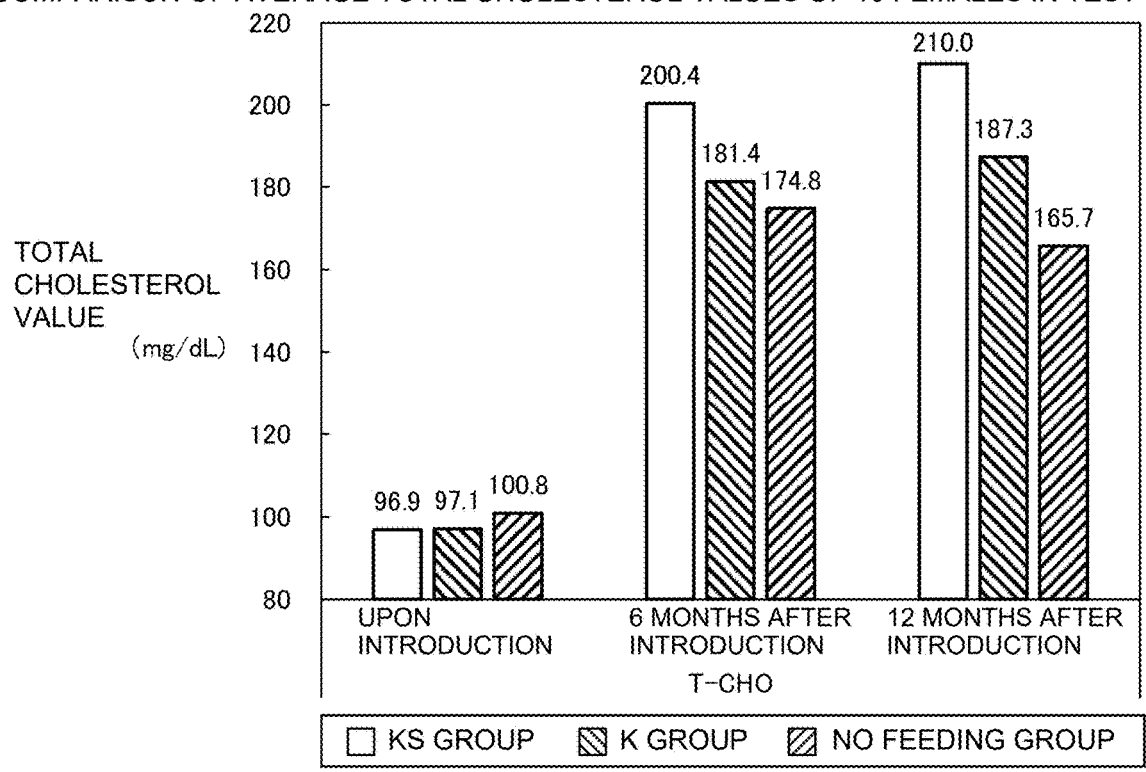
FIG. 22 is a graph showing average total cholesterol values of 10 females in each group in Test 2.
Figure 23:
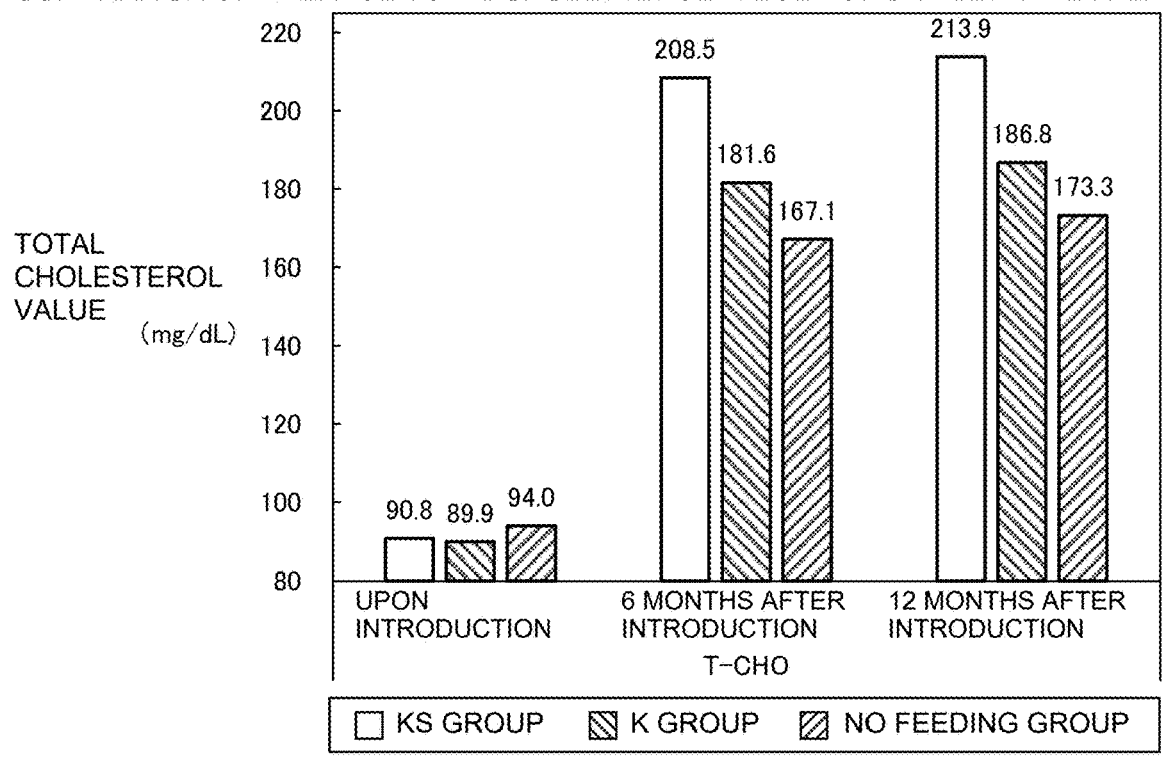
FIG. 23 is a graph showing average total cholesterol values of eight males in each group in Test 2.
Figure 24:
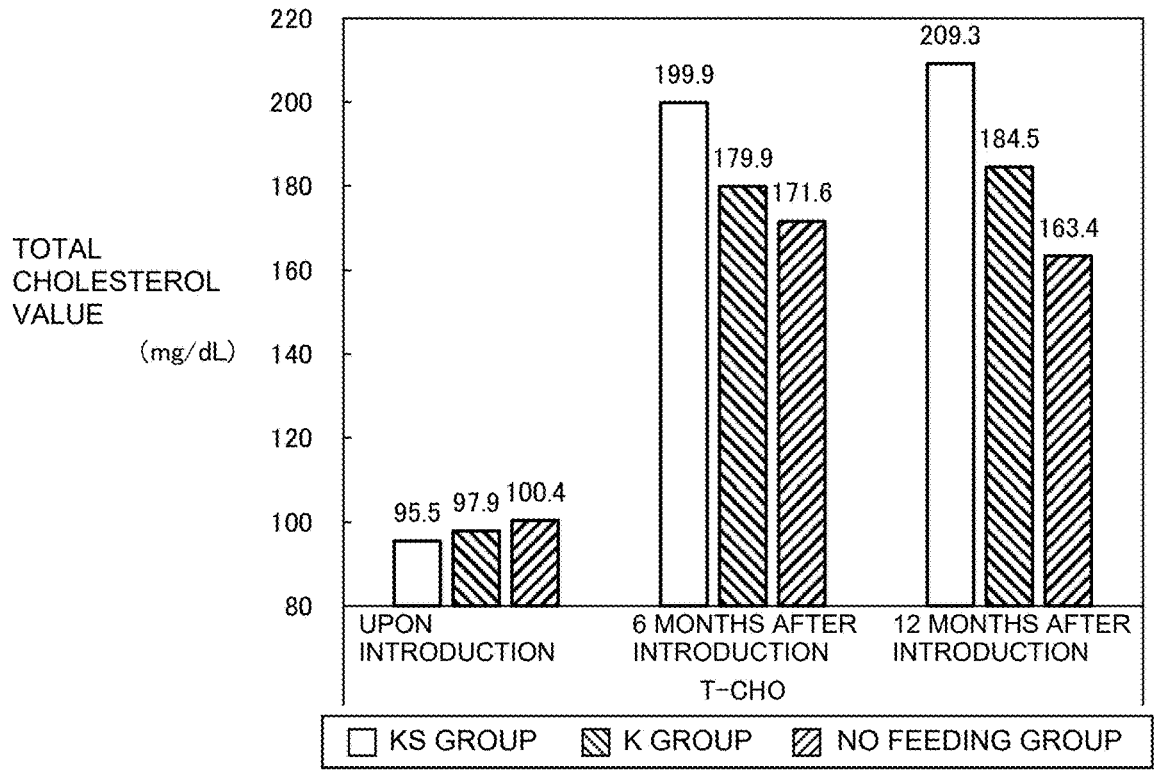
FIG. 24 is a graph showing average total cholesterol values of eight females in each group in Test 2.
Figure 25:
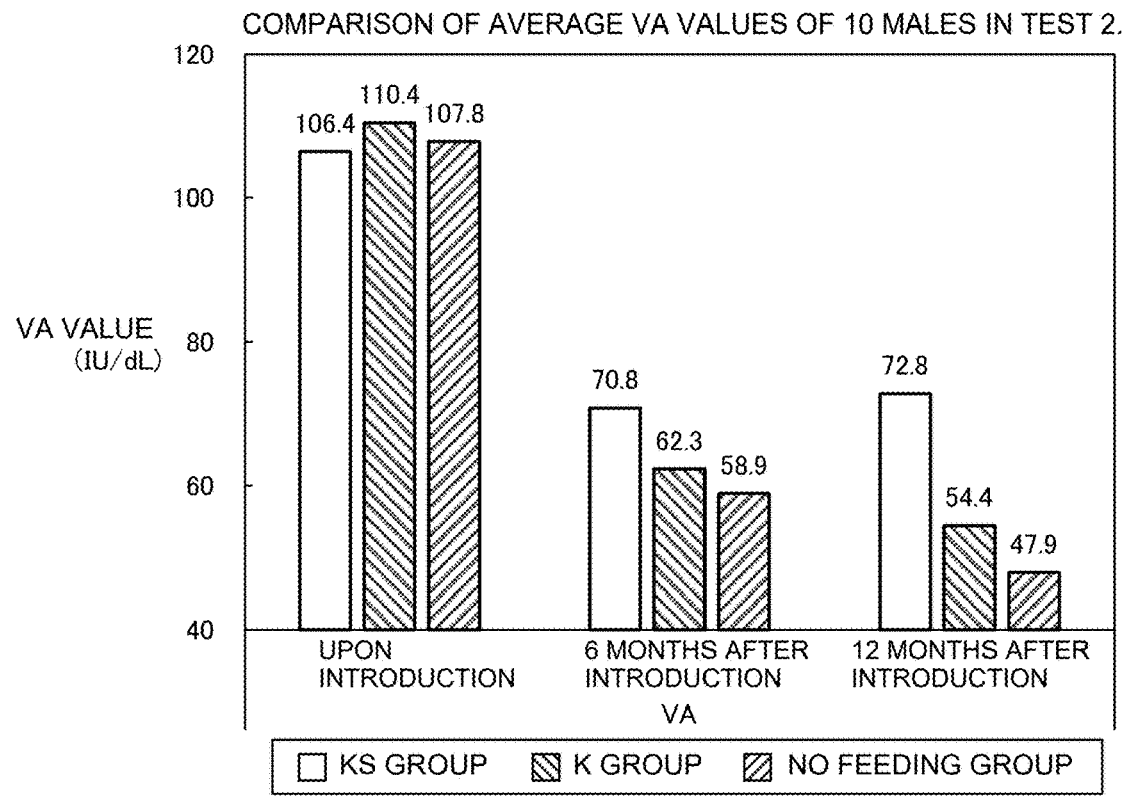
FIG. 25 is a graph showing average vitamin A values of 10 males in each group in Test 2.
Figure 26:
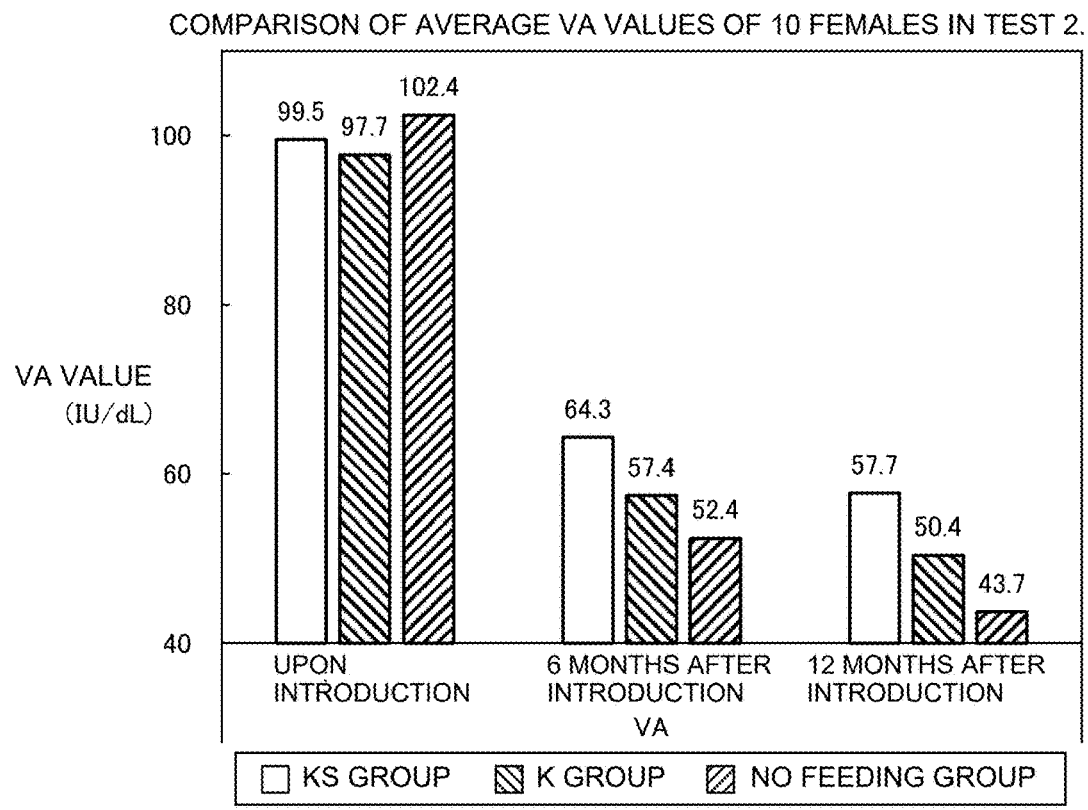
FIG. 26 is a graph showing average vitamin A values of 10 females in each group in Test 2.
Figure 27:
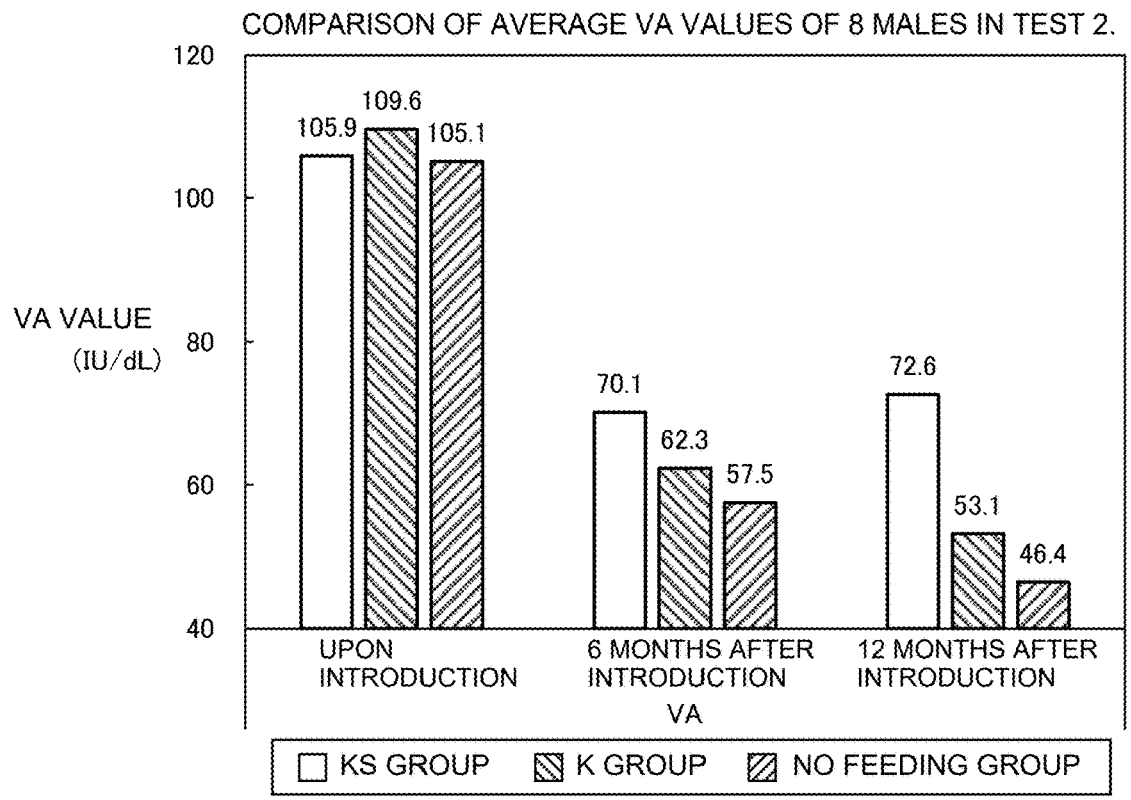
FIG. 27 is a graph showing average vitamin A values of eight males in each group in Test 2.
Figure 28:
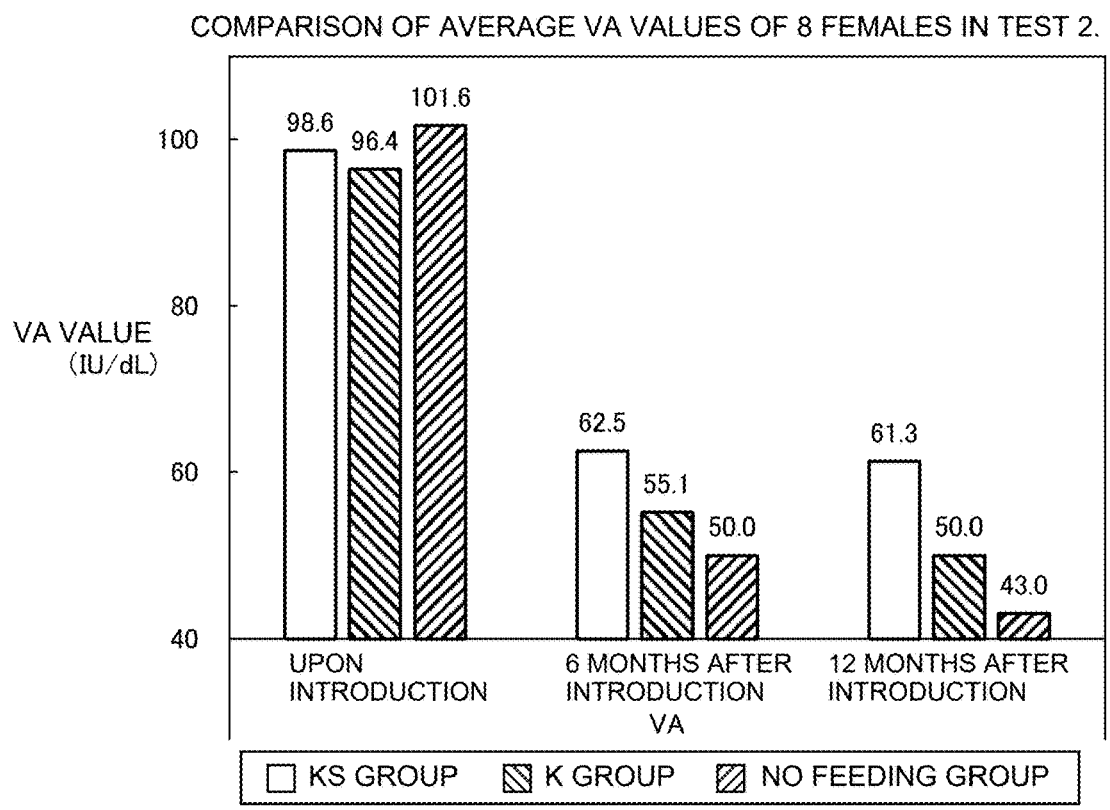
FIG. 28 is a graph showing average vitamin A values of eight females in each group in Test 2.
Figure 29:
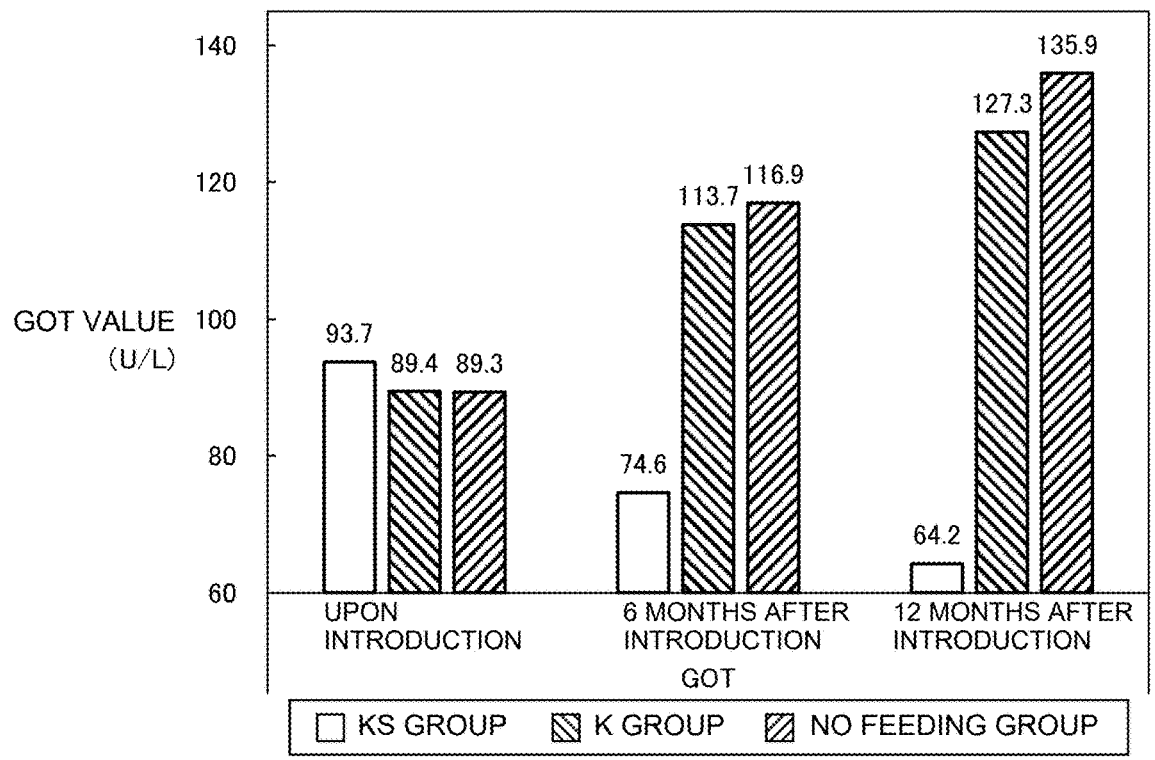
FIG. 29 is a graph showing average GOT values of 10 males in each group in Test 2.
Figure 30:
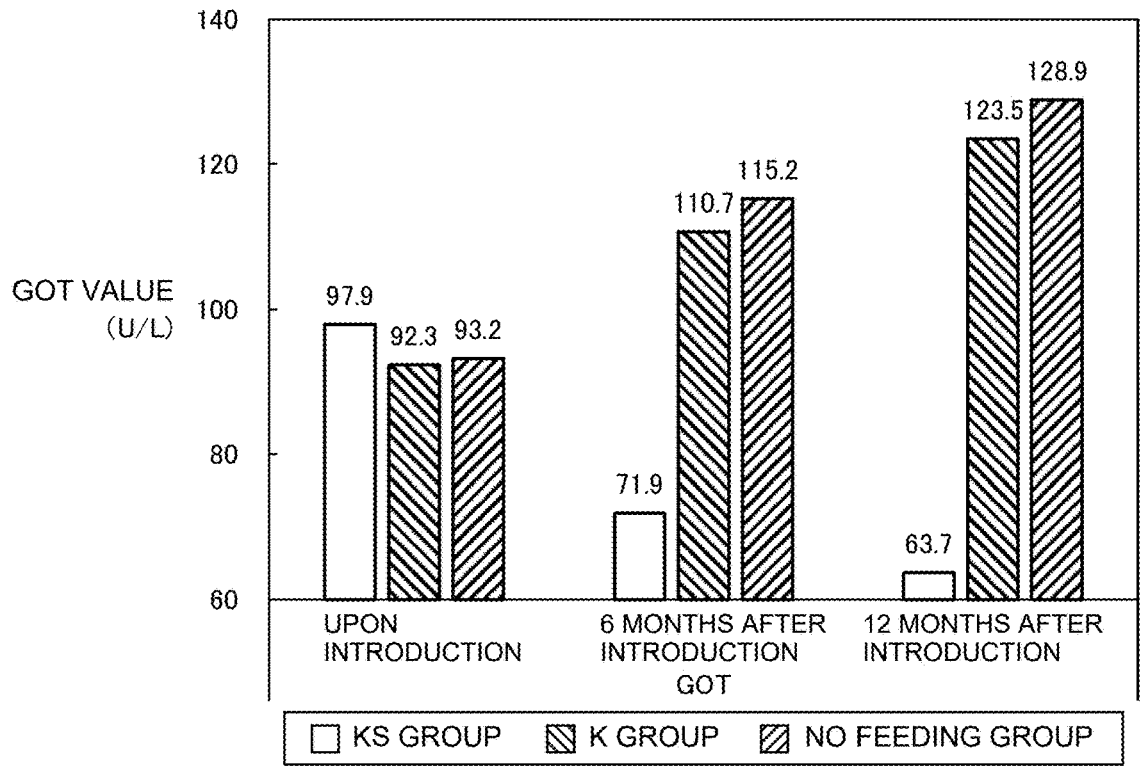
FIG. 30 is a graph showing average GOT values of 10 females in each group in Test 2.
Figure 31:
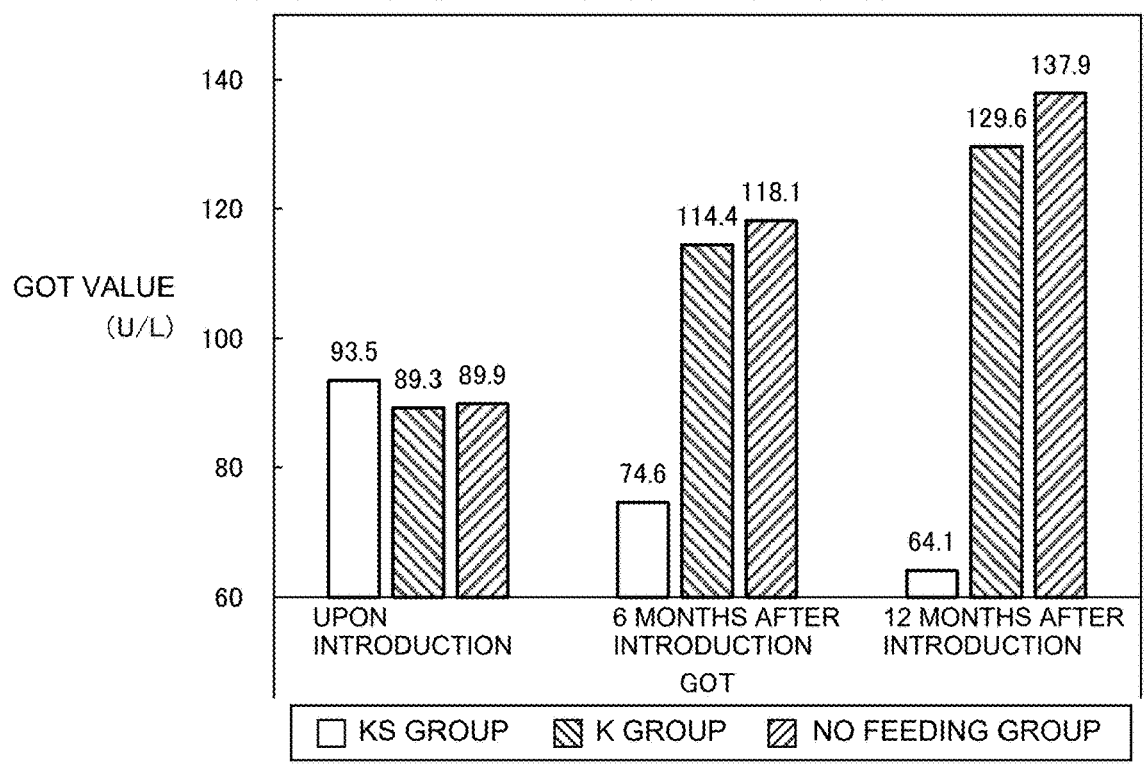
FIG. 31 is a graph showing average GOT values of eight males in each group in Test 2.
Figure 32:
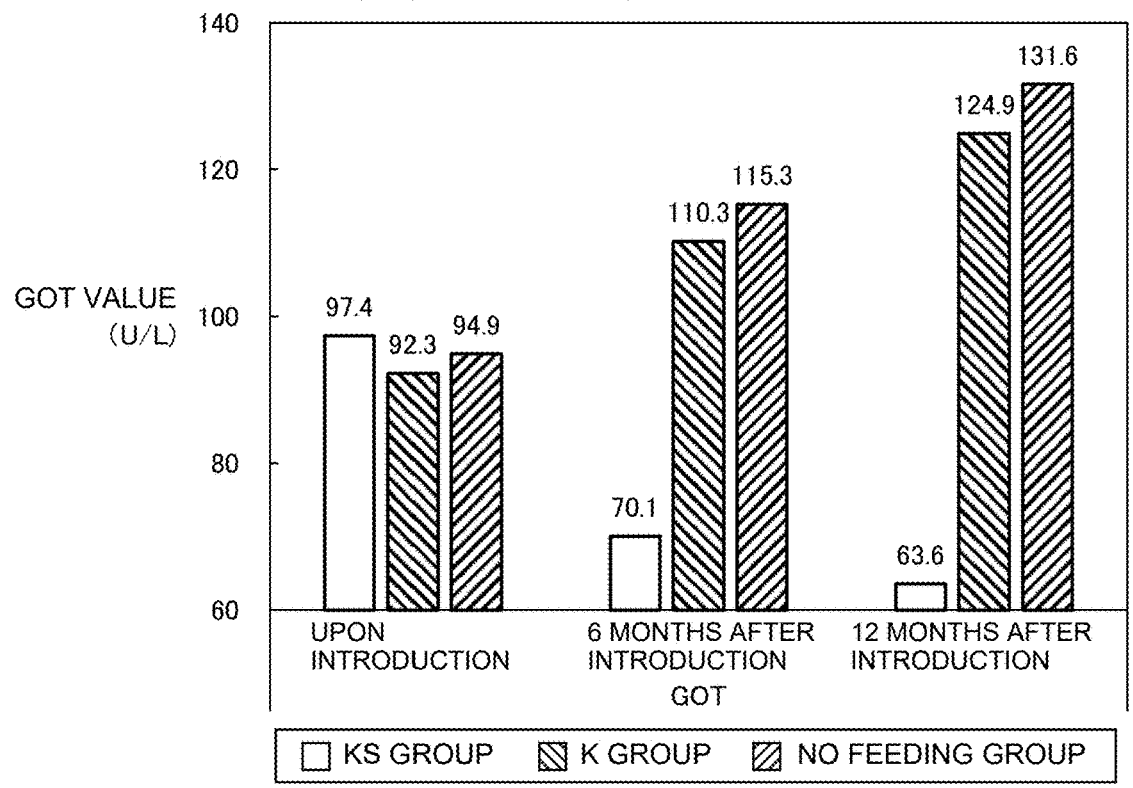
FIG. 32 is a graph showing average GOT values of eight females in each group in Test 2.
Figure 33:
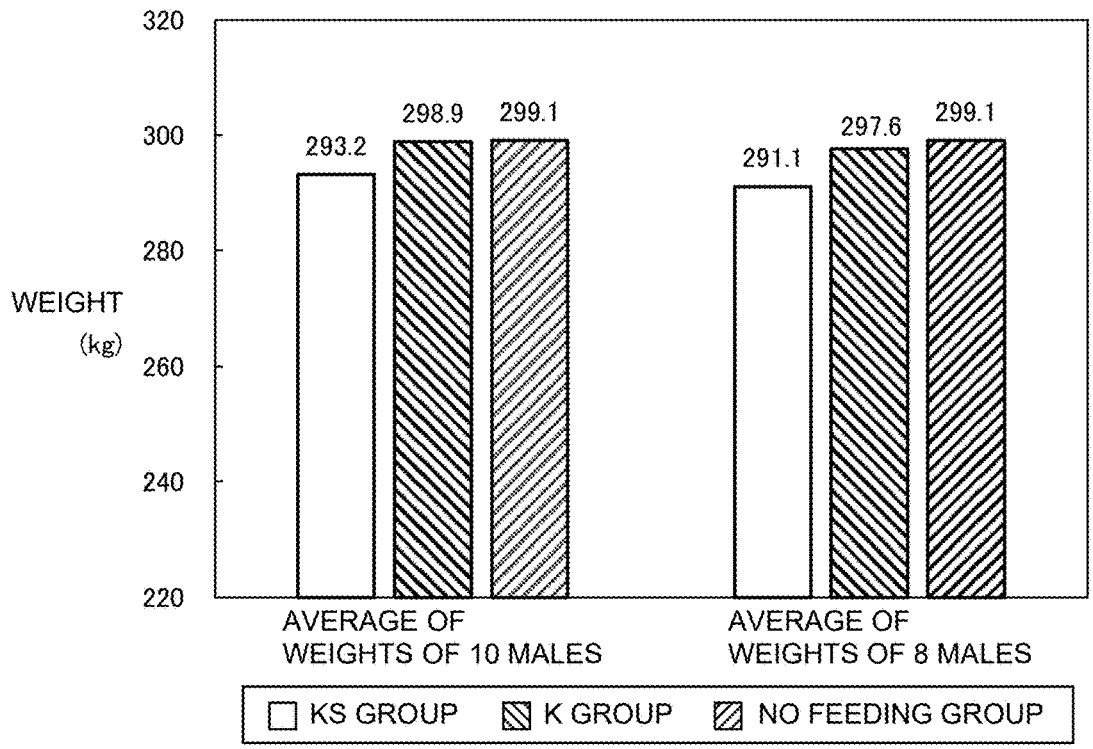
FIG. 33 is a graph showing upon-introduction weights of males in each group in Test 2.
Figure 34:
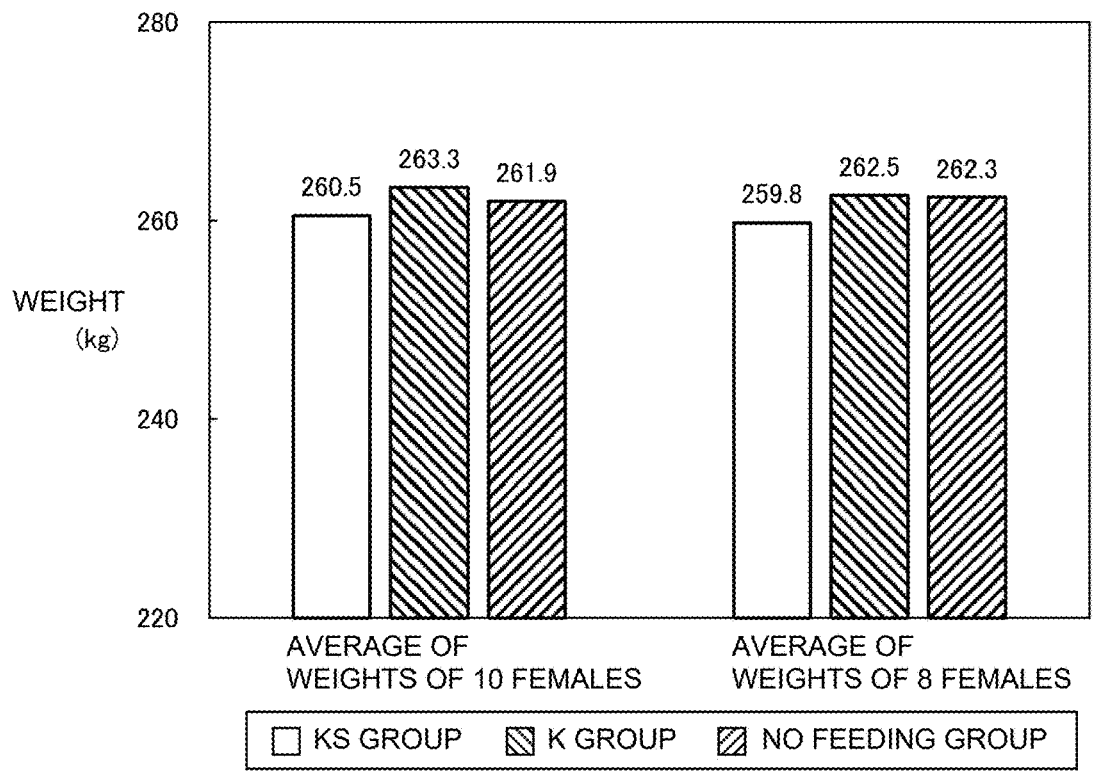
FIG. 34 is a graph showing upon-introduction weights of females in each group in Test 2.
Figure 35:
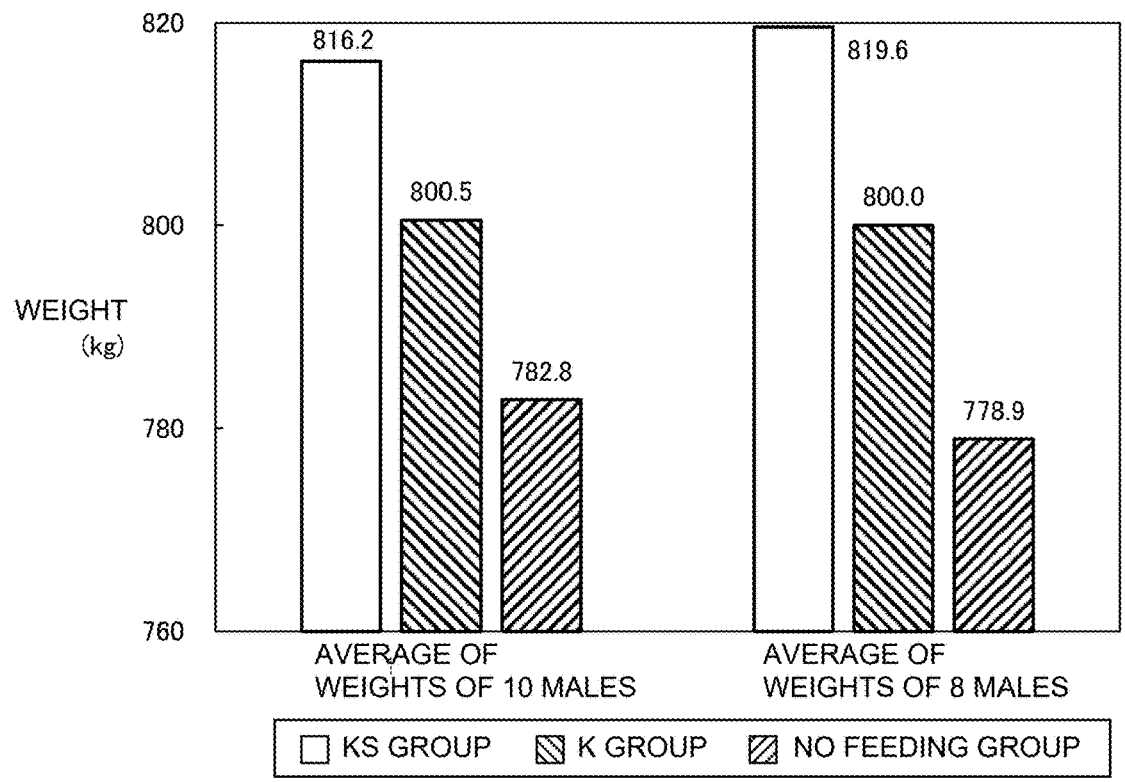
FIG. 35 is a graph showing upon-arrival weights of males in each group in Test 2.
Figure 36:
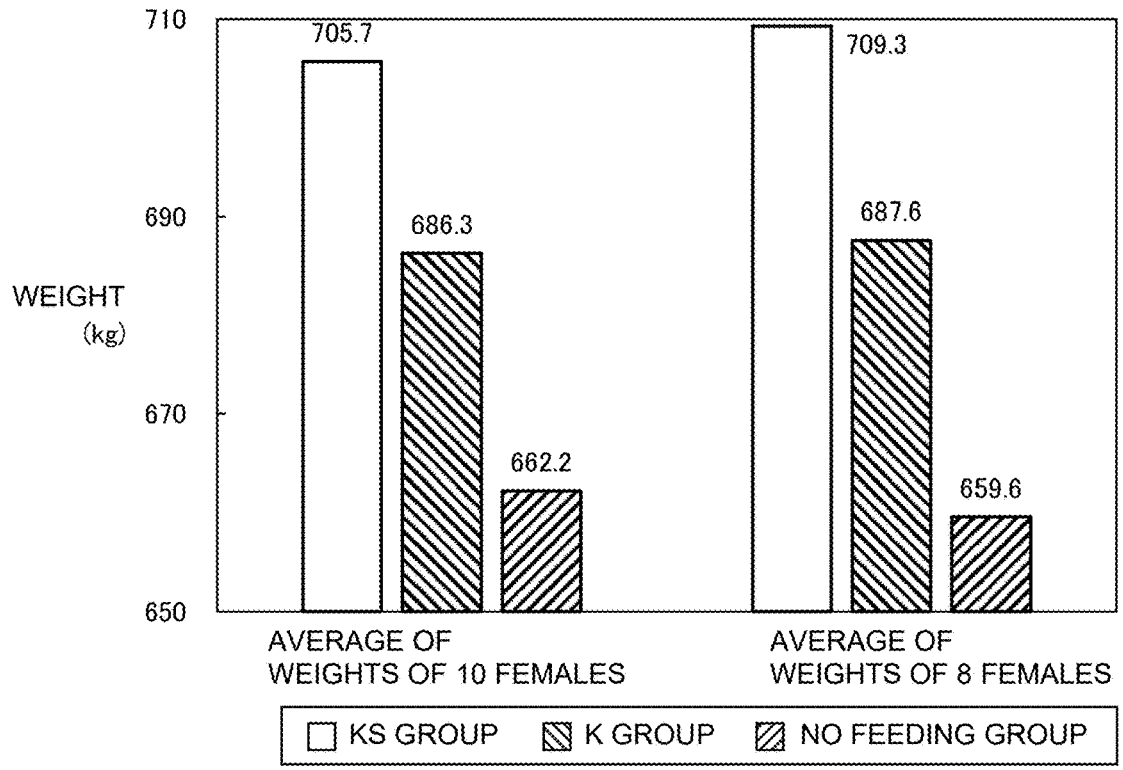
FIG. 36 is a graph showing upon-arrival weights of females in each group in Test 2.
Figure 37:
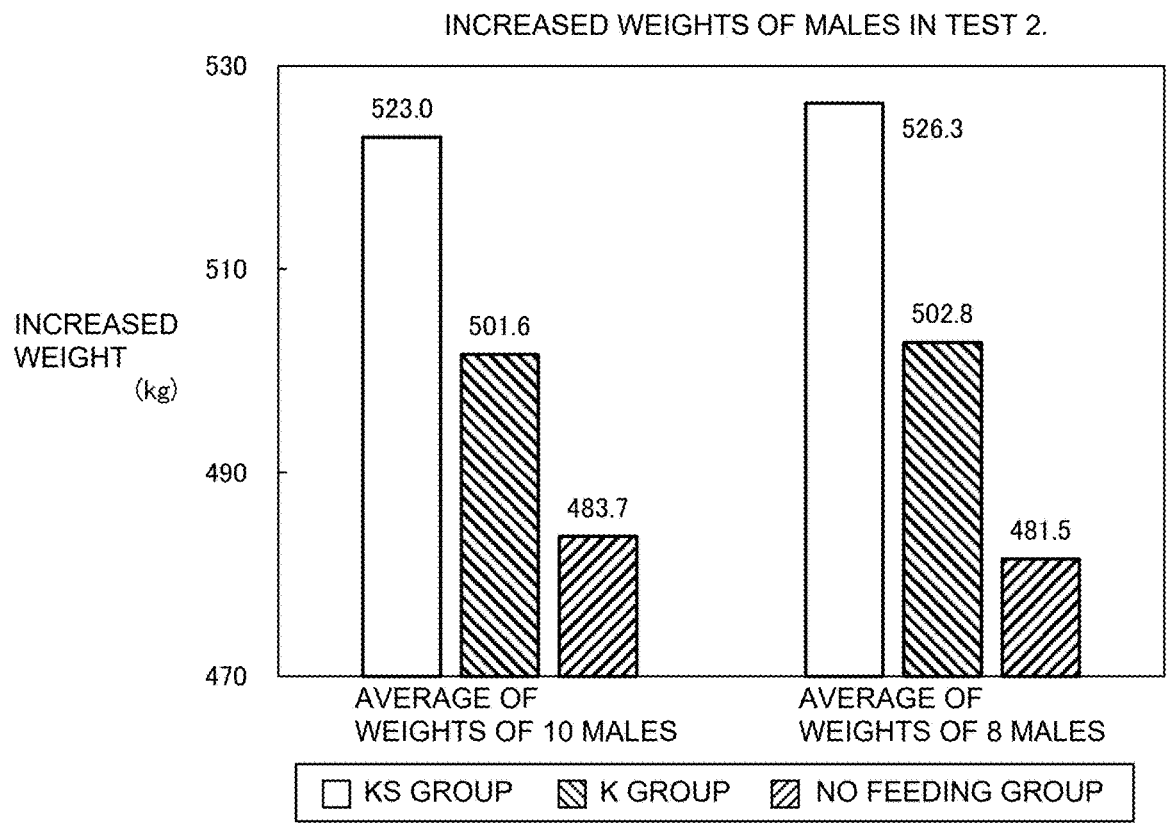
FIG. 37 is a graph showing increased weights of males in each group in Test 2.
Figure 38:
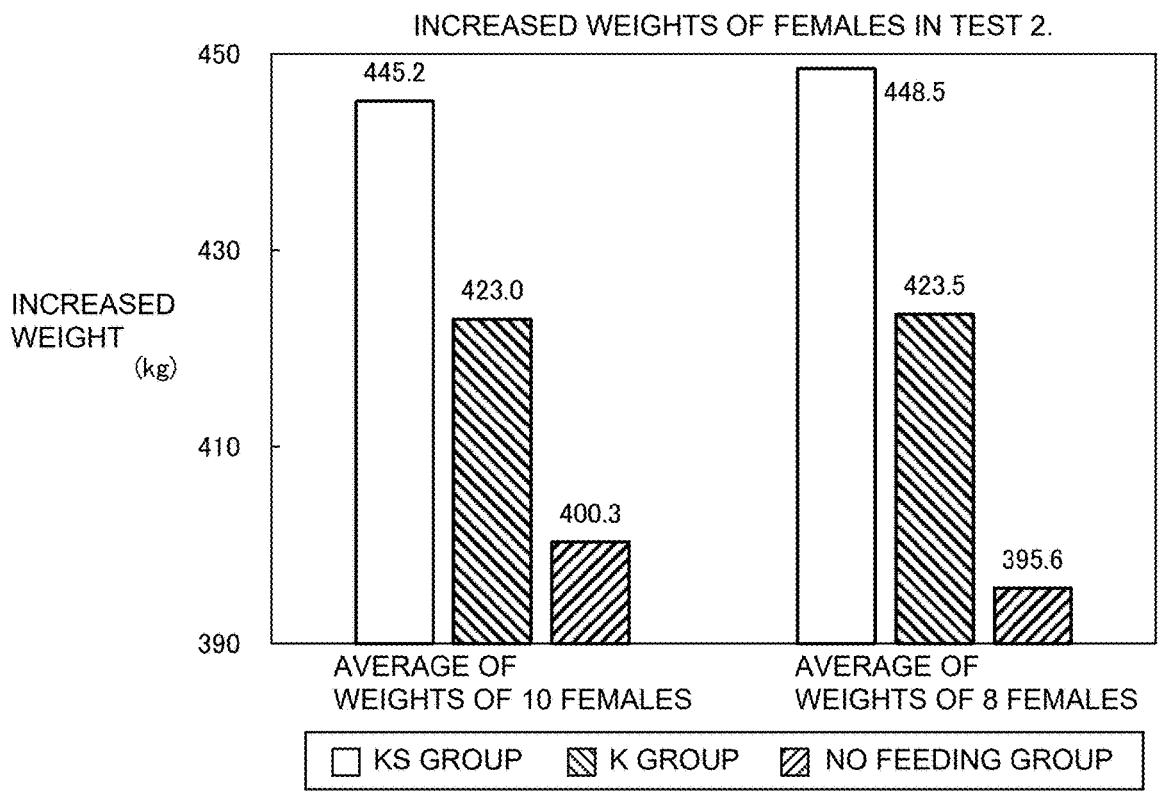
FIG. 38 is a graph showing increased weights of females in each group in Test 2.

As shown in FIG. 20, in the KS group, it took four days for females to completely eat after the feeding was started; in the K group, it took 10 days for females to completely eat; and in the no feeding group, it took 14 days for females to completely eat, as with the males.

Even when feeding of the licorice extract of the present invention was started after the introduction of fattening, even as compared with the K group to which the licorice extract including 13% or more of the glycyrrhizic acid was fed, high effects were confirmed, whereby synergy effect of the glycyrrhizic acid, the licorice saponins, and the licorice flavonoids, which are included in the licorice extract in Example 5, was confirmed.

It is considered that in the KS group, the cattle completely ate from immediately after the introduction of fattening and the amounts of feed intakes were large, as compared with the K group and the no feeding group, stress on the cattle is reduced, burdens on the digestive organs are decreased, and functions and states of the digestive organs are fine.

2.2 Blood Test Results (Total Cholesterol Values, VA Values, and GOT Values)

Blood tests (total cholesterol values, VA values, and GOT values) on all of the cattle were conducted three times: upon the introduction to the fattening ranch, six months after the introduction thereto, and 12 months after the introduction thereto, the total cholesterol values, the GOT values, and the VA values were measured.

Average values of 10 males and 10 females and average values of values of eight males and females excluding two males and two female among 10 males and 10 females, each of which had the highest value and the lowest value, in each of the groups are shown in FIGS. 21 to 24 (total cholesterol values), FIGS. 25 to 28 (VA values), and FIGS. 29 to 32 (GOT value).

As shown in FIGS. 21 to 24, in the KS group, the total cholesterol values of both of the males and the females were high. It is seen from this result that as described above, in the KS group, after the introduction of fattening, the amounts of the feed intakes were large from an earlier stage than the other groups and in addition thereto, digestion and absorption and metabolism of the ingested feed were fine.

As shown in FIGS. 25 to 28, in the KS group, the VA values of both of the males and the females were also high. Although as compared with the introduction of fattening six months after the introduction thereof and 12 months after the introduction thereof, in all of the groups, the VA values were reduced, in the KS group, the VA values six months after the introduction thereof and 12 months after the introduction thereof remained nearly at the same level or were rather enhanced. On the other hand, in the K group and the no feeding group, from six months after the introduction thereof to 12 months after the introduction thereof, the VA values were further reduced.

As shown in FIGS. 29 to 32, in the KS group, at both of six months after the introduction of fattening and 12 months after the introduction of fattening, as compared with the other groups, the GOT values were low. In the K group and the no feeding group, six month after the introduction of fattening, the GOT values were increased and 12 month after the introduction of fattening, the GOT values were further increased.

It was found from the above-described results that even when feeding of the licorice extract of the present invention is started after the introduction of fattening, favorable influence is exerted on nutrition states, metabolism (total cholesterol values), growing states, immune strength (vitamin A values), and a liver function (GOT values) by composite effects of the glycyrrhizic acid, the licorice saponins other than the glycyrrhizic acid, and the licorice flavonoids.

2.3 Weights

Weights and increased weights upon the introduction to the fattening ranch and upon arriving at the carcass market were measured. The weights measured at the calf auction market were defined as weights upon the introduction to the fattening ranch. The weights measured upon arriving at the carcass market from the fattening ranch were defined as upon-arrival weights. A difference of each of the upon-introduction weights and each of the upon-arrival weights was defined as an increased weight.

As shown in FIGS. 32 to 38, in the KS group, the upon-arrival weights and the increased weights of both of the males and the females were the largest. It is considered that the large increased weights are due to the development of a virtuous cycle as described below. In other words, as described above, in the KS group, the feed intakes were large from the earlier stage after the introduction of fattening than the other groups and in addition thereto, because the digestion and absorption, the metabolism, the growing, the immune strength, and the liver function are also fine, adverse influence of stress is hardly received even when there are changes in the environment and the feed and states of internal organs such as the digestive organs can be maintained in a favorable state. Consequently, diseases can be prevented and anorexia due to the diseases can be prevented. It is considered that in this way, in the KS group, the feed intakes are stably large and the larger somatic growth than those in the other groups can be obtained until the shipping to the carcass market.

As described in Test 1., it is seen that even by starting the feeding of the licorice extract of the present invention as the feed additive after the introduction to the fattening ranch, feed efficiency can be increased because despite the feeding manner in which in the KS group, the K group, and the no feeding group, the same kinds of the feed, other than the licorice extract, in the same amounts were fed, the somatic growth in the KS group was larger than those in the other groups.

2.4 Edible Liver Discard Rate

Edible liver discard rates upon slaughter were confirmed. Discarding of edible livers incurs economic loss. Liver lesions such as a sawdust liver and hepatic hemorrhage upon shipping to a carcass market are caused due to an increase in burdens on livers during a fattening period. Few liver lesions show that a liver function has been maintained in a healthy state.

Figure 39:
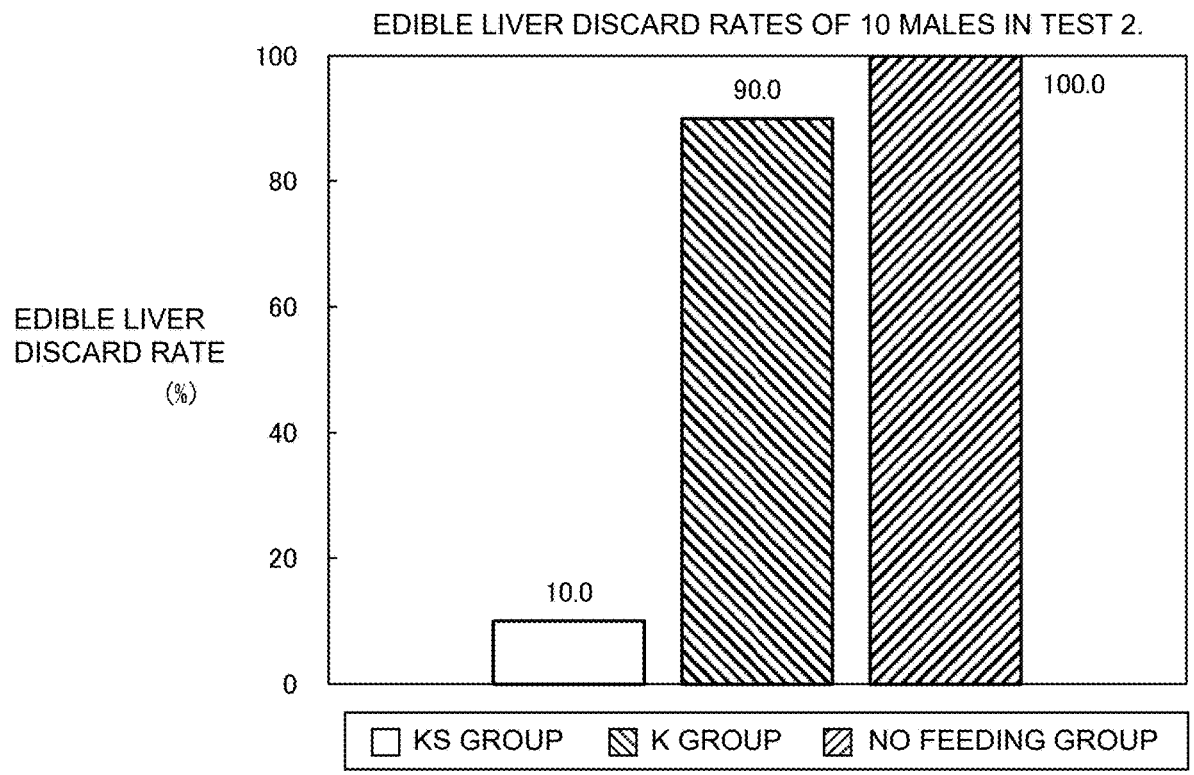
FIG. 39 is a graph showing an edible liver discard rate of males in each group in Test 2.
Figure 40:
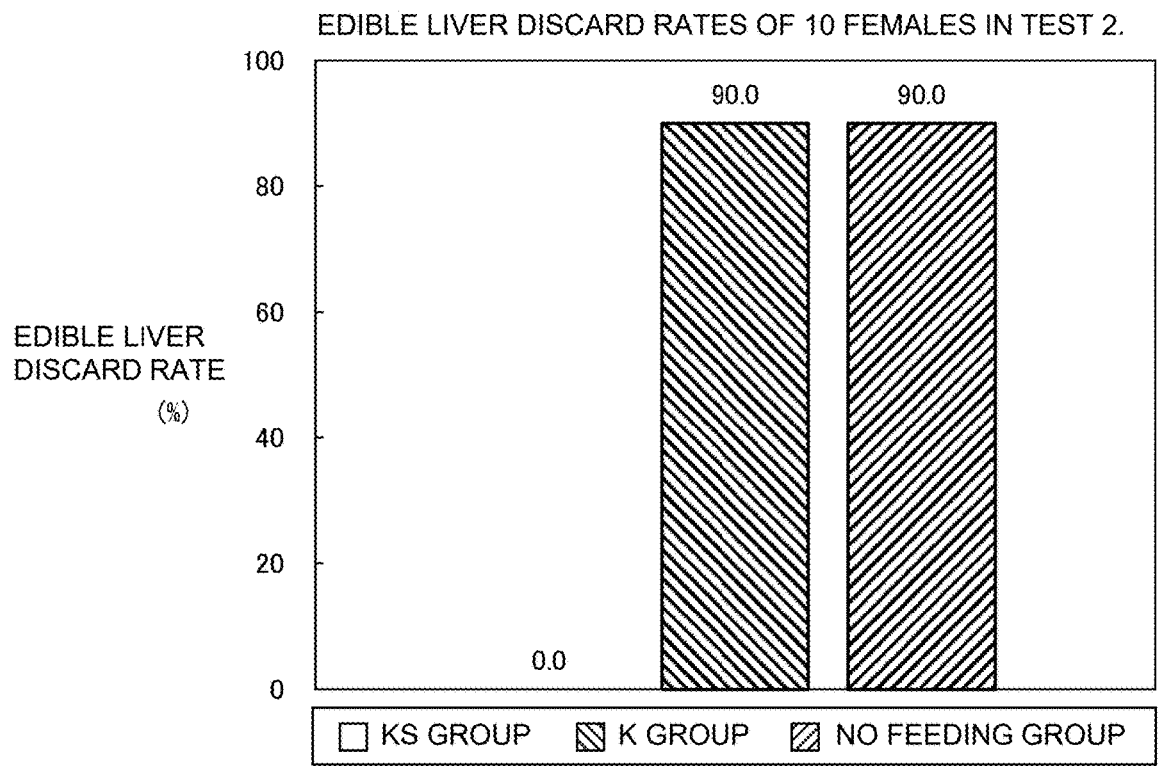
FIG. 40 is a graph showing an edible liver discard rate of females in each group in Test 2.

As shown in FIGS. 39 to 40, in the KS group, edible liver discard rates of both of the males and the females were extremely low, as compared with the other groups. Also in the K group to which the licorice extract including 13% or more of the glycyrrhizic acid was fed, edible liver discard rates were at substantially the same level as that in the no feeding group. It was found that effects of the licorice extract of the present invention to maintain the liver function in the healthy state are extremely large.

2.5 Carcass Weights and Yield Rates

Carcass weights were measured at a carcass market. In addition, carcass yield rates ((carcass weight/weight upon arriving at the carcass market)×100) were calculated from weights upon arriving at the carcass market and the carcass weights. Note that a dressed carcass is cattle in a state in which a head, skin, internal organs, blood, and the like are removed from a living body and constitutes an edible part.

Figure 41:
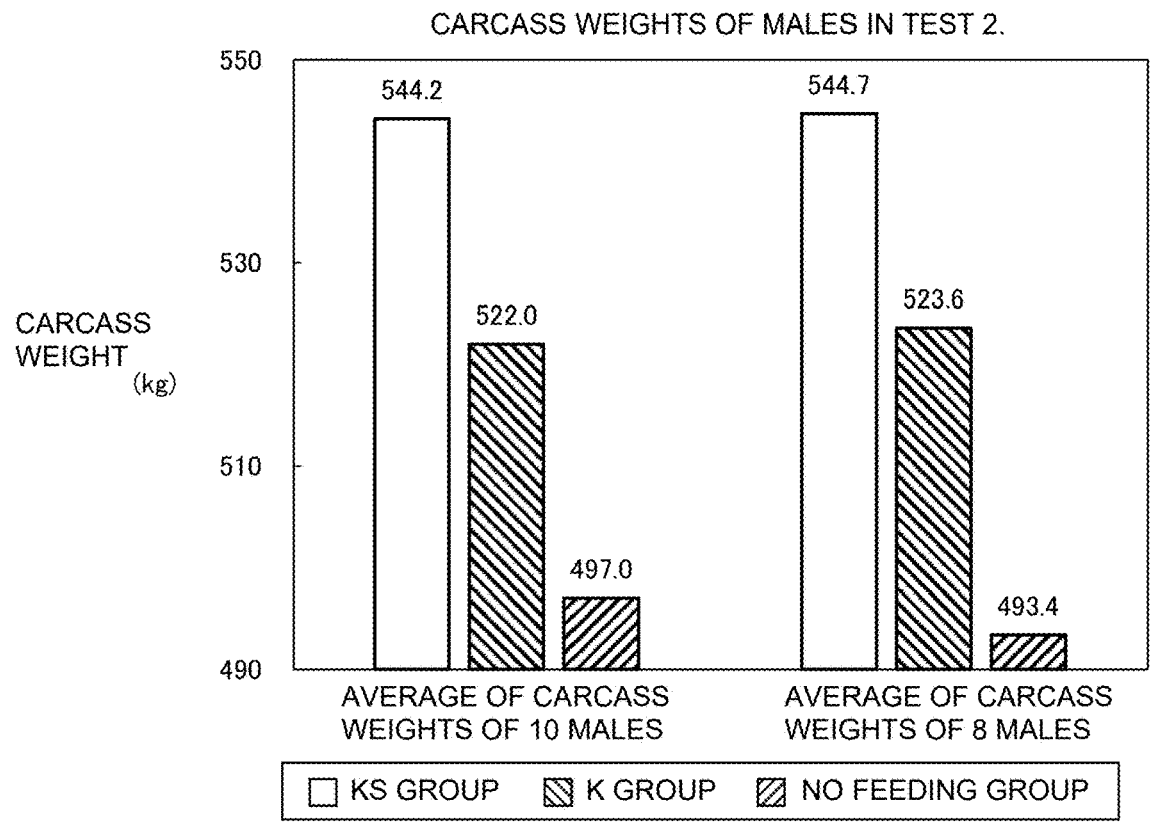
FIG. 41 is a graph showing a carcass weight of males in each group in Test 2.
Figure 42:
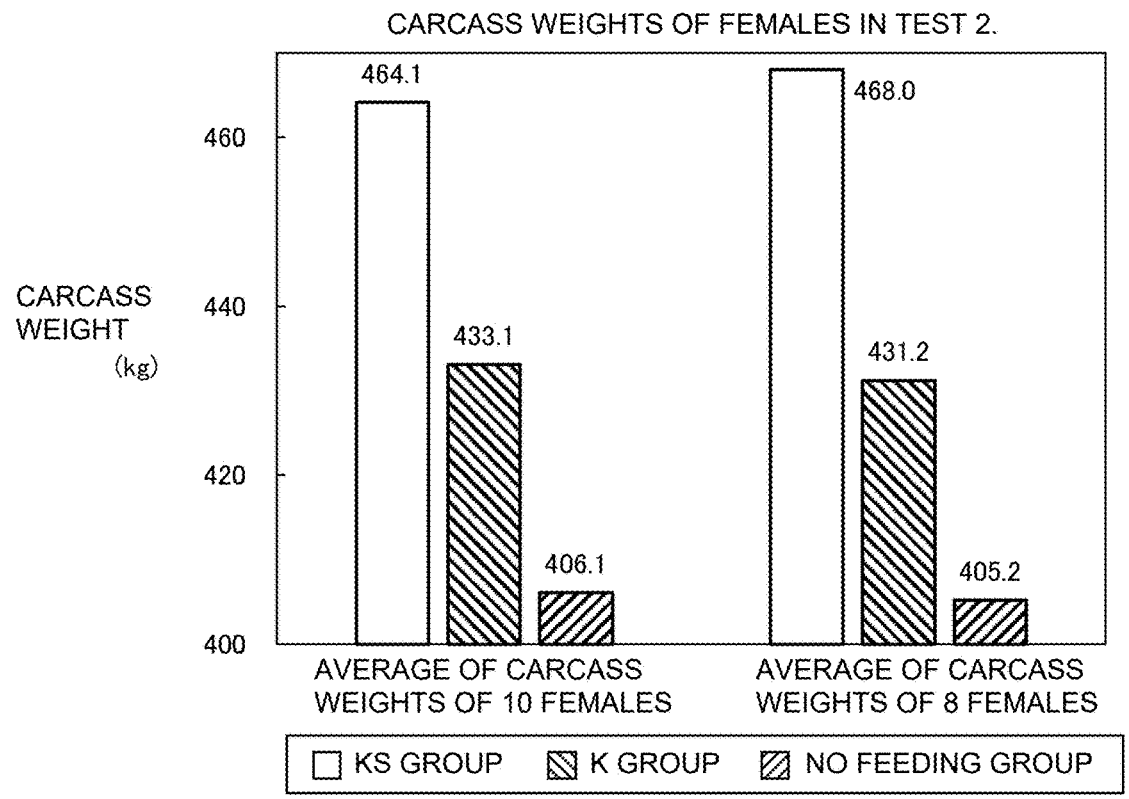
FIG. 42 is a graph showing a carcass weight of females in each group in Test 2.
Figure 43:
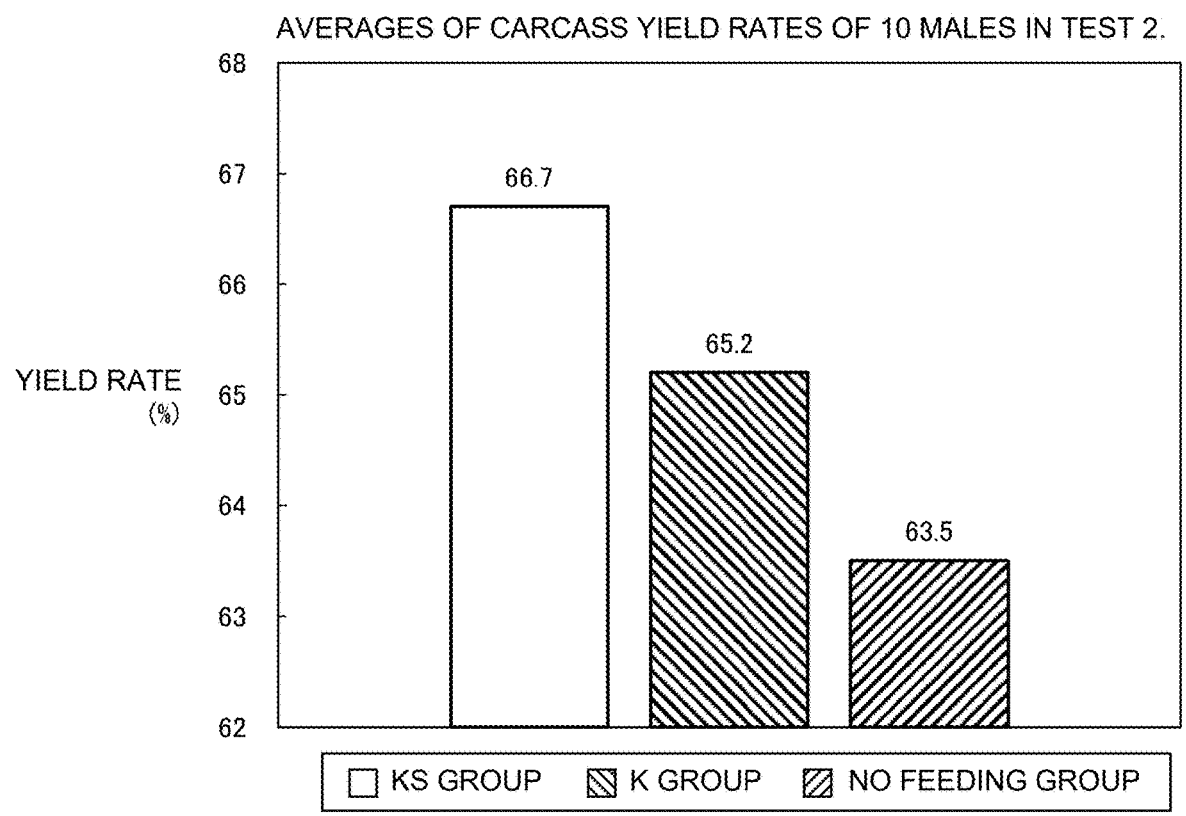
FIG. 43 is a graph showing an average carcass yield rate of 10 males in each group in Test 2.
Figure 44:
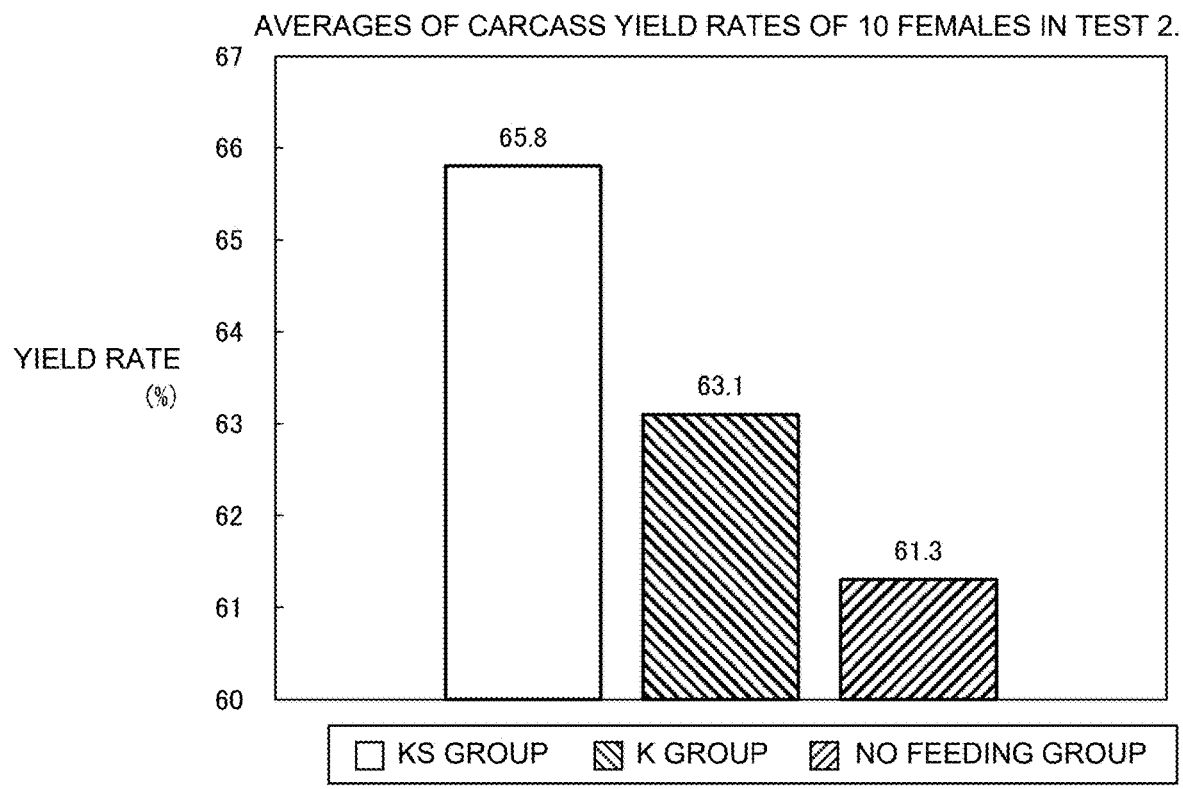
FIG. 44 is a graph showing an average carcass yield rate of 10 females in each group in Test 2.
Figure 45:
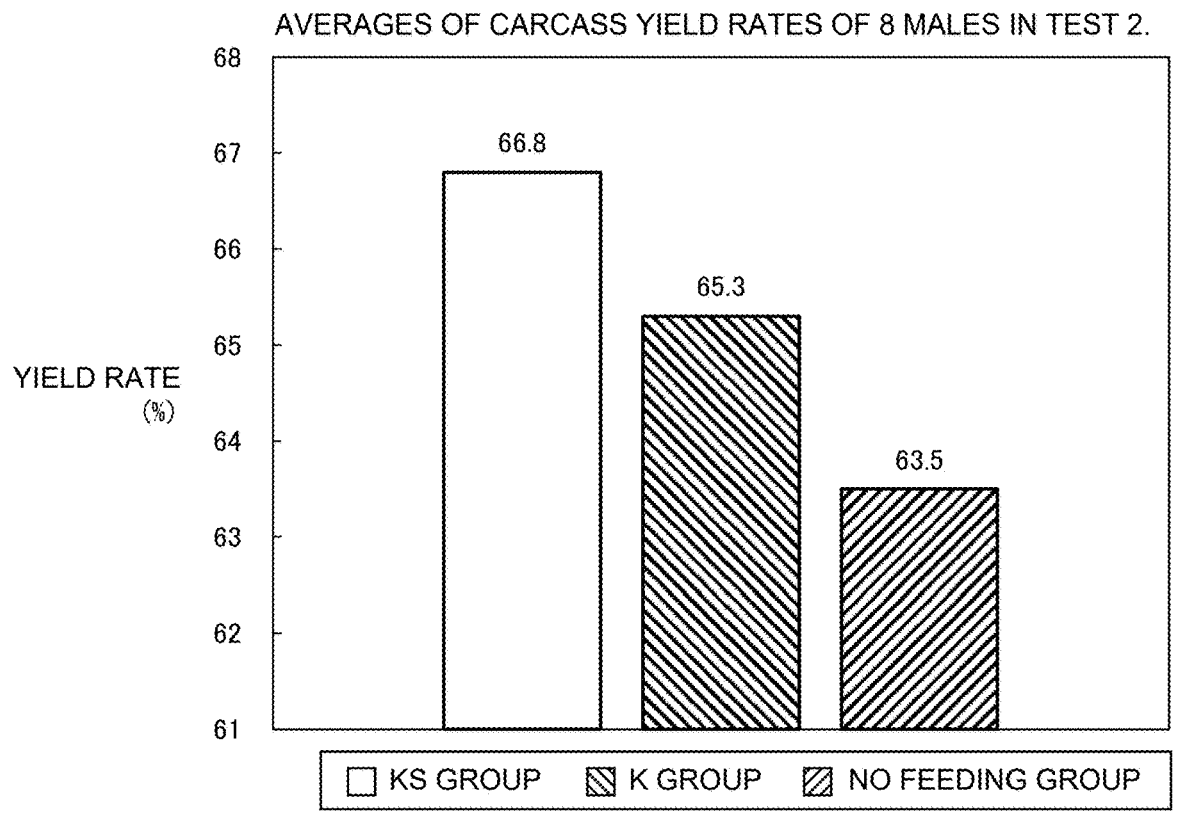
FIG. 45 is a graph showing an average carcass yield rate of eight males in each group in Test 2.
Figure 46:
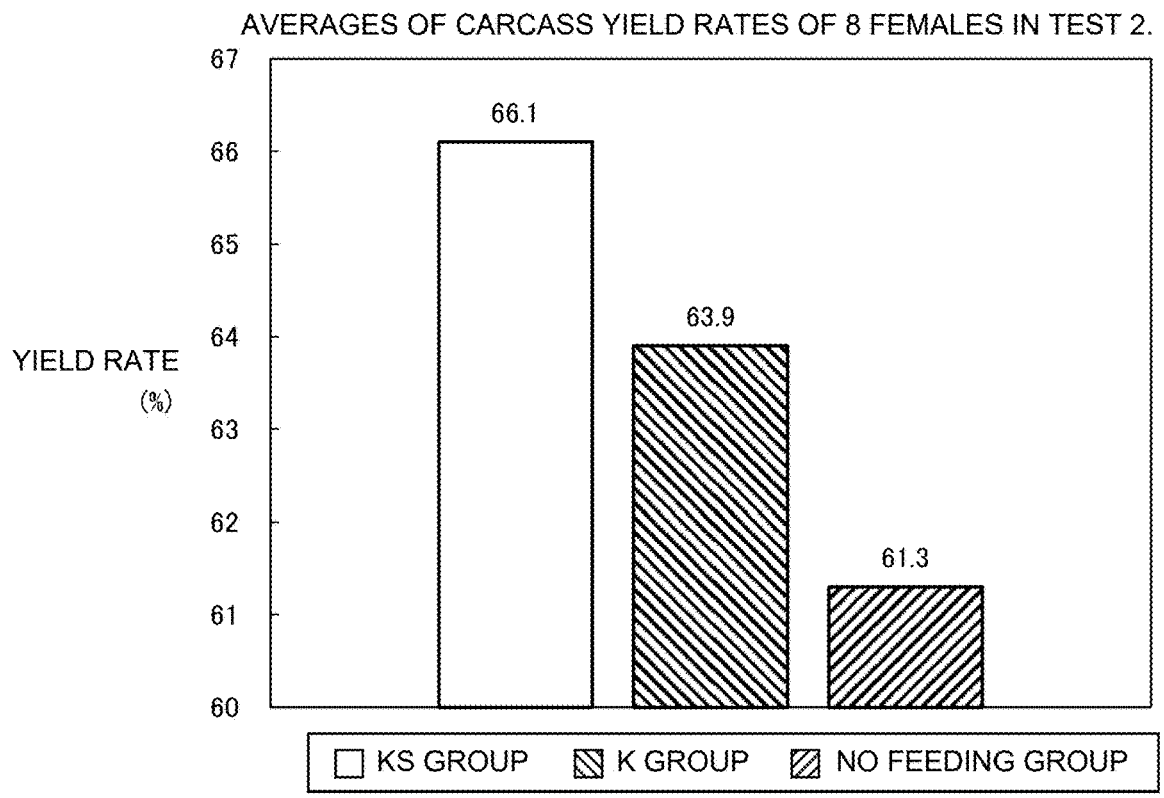
FIG. 46 is a graph showing an average carcass yield rate of eight females in each group in Test 2.

As shown in FIGS. 41 to 42, it is seen that in the KS group, carcass weights constituting the edible parts are large, as compared with those in the other groups. Furthermore, as shown in FIGS. 43 to 46, in the KS group, carcass yield rates are high, as compared with those in the other groups. Even if somatic growth is good, but if a yield rate is not good, dressed carcasses cannot be obtained considering weights. It is considered that by feeding the licorice extract of the present invention, after the introduction of fattening, stably high feed intakes can be maintained from an early stage and health of digestive organs and livers can be maintained, thereby bringing about enhancement in the somatic growth, the carcass weights, and the carcass yield rates.

As described above, it was confirmed that even by starting the feeding of the licorice extract of the present invention as the feed additive after the introduction to the fattening ranch, feed efficiency can be increased because despite the feeding manner in which in the KS group, the K group, and the no feeding group, the same kinds of the feed, other than the licorice extract, in the same amounts were fed, the carcass weights and the carcass yield rates in the KS group were larger than those in the other groups.

Test 3. Feeding for Only 10 Days from Day of Introduction of Fattening

As described in "Test 2. From Time of Introduction of Fattening to Shipping to Carcass Market", the calves upon the introduction to the fattening ranch in particular receive the stress due to the movement and the environmental changes. In addition, upon the introduction to the fattening ranch, the internal organs such as the digestive organs, the liver function, and the like have already been damaged due to the feeding for the purpose of the somatic growth. Therefore, by feeding the licorice extract for only 10 days from the day of the introduction to the fattening ranch, influence of the licorice extract of the present invention exerted on leftover amounts of the feed, numbers of days up to complete eating of the feed, and nutrition states (total cholesterol values, vitamin A values, and GOT values in blood tests) was examined.

Targets were 36 male head of Japanese Black Cattle at approximately 9 months of age to approximately 10 months of age (from 275 days of age to 308 days of age after birth) and 36 female head of Japanese Black Cattle at approximately 9 months of age to approximately 10 months of age (279 days of age to 309 days of age after birth), which were purchased at the calf auction market for the purpose of fattening and were introduced to the fattening ranch. The males and females were divided into three groups from the time of the introduction to the fattening ranch as shown in Table 9 with one frame constituting four head×three frames=12 head in each of the groups.

TABLE 9

|  | Male | Female | Total |
| --- | --- | --- | --- |
| KS group | 12 head | 12 head | 24 head |
| K group | 12 head | 12 head | 24 head |
| No feeding group | 12 head | 12 head | 24 head |

In the KS group, the licorice extract in Example 5 was added to the feed as the feed additive, and in the K group, the licorice extract in Comparative Example 1 was added to the feed as the feed additive. In the no feeding group, any licorice extract was not added to the feed. As to feed other than the licorice extracts, 3.0 kg of formula feed, 0.4 kg of rice straws, 2.0 kg of beer lees (moisture 50%), and 6.0 kg of oat hay per male head were fed and 3.0 kg of formula feed, 0.4 kg of rice straws, 2.0 kg of beer lees (moisture 50%), and 5.0 kg of oat hay per female head were fed with each amount divided into three parts a day in the order of the formula feed, the rice straws, the beer lees, and the oat hay and with the same amount fed to each of the groups at the same time. In order to confirm an increase in feed intakes and feeding properties, amounts of the feed additive (licorice extract) were increased than usual.

In the KS group, the licorice extract in Example 5 was fed for 10 days from the day of the introduction to the fattening ranch by adding 5 g/day/head thereof to the feed as the feed additive. In the K group, the licorice extract in Comparative Example 1 was fed for 10 days from the day of the introduction to the fattening ranch by adding 5 g/day/head thereof to the feed as the feed additive. The present test was terminated after 10 days.

3.1 Leftover Amounts and Numbers of Days Up to Complete Eating

Figure 47:
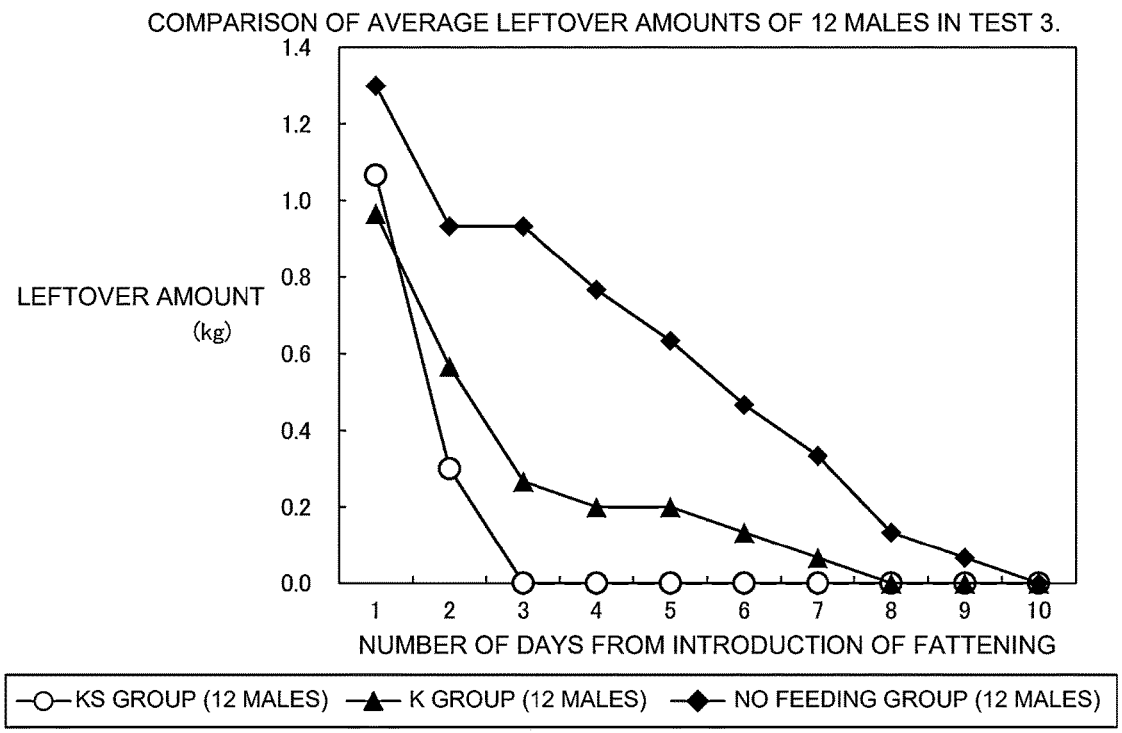
FIG. 47 is a graph showing average leftover amounts of 12 males in each group in Test 3.
Figure 48:
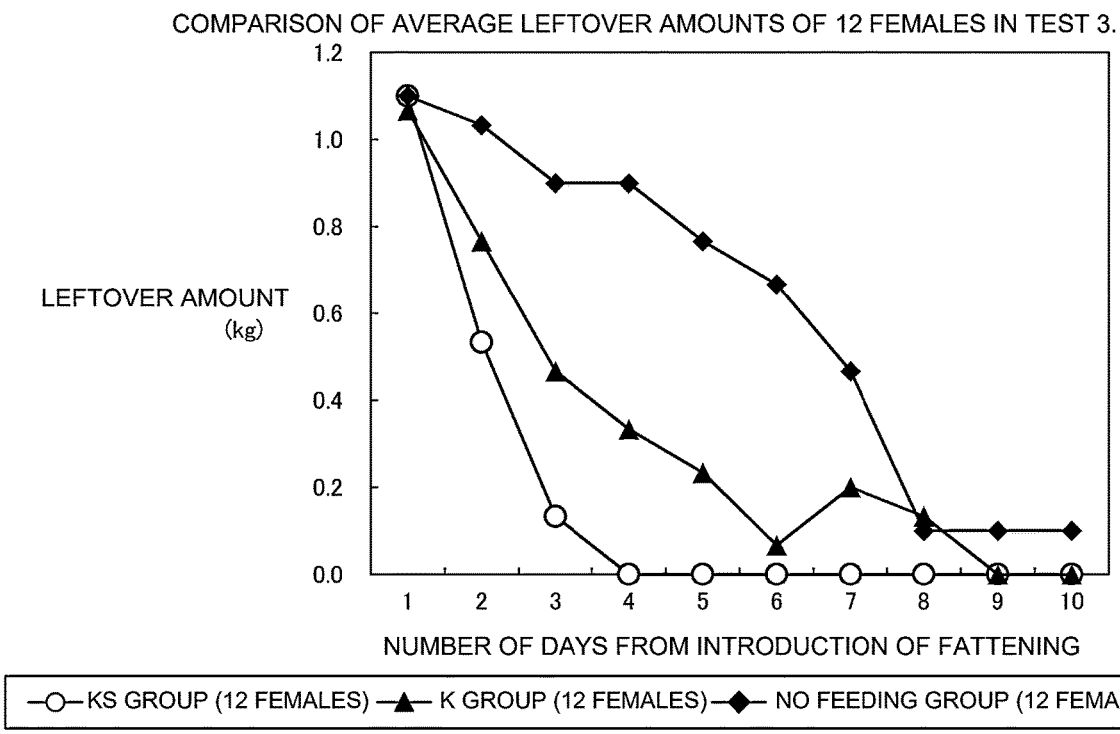
FIG. 48 is a graph showing average leftover amounts of 12 females in each group in Test 3.
Figure 49:
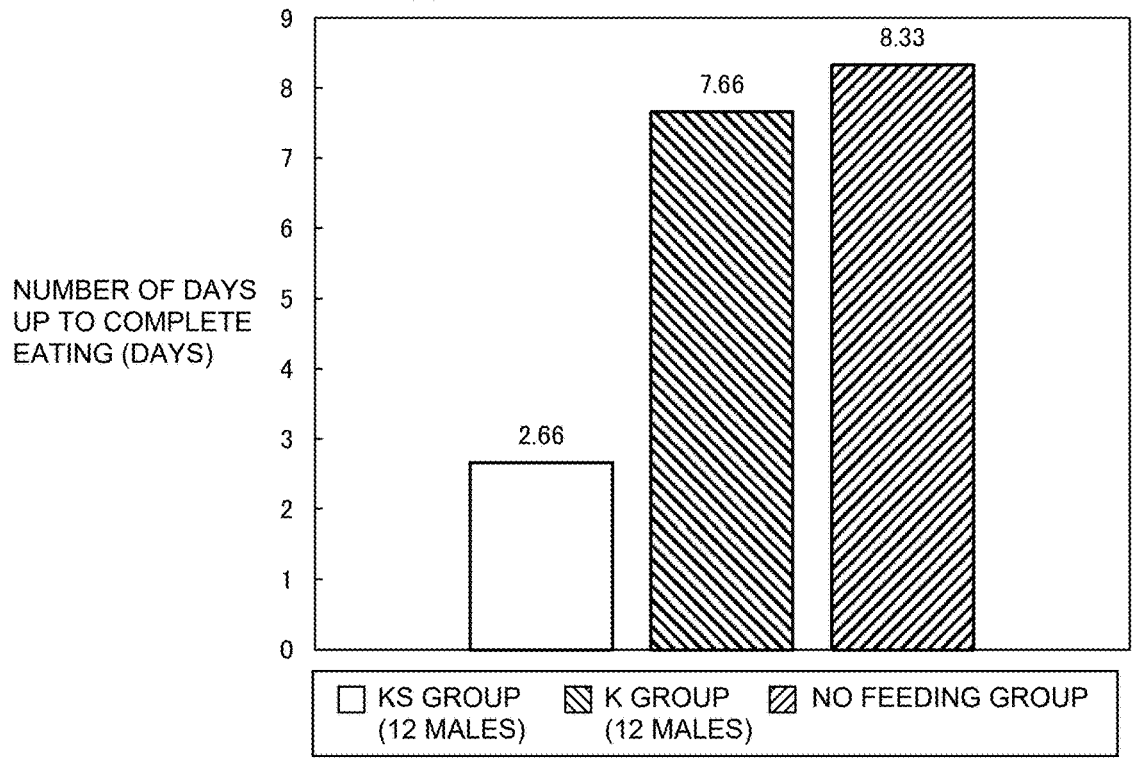
FIG. 49 is a graph showing an average number of days of 12 males up to complete eating in each group in Test 3.
Figure 50:
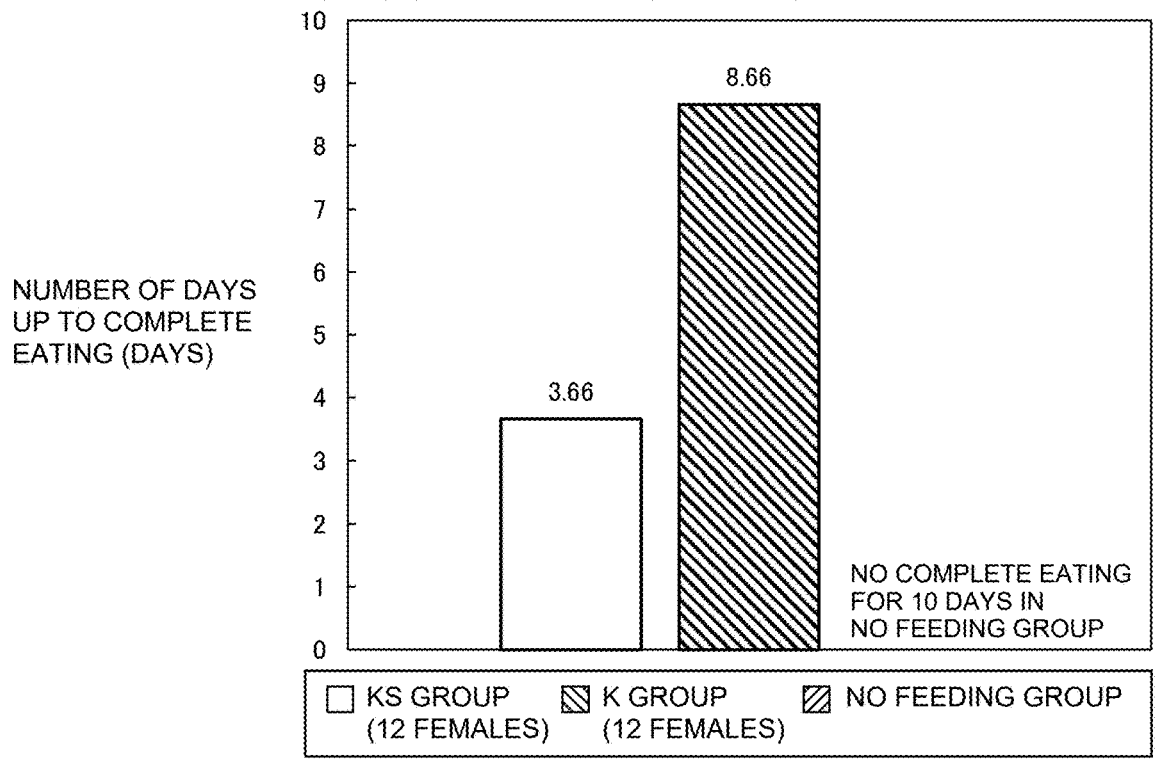
FIG. 50 is a graph showing an average number of days of 12 females up to complete eating in each group in Test 3.

As described above, since the feed was fed in the order of the formula feed, the rice straws, and the oat hay, in a case where remaining feed is caused, the oat hay becomes the remaining feed. Accordingly, weights of the remaining feed of the oat hay were measured as leftover amounts. Transition of the leftover amounts is shown in FIGS. 47 and 48 and numbers of days up to complete eating are shown in FIGS. 49 and 50.

As shown in FIGS. 47 to 50, in the KS group, it took three days for all of the 12 head of male fattening cattle to complete eat; in the K group, it took eight days for all of the 12 head of male fattening cattle to complete eat; and in the no feeding group, it took 10 days for all of the 12 head of male fattening cattle to complete eat. Average numbers of days up to the complete eating of the males was 2.66 days in the KS group, 7.66 days in the K group, and 8.33 days in the no feeding group. In the KS group, it took four days for all of the 12 head of female fattening cattle to complete eat; in the K group, it took nine days for all of the 12 head of female fattening cattle to complete eat; and in the no feeding group, there was some cattle which did not reach the complete eating even after 10 days. The average number of days up to the complete eating was 3.66 days in the KS group and was 8.66 days in the K group (in the no feeding group, the fattening cattle did not complete eat for 10 days).

It can be said from this result that the licorice extract of the present invention can improve stress on the calves upon the introduction of fattening and can improve the internal organs and the liver function. In addition, by decreasing the leftovers of the calves upon the introduction of fattening, the somatic growth can be brought about from an early stage after the introduction of fattening.

Since Test 3. was conducted for only 10 days from the day of the introduction of fattening, the cattle were in the middle of fattening upon finishing the test (at the 10th day from the introduction of fattening) and at this point of time, amounts of production of edible meat and weight ratios of amounts of the given feed and the amounts of meat production (feed efficiency) are unknown. However, as with Test 1, and Test 2., it is considered that even by feeding the licorice extract of the present invention as the feed additive for only 10 days after the introduction to the fattening ranch, feed efficiency can be increased because despite the feeding manner in which in the KS group, the K group, and the no feeding group, the same kinds of the feed, other than the licorice extract, in the same amounts were fed, in the KS group, the leftover amounts were smaller than those in the other groups (large dietary intakes) and the numbers of days up to the complete eating were small.

Test 4. From Approximately 91 Days of Age to Approximately 150 Days of Age After Birth As described above, the calves are weaned at approximately 90 days of age after birth as a rough standard. In a period from approximately 91 days of age after birth after being weaned to the time of shipping to the calf auction market, loads, burdens, and stress are exerted on digestive organs, thereby reducing feed intakes and delaying development of the digestive organs. The development of the digestive organs is delayed, thereby reducing the feed intakes and resulting in a vicious cycle. This leads to a reduction in somatic growth and feed efficiency.

Therefore, by feeding the licorice extract of the present invention as a feed additive to cattle from approximately 91 days of age to approximately 150 days of age after birth, influence of the licorice extract of the present invention exerted on leftover amounts and nutrition states (total cholesterol values, vitamin A values, and GOT values in blood tests) of the calves after being weaned was examined.

Targets were a total of 60 head of Japanese Black Cattle including 30 male calves and 30 female calves at approximately 91 days of age to approximately 150 days of age after birth. The targets were divided into three groups shown in Table 10. Here, at approximately 70 days of age after birth, the first blood tests were conducted, and the targets were divided into three groups so as to make average values of the total cholesterol values, VA values, and GOT values measured by the blood tests equivalent. A group whose average value of the GOT values among these values was high was defined as a KS group.

TABLE 10

|  | Male | Female | Total |
| --- | --- | --- | --- |
| KS group | 10 head | 10 head | 20 head |
| K group | 10 head | 10 head | 20 head |
| No feeding group | 10 head | 10 head | 20 head |

In the KS group, the licorice extract in Example 5 was added to feed as a feed additive, and in the K group, the licorice extract in Comparative Example 1 was added to feed as a feed additive. In the no feeding group, any licorice extract was not added to feed. As to feed other than the licorice extracts (substitute milk, creep feed, formula feed, and oat hay), feed shown in Table 11 (feed fed to one male head of cattle) and feed shown in Table 12 (feed fed to one female head of cattle) were fed by dividing each amount shown therein into three parts a day, and at and after approximately 91 days of age, the same amount was fed to each of the groups at the same time in the order of the formula feed and the oat hay.

TABLE 11

|  | Substitute milk | Creep feed | Formula feed | Oat hay |
| --- | --- | --- | --- | --- |
| 81 to 90 days | Fed | 3.2 kg | — | 0.4 kg |
| 91 to 120 days | — | — | 4.5 kg | 1.8 kg |
| 121 to 150 days | — | — | 5.0 kg | 2.0 kg |

TABLE 12

|  | Substitute milk | Creep feed | Formula feed | Oat hay |
|---|---|---|---|---|
| 81 to 90 days | Fed | 2.8 kg | — | 0.3 kg |
| 91 to 120 days | — | — | 3.5 kg | 1.5 kg |
| 121 to 150 days | — | — | 4.5 kg | 2.0 kg |

In the KS group, in a period from approximately 91 days of age to approximately 150 days of age after birth, 3 g/day/head of the licorice extract in Example 5 was added to the feed as a feed additive and fed. In the K group, in a period from approximately 91 days of age to approximately 150 days of age after birth, 3 g/day/head of the licorice extract in Comparative Example 1 was added to the feed as a feed additive and fed.

4.1 Leftover Amounts

As described above, since at and after the approximately 91 days of age after birth, the feed was fed in the order of the formula feed and the oat hay, in a case where remaining feed is caused, the oat hay becomes the remaining feed. Accordingly, weights of the remaining feed of the oat hay were measured as leftover amounts. Transition of the leftover amounts is shown in FIGS. 51 and 52.

Figure 51:
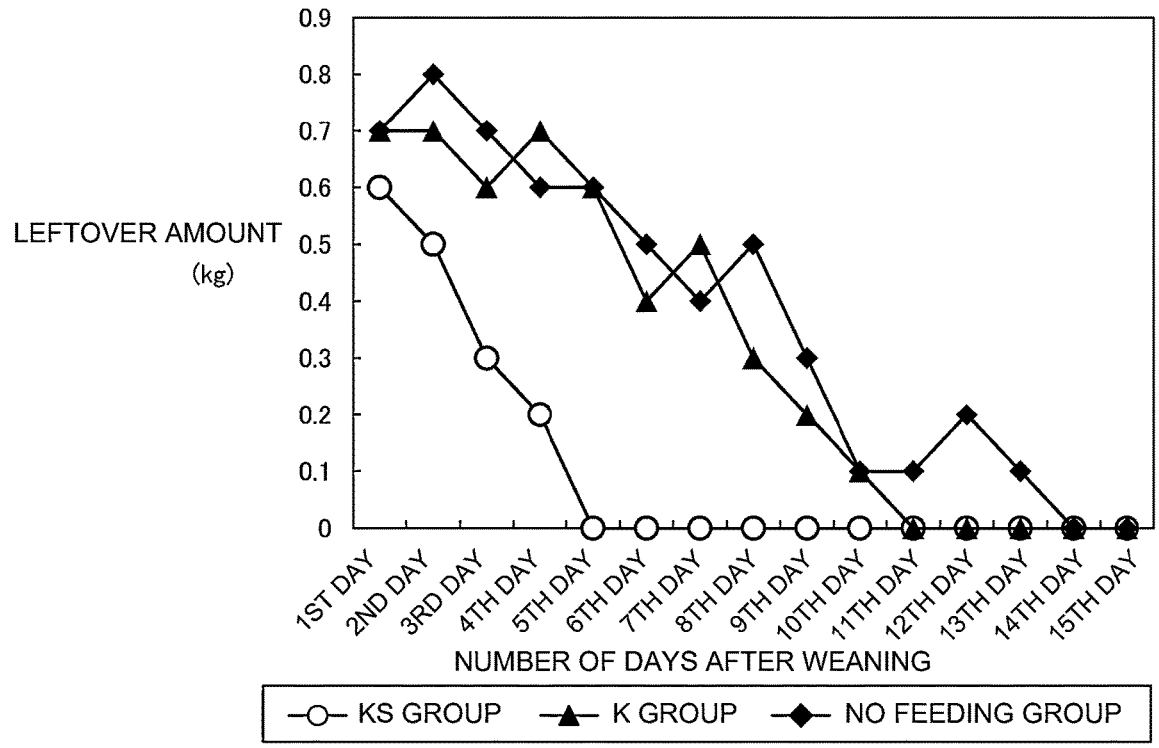
FIG. 51 is a graph showing comparison of average leftover amounts of 10 males in each group in Test 4.
Figure 52:
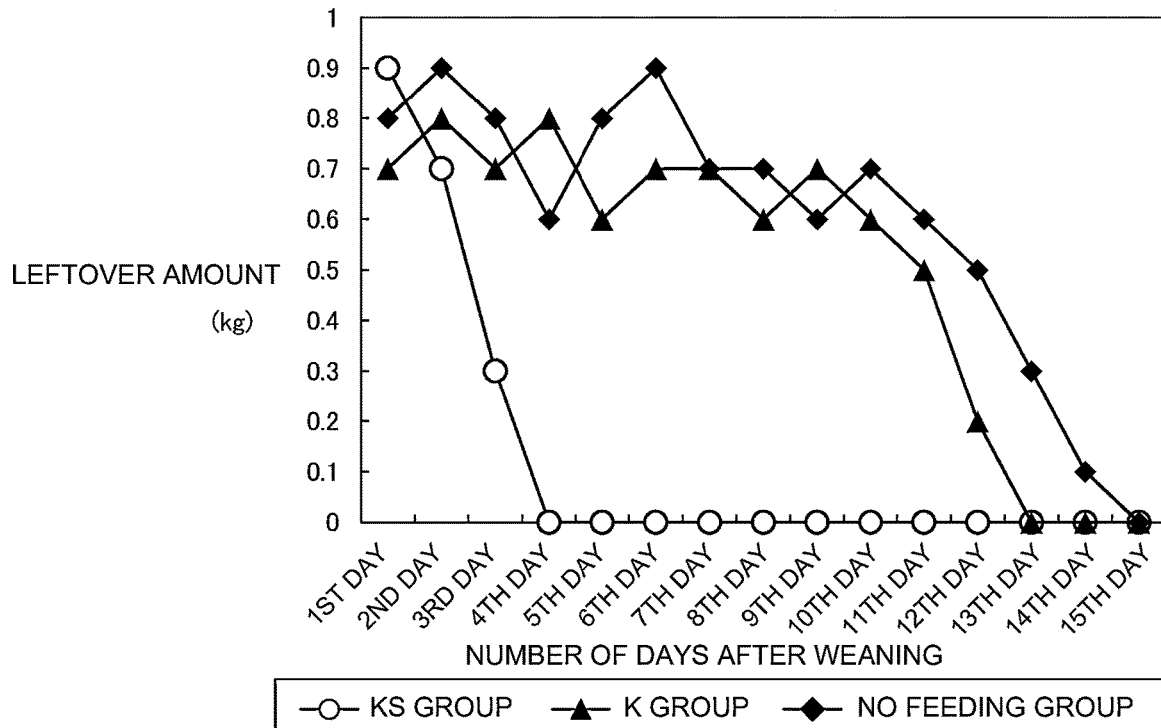
FIG. 52 is a graph showing comparison of average leftover amounts of 10 females in each group in Test 4.
Figure 53:
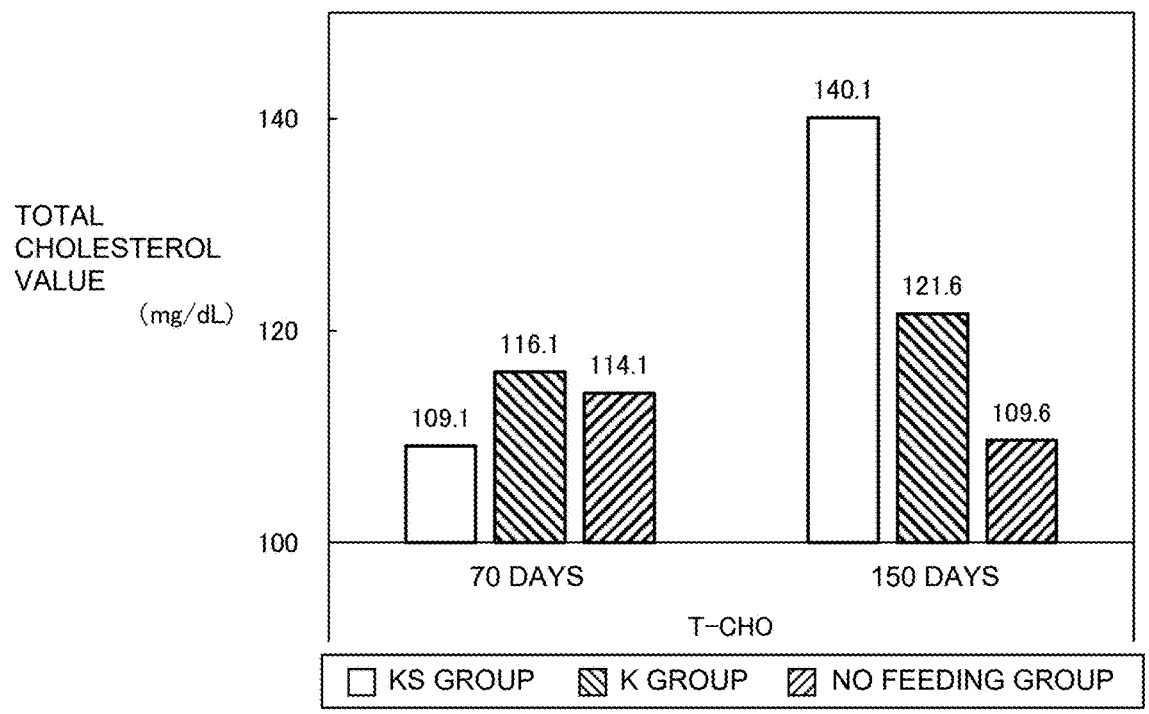
FIG. 53 is a graph showing average total cholesterol values of 10 males in each group in Test 4.
Figure 54:
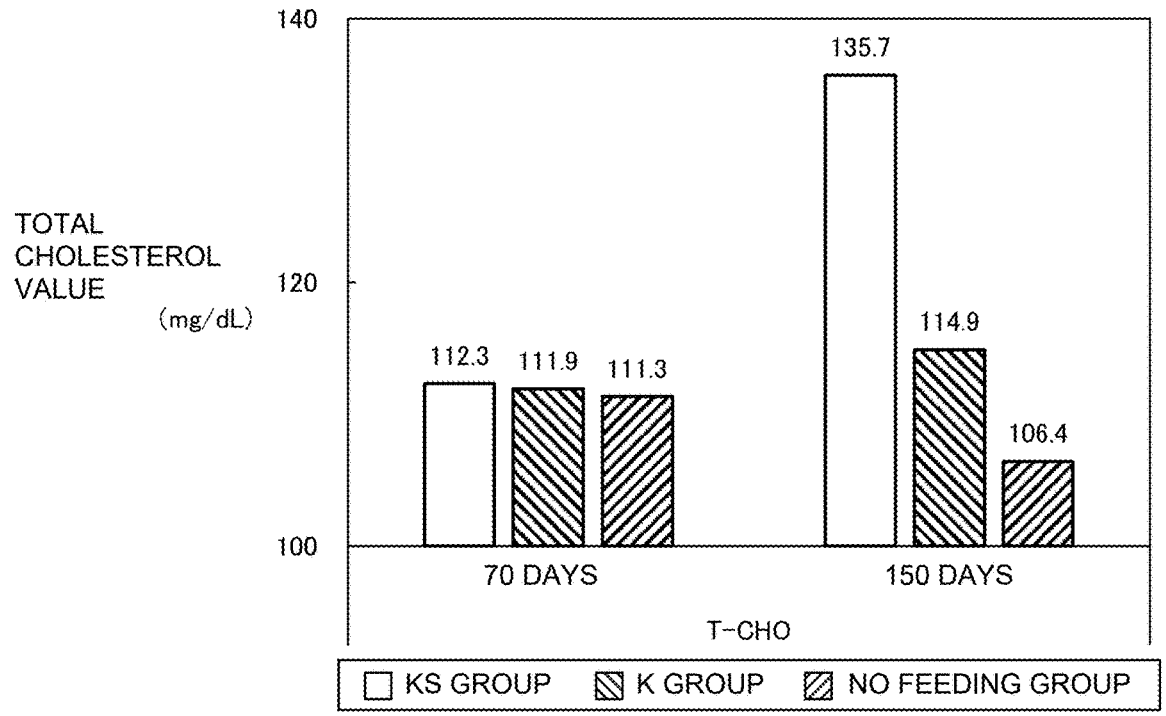
FIG. 54 is a graph showing average total cholesterol values of 10 females in each group in Test 4.
Figure 55:
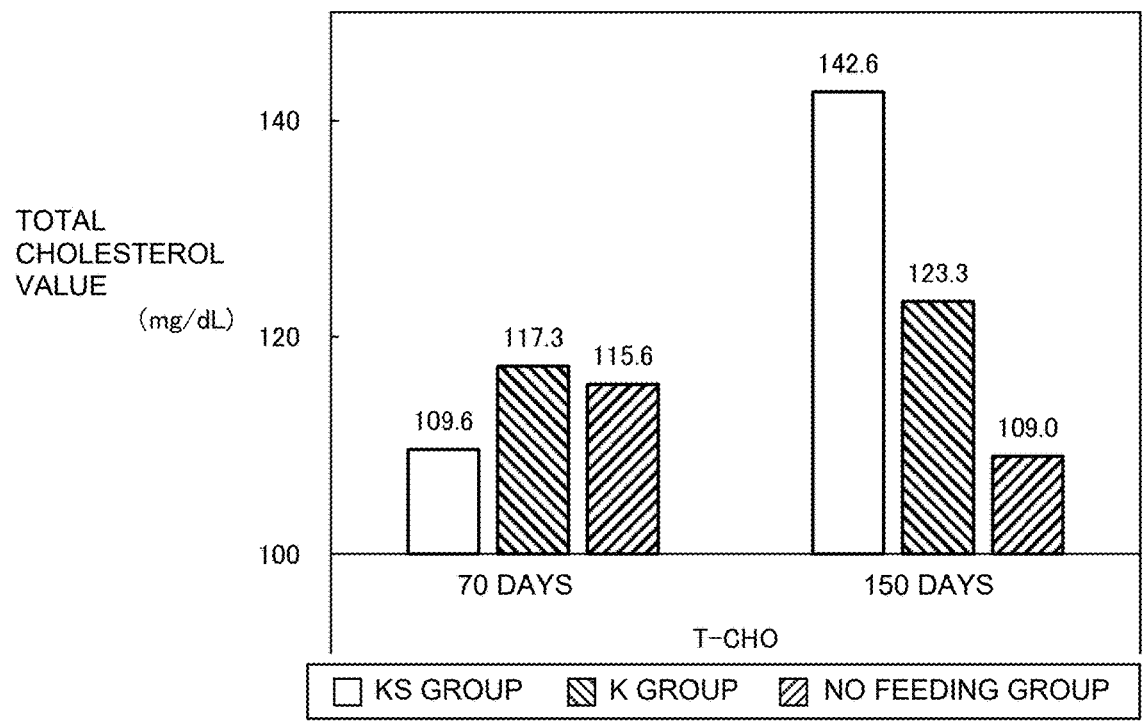
FIG. 55 is a graph showing average total cholesterol values of eight males in each group in Test 4.
Figure 56:
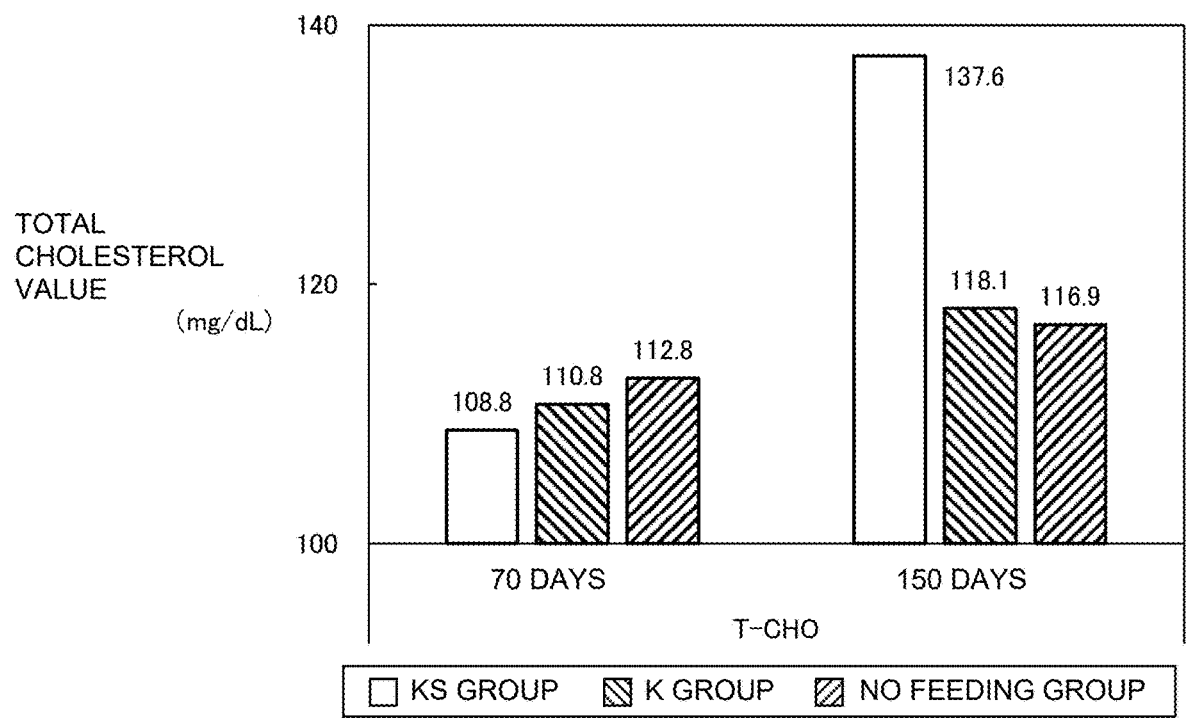
FIG. 56 is a graph showing average total cholesterol values of eight females in each group in Test 4.
Figure 57:
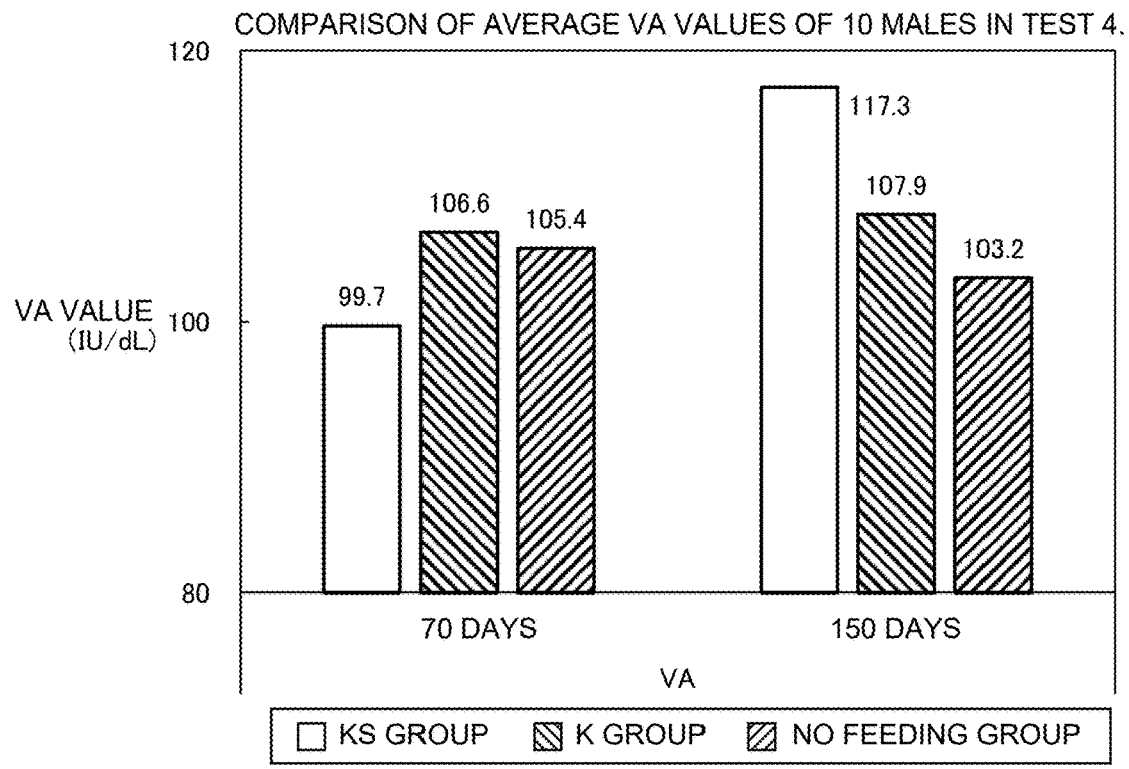
FIG. 57 is a graph showing average vitamin A values of 10 males in each group in Test 4.
Figure 58:
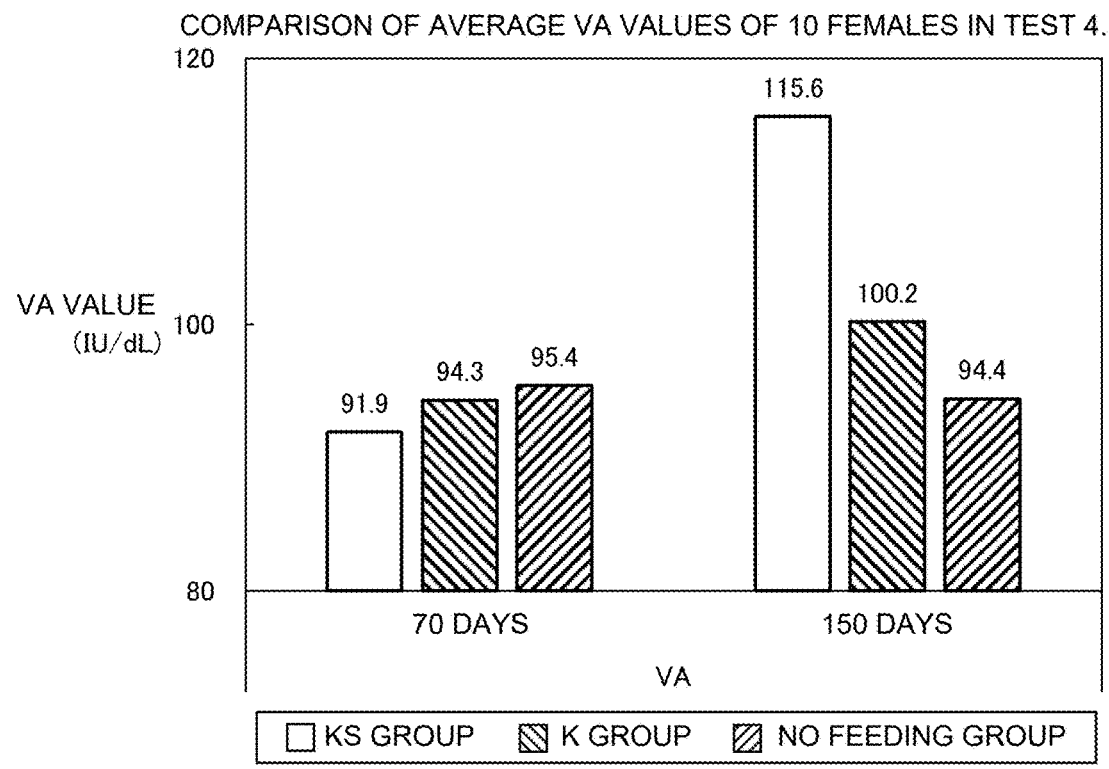
FIG. 58 is a graph showing average vitamin A values of 10 females in each group in Test 4.
Figure 59:
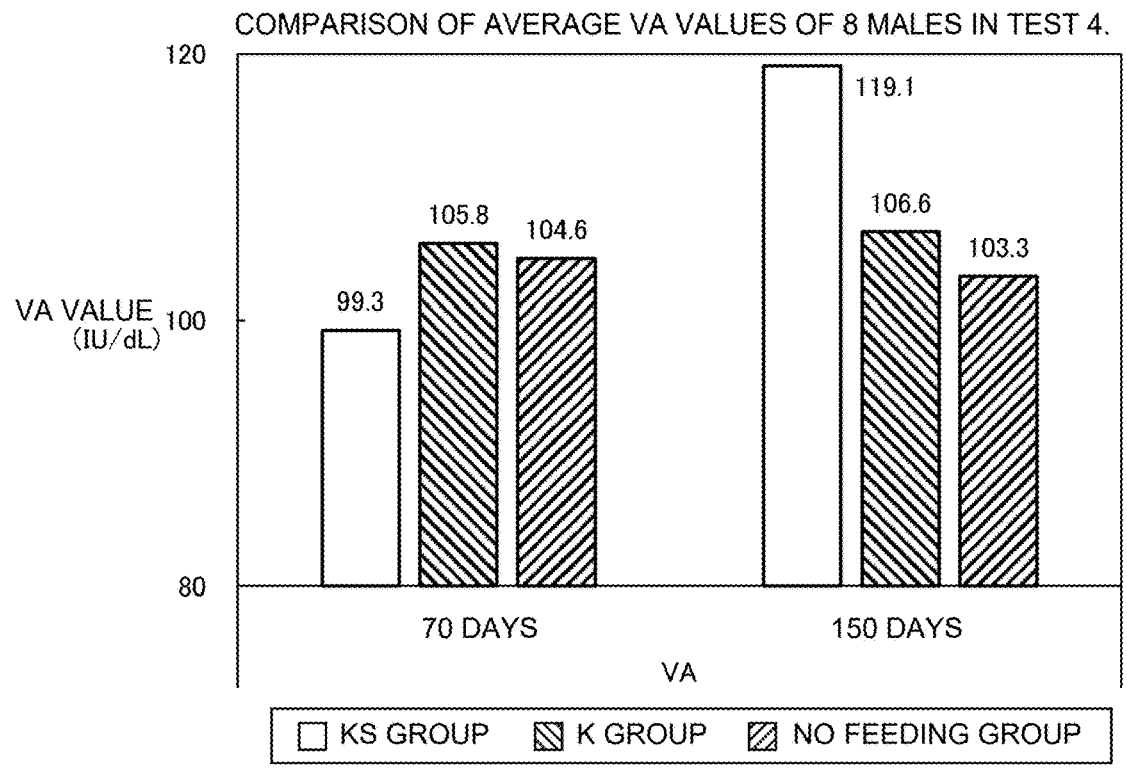
FIG. 59 is a graph showing average vitamin A values of eight males in each group in Test 4.
Figure 60:
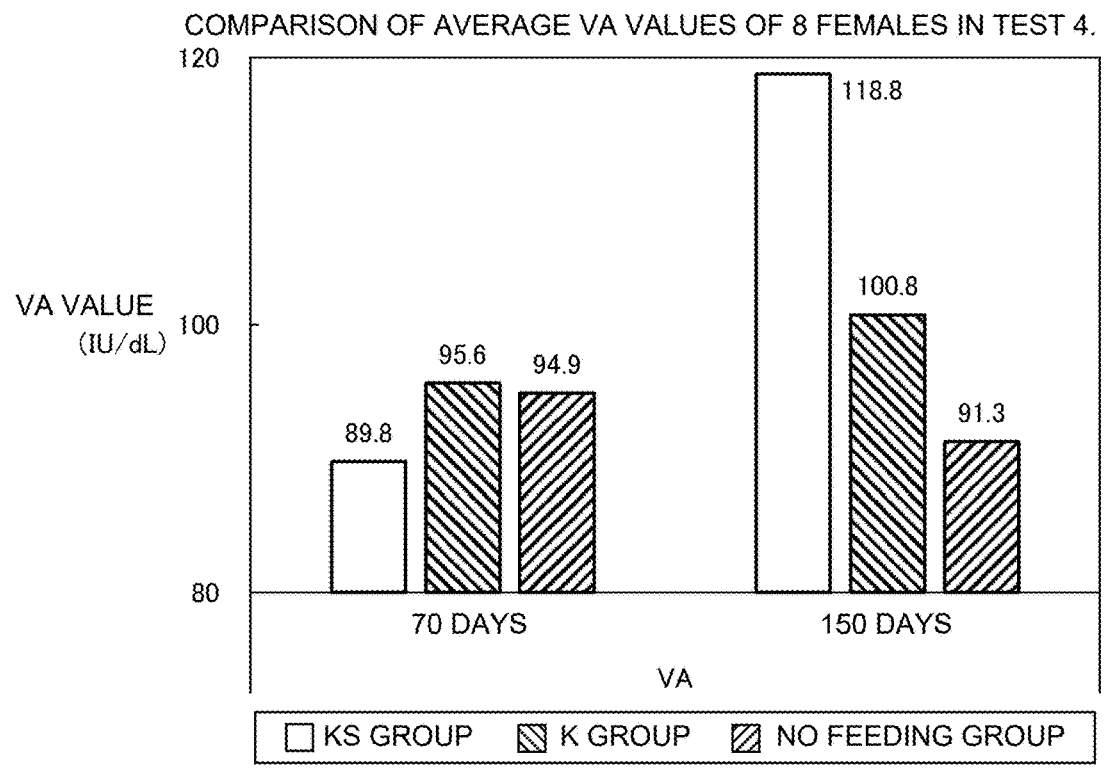
FIG. 60 is a graph showing average vitamin A values of eight females in each group in Test 4.
Figure 61:
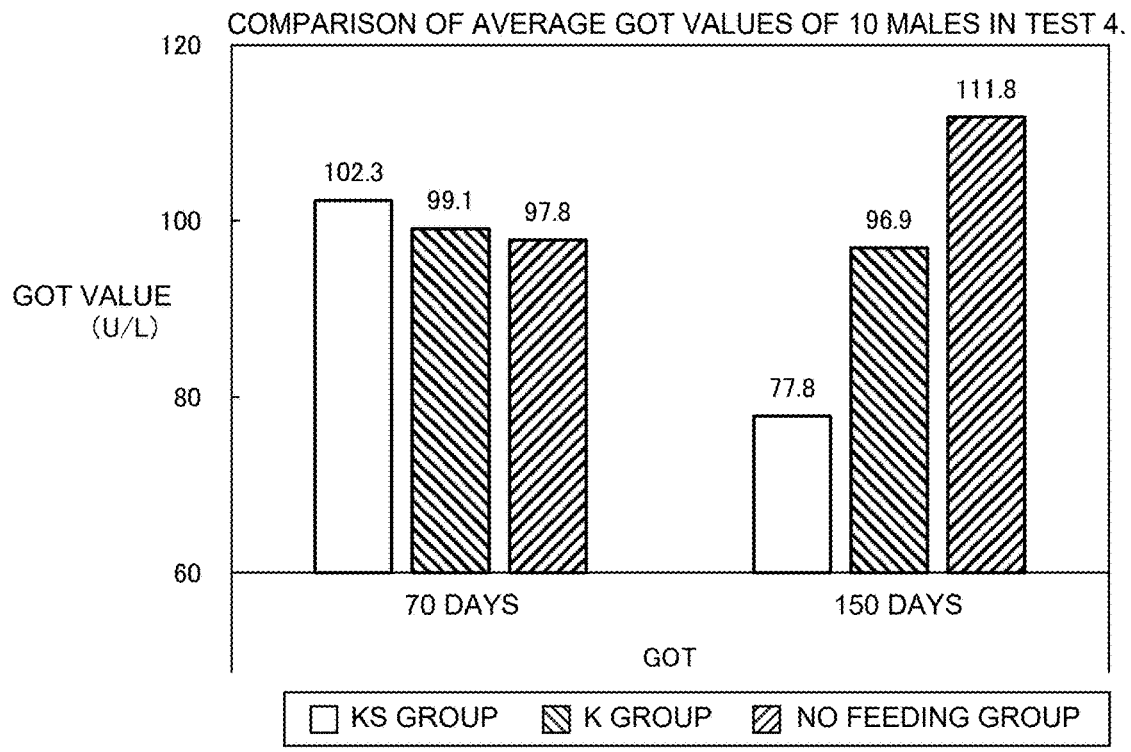
FIG. 61 is a graph showing average GOT values of 10 males in each group in Test 4.
Figure 62:
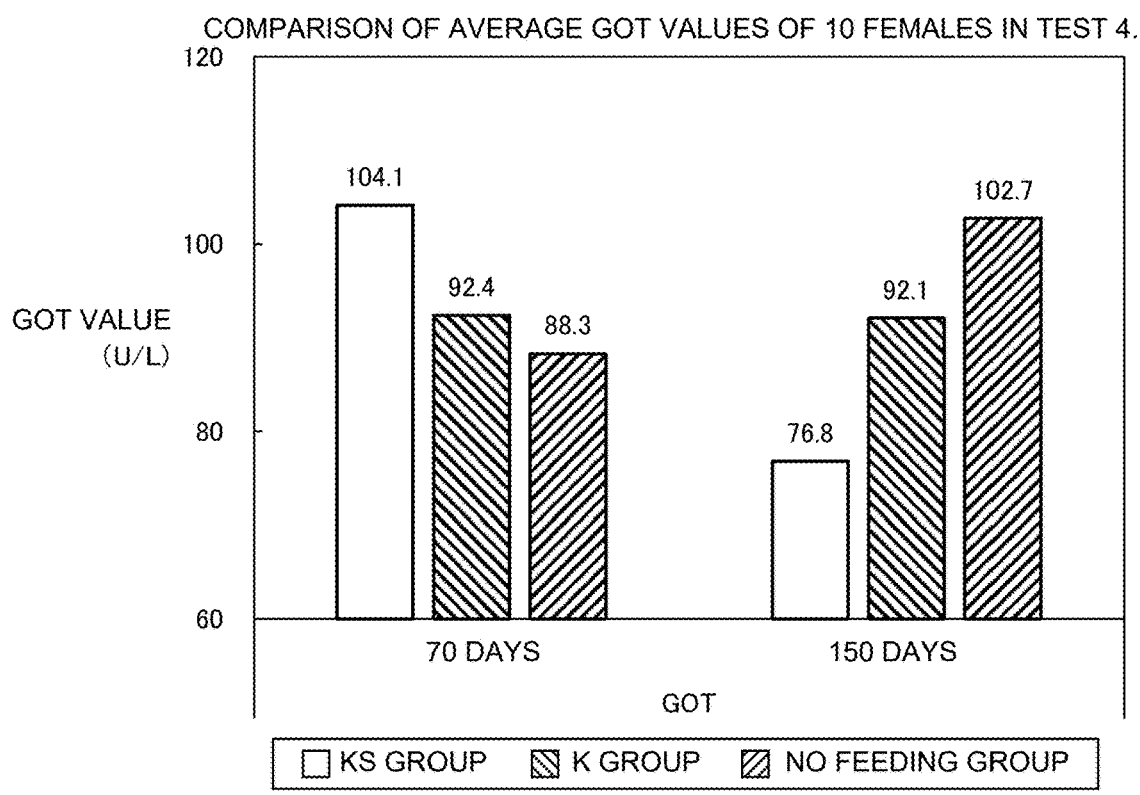
FIG. 62 is a graph showing average GOT values of 10 females in each group in Test 4.
Figure 63:
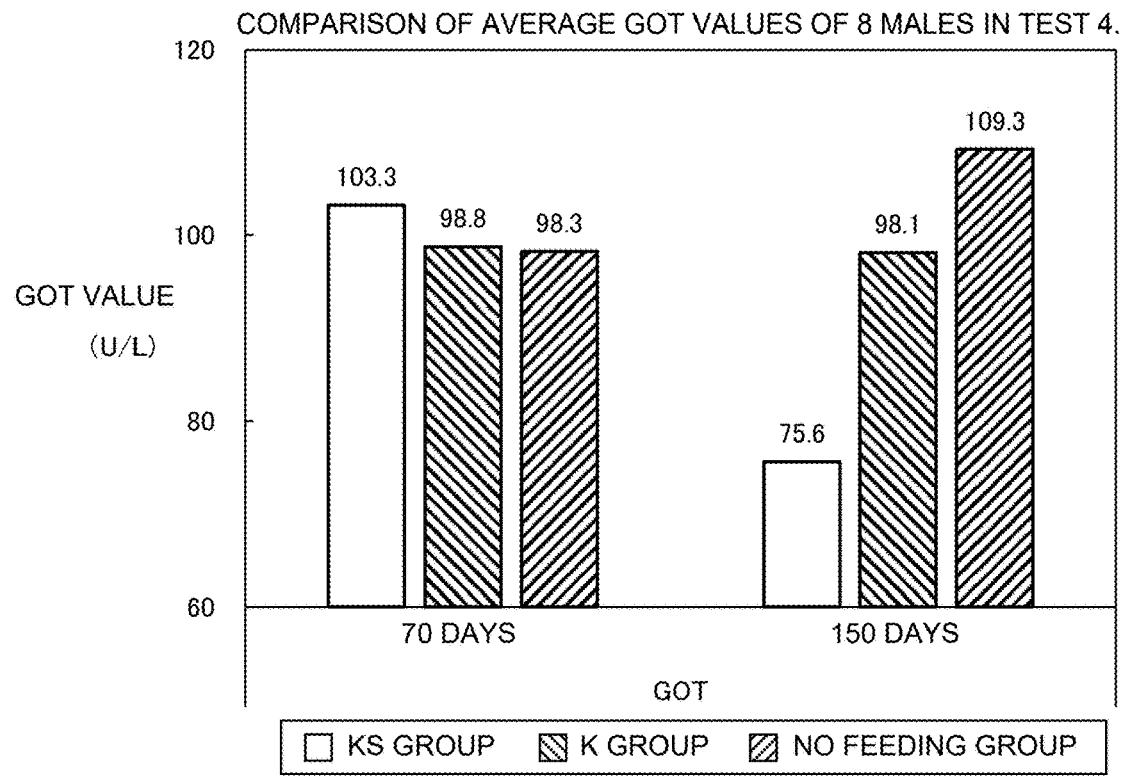
FIG. 63 is a graph showing average GOT values of eight males in each group in Test 4.
Figure 64:
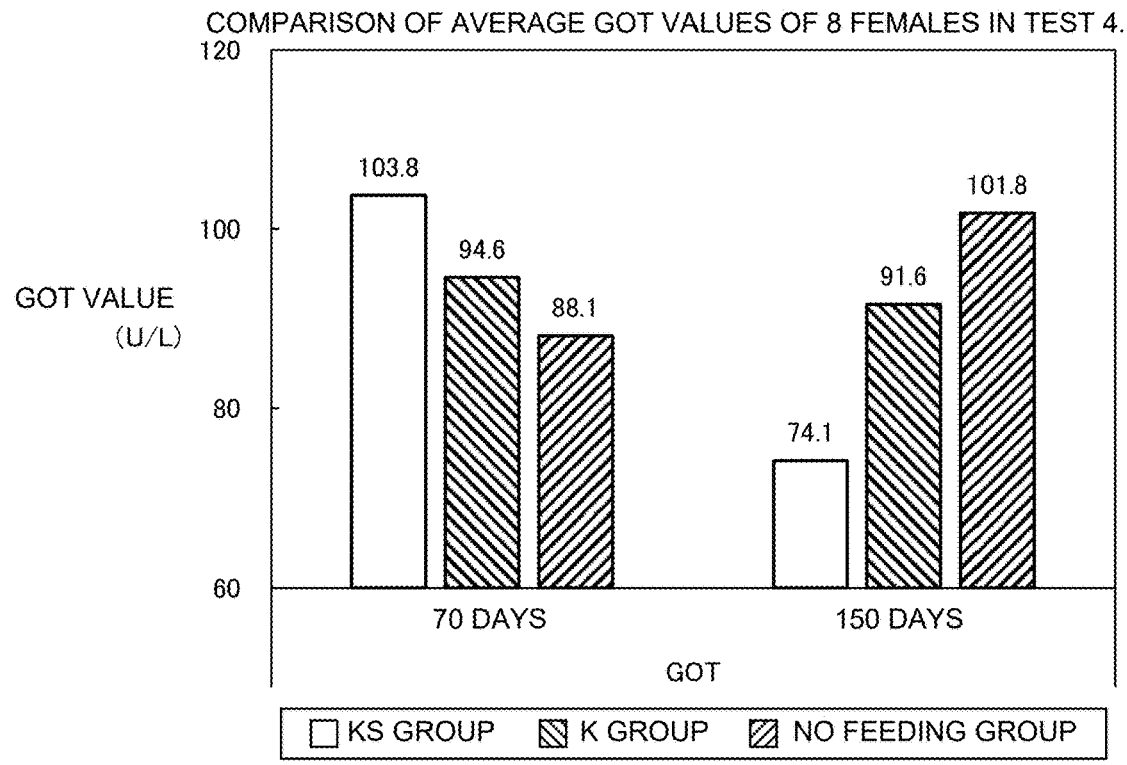
FIG. 64 is a graph showing average GOT values of eight females in each group in Test 4.

As shown in FIGS. 51 and 52, in the KS group, the males completely ate on the fifth day and the complete eating was continued. In the K group, it took 11 days up to the continuation of the complete eating. In the no feeding group, it took further days and it took 14 days up to the continuation of the complete eating. In the KS group, the females complete ate on the fourth day, one day earlier than the males, and also thereafter, the complete eating was continued. In the K group, while variation from the first day to the ninth day was shown, the female completely ate on the 13th day and also thereafter, the complete eating was continued. In the KS group, even as compared with the K group, the numbers of days required up to the complete eating were small.

It was found that even when the feeding of the licorice extract of the present invention is started after weaning, the licorice extract of the present invention has effects to enhance feed intakes.

4.2 Blood Test Results (Total Cholesterol Values, VA Values, and GOT Values)

In order to comprehend nutrition states and metabolism states of the cattle, blood tests were conducted and total cholesterol values, vitamin A values (VA values), and GOT value were measured.

The blood tests (total cholesterol values, VA values, and GOT values) of all of the cattle were conducted two times at approximately 70 days of age and approximately 150 days of age after birth.

Average values of 10 males and 10 females and average values of values of eight males and females excluding two males and two females among 10 males and 10 females, each of which had the highest value and the lowest value, in each of the groups are shown in FIGS. 53 to 56 (total cholesterol values), FIGS. 57 to 60 (VA values), and FIGS. 61 to 64 (GOT values).

As shown in FIGS. 53 to 56, in the blood tests conducted at the approximately 70 days of age before starting the feeding of the licorice extract, there was little difference in the total cholesterol values of both of the males and the females among the groups. On the other hand, in the blood tests conducted at the approximately 150 days of age, in the KS group, the total cholesterol values of both of the males and females were the highest. In the K group, in the blood tests conducted at the approximately 70 days of age and the approximately 150 days of age, the total cholesterol values remained nearly at the same level, and in the no feeding group, the total cholesterol values at the approximately 150 days of age were lower than those at the approximately 70 days of age.

As shown in FIGS. 57 to 60, in the blood tests conducted at the approximately 70 days of age before starting the feeding of the licorice extract, there was little difference in the VA values of both of the males and the females among the groups, and in the KS group, the values were rather lower than those in the other groups. On the other hand, the blood tests conducted at the approximately 150 days of age, in the KS group, the VA values of both of the males and the females were the highest. In the K group, in the blood tests conducted at the approximately 70 days of age and the approximately 150 days of age, the VA values remained nearly at the same level, and in the no feeding group, the VA values in the blood tests conducted at the approximately 150 days of age were lower than those in the in the blood tests conducted at the approximately 70 days of age.

As shown in FIGS. 61 to 64, in the blood tests conducted at the approximately 70 days of age before starting the feeding of the licorice extract, in the KS group, the GOT values were higher than those in the other groups. On the other hand, in the blood tests conducted at the approximately 150 days of age, in the KS group, the GOT values of both of the males and the females were the lowest. In the K group, in the blood tests conducted at the approximately 70 days of age and the approximately 150 days of age, the GOT values remained nearly at the same level, and in the no feeding group, the GOT values in the blood tests conducted at the approximately 150 days of age were higher than those in the blood test conducted at the approximately 70 days of age.

It was found from the above-described results that even when the feeding of the licorice extract of the present invention is started after weaning, the licorice extract (Example 5) in the KS group, which contains the licorice flavonoids and the licorice saponins other than the glycyrrhizic acid, exerts favorable influence on the nutrition states, the metabolism (total cholesterol values), the growing states (vitamin A values), and the liver function (GOT values) by composite effects of the glycyrrhizic acid, the licorice saponins other than the glycyrrhizic acid, the licorice flavonoids, not by the effects of the glycyrrhizic acid.

Since Test 4. was conducted in only the period from the approximately 91 days of age to the approximately 150 days of age after birth, upon finishing the test, amounts of production of edible meat and weight ratios of amounts of the given feed and the amounts of meat production (feed efficiency) are unknown. However, as with Test 1, and Test 2, it is considered that even by feeding the licorice extract of the present invention as the feed additive after weaning, feed efficiency can be increased because despite the feeding manner in which in the KS group, the K group, and the no feeding group, the same kinds of the feed, other than the licorice extract, in the same amounts were fed, in the KS group, the leftover amounts were smaller than those in the other groups (the dietary intakes were large) and the numbers of days up to the complete eating were small.

Test 5. Approximately Two Months from Approximately Five Days of Age to Approximately 60 Days of Age After Birth When in a suckling period of cattle, loads are exerted on internal organs such as digestive organs and a liver function, immune strength and metabolic ability are reduced and diarrhea and colds are caused. There may be a case where the loads on the internal organs and the liver function are caused by injecting high-concentration substitute milk or formula feed in the suckling period. In addition, there may be a case where loads are exerted on the internal organs and the liver function, and the immune strength and the metabolism are reduced by stress caused by separation from mother cows soon after birth and nurturing by a breeding staff, stress caused by changes in kinds and amounts of the feed in accordance with growing, and also stress on bodies caused by environmental changes such as heat stress and cold stress in a heat period and a cold period and difference in cold and warm temperatures. In particular, since the growing of calves is not sufficient, the calves are liable to anorexia due to the loads and the stress exerted on the internal organs and the liver function, nutritional deficiency is caused, and a vicious cycle in which the loads and the stress exerted on the internal organs and the liver function are further increased results, thereby making the calves liable to diarrhea and colds.

When symptoms of the diarrhea are caused, in many cases, treatment such as administration of drug, administration of an antimicrobial agent, and continuous administration of a probiotic agent is conducted. The diarrhea deprives the body of moisture, a symptom of dehydration can also be caused, and when the treatment is prolonged, a reduction in immune strength and resistance is incurred, and colds are often concurrently developed.

Here, two types into which the diarrhea often seen in the calves is roughly divided in general are known. One type of the diarrhea is due to suffering of indigestion, which is caused by loads exerted on the internal organs and the digestive organs and a reduction in metabolic ability and immune strength due to ingestion of high-concentration milk and feed, meteorological conditions such as a heat period and a cold period and difference in cold and warm temperatures, deficiency in an intake of colostrum, changes in feed, and the like. Another type is caused by mixing of germs, viruses, parasites, and the like into fine-quality drying cured hay and feed, and since this can be prevented by frequently making replacement of the feed and the like, it can be said that this type is caused by poor hygiene control of cattle barns.

Therefore, by feeding the licorice extract of the present invention as a feed additive to calves from approximately five days of age to approximately 60 days of age after birth, influence of the licorice extract of the present invention exerted on onset ratios of diarrhea due to indigestion, numbers of treatment days of diarrhea due to the indigestion, onset ratios of colds, and numbers of treatment days of the colds was examined.

Targets were 150 calves of Japanese Black Cattle and 30 calves of Holstein in a period from approximately five days of age to approximately 60 days of age after birth. The targets were divided into three groups shown in Table 13.

In the KS group, the licorice extract in Example 5 was added to feed as a feed additive, and in the K group, the licorice extract in Comparative Example 1 was added to feed as a feed additive. In the no feeding group, any licorice extract was not added to feed. As to feed other than the licorice extracts (substitute milk, creep feed, and oat hay), the feed was fed to both of the males and the females with the same amount fed to each of the groups at the same time by dividing each amount into three parts a day. The creep feed and the oat hay were fed from after approximately two weeks after birth.

In the KS group, from approximately five days of age after birth to approximately 60 days of age after birth, 2 g/day/head of the licorice extract in Example 5 was added to the feed as the feed additive and fed. In the K group, from approximately five days of age after birth to approximately 60 days of age after birth, 2 g/day/head of the licorice extract in Comparative Example 1 was added to the feed as the feed additive and fed.

Figure 65:
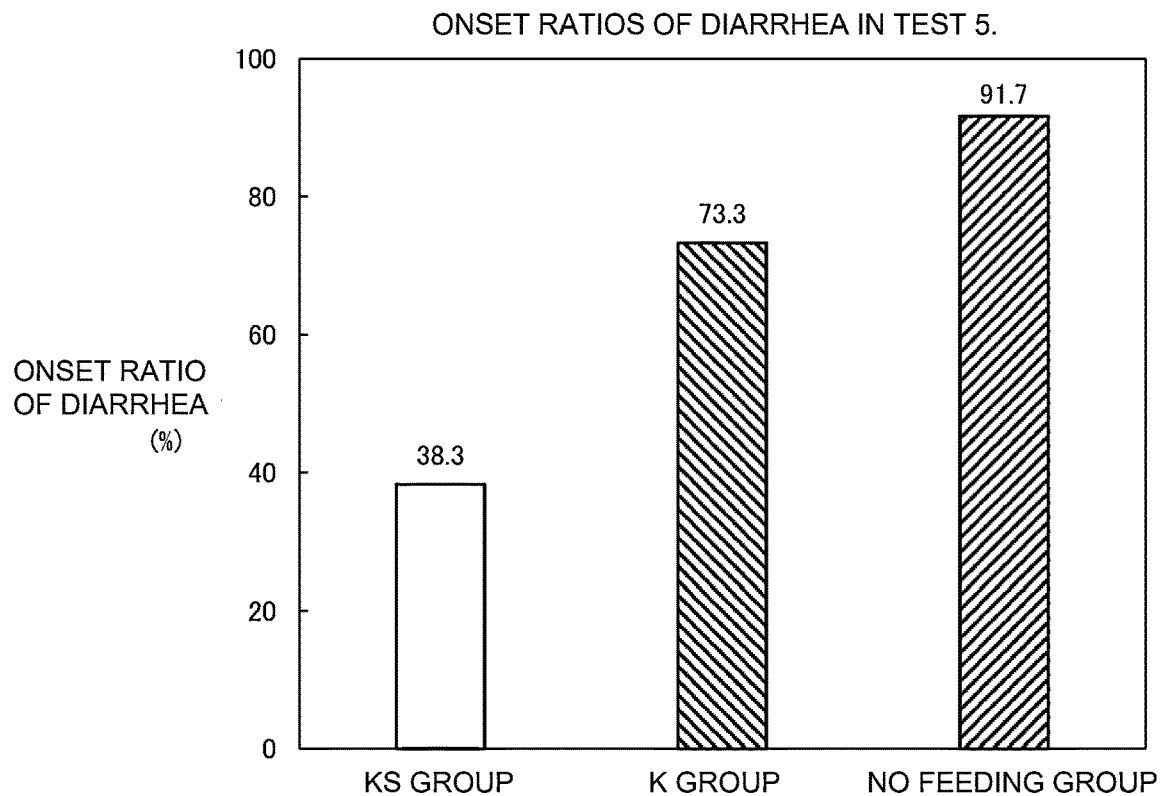
FIG. 65 is a graph showing onset ratios of diarrhea in Test 5.
Figure 66:
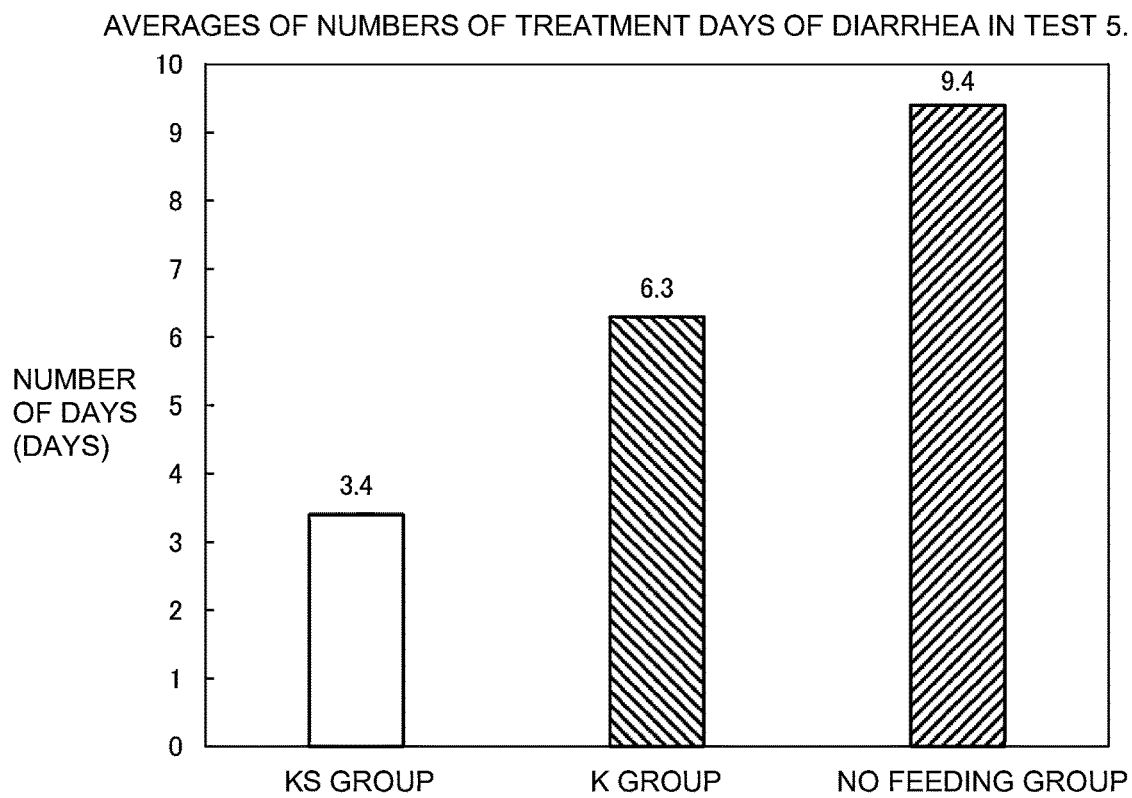
FIG. 66 is a graph showing an average number of treatment days of the diarrhea in Test 5.

Numbers of cases of onset of the diarrhea (numbers of head) among the total of 180 head of cattle due to the indigestion are shown in Table 14 and FIG. 65, and the numbers of treatment days of the diarrhea are shown in table 15 and FIG. 66.

TABLE 14

|  | KS group | K group | No feeding group |
|---|---|---|---|
| 1st to 7th day | 1 | 3 | 3 |
| 8th to 14th day | 7 | 15 | 19 |
| 15th to 21st day | 1 | 4 | 3 |
| 22nd to 28th day | 5 | 8 | 11 |
| 29th to 35th day | 3 | 6 | 7 |
| 36th to 42nd day | 2 | 3 | 4 |
| 43rd to 49th day | 1 | 3 | 4 |
| 50th to 56th day | 2 | 1 | 2 |
| 57th to 60th day | 1 | 1 | 2 |
| No onset (number of cases) | 37 | 16 | 5 |
| Onset ratio | 38.3% | 73.3% | 91.7% |

TABLE 15

|  | KS group | | TK group | | K group | |
|---|---|---|---|---|---|---|
| Number of treatment days | Number of head | Number of treatment days × Number of head | Number of head | Number of treatment days × Number of head | Number of head | Number of treatment days × Number of head |
| 1 day | 0 | 0 | 0 | 0 | 0 | 0 |
| 2 days | 5 | 10 | 2 | 4 | 0 | 0 |
| 3 days | 10 | 30 | 2 | 6 | 0 | 0 |
| 4 days | 5 | 20 | 3 | 12 | 1 | 4 |
| 5 days | 1 | 5 | 10 | 50 | 2 | 10 |
| 6 days | 1 | 6 | 8 | 48 | 4 | 24 |

TABLE 13

|  | A Farm | | B Farm | | C Farm | | |
|---|---|---|---|---|---|---|---|
|  | Male | Female | Male | Female | Male | Female | Total |
| KS group | 15 head | 15 head | 10 head | 10 head | 5 head | 5 head | 60 head |
| K group | 15 head | 15 head | 10 head | 10 head | 5 head | 5 head | 60 head |
| No feeding group | 15 head | 15 head | 10 head | 10 head | 5 head | 5 head | 60 head |

TABLE 15-continued

| Number of treatment days | KS group | | TK group | | K group | |
|---|---|---|---|---|---|---|
| | Number of head | Number of treatment days × Number of head | Number of head | Number of treatment days × Number of head | Number of head | Number of treatment days × Number of head |
| 7 days | 1 | 7 | 7 | 49 | 6 | 42 |
| 8 days | 0 | 0 | 5 | 40 | 8 | 64 |
| 9 days | 0 | 0 | 3 | 27 | 8 | 72 |
| 10 days | 0 | 0 | 2 | 20 | 8 | 80 |
| 11 days | 0 | 0 | 1 | 11 | 8 | 88 |
| 12 days | 0 | 0 | 1 | 12 | 3 | 36 |
| 13 days | 0 | 0 | 0 | 0 | 4 | 52 |
| 14 days | 0 | 0 | 0 | 0 | 2 | 28 |
| 15 days | 0 | 0 | 0 | 0 | 1 | 15 |
| | Total 23 head | Average 3.4 days | Total 44 head | Average 6.3 days | Total 55 head | Average 9.4 days |

As shown in Table 14 and FIG. 65, in the KS group, the number of cases of onset of the diarrhea up to approximately 60 days of age was approximately 52% of that in the K group and approximately 42% of that in the no feeding group. In addition, in the KS group, in substantially all of the weeks, the numbers of cases of the onset of the diarrhea were smaller than those in the other groups. It was only in the KS group that the majority of the cattle did not have the diarrhea.

As shown in Table 15 and FIG. 66, in the KS group, the number of treatment days was small, as compared with those in the other groups. It was found that by feeding the licorice extract of the present invention as the feed additive, the onset of the diarrhea is suppressed, the diarrhea hardly becomes severe even if the cattle get the diarrhea, and the cattle recover in a comparatively short treatment period.

Conventionally, the licorice is used in the crude drug "Rhubarb and Licorice Decoction", and it is known that the licorice has purging action (contracting of the diarrhea or causing of the diarrhea). However, it was confirmed that the licorice extract of the present invention has new effects, which cause the diarrhea not to be contracted (do not cause the diarrhea) and cannot be expected from the conventional common technical knowledge.

The licorice extract of the present invention includes not only the glycyrrhizic acid but also the licorice saponins other than the glycyrrhizic acid and the licorice flavonoids. As described above, it is considered that making the cattle hardly susceptible to the influence of the stress, increasing the feed intakes, enhancing the digestion and absorption, the immune strength, and the metabolism, and thereby promoting the somatic growth by the synergy effect of the above-mentioned components are also factors contributing to making the cattle hardly susceptible to the diarrhea.

Figure 67:
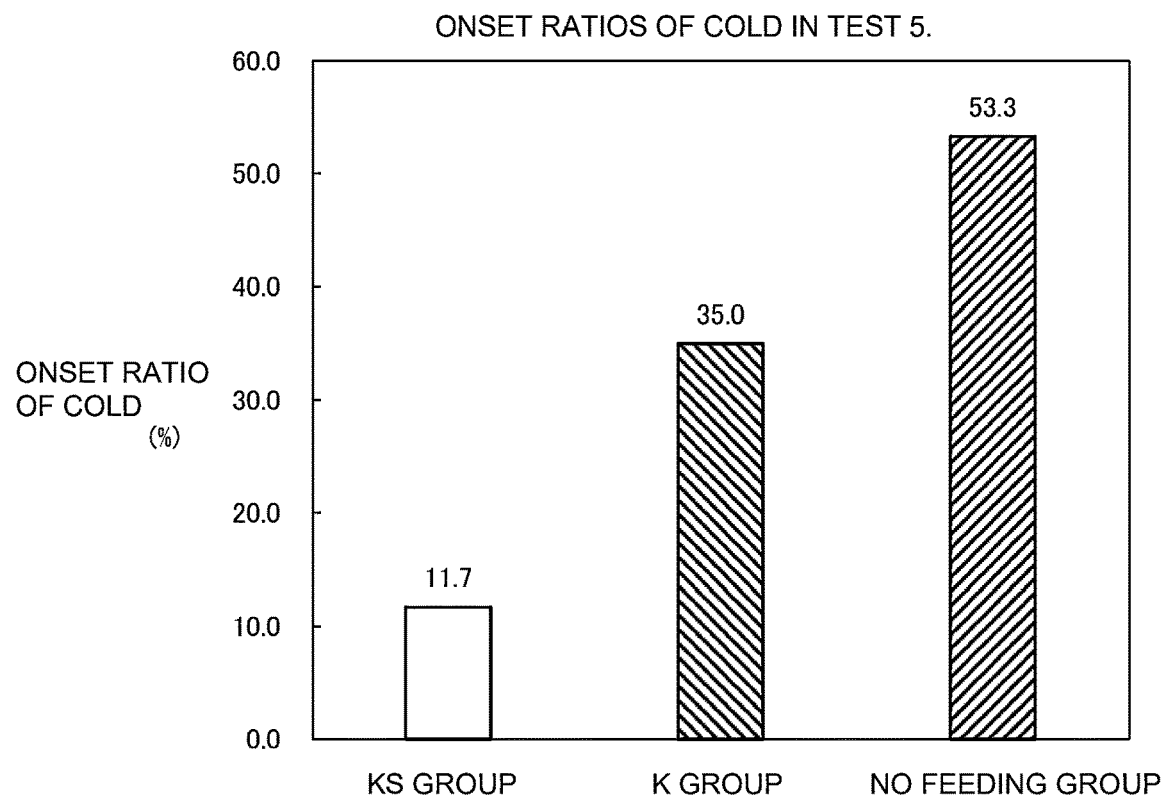
FIG. 67 is a graph showing onset ratios of colds in Test 5.
Figure 68:
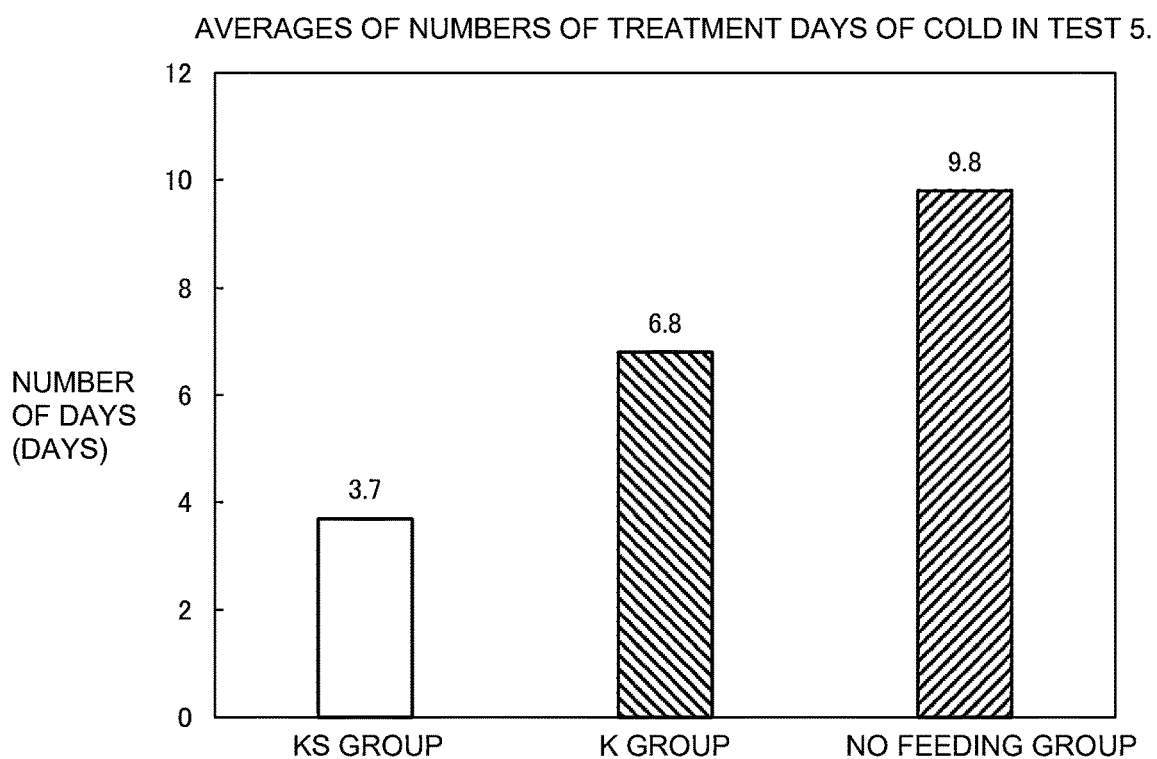
FIG. 68 is a graph showing an average number of treatment days of the colds in Test 5.

The numbers of cases of the onset of colds of the total of 180 head of cattle (numbers of head) are shown in Table 16 and FIG. 67, and numbers of treatment days of the colds are shown in Table 17 and FIG. 68.

TABLE 16

| | KS group | K group | No feeding group |
|---|---|---|---|
| 1st to 7th day | 0 | 1 | 1 |
| 8th to 14th day | 1 | 3 | 5 |

TABLE 16-continued

| | KS group | K group | No feeding group |
|---|---|---|---|
| 15th to 21st day | 1 | 2 | 4 |
| 22nd to 28th day | 1 | 4 | 8 |
| 29th to 35th day | 0 | 3 | 5 |
| 36th to 42nd day | 0 | 2 | 2 |
| 43rd to 49th day | 1 | 1 | 2 |
| 50th to 56th day | 2 | 3 | 2 |
| 57th to 60th day | 1 | 2 | 3 |
| No onset (number of cases) | 53 | 39 | 28 |
| Onset ratio | 11.7% | 35.0% | 53.3% |

TABLE 17

| Number of treatment days | KS group | | TK group | | K group | |
|---|---|---|---|---|---|---|
| | Number of head | Number of treatment days × Number of head | Number of head | Number of treatment days × Number of head | Number of head | Number of treatment days × Number of head |
| 1 day | 0 | 0 | 0 | 0 | 0 | 0 |
| 2 days | 1 | 2 | 0 | 0 | 0 | 0 |
| 3 days | 3 | 9 | 1 | 3 | 0 | 0 |
| 4 days | 1 | 4 | 1 | 4 | 0 | 0 |
| 5 days | 1 | 5 | 3 | 15 | 1 | 5 |
| 6 days | 1 | 6 | 7 | 42 | 1 | 6 |
| 7 days | 0 | 0 | 4 | 28 | 0 | 0 |
| 8 days | 0 | 0 | 1 | 8 | 5 | 40 |
| 9 days | 0 | 0 | 1 | 9 | 8 | 72 |
| 10 days | 0 | 0 | 1 | 10 | 8 | 80 |
| 11 days | 0 | 0 | 1 | 11 | 5 | 55 |
| 12 days | 0 | 0 | 1 | 12 | 1 | 12 |
| 13 days | 0 | 0 | 0 | 0 | 1 | 13 |
| 14 days | 0 | 0 | 0 | 0 | 1 | 14 |
| 15 days | 0 | 0 | 0 | 0 | 1 | 15 |
| | Total 7 head | Average 3.7 days | Total 21 head | Average 6.8 days | Average 32 head | Average 9.8 days |

As shown in Table 16 and FIG. 67, in the KS group, the number of cases of the onset of the colds at up to the approximately 60 days of age was approximately 33% of that in the K group and was approximately 22% that in the no feeding group. In addition, in the KS group, in substantially all of the weeks, the numbers of cases of the onset of the colds were smaller than those in the other groups.

As shown in Table 17 and FIG. 68, in the KS group, the number of treatment days was small, as compared with those in the other groups. It was found that by feeding the licorice extract of the present invention as the feed additive, the onset of the colds is suppressed, the colds hardly become severe even if the cattle get the colds, and the cattle recover in a comparatively short treatment period.

In addition, although in the K group and the no feeding group, the diarrhea and the colds were contracted over all the periods, it is seen that the increases and the decreases in the numbers of the onset of the cases are similar between the diarrhea and the colds. Cattle whose immune strength and resistance are weak easily concurrently contract the colds and the diarrhea. By feeding the licorice extract of the present invention as the feed additive, both of the diarrhea and the colds can be prevented, the diarrhea and the colds hardly become severe even if the diarrhea and the colds are contracted, and the number of treatment days can be reduced.

The colds of the calves are caused by a reduction in transfer immunity from mother cows, stress due to changes in a climate and the environment, and insufficient hygiene control of cattle barns such as suction of ammonia gas and dust due to poor ventilation. When the immune strength and the resistance are reduced by these causes, the calves are infected with viruses and germs and thereby catch the colds. Although a body temperature of a healthy calf is 38.5° C. to 39° C., when a calf catches the colds, symptoms such as a fever of 39.5° C. to 40° C., coughs, snivel, and rapid breathing are seen. In addition, since disappearance of vigor, ananastasia, suckling difficulty, fragility, and anorexia are caused and when the symptoms become severe, cattle may die or even after recovery, growth insufficiency may be caused, early treatment and prevention are required.

Conventionally, as one method of the prevention, colostrum is fed and immune strength and resistance are thereby raised. However, cattle to which the colostrum is insufficiently fed or cattle which do not eat feed get nutritional deficiency. In addition, as described above, loads are exerted on internal organs such as digestive organs and a liver function by ingestion of high-concentration milk and high-concentration feed for the purpose of somatic growth, the immune strength and the resistance are reduced, and the cattle may catch the colds.

As shown in the results in Test 1. to 5., the licorice extract of the present invention has the effects of increasing the feed intakes, improving the digestion and the absorption of the nutrition and the metabolism, improving the growing states and the immune strength, improving the liver function, increasing the weights, and the like. By feeding the licorice extract of the present invention as the feed additive, the nutritional deficiency and lowering of immune strength, which cause the colds, can be prevented, the colds can be prevented, and the number of treatment days can be reduced.

The licorice extract of the present invention can be used as a raw material of a multifunctional feed additive for the purpose of increasing the feed intakes, improving the digestion and absorption of the nutrition, improving the metabolism, improving the growing states and the immune strength, improving of the liver function, increasing the weights, increasing the carcass weights, enhancing the carcass yield rates, preventing the diarrhea, reducing the number of treatment days of the diarrhea, preventing the colds, and/or reducing the number of treatment days of the colds.

Test. 6 Feeding of Feed Additive Including Licorice Extract and Water-Soluble Dietary Fiber.
6.1 Numbers of Cases of Onset of Diarrhea With a total of 120 head including 60 head of male calves of Japanese Black Cattle and 60 head of female calves of Japanese Black Cattle at approximately five days of age to approximately 60 days of age after birth as targets, onset ratios of diarrhea for a period of approximately 60 days after birth and numbers of treatment days up to complete recovery were examined.

The targeted cattle were divided into a feeding group and no feeding group shown in Table 18. A feed additive A and a feed additive B which include the licorice extract in Example 5 were added to feed and fed to the cattle in the feeding group. No licorice extract was added to feed in no feeding group.

TABLE 18

|  | Feeding group | No feeding group | Total |
| --- | --- | --- | --- |
| Male calves | 30 head | 30 head | 60 head |
| Female calves | 30 head | 30 head | 60 head |

The feed additive A was prepared by uniformly mixing 10% by mass of the licorice extract in Example 5, 30% by mass of glucomannan (an average particle diameter of 150 to 200-mesh) as water-soluble dietary fiber, and 60% by mass of a starch decomposition product (Pinedex #1 manufactured by Matsutani Chemical Industry Co., Ltd.).

The feed additive B was prepared by uniformly mixing 40% by mass of the licorice extract in Example 5 and 60% by mass of glucomannan (an average particle diameter of 150 to 200-mesh) as water-soluble dietary fiber.

Components of the feed additives A and B were as shown in Table 19.

TABLE 19

|  | Feed additive A | (per 100 g)<br>Feed additive B |
| --- | --- | --- |
| Protein | 3.8 g | 1.1 g |
| Fat | 21.1 g | 7.9 g |
| Carbohydrate | 68.8 g | 67.2 g |
| Ash | 0.1 g | 14.7 g |
| Sodium | 12 mg | 844 mg |

In a period of approximately five days of age after birth to approximately 30 days of age after birth, the feed additive A was uniformly dispersed in substitute milk, 5 g/head of the feed additive A was fed two times in the morning and the evening, and a total of 10 g/day/head thereof was fed. In a period of approximately 31 days of age after birth to approximately 60 days of age after birth, a proper amount of water was added to the feed additive B, the resultant was formed into balls, 2.5 g/head of the balls was orally fed two times in the morning and the evening, and a total of 5 g/day/head thereof was fed.

Numbers of cases of onset of the diarrhea (numbers of head) and onset ratios are shown in Table 20.

TABLE 20

| After birth | Feeding group | No feeding group |
| --- | --- | --- |
| 1st to 7th day | 1 | 3 |
| 8th to 14th day | 0 | 10 |
| 15th to 21st day | 2 | 2 |
| 22nd to 28th day | 2 | 8 |
| 29th to 35th day | 3 | 5 |
| 36th to 42nd day | 3 | 3 |
| 43rd to 49th day | 1 | 3 |
| 50th to 56th day | 0 | 2 |
| 57th to 60th day | 1 | 2 |
| Number of cases | 13 | 38 |
| Onset ratio | 21.6% | 63.3% |

As shown in Table 20, in the feeding group, the onset of the diarrhea was suppressed to approximately ⅓ of that in the no feeding group.

6.2 Numbers of Treatment Days of Diarrhea

With calves, which had the diarrhea, as targets, by feeding the feed additive A and the feed additive B, numbers of treatment days were examined. The targets were a total of 64 head including 36 head of male calves and 28 head of female calves, which had the diarrhea, regardless of days of age after birth, and as shown in Table 21, the targets were divided into a feeding group and no feeding group.

TABLE 21

|  | Feeding group | No feeding group | Total |
|---|---|---|---|
| Male calves which had diarrhea | 18 head | 18 head | 36 head |
| Female calves hich had diarrhea | 14 head | 14 head | 28 head |

In a period from approximately five days of age after birth to approximately 30 days of age after birth, the feed additive A was uniformly dispersed in substitute milk, 5 g/head thereof was fed two times in the morning and the evening, and a total of 10 g/day/head thereof was fed. In a period from approximately 31 days of age after birth to approximately 60 days of age after birth, a proper amount of water was added to the feed additive B, the resultant was formed into balls, 2.5 g/head of the balls was orally fed two times in the morning and the evening, a total of 5 g/day/head thereof was fed.

The numbers of treatment days of the diarrhea and average numbers of treatment days are shown in Table 22.

TABLE 22

| Number of treatment days | Feeding group | No feeding group |
|---|---|---|
| 1 day | 4 | 0 |
| 2 days | 17 | 0 |
| 3 days | 3 | 4 |
| 4 days | 2 | 1 |
| 5 days | 1 | 4 |
| 6 days | 0 | 6 |
| 7 days | 0 | 8 |
| 8 days | 0 | 4 |
| 9 days | 0 | 6 |
| 10 days | 0 | 2 |
| 11 days | 0 | 1 |
| 12 days | 0 | 1 |
| 13 days | 0 | 0 |
| 14 days | 0 | 0 |
| 15 days | 0 | 0 |
| Total (number of head) | 27 | 37 |
| Average days up to complete recovery | 2.22 days | 6.94 days |

As shown in Table 22, in the feeding group, it was made possible to reduce the number of treatment days of diarrhea to ⅓ or less of that in the no feeding group. By the feed additive of the present invention in which the glucomannan was added to the licorice extract of the present invention, it was made possible to effectively suppress the onset of the diarrhea and to reduce the number of treatment days owing to the effects of the licorice extract and intestinal regulation action by the glucomannan added thereto.

Test 7. From after Birth Up to Approximately 240 Days of Age to Approximately 270 Days of Age (Comparison among KS group, KK group, K group, and No Feeding Group)

By feeding the licorice extract of the present invention as a feed additive to calves at approximately 240 days of age to approximately 270 days of age after birth, influence of the licorice extract of the present invention exerted on a reduction in leftover amounts of feed upon being weaned (an increase in dietary intakes), nutrition states (GOT values in blood tests), and weights was examined.

In the present test, as with Test 1., in order to clearly confirm the effects obtained by the licorice extract, the calves were completely weaned at approximately 80 days of age.

Targets were a total of 40 head of Japanese Black Cattle including 20 head of castrated male calves and 20 head of female calves at 0 day of age after birth up to days of age at the time of the shipping to a calf auction market. The targets were divided into four groups shown in Table 23.

In a KS group, the licorice extract in Example 5 was added as a feed additive from approximately five days of age after birth, in a KK group, the licorice extract in Example 11 was added as a feed additive, and in a K group, the licorice extract in Comparative Example 1 was added as a feed additive. In a no feeding group, any licorice extract was not added to feed. As to feed other than the licorice extracts (substitute milk, artificial milk, formula feed, and coarse feed such as pasture), feed shown in Table 24 was fed with each amount shown therein divided into three parts a day, and the feed of the formula feed, the rice straws, and the oat hay were fed at and after 81 days of age in this order with the same amount fed to each of the groups at the same time. The creep feed and the oat hay were fed from approximately two weeks after birth.

TABLE 23

|  | Licorice extract | Male | Female | Total |
|---|---|---|---|---|
| KS group | Example 5 | 5 head | 5 head | 10 head |
| KK group | Example 11 | 5 head | 5 head | 10 head |
| K group | Comparative Example 1 | 5 head | 5 head | 10 head |
| No feeding group | Not added | 5 head | 5 head | 10 head |

TABLE 24

|  | Substitute milk Artificial milk | Creep feed | Formula feed | Rice straws | Oat hay |
|---|---|---|---|---|---|
| 0 to 30 days | Fed | 0.3 kg | — | — | 0.03 kg |
| 31 to 60 days | Fed | 1.5 kg | — | — | 0.2 kg |
| 61 to 80 days | Fed | 3.2 kg | — | — | 0.4 kg |
| 81 to 120 days | — | — | 4.5 kg | 0.4 kg | 1.8 kg |
| 121 to 150 days | — | — | 5.5 kg | 0.4 kg | 2.5 kg |
| 151 to 180 days | — | — | 4.5 kg | 0.4 kg | 4.0 kg |
| 181 to 210 days | — | — | 4.5 kg | 0.4 kg | 4.5 kg |
| 211 to 240 days | — | — | 4.5 kg | 0.4 kg | 5.0 kg |

TABLE 25

|  | Substitute milk Artificial milk | Creep feed | Formula feed | Rice straws | Oat hay |
|---|---|---|---|---|---|
| 0 to 30 days | Fed | 0.3 kg | — | — | 0.03 kg |
| 31 to 60 days | Fed | 1.5 kg | — | — | 0.2 kg |
| 61 to 80 days | Fed | 3.0 kg | — | — | 0.4 kg |
| 81 to 120 days | — | — | 4.0 kg | 0.4 kg | 1.5 kg |
| 121 to 150 days | — | — | 4.5 kg | 0.4 kg | 3.5 kg |
| 151 to 180 days | — | — | 4.0 kg | 0.4 kg | 4.0 kg |
| 181 to 210 days | — | — | 4.0 kg | 0.4 kg | 4.5 kg |
| 211 to 240 days | — | — | 4.0 kg | 0.4 kg | 4.5 kg |
| (241 to 270 days) | — | — | (4.0 kg) | (0.4 kg) | (4.5 kg) |

In the KS group, 1 g/day/head of the licorice extract in Example 5 was added to feed as the feed additive and fed from approximately the fifth day after birth, 2 g/day/head thereof was added to the feed as the feed additive and fed from approximately the 41st day after birth, and 3 g/day/head thereof was added to the feed as the feed additive and fed from approximately the 81st day to approximately the 240th day after birth. In the KK group, 1 g/day/head of the licorice extract in Example 11 was added to feed as the feed additive and fed from approximately the fifth day after birth, 2 g/day/head thereof was added to the feed as the feed additive and fed from approximately the 41st day after birth, and 3 g/day/head thereof was added to the feed as the feed additive and fed from approximately the 81st day to approximately the 240th day after birth. In the K group, 1 g/day/head of the licorice extract in Comparative Example 1 was added to feed as the feed additive and fed from approximately the fifth day after birth, 2 g/day/head thereof was added to the feed as the feed additive and fed from approximately the 41st day after birth, and 3 g/day/head thereof was added to the feed as the feed additive and fed from approximately the 81st day to approximately the 240th day after birth.

7.1 Leftover Amounts

As described above, since the formula feed, the rice straws, and the oat hay were fed as the feed at and after approximately 81 days of age in this order, in a case where remaining feed is caused, the oat hay becomes the remaining feed. Accordingly, weights of the remaining feed of the oat hay were measured as leftover amounts. The first day when the approximately 81-day-old calves were weaned is defined as the first day, and transition of leftover amounts is shown in FIG. 69 and FIG. 70.

Figure 69:
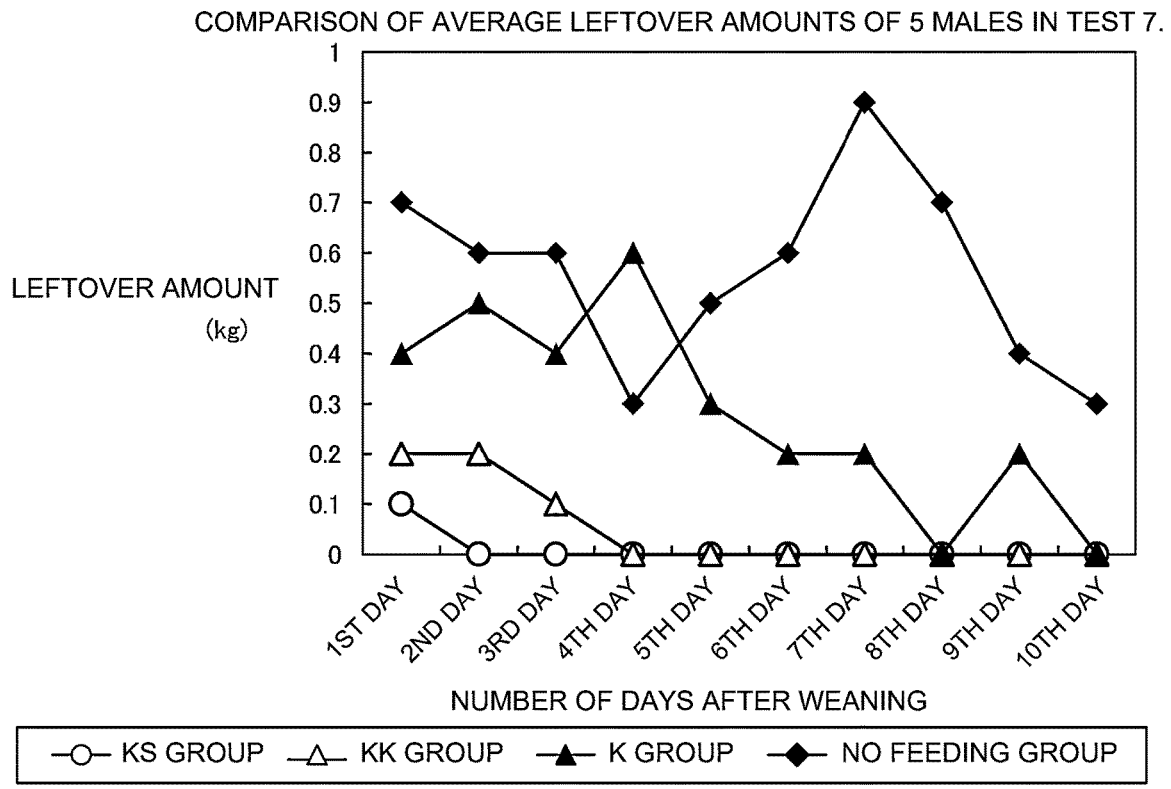
FIG. 69 is a graph showing comparison of average leftover amounts of five males in each group in Test 7.

As shown in FIG. 69, in the KS group, the male calves had no leftover from the second day of weaning and kept complete eating, and in the KK group, the male calves had no leftover from the fourth day of weaning and kept complete eating. In the K group, although the male calves once completely ate on the eighth day, the leftover was caused again, and it took 10 days until complete eating was continued. In the no feeding group, the male calves did not reach the complete eating by the 10th day.

Figure 70:
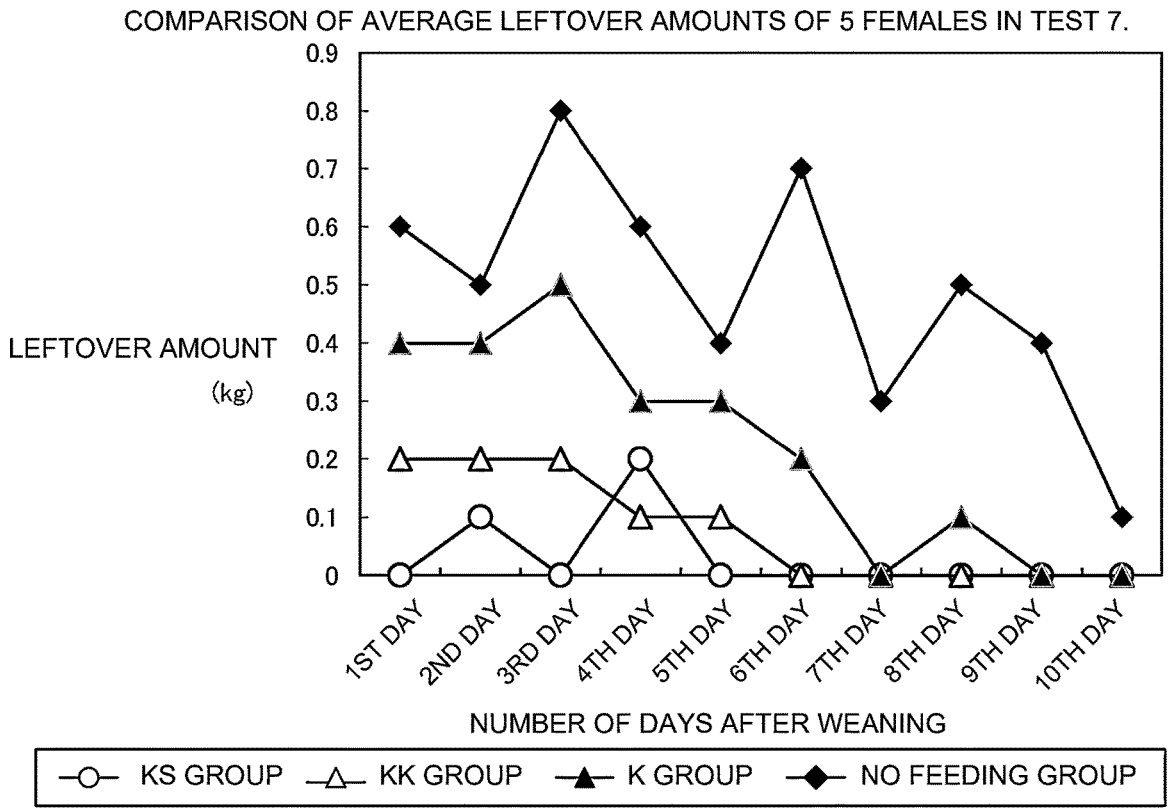
FIG. 70 is a graph showing comparison of average leftover amounts of five females in each group in Test 7.
Figure 71:
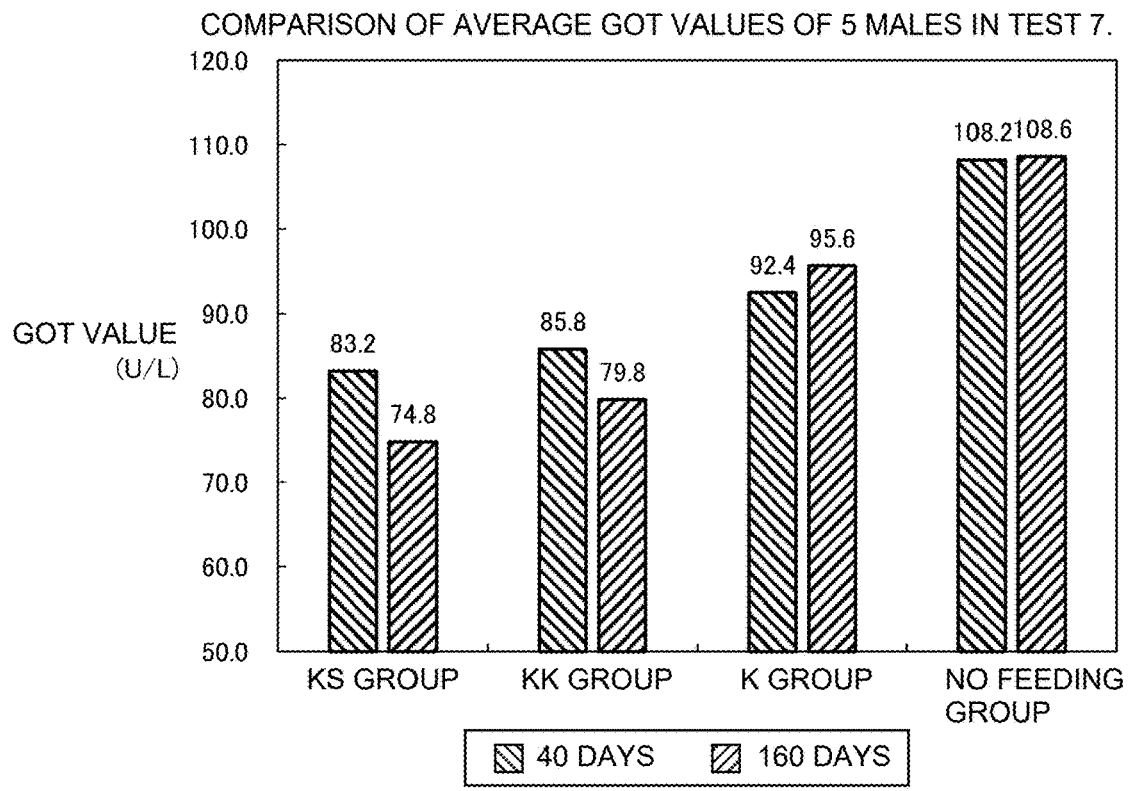
FIG. 71 is a graph showing average GOT values of five males in each group in Test 7.
Figure 72:
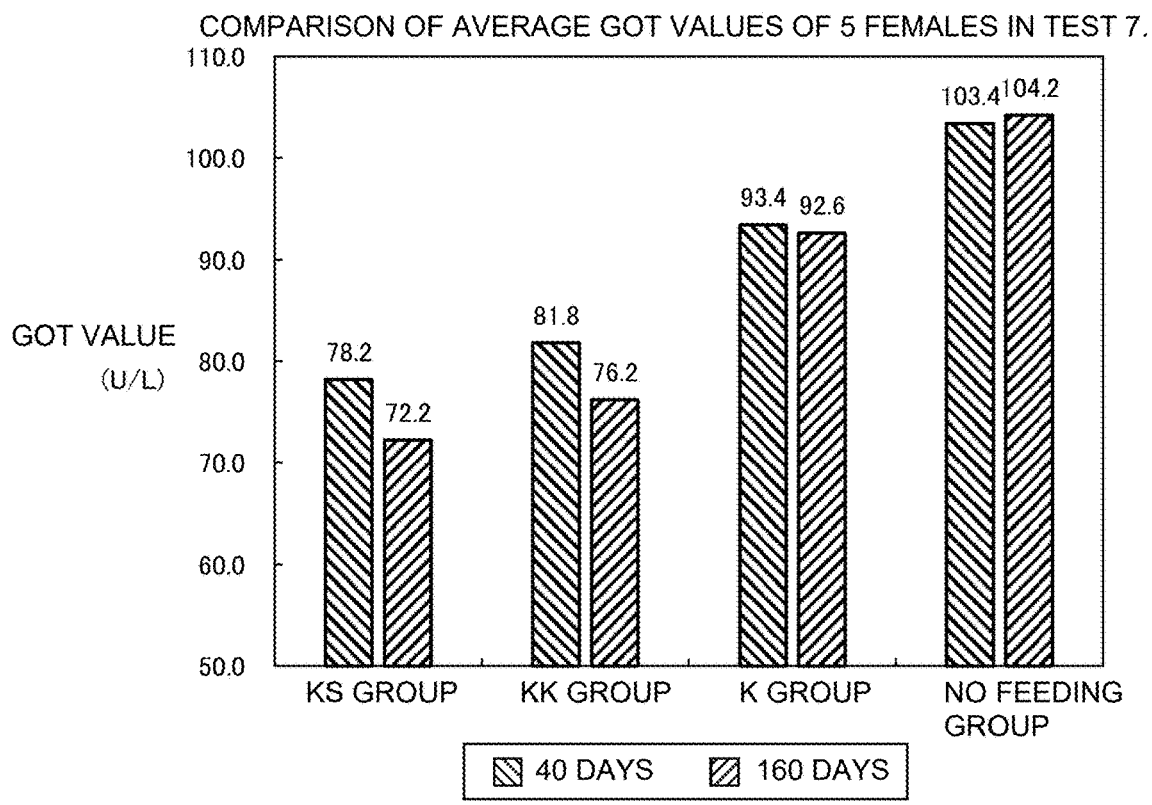
FIG. 72 is a graph showing average GOT values of five females in each group in Test 7.
Figure 73:
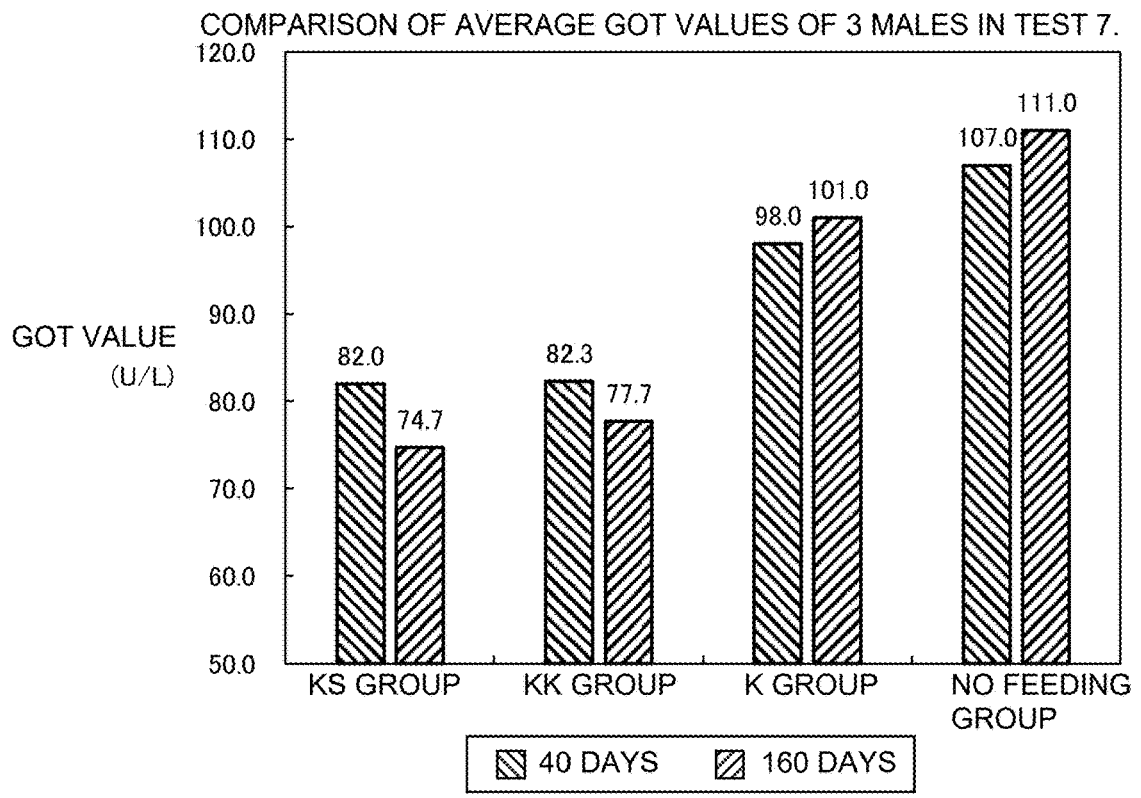
FIG. 73 is a graph showing average GOT values of three males in each group in Test 7.
Figure 74:
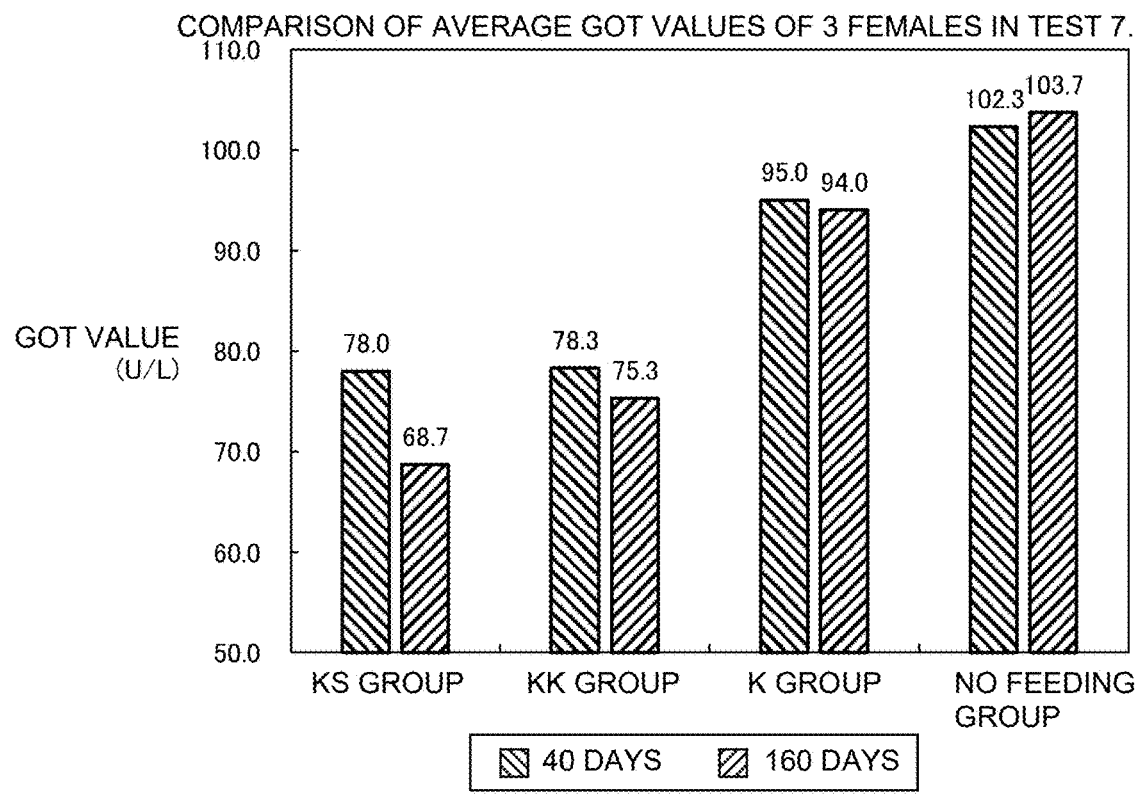
FIG. 74 is a graph showing average GOT values of three females in each group in Test 7.
Figure 75:
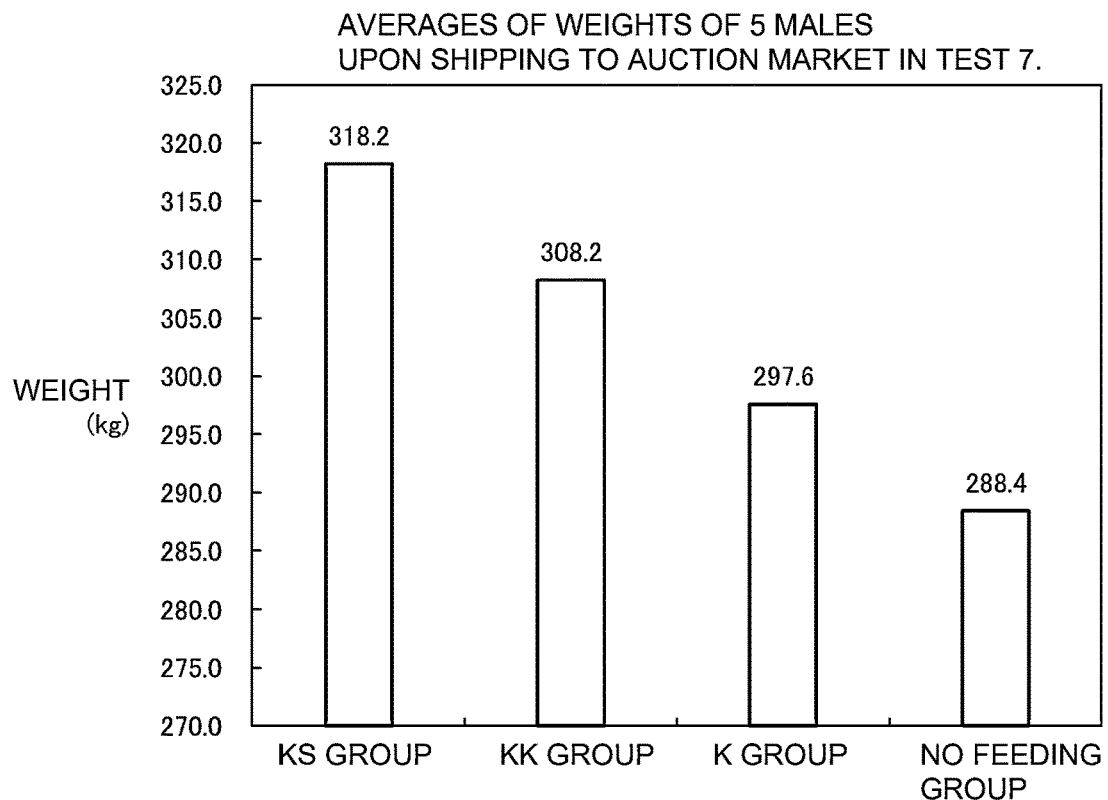
FIG. 75 is a graph showing an average weight of five males in each group upon shipping to an auction market in Test 7.
Figure 76:
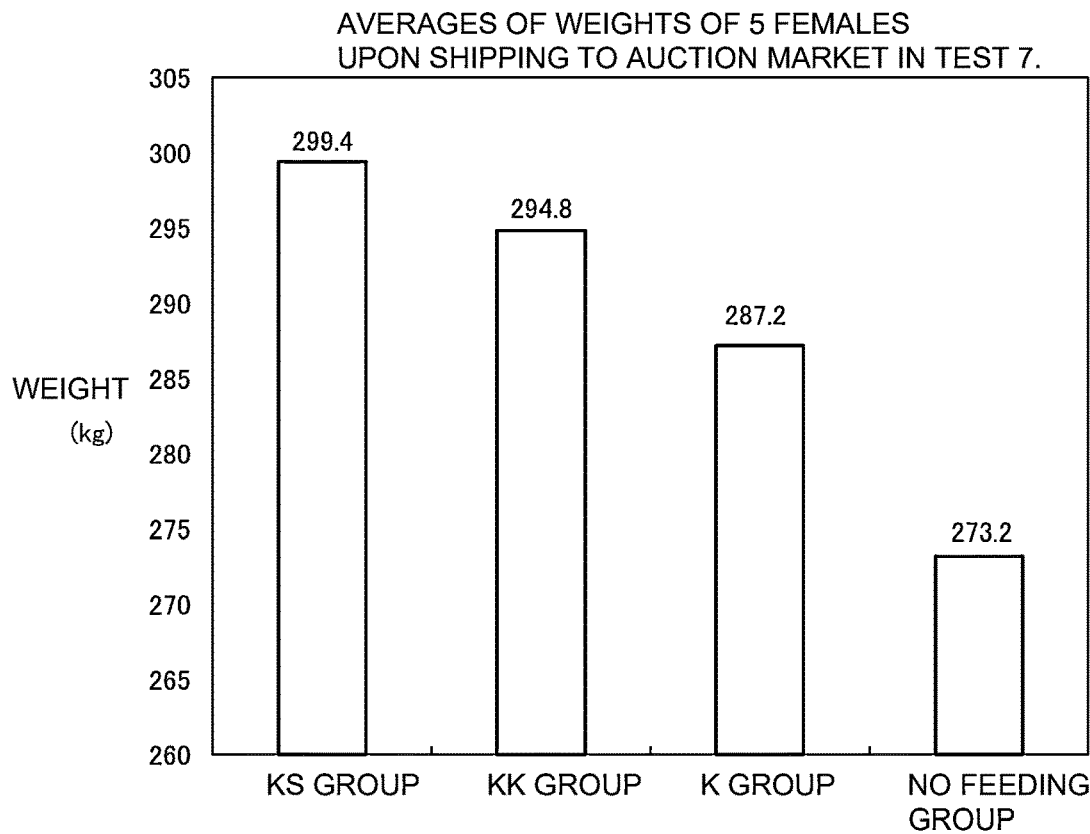
FIG. 76 is a graph showing an average weight of five females in each group upon shipping to the auction market in Test 7.
Figure 77:
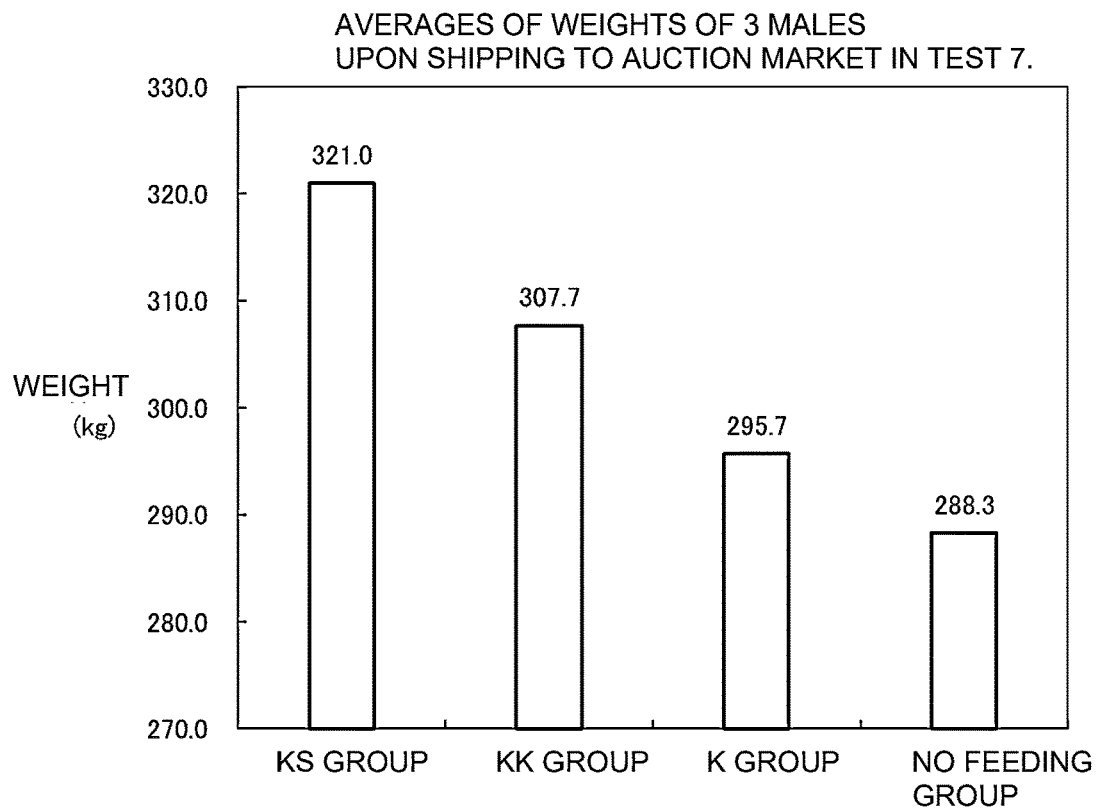
FIG. 77 is a graph showing an average weight of three males in each group upon shipping to the auction market in Test 7.
Figure 78:
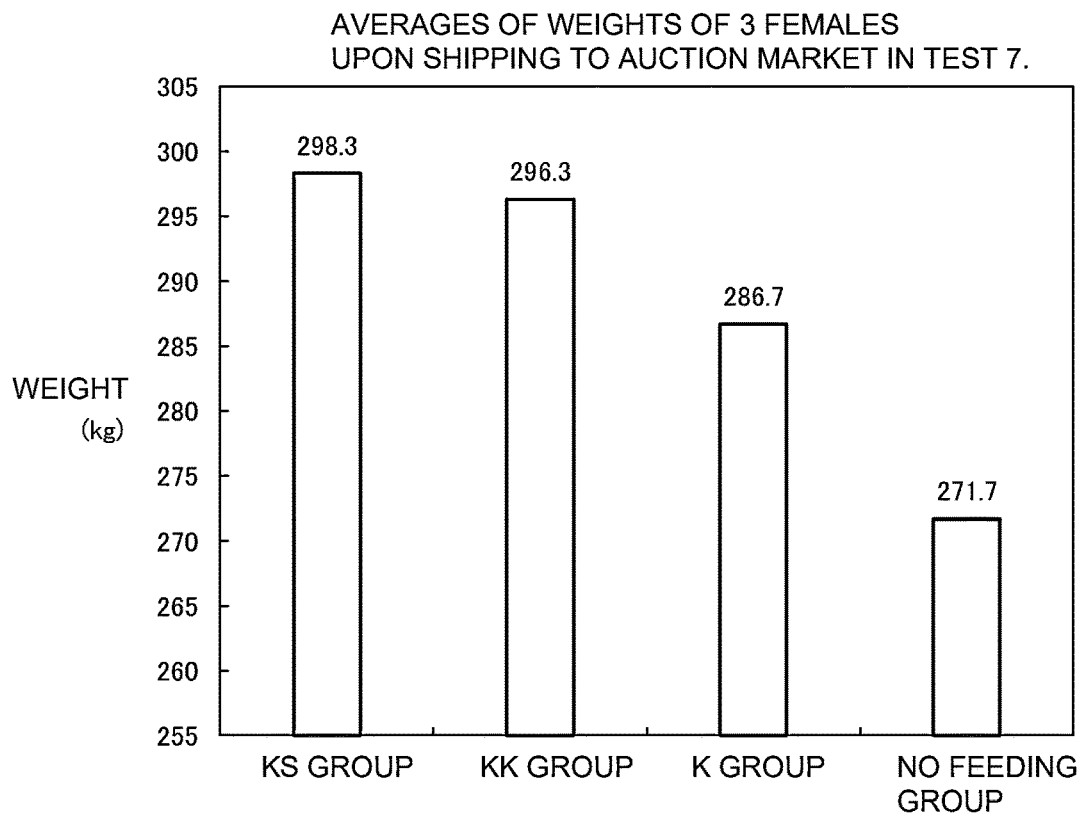
FIG. 78 is a graph showing an average weight of three females in each group upon shipping to the auction market in Test 7.

As shown in FIG. 70, in the KS group, the female calves had no leftover from the fifth day of weaning and kept complete eating, and in the KK group, the female calves had no leftover from the sixth day of weaning and kept complete eating. In the K group, although the female calves once completely ate on the seventh day, the leftover was caused again, and it took nine days until complete eating was continued. In the no feeding group, the female calves did not reach the complete eating by the 10th day.

As described above, in the KS group to which the licorice extract in Example 5 was fed and in the KK group to which the licorice extract in Example 11 was fed from approximately five days of age after birth, effects by feeding of the licorice extract were exhibited from approximately 81 days of age after weaning. Even as compared with the K group to which the licorice extract including 13% or more of the glycyrrhizic acid was fed, high effects were confirmed, whereby synergy effect of the glycyrrhizic acid, the licorice saponins, and the licorice flavonoids included in the licorice extract in Example 5 with respect to the reduction in the leftover amounts (an increase in dietary intakes) was confirmed.

Although amounts of all of the glycyrrhizic acid, the licorice saponins, and the licorice flavonoids in the licorice extract in Example 11, which was fed in the KK group, are smaller than those in Example 5, in the KK group, effects comparable to those in the KS group were obtained and even compared with the K group, high effects were confirmed.

As described above, it is considered that the feed intakes reflect the stress exerted on the calves, the burdens on the digestive organs, and degrees of development of the digestive organs. It is considered that in the KS group and in the KK group, in each of which the calves completely ate immediately after the weaning and the amounts of the feed intakes were large, as compared with the K group and the no feeding group, the stress of the calves was reduced, the burdens exerted on the digestive organs were decreased, and development states of the digestive organs were fine.

7.2 Blood Test Results (GOT values)

The blood test (GOT values) on all of the cattle was conducted twice at approximately 40 days of age and approximately 160 days of age after birth.

Average values of GOT values of five head and average values of GOT values of three head excluding two head among the five head, which had the highest value and the lowest value, in each of the groups are shown in FIGS. 71 to 74.

As shown in FIGS. 71 to 74, in the KS group and the KK group, at both of the approximately 40 days of age after birth and the approximately 160 days of age after birth, the GOT values were low, as compared with those in the other groups. In the KS group and the KK group, further, the GOT values at the approximately 160 days of age after birth were lower than those at the approximately 40 days of age after birth. On the other hand, in the K group and the no feeding group, the GOT values at the approximately 40 days of age after birth and those at the approximately 160 days of age after birth remained nearly at the same level or the GOT values at the approximately 160 days of age after birth were slightly higher than those at the approximately 40 days of age after birth. Although contents of the (A) the glycyrrhizic acid, (B) the licorice saponins other than the glycyrrhizic acid, and (C) the licorice flavonoids in the licorice extract in Example 11, which was fed in the KK group, are low, as compared with those of the licorice extract in Example 5, which was fed in the KS group, it was made possible to obtain approximately the same effects as those in the KS group.

It was found from the above-described results that favorable influence is exerted on the liver function (GOT values) by composite effects of the glycyrrhizic acid, the licorice saponins other than the glycyrrhizic acid, and the licorice flavonoids, not by the effects of the glycyrrhizic acid.

7.3 Weights

Average values of weights of five males and five females and average values of weights of three males and three females excluding two males and two females among the five males and the five females, each of which had the highest value and the lowest value, the weight measured upon shipping to an auction market, in each of the groups are shown in FIGS. 75 to 78. In the no feeding group of females, due to weight shortage on the 240th day, the females were shipped on the 270th day. Note that since auction market dates are limited, there are some differences in days of age upon shipping.

As shown in FIGS. 75 to 78, the weights in the KS group were larger than those in the other groups. Also in the KK group, somatic growth was large, as compared with that in the no feeding group. Although as to the females in the no feeding group in particular, a shipping date was extended to approximately 270 days of age, the weights did not reach those at the females at 240 days of age in the KS group and the KK group.

Test 8. Onset of Diarrhea and Onset of Colds and Numbers of Treatment Days (Comparison Among KS Group, KK Group, K Group, and No Feeding Group)

By feeding the licorice extract of the present invention as a feed additive to calves from approximately five days of age to approximately 60 days of age after birth, influence of the licorice extract of the present invention exerted on onset ratios of diarrhea due to indigestion, numbers of treatment days of diarrhea due to the indigestion, onset ratios of colds, and numbers of treatment days of the colds was examined.

Targets were 80 head of Japanese Black Cattle calves in a period of approximately five days of age to approximately 60 days of age after birth. The targets were divided into four groups shown in Table 26.

TABLE 26

|  | A Farm | | B Farm | | |
| --- | --- | --- | --- | --- | --- |
|  | Male | Female | Male | Female | Total |
| KS group | 5 head | 5 head | 5 head | 5 head | 20 head |
| KK group | 5 head | 5 head | 5 head | 5 head | 20 head |
| K group | 5 head | 5 head | 5 head | 5 head | 20 head |
| No feeding group | 5 head | 5 head | 5 head | 5 head | 20 head |

In the KS group, the licorice extract in Example 5 was added to feed as a feed additive, in the KK group, the licorice extract in Example 11 was added to feed as a feed additive, and in the K group, the licorice extract in Comparative Example 1 was added to feed as a feed additive. In the no feeding group, any licorice extract was not added to feed. As to feed other than the licorice extracts (substitute milk, creep feed, and oat hay), the feed was fed to both of the males and the females with the same amount fed to each of the groups at the same time by dividing each amount into three parts a day. The creep feed and the oat hay were fed from after approximately two weeks after birth.

In the KS group, from approximately five days of age after birth to approximately 60 days of age after birth, 2 g/day/head of the licorice extract in Example 5 was added to the feed as the feed additive and fed. In the KK group, from approximately five days of age after birth to approximately 60 days of age after birth, 2 g/day/head of the licorice extract in Example 11 was added to the feed as the feed additive and fed. In the K group, from approximately five days of age after birth to approximately 60 days of age after birth, 2 g/day/head of the licorice extract in Comparative Example 1 was added to the feed as the feed additive and fed.

Figure 79:
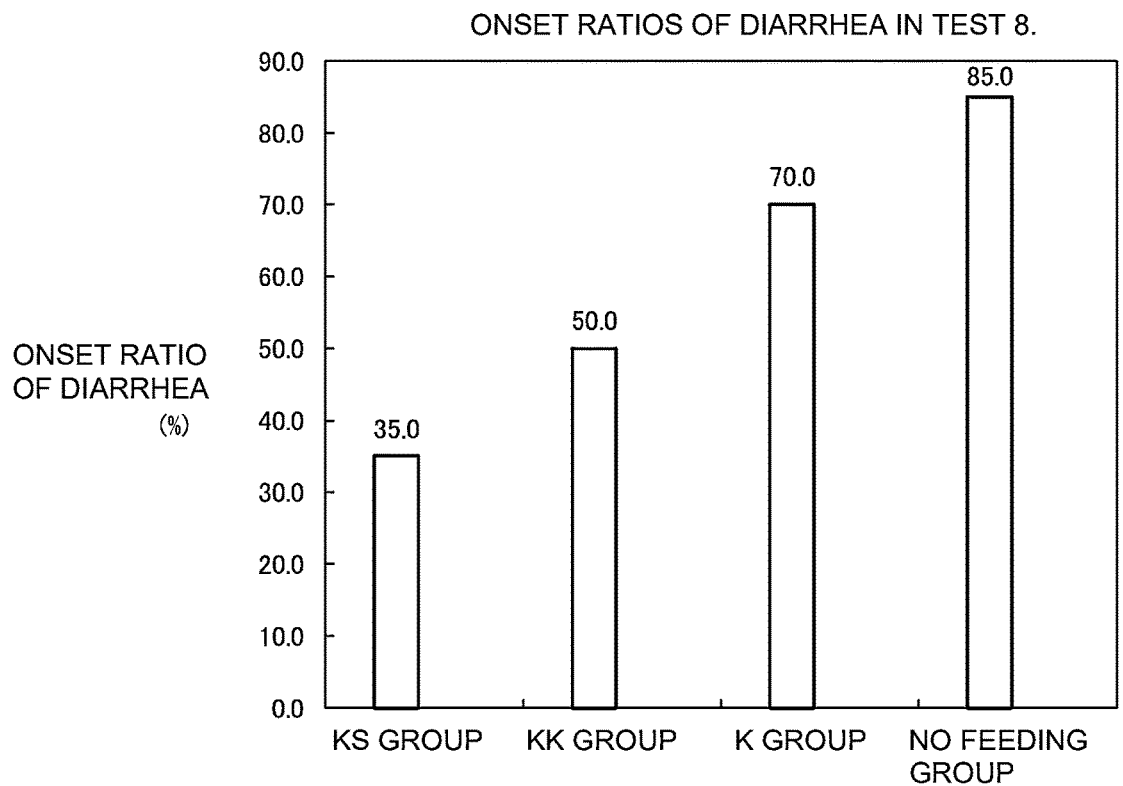
FIG. 79 is a graph showing onset ratios of diarrhea in Test 8.
Figure 80:
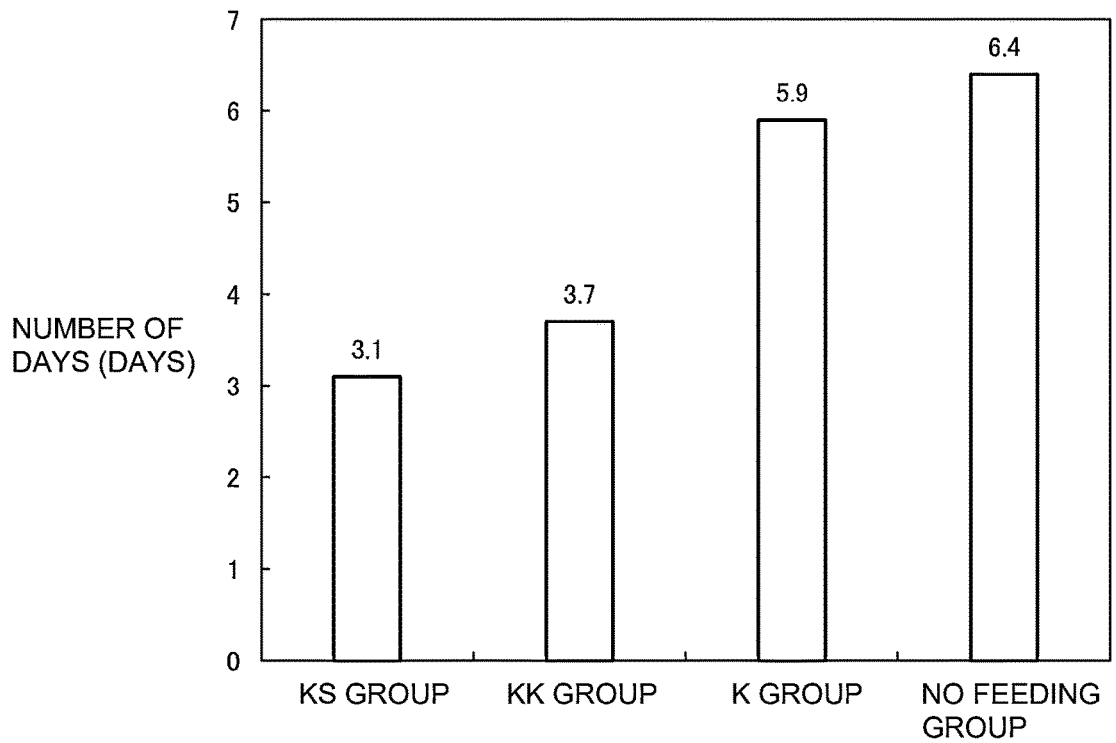
FIG. 80 is a graph showing an average number of treatment days of the diarrhea in Test 8.

Numbers of cases of onset of the diarrhea (numbers of head) among the total of 80 head of cattle due to the indigestion are shown in Table 27 and FIG. 79, and the numbers of treatment days of the diarrhea are shown in table 28 and FIG. 80.

TABLE 27

|  | KS group | KK group | K group | No feeding group |
| --- | --- | --- | --- | --- |
| 1st to 7th day | 1 | 2 | 0 | 2 |
| 8th to 14th day | 1 | 1 | 3 | 2 |
| 15th to 21st day | 1 | 1 | 3 | 1 |
| 22nd to 28th day | 1 | 2 | 2 | 4 |
| 29th to 35th day | 0 | 1 | 1 | 4 |
| 36th to 42nd day | 1 | 1 | 1 | 0 |
| 43rd to 49th day | 1 | 0 | 1 | 2 |
| 50th to 56th day | 0 | 1 | 2 | 1 |
| 57th to 60th day | 1 | 1 | 1 | 1 |
| No onset (number of cases) | 13 | 9 | 6 | 3 |
| Onset ratio of diarrhea | 35.0% | 50.0% | 70.0% | 85.0% |

TABLE 28

|  | KS group | | TK group | | K group | | No feeding group | |
| --- | --- | --- | --- | --- | --- | --- | --- | --- |
| Diarrhea Number of treatment days | Number of head | Number of treatment days × Number of head | Number of head | Number of treatment days × Number of head | Number of head | Number of treatment days × Number of head | Number of head | Number of treatment days × Number of head |
| 1 day | 0 | 0 | 0 | 0 | 0 | 0 | 0 | 0 |
| 2 days | 2 | 4 | 2 | 4 | 2 | 4 | 1 | 2 |
| 3 days | 2 | 6 | 3 | 9 | 0 | 0 | 1 | 3 |
| 4 days | 3 | 12 | 2 | 8 | 2 | 8 | 2 | 8 |
| 5 days | 0 | 0 | 2 | 10 | 3 | 15 | 3 | 15 |
| 6 days | 0 | 0 | 1 | 6 | 2 | 12 | 1 | 6 |
| 7 days | 0 | 0 | 0 | 0 | 1 | 7 | 3 | 21 |
| 8 days | 0 | 0 | 0 | 0 | 1 | 8 | 3 | 24 |
| 9 days | 0 | 0 | 0 | 0 | 2 | 18 | 1 | 9 |
| 10 days | 0 | 0 | 0 | 0 | 1 | 10 | 1 | 10 |
| 11 days | 0 | 0 | 0 | 0 | 0 | 0 | 1 | 11 |
| 12 days | 0 | 0 | 0 | 0 | 0 | 0 | 0 | 0 |
| 13 days | 0 | 0 | 0 | 0 | 0 | 0 | 0 | 0 |
| 14 days | 0 | 0 | 0 | 0 | 0 | 0 | 0 | 0 |
| 15 days | 0 | 0 | 0 | 0 | 0 | 0 | 0 | 0 |
|  | Total 7 head | Average 3.1 days | Total 10 head | Average 3.7 days | Total 14 head | Average 5.9 days | Total 17 head | Average 6.4 days |

As shown in Tables 27 to 28 and FIGS. 79 to 80, it was made possible to suppress the numbers of cases of onset of the diarrhea in the KS group and the KK group to the half or less of the numbers of head of the cattle.

In the KS group and the KK group, the numbers of treatment days were also small, as compared with those in the other groups. It was found that by feeding the licorice extract of the present invention as the feed additive, the onset of the diarrhea is suppressed, the diarrhea hardly becomes severe even if the cattle get the diarrhea, and the cattle recover in a comparatively short treatment period.

Figure 81:
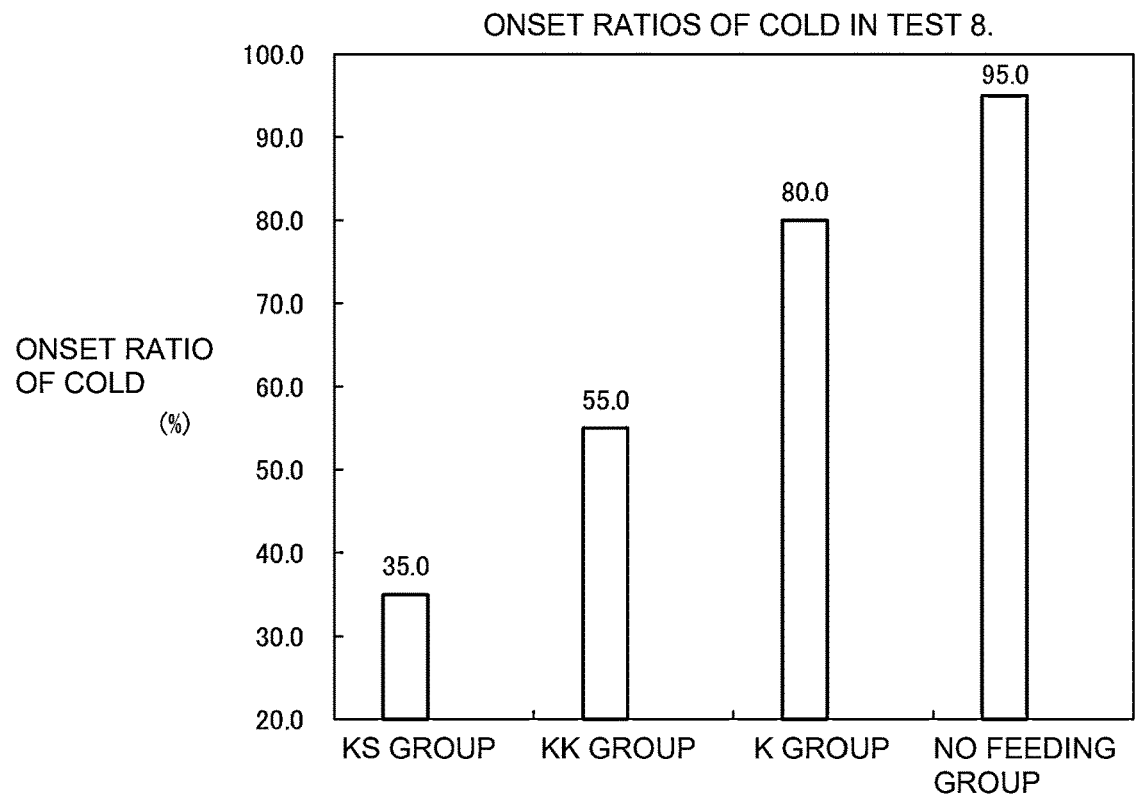
FIG. 81 is a graph showing onset ratios of colds in Test 8.
Figure 82:
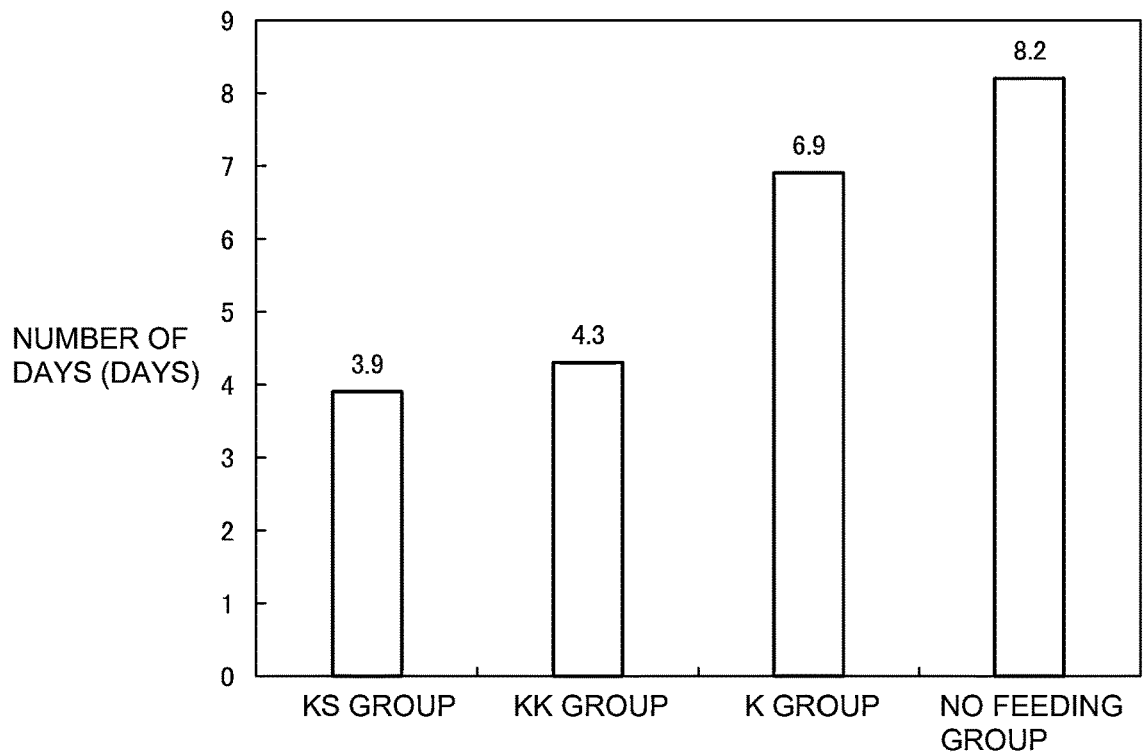
FIG. 82 is a graph showing an average number of treatment days of the colds in Test 8.

Next, the numbers of cases of the onset of colds of the total of 20 head of cattle (numbers of head) are shown in Table 29 and FIG. 81, and the numbers of treatment days of the colds are shown in Table 30 and FIG. 82.

TABLE 29

|  | KS group | KK group | K group | No feeding group |
|---|---|---|---|---|
| 1st to 7th day | 2 | 2 | 1 | 2 |
| 8th to 14th day | 1 | 0 | 1 | 1 |
| 15th to 21st day | 0 | 1 | 3 | 2 |
| 22nd to 28th day | 2 | 1 | 1 | 3 |
| 29th to 35th day | 0 | 3 | 2 | 3 |
| 36th to 42nd day | 0 | 2 | 2 | 2 |
| 43rd to 49th day | 2 | 0 | 2 | 1 |
| 50th to 56th day | 0 | 1 | 1 | 3 |
| 57th to 60th day | 0 | 1 | 3 | 2 |
| No onset (number of cases) | 13 | 9 | 4 | 1 |
| Onset ratio of colds | 35.0% | 55.0% | 80.0% | 95.0% |

TABLE 30

| Colds Number of treatment days | KS group | | TK group | | K group | | No feeding group | |
|---|---|---|---|---|---|---|---|---|
| | Number of head | Number of treatment days × Number of head | Number of head | Number of treatment days × Number of head | Number of head | Number of treatment days × Number of head | Number of head | Number of treatment days × Number of head |
| 1 day | 0 | 0 | 0 | 0 | 0 | 0 | 0 | 0 |
| 2 days | 1 | 2 | 2 | 4 | 0 | 0 | 0 | 0 |
| 3 days | 2 | 6 | 3 | 9 | 1 | 3 | 1 | 3 |
| 4 days | 2 | 8 | 2 | 8 | 2 | 8 | 1 | 4 |
| 5 days | 1 | 5 | 0 | 0 | 1 | 5 | 1 | 5 |
| 6 days | 1 | 6 | 2 | 12 | 2 | 12 | 1 | 6 |
| 7 days | 0 | 0 | 2 | 14 | 4 | 28 | 4 | 28 |
| 8 days | 0 | 0 | 0 | 0 | 3 | 24 | 2 | 16 |
| 9 days | 0 | 0 | 0 | 0 | 1 | 9 | 2 | 18 |
| 10 days | 0 | 0 | 0 | 0 | 1 | 10 | 2 | 20 |
| 11 days | 0 | 0 | 0 | 0 | 1 | 11 | 4 | 44 |
| 12 days | 0 | 0 | 0 | 0 | 0 | 0 | 1 | 12 |
| 13 days | 0 | 0 | 0 | 0 | 0 | 0 | 0 | 0 |
| 14 days | 0 | 0 | 0 | 0 | 0 | 0 | 0 | 0 |
| 15 days | 0 | 0 | 0 | 0 | 0 | 0 | 0 | 0 |
| | Total 7 head | Average 3.9 days | Total 11 head | Average 4.3 days | Total 16 head | Average 6.9 days | Total 19 head | Average 8.2 days |

As shown in Tables 29 to 30 and FIGS. 81 to 82, in the KS group, it was made possible to suppress the number of cases of onset of the colds to the half or less of the number of the cattle. Also in the KK group, it was made possible to substantially suppress the number of cases of onset of the colds, as compared with the K group and the no feeding group, in each of which 80 percent or more of the cattle caught the colds.

In the KS group and the KK group, the numbers of treatment days were also small, as compared with those in the other groups. It was found that by feeding the licorice extract of the present invention as the feed additive, the onset of the colds is suppressed, the colds hardly become severe even if the cattle catch the colds, and the cattle recover in a comparatively short treatment period.

Test 9. From after Birth Up to Approximately 240 Days of Age to Approximately 270 Days of Age (Comparison Among KS Group, TK Group, K Group, and No Feeding Group)

By feeding the licorice extract of the present invention as a feed additive to calves at approximately 240 days of age to approximately 270 days of age after birth, influence of the licorice extract of the present invention exerted on a reduction in leftover amounts of feed upon being weaned (an increase in dietary intakes), nutrition states (GOT values in blood tests), and weights was examined.

In the present test, as with Test 1., in order to clearly confirm the effects obtained by the licorice extract, the calves were completely weaned at approximately 80 days of age.

Targets were a total of 40 head of Japanese Black Cattle including 20 head of castrated male calves and 20 head of female calves at 0 day of age after birth up to days of age at the time of the shipping to a calf auction market. The targets were divided into four groups shown in Table 31.

In a KS group, the licorice extract in Example 5 was added as a feed additive from approximately five days of age after birth, in a TK group, the licorice extract in Example 12 was added as a feed additive, and in a K group, the licorice extract in Comparative Example 1 was added as a feed additive. In a no feeding group, any licorice extract was not added to feed. As to feed other than the licorice extracts (substitute milk, artificial milk, formula feed, and coarse feed such as pasture), feed shown in Table 32 was fed with each amount shown therein divided into three parts a day, and the feed of the formula feed, the rice straws, and the oat hay were fed at and after 81 days of age in this order with the same amount fed to each of the groups at the same time. The creep feed and the oat hay were fed from approximately two weeks after birth.

TABLE 31

| | Licorice extract | Male | Female | Total |
|---|---|---|---|---|
| KS group | Example 5 | 5 head | 5 head | 10 head |
| TK group | Example 12 | 5 head | 5 head | 10 head |
| K group | Comparative Example 1 | 5 head | 5 head | 10 head |
| No feeding group | Not added | 5 head | 5 head | 10 head |

TABLE 32

| | Substitute milk Artificial milk | Creep feed | Formula feed | Rice straws | Oat hay |
|---|---|---|---|---|---|
| 0 to 30 days | Fed | 0.3 kg | — | — | 0.03 kg |
| 31 to 60 days | Fed | 1.5 kg | — | — | 0.2 kg |
| 61 to 80 days | Fed | 3.2 kg | — | — | 0.4 kg |
| 81 to 120 days | — | — | 4.5 kg | 0.4 kg | 1.8 kg |
| 121 to 150 days | — | — | 5.5 kg | 0.4 kg | 2.5 kg |
| 151 to 180 days | — | — | 4.5 kg | 0.4 kg | 4.0 kg |
| 181 to 210 days | — | — | 4.5 kg | 0.4 kg | 4.5 kg |
| 211 to 240 days | — | — | 4.5 kg | 0.4 kg | 5.0 kg |

TABLE 33

| | Substitute milk Artificial milk | Creep feed | Formula feed | Rice straws | Oat hay |
|---|---|---|---|---|---|
| 0 to 30 days | Fed | 0.3 kg | — | — | 0.03 kg |
| 31 to 60 days | Fed | 1.5 kg | — | — | 0.2 kg |
| 61 to 80 days | Fed | 3.0 kg | — | — | 0.4 kg |
| 81 to 120 days | — | — | 4.0 kg | 0.4 kg | 1.5 kg |
| 121 to 150 days | — | — | 4.5 kg | 0.4 kg | 3.5 kg |
| 151 to 180 days | — | — | 4.0 kg | 0.4 kg | 4.0 kg |
| 181 to 210 days | — | — | 4.0 kg | 0.4 kg | 4.5 kg |
| 211 to 240 days | — | — | 4.0 kg | 0.4 kg | 4.5 kg |
| (241 to 270 days) | — | — | (4.0 kg) | (0.4 kg) | (4.5 kg) |

In the KS group, 1 g/day/head of the licorice extract in Example 5 was added to feed as the feed additive and fed from approximately the fifth day after birth, 2 g/day/head thereof was added to the feed as the feed additive and fed from approximately the 41st day after birth, and 3 g/day/head thereof was added to the feed as the feed additive and fed from approximately the 81st day to approximately the 240th day after birth. In the TK group, 1 g/day/head of the licorice extract in Example 12 was added to feed as the feed additive and fed from approximately the fifth day after birth, 2 g/day/head thereof was added to the feed as the feed additive and fed from approximately the 41st day after birth, and 3 g/day/head thereof was added to the feed as the feed additive and fed from approximately the 81st day to approximately the 240th day after birth. In the K group, 1 g/day/head of the licorice extract in Comparative Example 1 was added to feed as the feed additive and fed from approximately the fifth day after birth, 2 g/day/head thereof was added to the feed as the feed additive and fed from approximately the 41st day after birth, and 3 g/day/head thereof was added to the feed as the feed additive and fed from approximately the 81st day to approximately the 240th day after birth.

9.1 Leftover Amounts

As described above, since the formula feed, the rice straws, and the oat hay were fed as the feed at and after 81 days of age in this order, in a case where remaining feed is caused, the oat hay becomes the remaining feed. Accordingly, weights of the remaining feed of the oat hay were measured as leftover amounts. The first day when the approximately 81-day-old calves were weaned is defined as the first day, and transition of leftover amounts is shown in FIGS. 83 and 84.

Figure 83:
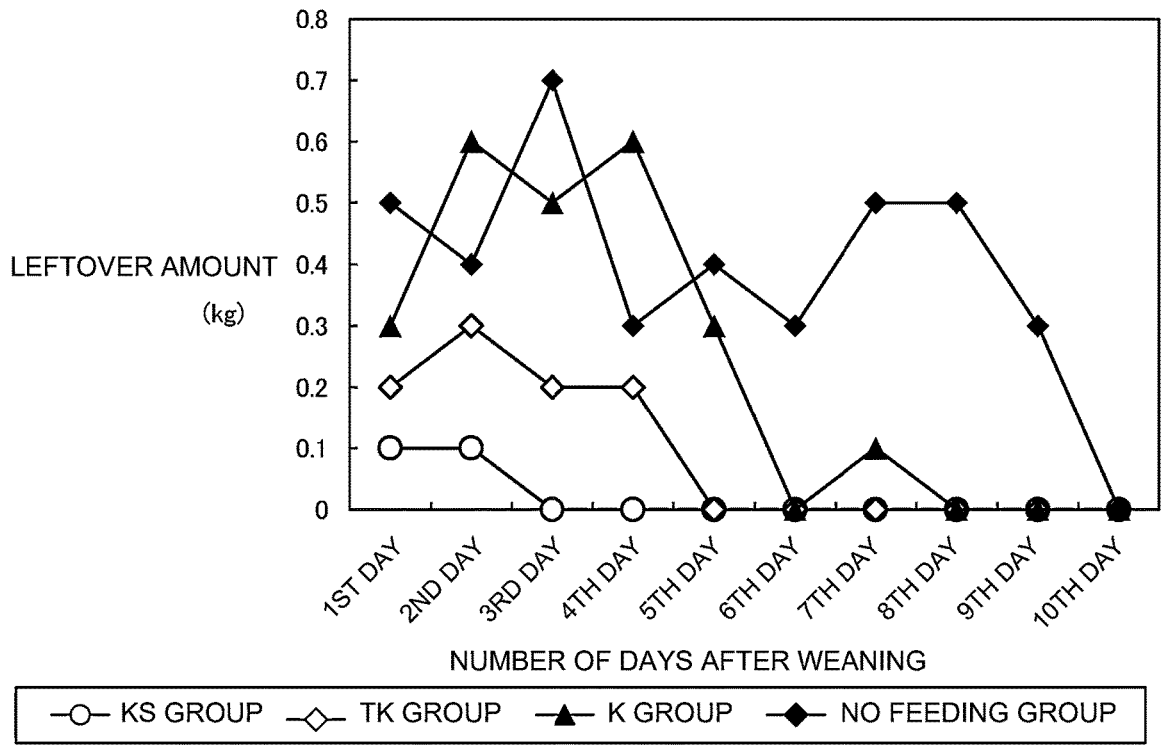
FIG. 83 is a graph showing comparison of average leftover amounts of five males in each group in Test 9.

As shown in FIG. 83, in the KS group, the male calves had no leftover from the third day of weaning and kept complete eating, and in the TK group, the male calves had no leftover from the fifth day of weaning and kept complete eating. In the K group, although the male calves once completely ate on the sixth day, the leftover was caused again, and it took eight days until complete eating was continued. In the no feeding group, the male calves completely ate on the 10th day from weaning.

Figure 84:
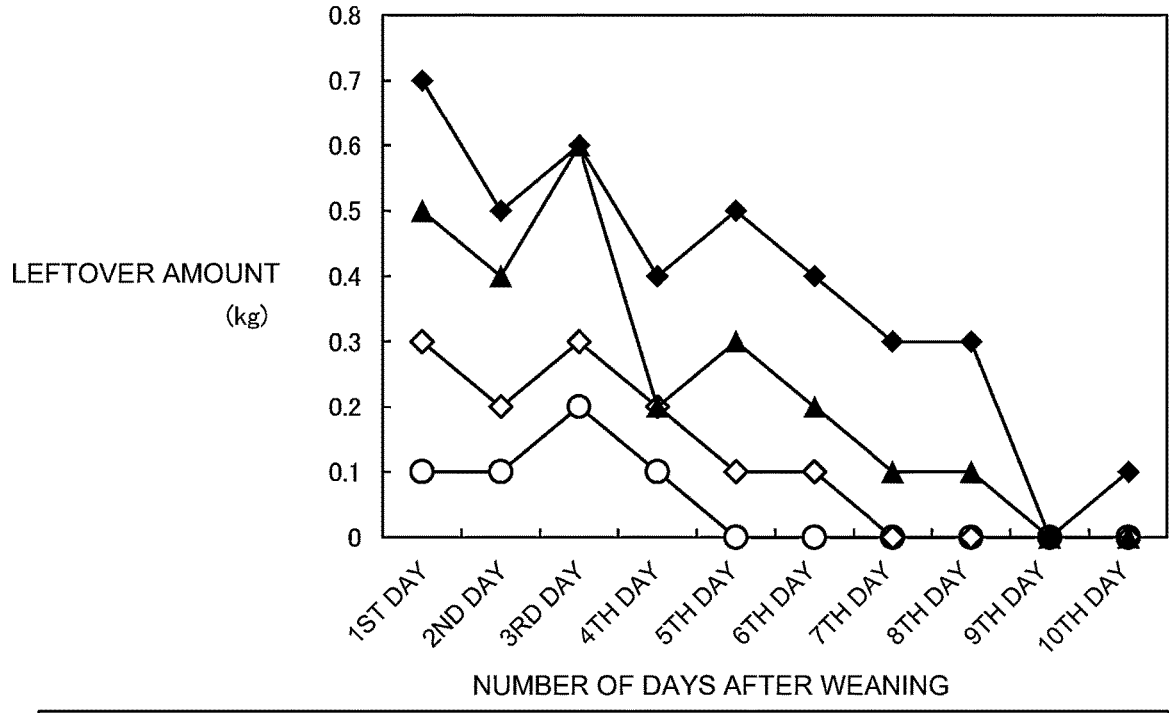
FIG. 84 is a graph showing comparison of average leftover amounts of five females in each group in Test 9.
Figure 85:
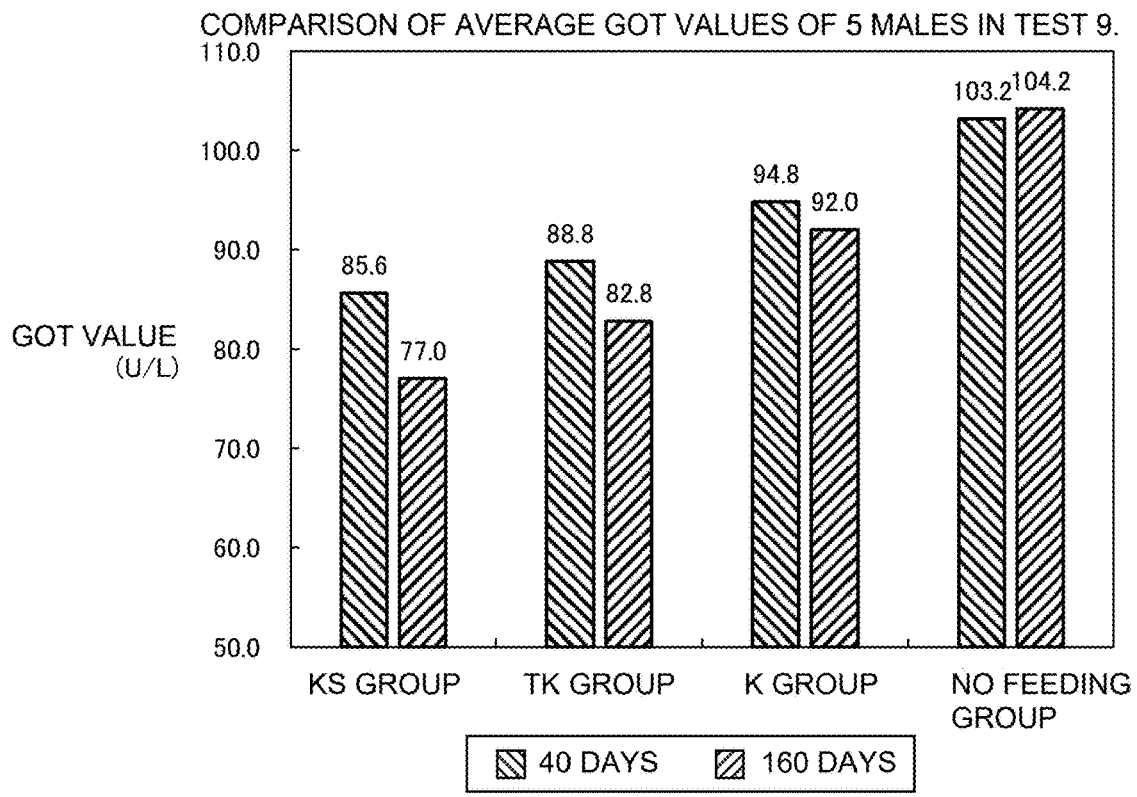
FIG. 85 is a graph showing average GOT values of five males in each group in Test 9.
Figure 86:
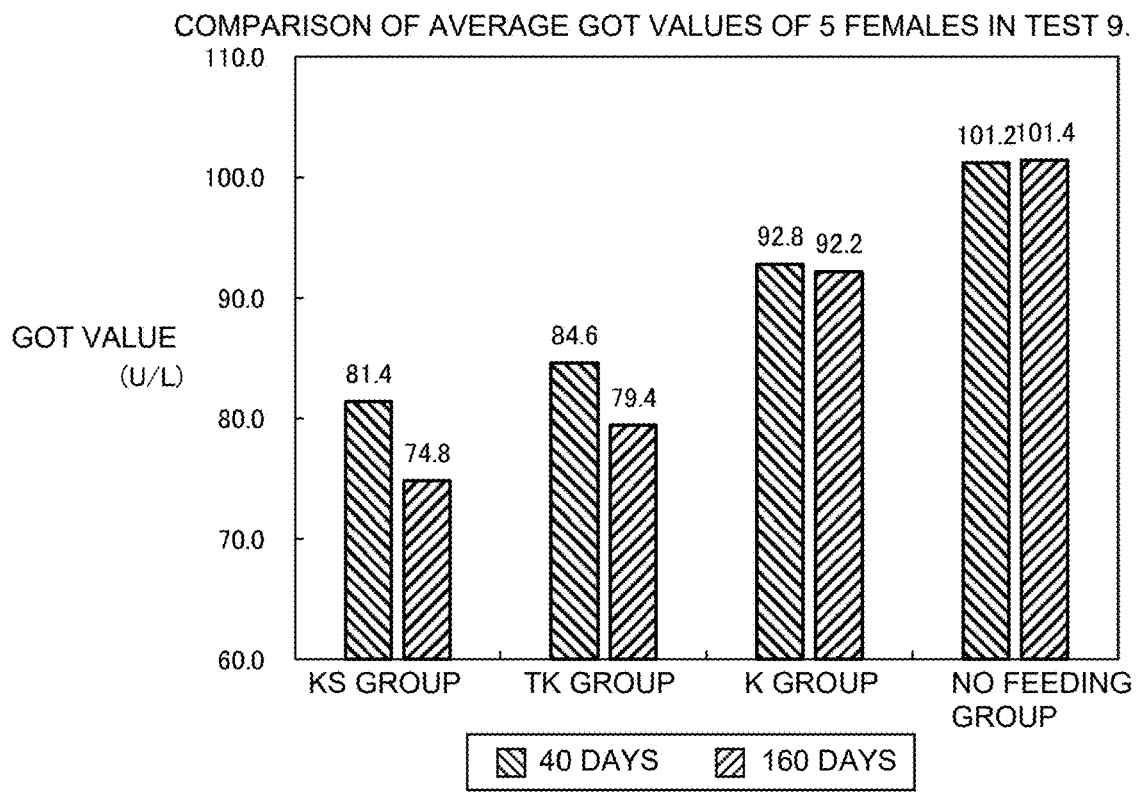
FIG. 86 is a graph showing average GOT values of five females in each group in Test 9.
Figure 87:
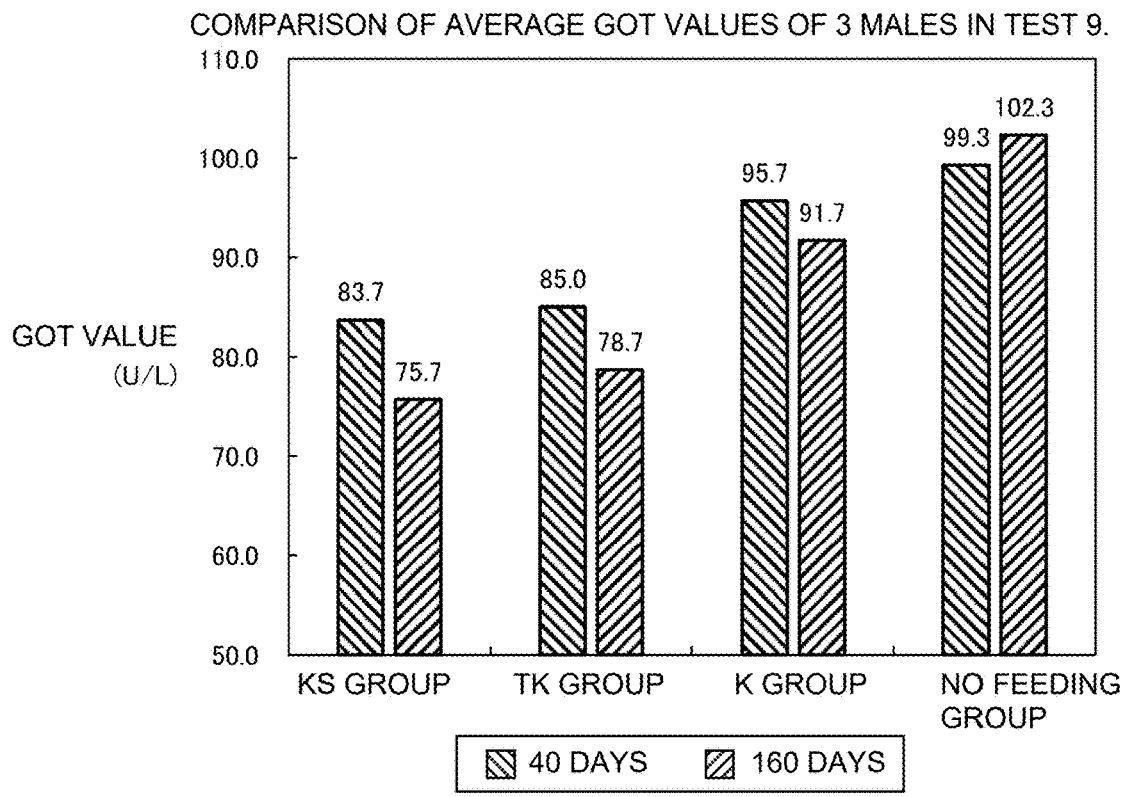
FIG. 87 is a graph showing average GOT values of three males in each group in Test 9.
Figure 88:
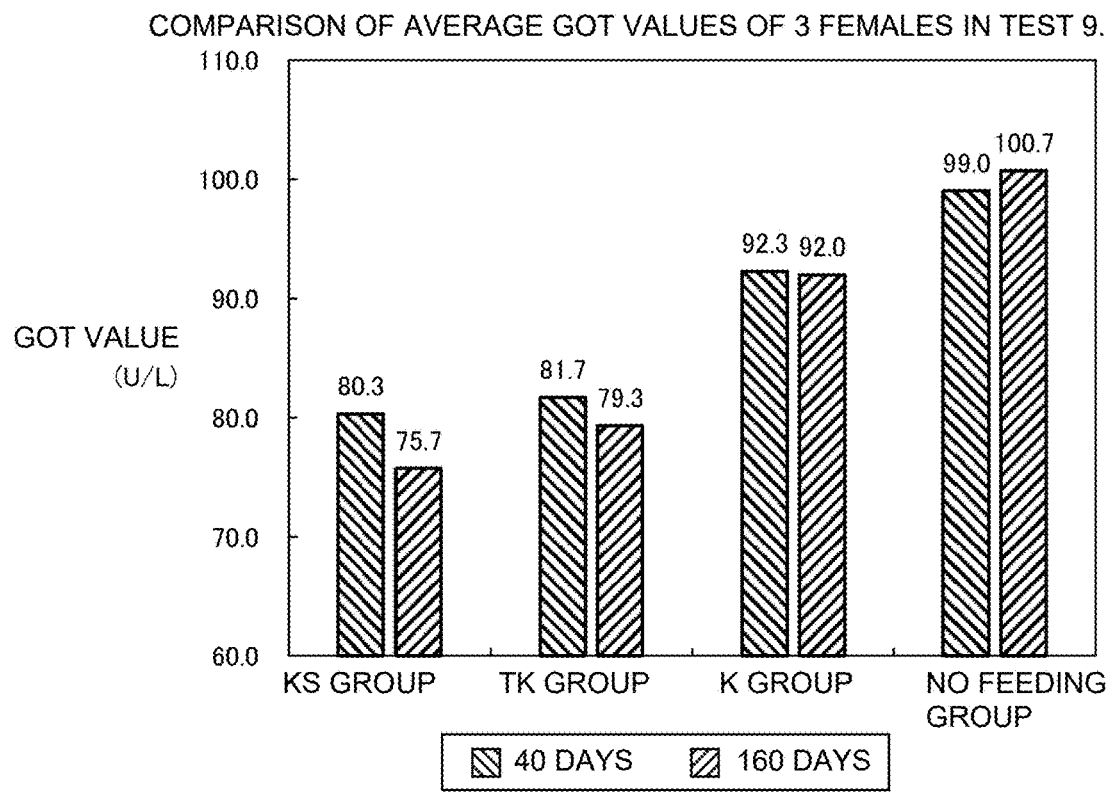
FIG. 88 is a graph showing average GOT values of three females in each group in Test 9.
Figure 89:
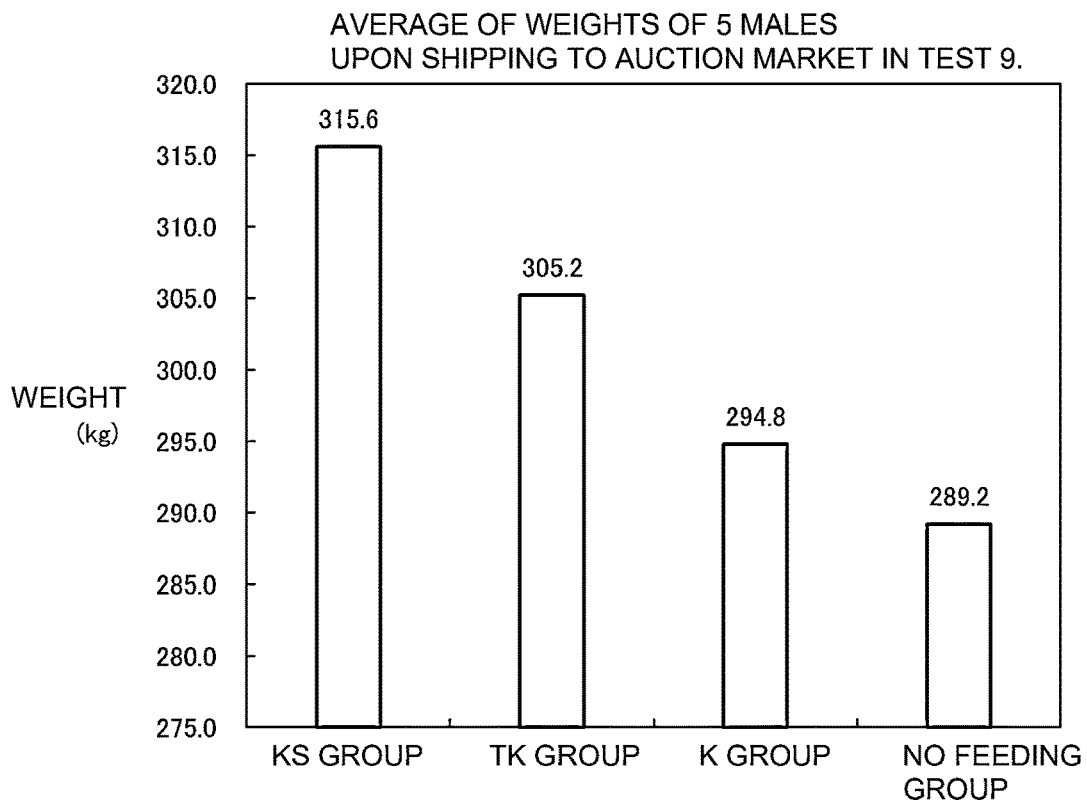
FIG. 89 is a graph showing an average weight of five males in each group upon shipping to an auction market in Test 9.
Figure 90:
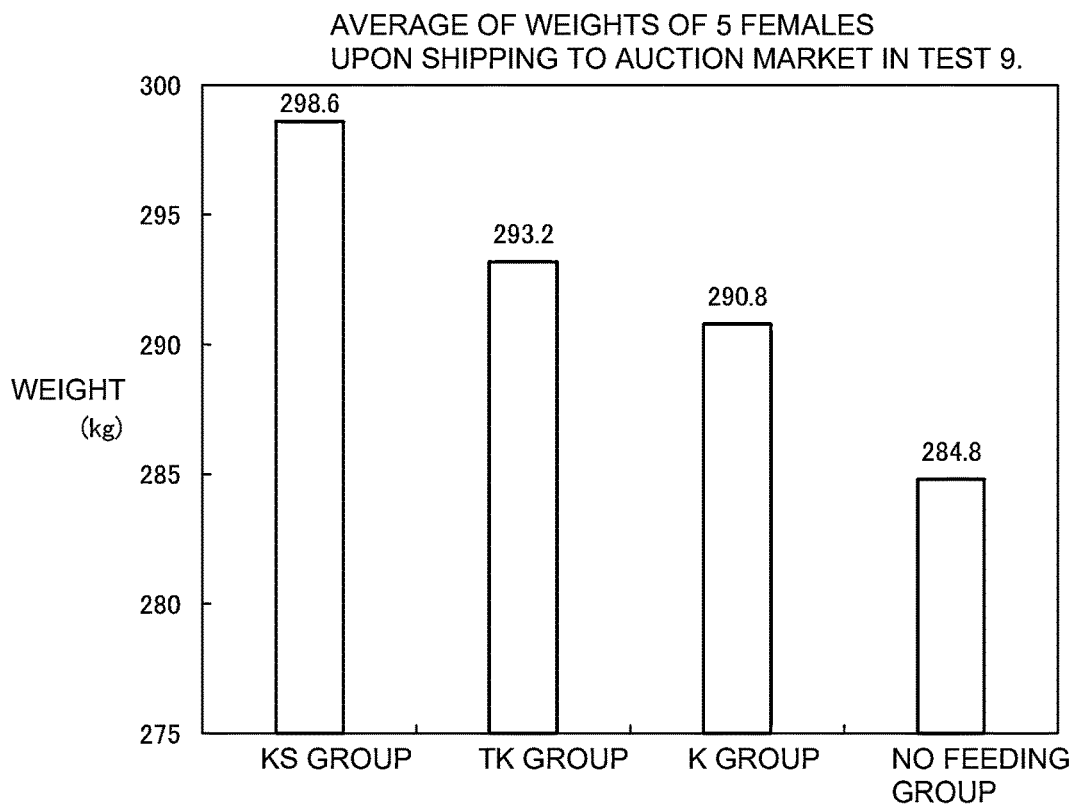
FIG. 90 is a graph showing an average weight of five females in each group upon shipping to the auction market in Test 9.
Figure 91:
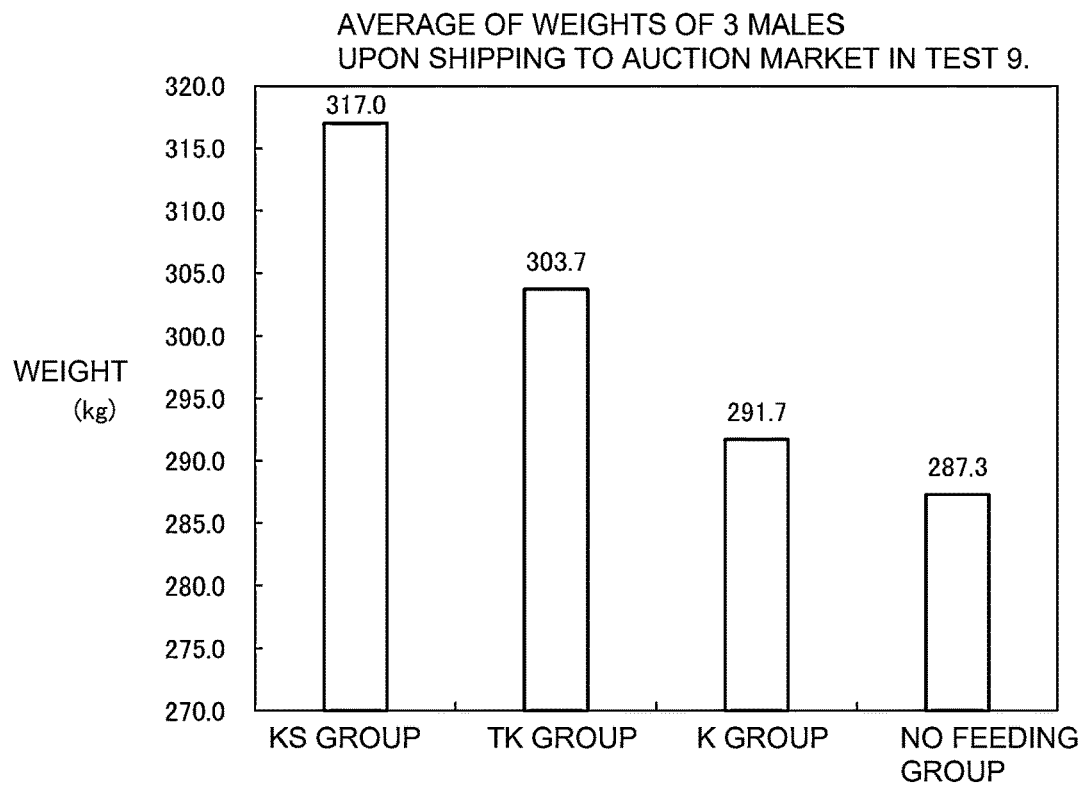
FIG. 91 is a graph showing an average weight of three males in each group upon shipping to the auction market in Test 9.
Figure 92:
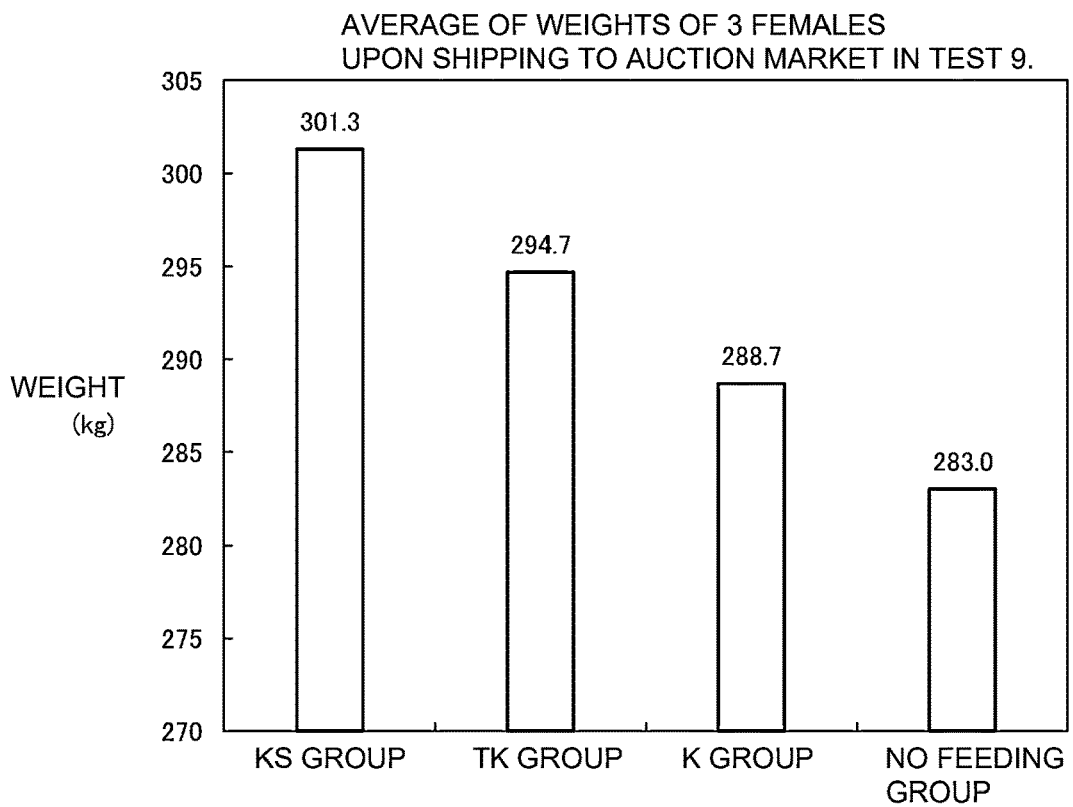
FIG. 92 is a graph showing an average weight of three females in each group upon shipping to the auction market in Test 9.

As shown in FIG. 84, in the KS group, the female calves had no leftover from the fifth day of weaning and kept complete eating, and in the TK group, the female calves had no leftover from the seventh day of weaning and kept complete eating. In the K group, the female calves completely ate on the ninth day from weaning. Also in the no feeding group, the female calves completely ate on the ninth day from weaning but did not completely eat on the 10th day.

As described above, in the KS group to which the licorice extract in Example 5 was fed and in the TK group to which the licorice extract in Example 12 was fed from approximately five days of age after birth, effects by feeding of the licorice extract were exhibited from approximately 81 days of age after weaning. Even as compared with the K group to which the licorice extract including 13% or more of the glycyrrhizic acid was fed, high effects were confirmed, whereby synergy effect of the glycyrrhizic acid, the licorice saponins, and the licorice flavonoids included in the licorice extract in Example 5 with respect to the reduction in the leftover amounts (an increase in dietary intakes) was confirmed.

In the licorice extract in Example 12 fed in the TK group, 15.3% glycyrrhizic acid, which is larger than that contained in the licorice extract in Example 5 fed in the KS group, is contained. On the other hand, amounts of the licorice saponins and the licorice flavonoids, contained in the licorice extract in Example 12, are smaller than those in the licorice extract in Example 5. It is shown in FIG. 83 to FIG. 84 that when the KS group and the TK group are compared, the licorice extract in the KS group in which amounts of the licorice saponins and the licorice flavonoids other than the glycyrrhizic acid are large was effective for the somatic growth despite the small amount of the glycyrrhizic acid, that is, that effectiveness was due to composite effects of the components, not due to the large content of the glycyrrhizic acid.

As described above, it is considered that the feed intakes reflect the stress exerted on the calves, the burdens on the digestive organs, and degrees of development of the digestive organs. It is considered that in the KS group and in the TK group, in each of which the calves completely ate immediately after the weaning and the amounts of the feed intakes were large, as compared with the K group and the no feeding group, the stress of the calves was reduced, the burdens exerted on the digestive organs were decreased, and development states of the digestive organs were fine.

9.2 Blood Test Results (GOT Values)

The blood test (GOT values) on all of the cattle was conducted twice at approximately 40 days of age and approximately 160 days of age after birth.

Average values of GOT values of five males and five females and average values of GOT values of three males and three females excluding two males and two females among the five males and the five females, each of which had the highest value and the lowest value, in each of the groups are shown in FIGS. 85 to 88.

As shown in FIG. 85 to FIG. 88, in the KS group and the TK group, at both of the approximately 40 days of age after birth and the approximately 160 days of age after birth, the GOT values were low, as compared with those in the other groups. In the KS group and the TK group, further, the GOT values at the approximately 160 days of age after birth were lower than those at the approximately 40 days of age after birth. On the other hand, in the K group and the no feeding group, the GOT values at the approximately 40 days of age after birth and those at the approximately 160 days of age after birth remained nearly at the same level or the GOT values at the approximately 160 days of age after birth were slightly higher than those at the approximately 40 days of age after birth.

It was found from the above-described results that favorable influence is exerted on the liver function (GOT values) by composite effects of the glycyrrhizic acid, the licorice saponins other than the glycyrrhizic acid, and the licorice flavonoids, not by the effects of the glycyrrhizic acid.

9.3 Weights

Average values of weights of five males and five females and average values of weights of three males and three females excluding two males and two females among the five males and the five females, each of which had the highest value and the lowest value, the weight measured upon shipping to an auction market, in each of the groups are shown in FIGS. 89 to 92. In the no feeding group of females, due to weight shortage on the 240th day, the females were shipped on the 270th day. Note that since auction market dates are limited, there are some differences in days of age upon shipping.

As shown in FIGS. 89 to 92, the weights in the KS group were larger than those in the other groups. Also in the TK group, somatic growth was large, as compared with that in the no feeding group. Although as to the females in the no feeding group in particular, a shipping date was extended to approximately 270 days of age, the weights did not reach those at the females at 240 days of age in the KS group and TK group.

Test 10. Onset of Diarrhea and Onset of Colds and Numbers of Treatment Days (Comparison Among KS Group, TK Group, K Group, and No Feeding Group)

By feeding the licorice extract of the present invention as a feed additive to calves from approximately five days of age to approximately 60 days of age after birth, influence of the licorice extract of the present invention exerted on onset ratios of diarrhea due to indigestion, numbers of treatment days of diarrhea due to the indigestion, onset ratios of colds, and numbers of treatment days of the colds was examined.

Targets were 40 head of Japanese Black Cattle calves at approximately five days of age to approximately 60 days of age a after birth. The targets were divided into four groups shown in Table 34.

TABLE 34

|  | A Farm Male | B Farm Female | Total |
|---|---|---|---|
| KS group | 5 head | 5 head | 10 head |
| TK group | 5 head | 5 head | 10 head |
| K group | 5 head | 5 head | 10 head |
| No feeding group | 5 head | 5 head | 10 head |

In the KS group, the licorice extract in Example 5 was added to feed as a feed additive, in the TK group, the licorice extract in Example 12 was added to feed as a feed additive, and in the K group, the licorice extract in Comparative Example 1 was added to feed as a feed additive. In the no feeding group, any licorice extract was not added to feed. As to feed other than the licorice extracts (substitute milk, creep feed, and oat hay), the feed was fed to both of the males and the females with the same amount fed to each of the groups at the same time by dividing each amount into three parts a day. The creep feed and the oat hay were fed from after approximately two weeks after birth.

In the KS group, from approximately five days of age after birth to approximately 60 days of age after birth, 2 g/day/head of the licorice extract in Example 5 was added to the feed as the feed additive and fed. In the TK group, from approximately five days of age after birth to approximately 60 days of age after birth, 2 g/day/head of the licorice extract in Example 12 was added to the feed as the feed additive and fed. In the K group, from approximately five days of age after birth to approximately 60 days of age after birth, 2 g/day/head of the licorice extract in Comparative Example 1 was added to the feed as the feed additive and fed.

Figure 93:
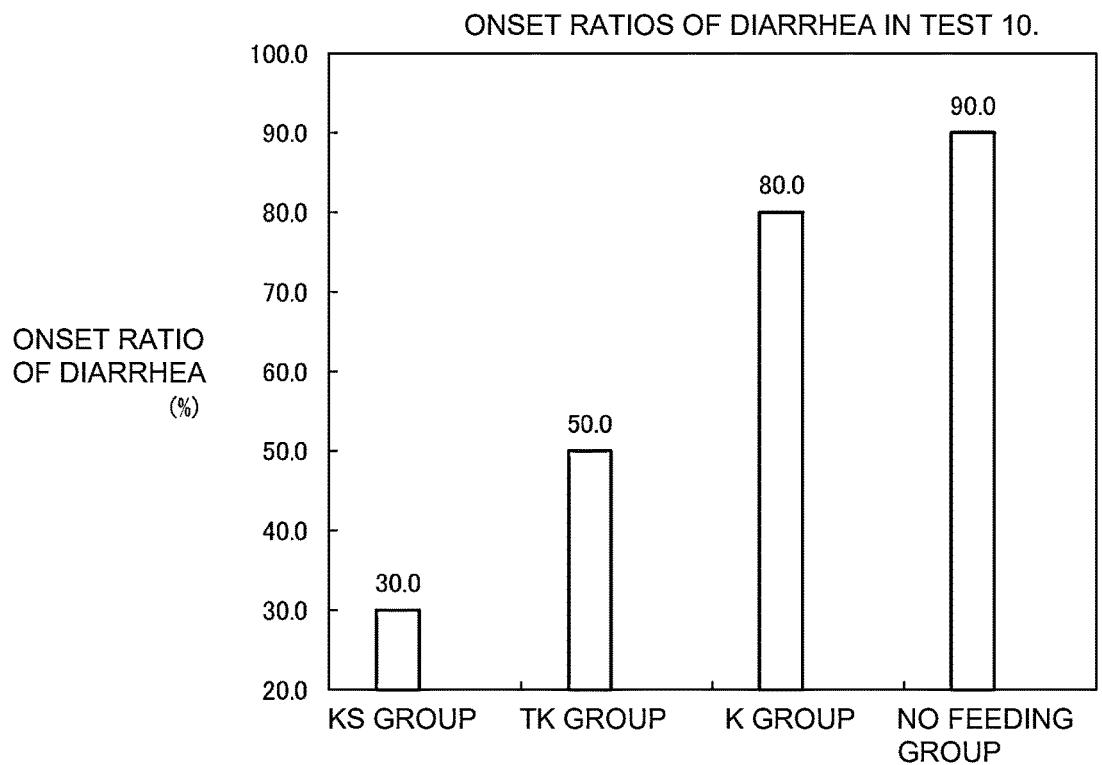
FIG. 93 is a graph showing onset ratios of diarrhea in Test 10.
Figure 94:
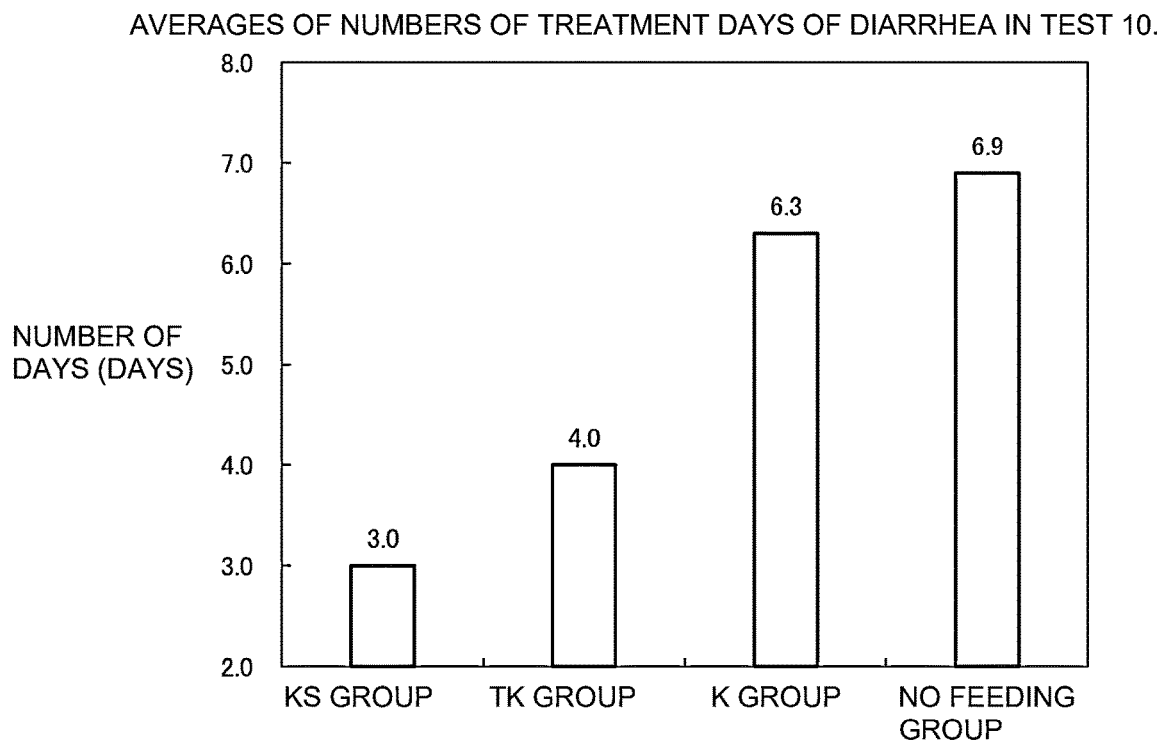
FIG. 94 is a graph showing an averages number of treatment days of the diarrhea in Test 10.

Numbers of cases of onset of the diarrhea (numbers of head) among the total of 40 head of cattle due to the indigestion are shown in Table 35 and FIG. 93, and numbers of treatment days of the diarrhea are shown in table 36 and FIG. 94.

TABLE 35

|  | KS group | TK group | K group | No feeding group |
|---|---|---|---|---|
| 1st to 7th day | 1 | 2 | 0 | 1 |
| 8th to 14th day | 0 | 1 | 2 | 1 |
| 15th to 21st day | 1 | 1 | 1 | 1 |
| 22nd to 28th day | 1 | 1 | 2 | 2 |
| 29th to 35th day | 0 | 0 | 0 | 1 |
| 36th to 42nd day | 0 | 0 | 2 | 1 |
| 43rd to 49th day | 0 | 0 | 0 | 1 |
| 50th to 56th day | 0 | 0 | 1 | 1 |
| 57th to 60th day | 0 | 0 | 0 | 0 |
| No onset (number of cases) | 7 | 5 | 2 | 1 |
| Onset ratio of diarrhea | 30.0% | 50.0% | 80.0% | 90.0% |

TABLE 36

|  | KS group | | TK group | | K group | | No feeding group | |
|---|---|---|---|---|---|---|---|---|
| Diarrhea Number of treatment days | Number of head | Number of treatment days × Number of head | Number of head | Number of treatment days × Number of head | Number of head | Number of treatment days × Number of head | Number of head | Number of treatment days × Number of head |
| 1 day | 0 | 0 | 0 | 0 | 0 | 0 | 0 | 0 |
| 2 days | 1 | 2 | 0 | 0 | 1 | 2 | 0 | 0 |
| 3 days | 1 | 3 | 2 | 6 | 0 | 0 | 1 | 3 |

TABLE 36-continued

|  | KS group | | TK group | | K group | | No feeding group | |
|---|---|---|---|---|---|---|---|---|
| Diarrhea Number of treatment days | Number of head | Number of treatment days × Number of head | Number of head | Number of treatment days × Number of head | Number of head | Number of treatment days × Number of head | Number of head | Number of treatment days × Number of head |
| 4 days | 1 | 4 | 2 | 8 | 0 | 0 | 0 | 0 |
| 5 days | 0 | 0 | 0 | 0 | 2 | 10 | 2 | 10 |
| 6 days | 0 | 0 | 1 | 6 | 1 | 6 | 2 | 12 |
| 7 days | 0 | 0 | 0 | 0 | 1 | 7 | 0 | 0 |
| 8 days | 0 | 0 | 0 | 0 | 2 | 16 | 1 | 8 |
| 9 days | 0 | 0 | 0 | 0 | 1 | 9 | 2 | 18 |
| 10 days | 0 | 0 | 0 | 0 | 0 | 0 | 0 | 0 |
| 11 days | 0 | 0 | 0 | 0 | 0 | 0 | 1 | 11 |
| 12 days | 0 | 0 | 0 | 0 | 0 | 0 | 0 | 0 |
| 13 days | 0 | 0 | 0 | 0 | 0 | 0 | 0 | 0 |
| 14 days | 0 | 0 | 0 | 0 | 0 | 0 | 0 | 0 |
| 15 days | 0 | 0 | 0 | 0 | 0 | 0 | 0 | 0 |
|  | Total 3 head | Average 3.0 days | Total 5 head | Average 4.0 days | Total 8 head | Average 6.3 days | Total 9 head | Average 6.9 days |

As shown in Tables 35 to 36 and FIGS. 93 to 94, it was made possible to suppress the numbers of cases of onset of the diarrhea in the KS group and the TK group to the half or less of the numbers of head of the cattle.

In the KS group and the TK group, the numbers of treatment days were also small, as compared with those in the other groups. It was found that by feeding the licorice extract of the present invention as the feed additive, the onset of the diarrhea is suppressed, the diarrhea hardly becomes severe even if the cattle get the diarrhea, and the cattle recover in a comparatively short treatment period. In particular, in the KS group, although when only the amount of the glycyrrhizic acid is seen, the amount thereof was smaller than those in the TK group and the K group, the number of cases of onset of the diarrhea and also the number of treatment days were the smallest. Also in this Test, composite effects of (A) glycyrrhizic acid, (B) licorice saponins other than the glycyrrhizic acid, and (C) licorice flavonoids were shown, not by effects of the glycyrrhizic acid alone.

Figure 95:
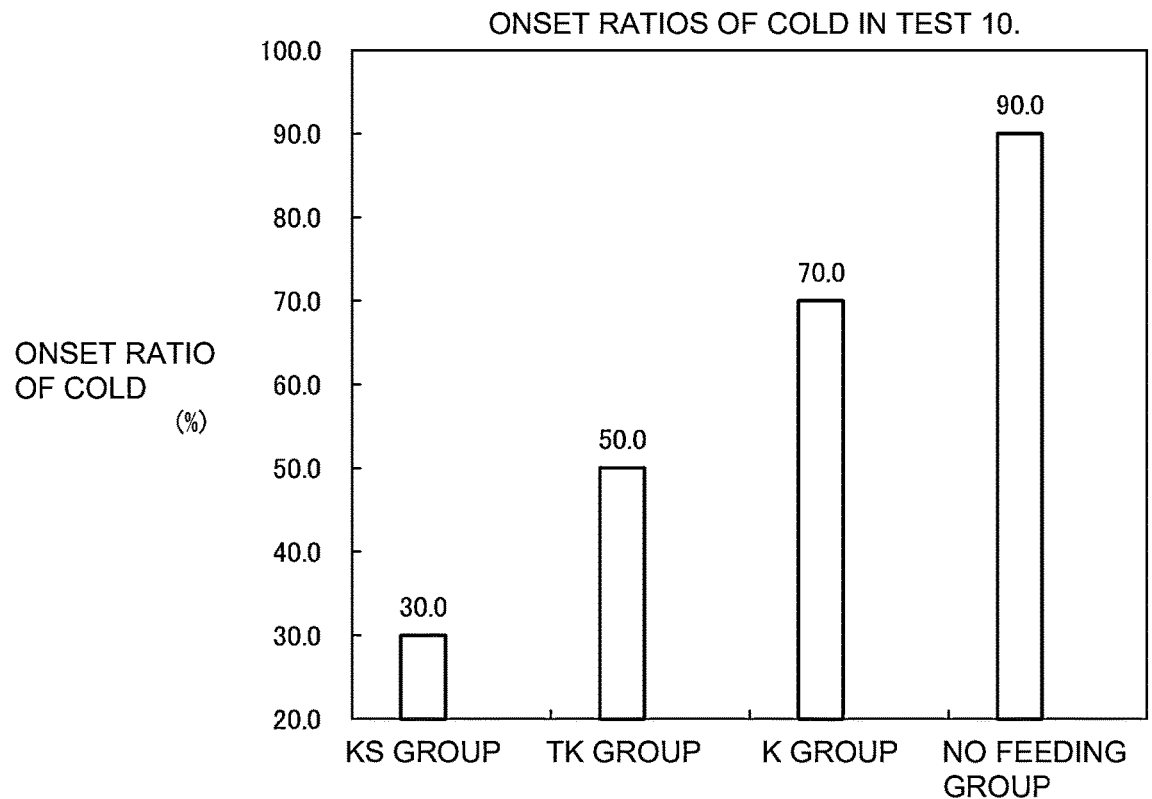
FIG. 95 is a graph showing onset ratios of colds in Test 10.
Figure 96:
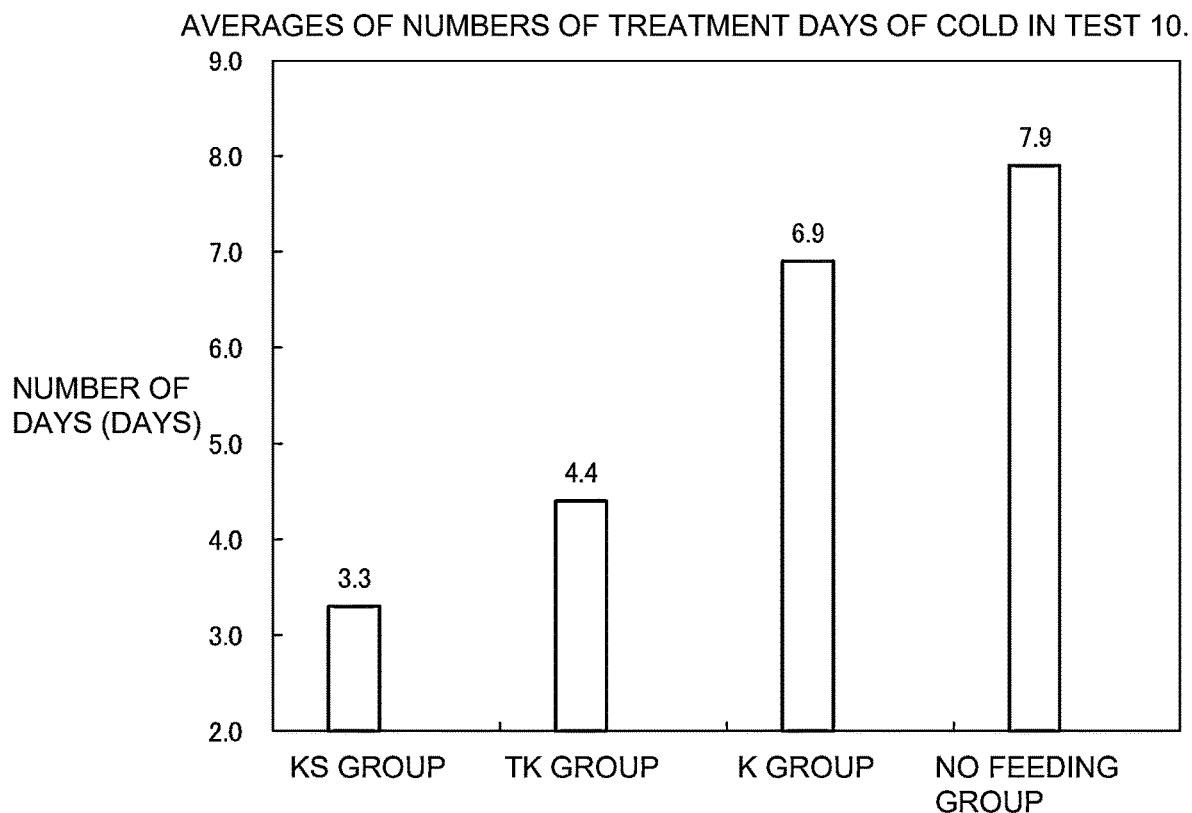
FIG. 96 is a graph showing an averages number of treatment days of the colds in Test 10.

Next, the numbers of cases of the onset of the colds of the total of 40 head of cattle (numbers of head) are shown in Table 37 and FIG. 95, and the numbers of treatment days of the colds are shown in Table 38 and FIG. 96.

TABLE 37

|  | KS group | TK group | K group | No feeding group |
|---|---|---|---|---|
| 1st to 7th day | 1 | 1 | 0 | 2 |
| 8th to 14th day | 0 | 1 | 2 | 0 |
| 15th to 21st day | 1 | 0 | 1 | 2 |
| 22nd to 28th day | 0 | 1 | 1 | 1 |
| 29th to 35th day | 0 | 1 | 1 | 0 |
| 36th to 42nd day | 1 | 0 | 0 | 2 |
| 43rd to 49th day | 0 | 1 | 1 | 0 |
| 50th to 56th day | 0 | 0 | 1 | 1 |
| 57th to 60th day | 0 | 0 | 0 | 1 |
| No onset (number of cases) | 7 | 5 | 3 | 1 |
| Onset ratio of colds | 30.0% | 50.0% | 70.0% | 90.0% |

TABLE 38

|  | KS group | | TK group | | K group | | No feeding group | |
|---|---|---|---|---|---|---|---|---|
| Colds Number of treatment days | Number of head | Number of treatment days × Number of head | Number of head | Number of treatment days × Number of head | Number of head | Number of treatment days × Number of head | Number of head | Number of treatment days × Number of head |
| 1 day | 0 | 0 | 0 | 0 | 0 | 0 | 0 | 0 |
| 2 days | 1 | 2 | 1 | 2 | 0 | 0 | 0 | 0 |
| 3 days | 0 | 0 | 0 | 0 | 0 | 0 | 0 | 0 |
| 4 days | 2 | 8 | 2 | 8 | 1 | 4 | 2 | 8 |
| 5 days | 0 | 0 | 1 | 5 | 2 | 10 | 1 | 5 |
| 6 days | 0 | 0 | 0 | 0 | 0 | 0 | 0 | 0 |
| 7 days | 0 | 0 | 1 | 7 | 1 | 7 | 1 | 7 |
| 8 days | 0 | 0 | 0 | 0 | 1 | 8 | 0 | 0 |
| 9 days | 0 | 0 | 0 | 0 | 1 | 9 | 2 | 18 |
| 10 days | 0 | 0 | 0 | 0 | 1 | 10 | 1 | 10 |
| 11 days | 0 | 0 | 0 | 0 | 0 | 0 | 1 | 11 |

TABLE 38-continued

| Colds Number of treatment days | KS group | | TK group | | K group | | No feeding group | |
|---|---|---|---|---|---|---|---|---|
| | Number of head | Number of treatment days × Number of head | Number of head | Number of treatment days × Number of head | Number of head | Number of treatment days × Number of head | Number of head | Number of treatment days × Number of head |
| 12 days | 0 | 0 | 0 | 0 | 0 | 0 | 1 | 12 |
| 13 days | 0 | 0 | 0 | 0 | 0 | 0 | 0 | 0 |
| 14 days | 0 | 0 | 0 | 0 | 0 | 0 | 0 | 0 |
| 15 days | 0 | 0 | 0 | 0 | 0 | 0 | 0 | 0 |
| | Total 3 head | Average 3.3 days | Total 5 head | Average 4.4 days | Total 7 head | Average 6.9 days | Total 9 head | Average 7.9 days |

As shown in Tables 37 to 38 and FIGS. 95 to 96, it was made possible to suppress the numbers of cases of onset of the colds in the KS group and the TK group to the half or less of the numbers of head of the cattle.

In the KS group and the TK group, the numbers of treatment days were also small, as compared with those in the other groups. It was found that by feeding the licorice extract of the present invention as the feed additive, the onset of the colds is suppressed, the colds hardly become severe even if the cattle catch the colds, and the cattle recover in a comparatively short treatment period.

As described above, it was confirmed that by feeding the licorice extract of the present invention or the supplement or the feed additive which includes the licorice extract of the present invention to the mammals or the livestock, the health conditions can be improved by at least one selected from the group consisting of an increase in dietary intakes of the mammals or the livestock, an increase in total cholesterol values in the blood thereof, an increase in vitamin A values in the blood thereof, a reduction in GOT values in the blood thereof, an increase in weights thereof, prevention of diarrhea therefor, a reduction in the number of treatment days of the diarrhea therefor, prevention of colds therefor, and a reduction in the number of treatment days of the colds therefor.

In addition, as described above, also in the tests conducted at any stage of the suckling stage, the weaning stage, and the fattening stage, despite the feeding manner in which in the KS group, the K group, and the no feeding group, the same kinds of the feed, other than the licorice extract, in the same amounts were fed, the effects of the smaller leftover amounts in the KS group than those in the other groups (the large dietary intakes), the increases in the somatic growth and the carcass weights, the increase in the carcass yield rates and the reduction in the edible liver discard rates were obtained. It was confirmed that by feeding the licorice extract of the present invention or the supplement or the feed additive which includes the licorice extract of the present invention to the mammals or the livestock, the ratio by the weight of the given feed and the amount of meat production (feed efficiency) can be increased.

The described embodiment and examples are to be considered in all respects only as illustrative and not restrictive. It is intended that the scope of the invention is, therefore, indicated by the appended claims rather than the foregoing description of the embodiment and examples and that all modifications and variations coming within the meaning and equivalency range of the appended claims are embraced within their scope.

The invention claimed is:

1. A method for improving health conditions of mammals or livestock by feeding, to the mammals or livestock, a licorice extract including:
   (A) one or more selected from the group consisting of glycyrrhizic acid, a glycyrrhizic acid derivative, glycyrrhetinic acid, and a glycyrrhetinic acid derivative;
   (B) licorice saponins other than the (A); and
   (C) licorice flavonoids,
   the (B) including at least a licorice saponin H2, a licorice saponin G2, and macedonoside A,
   the (C) including at least liquiritin apioside, isoliquiritin apioside, and isoliquiritin,
   by feeding, to the mammals or livestock, 0.017 g/day/head or more of the licorice saponin H2, 0.002 g/day/head or more of the licorice saponin G2, and 0.002 g/day/head or more of the macedonoside A, and
   by feeding, to the mammals or livestock, 0.001 g/day/head or more of the liquiritin apioside, 0.001 g/day/head or more of the isoliquiritin apioside, and 0.001 g/day/head or more of the isoliquiritin,
   the method for improving the health conditions of the mammals or livestock by at least one selected from the group consisting of an increase in dietary intakes of the mammals or livestock, an increase in total cholesterol values in the blood of the mammals or livestock, an increase in vitamin A values in the blood of the mammals or livestock, a reduction in GOT values in the blood of the mammals or livestock, an increase in weights of the mammals or the livestock, prevention of diarrhea for the mammals or livestock, a reduction in numbers of treatment days of the diarrhea for the mammals or the livestock, prevention of colds for the mammals or livestock, and a reduction in numbers of treatment days of the colds for the mammals or livestock.

2. The method according to claim 1, comprising:
   feeding, to the mammals or livestock,
   0.017 g/day/head or more of the licorice saponin H2, 0.002 g/day/head or more of the licorice saponin G2, and 0.009 g/day/head or more of the macedonoside A; and
   0.001 g/day/head or more of the liquiritin apioside, 0.001 g/day/head or more of the isoliquiritin apioside, and 0.001 g/day/head or more of the isoliquiritin.

3. The method according to claim 1, comprising:
feeding, to the mammals or livestock,
- 0.029 g/day/head or more of the licorice saponin H2, 0.005 g/day/head or more of the licorice saponin G2, and 0.002 g/day/head or more of the macedonoside A; and
- 0.009 g/day/head or more of the liquiritin apioside, 0.001 g/day/head or more of the isoliquiritin apioside, and 0.001 g/day/head or more of the isoliquiritin.

4. The method according to claim 1, comprising:
feeding, to the mammals or livestock,
- 0.02 g/day/head or more of the licorice saponin H2, 0.005 g/day/head or more of the licorice saponin G2, and 0.005 g/day/head or more of the macedonoside A; and
- 0.024 g/day/head or more of the liquiritin apioside, 0.004 g/day/head or more of the isoliquiritin apioside, and 0.003 g/day/head or more of the isoliquiritin.

5. The method according to claim 1, comprising:
feeding, to the mammals or livestock,
- 0.063 g/day/head or more of the licorice saponin H2, 0.008 g/day/head or more of the licorice saponin G2, and 0.026 g/day/head or more of the macedonoside A; and
- 0.056 g/day/head or more of the liquiritin apioside, 0.018 g/day/head or more of the isoliquiritin apioside, and 0.027 g/day/head or more of the isoliquiritin.

6. The method according to claim 1, comprising feeding, to the mammals or livestock,
- 0.09 g/day/head or more of the (A), and/or
- 0.02 g/day/head or more of the (B), and/or
- 0.04 g/day/head or more of the (C).

7. The method according to claim 1, comprising feeding, to the mammals or livestock,
- 0.15 g/day/head or more of the (A), and/or
- 0.02 g/day/head or more of the (B), and/or
- 0.04 g/day/head or more of the (C).

8. The method according to claim 1, comprising feeding, to the mammals or livestock
- 0.09 g/day/head or more of the (A), and/or
- 0.03 g/day/head or more of the (B), and/or
- 0.10 g/day/head or more of the (C).

9. The method according to claim 1, comprising feeding, to the mammals or livestock,
- 0.14 g/day/head or more of the (A), and/or
- 0.09 g/day/head or more of the (B), and/or
- 0.19 g/day/head or more of the (C).

10. The method according to claim 1, wherein the licorice extract includes:
the (A) one or more selected from the group consisting of the glycyrrhizic acid, the glycyrrhizic acid derivative, the glycyrrhetinic acid, and the glycyrrhetinic acid derivative,
the (B) the licorice saponins other than the (A); and
the (C) the licorice flavonoids,
the (B) including at least 1.7% by mass or more of the licorice saponin H2, 0.2% by mass or more of the licorice saponin G2, and 0.2% by mass or more of the macedonoside A,
the (C) including at least 0.1% by mass or more of the liquiritin apioside, 0.1% by mass or more of the isoliquiritin apioside, and 0.1% by mass or more of the isoliquiritin.

11. The method according to claim 2, wherein the (B) includes at least 1.7% by mass or more of the licorice saponin H2, 0.2% by mass or more of the licorice saponin G2, and 0.9% by mass or more of the macedonoside A, and
the (C) includes at least 0.1% by mass or more of the liquiritin apioside, 0.1% by mass or more of the isoliquiritin apioside, and 0.1% by mass or more of the isoliquiritin.

12. The method according to claim 3, wherein the (B) includes at least 2.9% by mass or more of the licorice saponin H2, 0.5% by mass or more of the licorice saponin G2, and 0.2% by mass or more of the macedonoside A, and
the (C) includes at least 0.9% by mass or more of the liquiritin apioside, 0.1% by mass or more of the isoliquiritin apioside, and 0.1% by mass or more of the isoliquiritin.

13. The method according to claim 4, wherein the (B) includes at least 2% by mass or more of the licorice saponin H2, 0.5% by mass or more of the licorice saponin G2, and 0.5% by mass or more of the macedonoside A, and
the (C) includes at least 2.4% by mass or more of the liquiritin apioside, 0.4% by mass or more of the isoliquiritin apioside, and 0.3% by mass or more of the isoliquiritin.

14. The method according to claim 5, wherein the (B) includes at least 6.3% by mass or more of the licorice saponin H2, 0.8% by mass or more of the licorice saponin G2, and 2.6% by mass or more of the macedonoside A, and
the (C) includes at least 5.6% by mass or more of the liquiritin apioside, 1.8% by mass or more of the isoliquiritin apioside, and 2.7% by mass or more of the isoliquiritin.

15. The method according to claim 6, wherein
9% by mass or more of the (A) is included, and/or
2% by mass or more of the (B) is included, and/or
4% by mass or more of the (C) is included.

16. The method according to claim 1, wherein the licorice extract is included in a feed additive.

17. The method according to claim 16, wherein the feed additive includes water-soluble dietary fiber.

18. The method according to claim 17, wherein the feed additive includes the licorice extract and the water-soluble dietary fiber in a mass ratio of the licorice extract:the water-soluble dietary fiber=10:90 to 40:60.

19. The method according to claim 17, wherein the water-soluble dietary fiber is glucomannan.

\* \* \* \* \*